US012624068B2

(12) United States Patent
Chung et al.

(10) Patent No.: US 12,624,068 B2
(45) Date of Patent: *May 12, 2026

(54) EXON SKIPPING BY PEPTIDE NUCLEIC ACID DERIVATIVES

(71) Applicant: OliPass Corporation, Yongin-si (KR)

(72) Inventors: Shin Chung, Yongin-si (KR); Daram Jung, Hwaseong-Si (KR); Bongjun Cho, Yongin-Si (KR); Kangwon Jang, Yongin-Si (KR); Heungsik Yoon, Seongnam-Si (KR)

(73) Assignee: OliPass Corporation, Yongin-si (KR)

( * ) Notice: Subject to any disclaimer, the term of this patent is extended or adjusted under 35 U.S.C. 154(b) by 79 days.

This patent is subject to a terminal disclaimer.

(21) Appl. No.: 16/474,686

(22) PCT Filed: Dec. 29, 2017

(86) PCT No.: PCT/IB2017/001725

§ 371 (c)(1),
(2) Date: Jun. 28, 2019

(87) PCT Pub. No.: WO2018/122610

PCT Pub. Date: Jul. 5, 2018

(65) Prior Publication Data

US 2019/0337987 A1 Nov. 7, 2019

Related U.S. Application Data

(60) Provisional application No. 62/440,929, filed on Dec. 30, 2016.

(51) Int. Cl.

*C07K 14/00* (2006.01)
*C07K 7/02* (2006.01)
*C12N 15/113* (2010.01)
*A61K 38/00* (2006.01)

(52) U.S. Cl.

CPC .............. *C07K 14/003* (2013.01); *C07K 7/02* (2013.01); *C12N 15/113* (2013.01); *A61K 38/00* (2013.01); *C12N 2310/3181* (2013.01); *C12N 2320/33* (2013.01)

(58) Field of Classification Search

CPC ..... C12N 15/11; C12N 15/111; C12N 15/113; C12N 2310/11; C12N 2320/33; C12N 2310/31; C12N 2310/3181; C07K 14/003

See application file for complete search history.

(56) References Cited

U.S. PATENT DOCUMENTS

| | | | |
|---|---|---|---|
| 6,566,135 | B1 | 5/2003 | Watt |
| 6,617,422 | B1 | 9/2003 | Nielsen et al. |
| 8,183,221 | B2 | 5/2012 | Thakker et al. |
| 2003/0119767 | A1 | 6/2003 | Dobie et al. |
| 2003/0207804 | A1 | 11/2003 | Manoharan et al. |
| 2004/0096848 | A1 | 5/2004 | Thrue et al. |
| 2004/0101858 | A1 | 5/2004 | Ward et al. |
| 2004/0186071 | A1 | 9/2004 | Bennett et al. |
| 2005/0130924 | A1 | 6/2005 | Monia et al. |
| 2006/0106112 | A1 | 5/2006 | Ehring et al. |
| 2006/0204502 | A1 | 9/2006 | Borea et al. |
| 2006/0252081 | A1 | 11/2006 | Hyldig-Nielsen et al. |
| 2008/0145313 | A1 | 6/2008 | Watson et al. |
| 2009/0264353 | A1 | 10/2009 | Orum et al. |
| 2011/0152348 | A1 | 6/2011 | Worm et al. |
| 2013/0210884 | A1 | 8/2013 | MacDonald et al. |
| 2015/0159160 | A1 | 6/2015 | Krieg et al. |
| 2015/0284725 | A1 | 10/2015 | Hung |

FOREIGN PATENT DOCUMENTS

| | | | |
|---|---|---|---|
| CN | 1408881 | A | 4/2003 |
| CN | 101932709 | A | 12/2010 |
| KR | 2011/0087436 | A | 8/2011 |
| RU | 2588654 | C2 | 7/2016 |
| WO | WO-9418835 | A1 | 9/1994 |
| WO | WO-000183 | A2 | 1/2000 |
| WO | WO-2004/024757 | A2 | 3/2004 |
| WO | WO-2005027833 | A2 | 3/2005 |
| WO | WO-2007/109324 | A2 | 9/2007 |
| WO | WO-2009/033027 | A2 | 3/2009 |
| WO | WO-2009/101399 | A1 | 8/2009 |
| WO | WO-2009113828 | A2 | 9/2009 |
| WO | WO-2009/143277 | A2 | 11/2009 |
| WO | WO-2014/059364 | A1 | 4/2014 |
| WO | WO-2016/149659 | A2 | 9/2016 |
| WO | WO-2016/196670 | A1 | 12/2016 |
| WO | WO-2018/029517 | A1 | 2/2018 |
| WO | WO-2018/051175 | A1 | 3/2018 |
| WO | WO-2018/069764 | A1 | 4/2018 |
| WO | WO-2018/127733 | A1 | 7/2018 |
| WO | WO-2018/138585 | A1 | 8/2018 |

OTHER PUBLICATIONS

Pankratova et al., PNA-mediated modulation and redirection of Her-2 pre-mRNA splicing: Specific skipping of erbB-2 exon 19 coding for the ATP catalytic domain, International Journal of Oncology, vol. 36, pp. 29-38. (Year: 2010).*

(Continued)

*Primary Examiner* — Dana H Shin

(74) *Attorney, Agent, or Firm* — Foley Hoag LLP; David P. Halstead; Mi Cai

(57) ABSTRACT

A peptide nucleic acid derivative of Formula I is provided to tightly bind to a splice site within a pre-mRNA in a sequence specific manner. Given with excellent cell membrane permeability and strong affinity for RNA, the peptide nucleic acid derivative induces exon skipping in cells treated with the peptide nucleic acid at sub-femtomolar concentration as "naked" oligonucleotide. The compound shows therapeutic activity in subjects upon systemic administration even at 1 μg/Kg or less, and therefore is useful to treat a disease or symptom at affordable treatment cost.

8 Claims, 68 Drawing Sheets

Specification includes a Sequence Listing.

(56) References Cited

OTHER PUBLICATIONS

Bark et al., "Developmentally Regulated Switch in Alternatively Spliced SNAP-25 Isoforms Alters Facilitation of Synaptic Transmission," Journal of Neuroscience, 24(40): 8796-8805 (2004).
Chatelier et al., "Biophysical Properties of Human Nav1.7 Splice Variants and Their Regulation by Protein Kinase A," Journal of Neurophysiology, 99(5): 2241-2250 (2008).
Choi et al., "Alternative splicing may contribute to time-dependent manifestation of inherited erythromelalgia," Brain, 133(Pt 6):1823-1835 (2010).
Dehm et al., "Splicing of a novel androgen receptor exon generates a constitutively active androgen receptor that mediates prostate cancer therapy resistance," Cancer Res, 68(13):5469-5477 (2008).
Drenth et al., "Mutations in sodium-channel gene SCN9A cause a spectrum of human genetic pain disorders," The Journal Of Clinical Investigation, 117(12): 3603-3609 (2007).
Emery et al., "Nav1.7 and other voltage-gated sodium channels as drug targets for pain relief," Expert Opinion on Therapeutic Targets, 20(8): 975-983 (2016).
Extended European Search Report for EP Application No. 17838864.1 dated Mar. 30, 2020.
Extended European Search Report for EP Application No. 17850354.6 mailed Mar. 30, 2020.
Extended European Search Report for EP Application No. 17860878.2 dated Jun. 26, 2020.
Extended European Search Report for EP Application No. 17889309.5 dated Jul. 6, 2020.
Haaima et al., "Increased DNA binding and sequence discrimination of PNA oligomers containing 2,6-diaminopurine," Nucleic Acids Res, 25(22):4639-4643 (1997).
International Search Report and Written Opinion for International Application No. PCT/IB2017/000697 dated Sep. 29, 2017.
International Search Report and Written Opinion for International Application No. PCT/IB2017/000751 dated Sep. 29, 2017.
International Search Report and Written Opinion for International Application No. PCT/IB2017/001385 dated Mar. 12, 2018.
International Search Report and Written Opinion for International Application No. PCT/IB2017/001727 mailed May 31, 2018.
International Search Report and Written Opinion for International Application No. PCT/IB2018/000160 dated Jun. 22, 2018.
Karras et al., "Peptide nucleic acids are potent modulators of endogenous pre-mRNA splicing of the murine interleukin-5 receptor-α chain," Biochemistry, 40(26):7853-7859 (2001).
Kerr et al., "Novel mRNA Isoforms of the Sodium Channels Nav1. 2, Nav1. 3 and Nav1. 7 Encode Predicted Two-Domain, Truncated Proteins," Neuroscience, 155: 797-808 (2008).
Lee et al., "Antihepatoma activity of chaetocin due to deregulated splicing of hypoxia-inducible factor 1α pre-mRNA in mice and in vitro," Hepatology, 53(1):171-180 (2011).
Muroi et al., "Selective silencing of NaV1.7 decreases excitability and conduction in vagal sensory neurons," The Journal Of Physiology, 589(23): 5663-5676 (2011).
Nielsen., "Peptide Nucleic Acids (PNA) in Chemical Biology and Drug Discovery," Chemistry & Biodiversity, 7(4): 786-804 (2010).
Osen-Sand, "Inhibition of axonal growth by SNAP-25 antisense oligonucleotidse in vitro and in vivo," Nature, 364:445-448 (1993).
Pan et al., "Effect of down-regulation of voltage-gated sodium channel Nav1.7 on activation of astrocytes and microglia in DRG in rats with cancer pain," Asian Pacific Journal of Tropical Medicine, 8(5): 405-411 (2015).
Rajeev et al., "High-Affinity Peptide Nucleic Acid Oligomers Containing Tricyclic Cytosine Analogues," Org Lett, 4(25):4395-4398 (2002).
Shiraishi et al., "Modulation of mdm2 pre-mRNA Splicing by 9-aminoacridine-PNA (Peptide Nucleic Acid) Conjugates Targeting Intron-Exon Junctions," BMC Cancer, 10: Article 342 (2010).
Yamamoto et al., "Generation 2.5 antisense oligonucleotides targeting the androgen receptor and its splice variants suppress enzalutamide-resistant prostate cancer cell growth," Clin Cancer Res, 21(7):1675-1687 (2015).
Zhang et al., "Treatment with siRNA and antisense oligonucleotides targeted to HIF-lalpha induced apoptosis in human tongue squamous cell carcinomas," International Journal of Cancer, 111(6):849-857 (2004).
International Preliminary Report on Patentability for International Application No. PCT/IB2017/001725 mailed Jul. 2, 2019.
International Search Report and Written Opinion for International Application No. PCT/IB2017/001725 mailed May 31, 2018.
Peacey et al., "Targeting a pre-mRNA Structure with Bipartite Antisense Molecules Modulated Tau Alternative Splicing," Nucleic Acids Research, 40(19): 9836-9849 (2012).
Singh et al., "An Antisense Microwalk Reveals Critical Role of an Intronic Position Linked to a Unique Long-Distance Interaction in pre-mRNA Splicing," RNA, 16(6): 1167-1181 (2010).
Siwkowski et al., "Identification and Functional Validation of PNAs that Inhibit Murine CD40 Expression by Redirection of Splicing," Nucleic Acids Research, 32(9): 2695-2706 (2004).
Lai et al., "The role of androgen and androgen receptor in skin-related disorders," Arch Dermatol Res., 304(7):499-510 (2012).
Singapore Search Report for Application No. 11201900153X dated Apr. 15, 2020.
Singapore Search Report for Application No. 11201904794Q dated Apr. 15, 2020.
Singapore Search Report for Application No. 11201905373X dated Apr. 15, 2020.
Singapore Search Report for Application No. 11201905601V dated Apr. 15, 2020.
Antsypovich, "Peptide nucleic acids: structure, properties, applications, strategies and practice of chemical synthesis," Russian Chemical Reviews, 71(1): 71-83 (2002).
Hanvey et al., "Antisense and Antigene Properties of Peptide Nucleic Acids," Science, 258: 1481-1485 (1992).
Pardridge et al., "Vector-mediated delivery of a polyamide ("peptide") nucleic acid analogue through the blood-barrier in vivo," PNAS, 92: 5592-5596 (1995).
Haile et al., "Androgen receptor and its splice variants in prostate cancer," Cellular and Molecular Life Sciences, 68: 3971-3981 (2011).
Infante et al., "Complete androgen insensitivity syndrome caused by a novel splice donor site mutation and activation of a cryptic splice donor site in the androgen receptor gene," Journal of Steroid Biochemistry & Molecular Biology, 155: 63-66 (2016).
NCBI Reference Sequence: NM_001144884.2; "*Homo sapiens* solute carrier family 30 member 7 (SLC30a7), transcript variant 2, mRNA," NCBI: 9 pages (2021).
NCBI Reference Sequence: NM_001286680.2; "*Homo sapiens* nucleophosmin/nuceloplasmin 2 (NPM2), transcript variant 2, mRNA," NCBI: 5 pages (2021).
NCBI Reference Sequence: NM_001348958.2; "*Homo sapiens* small integral membrane protein 26 (SMIM26), transcript variant 2, mRNA," NCBI: 3 pages (2021).
NCBI Reference Sequence: NM_001388409.1; "*Homo sapiens* WSC domain containing 1 (WSCD1), transcript variant 6, mRNA," NCBI: 5 pages (2021).
NCBI Reference Sequence: NM_001395415.1; "*Homo sapiens* small integral membrane protein 42 (SMIM42), mRNA," NCBI: 2 pages (2022).
NCBI Reference Sequence: NM_005257.6; "*Homo sapiens* GATA binding protein 6 (GATA6), mrNA," NCBI: 6 pages (2022).
NCBI Reference Sequence: NM_005336.6; "*Homo sapiens* high density lipoprotein binding protein (HDLBP), transcript variant 1, mRNA," NCBI: 10 pages (2022).
NCBI Reference Sequence: NM_020815.3; "*Homo sapiens* protcadherin 10 (PCDH10), transcript variant 2, mRNA," NCBI: 6 pages (2022).
NCBI Reference Sequence: NM_020825.4; "*Homo sapiens* cramped chromatin regulator homolog 1 (CRAMP1), mRNA," NCBI: 8 pages (2022).

(56) References Cited

OTHER PUBLICATIONS

NCBI Reference Sequence: NM_033516.6; "*Homo sapiens* TPD52 like 3 (TPD52L3), transcript variant 1, mRNA," NCBI: 3 pages (2021).
NCBI Reference Sequence: NM_157593.1; "*Homo sapiens* ARHGAP11B divergent transcript (ARHGAP11B-DT), transcript varaitn 1, long non-coding RNA," NCBI: 3 pages (2022).
NCBI Reference Sequence: NM_194294.5; "*Homo sapiens* indoleamine 2,3-dioxygenase 2 (IDO2), transcript variant 1, mRNA," NCBI: 6 pages (2022).
Ris-Stalpers et al., "Substitution of Aspartic Acid-686 by Histidine or Asparagine in the Human Androgen Receptor Leads to a Functionally Inactive Protein with Altered Hormone-Binding Characteristics," Molecular Endocrinology, 5: 1562-1569 (1991).
Yin et al., "Effective exon skipping and restoration of dystrophin expression by peptide nucleic acid antisense oligonucleotides in mdx mice," Molecular Therapy, 16(1): 38-45 (2008).
U.S. Appl. No. 16/324,266, Published.
U.S. Appl. No. 16/341,272, Granted.
U.S. Appl. No. 16/333,855, Published.
U.S. Appl. No. 16/475,716, Granted.
U.S. Appl. No. 16/480,147, Granted.
Date et al., "Expression of constitutively stable hybrid hypoxia-inducible factor-1alpha protects cultured rat cardiomyocytes against simulated ischemia-reperfusion injury," Am J Physiol Cell Physiol, 288: C314-C320 (2005).
Extended European Search Report and Written Opinion for EP Application No. 17890613.7 dated Nov. 13, 2020.
Extended European Search Report and Written Opinion for EP Application No. 18744379.1 dated Nov. 13, 2020.
Schubert et al., "The induction of HIF-1 reduces astrocyte activation by amyloid beta peptide," European Journal of Neuroscience, 29(7): 1323-1334 (2009).
Zeng et al., "Progress of synthesis of modified peptide nucleic acid." Chinese Pharmaceutical Journal: 1936-1945 (2015).
Chenna et al., "A simple cytosine-to-G-clamp nucleobase substitution enables chiral γ-PNAs to invade mixed-sequence double helical B-form DNA." Chembiochem: a European Journal of Chemical Biology 9.15 (2008):2388-2391.

* cited by examiner

DNA PTO LNA PMO PNA

B : Nucleobase (N → C) X-$B_1B_2B_3$----$B_{(k-1)}B_k$-Z

X = $CH_2$, O, S, or NH
m = integer
n = integer

Thymine X = F, Cl, Br, or I Uracil

Cytosine

R = alkyl

Figure 7
(continued from previous page)
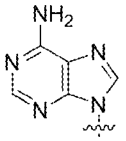 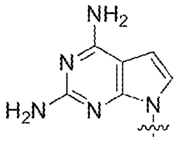 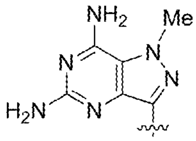 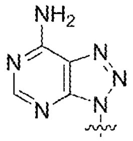 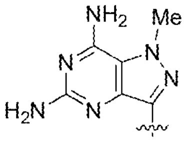
Adenine
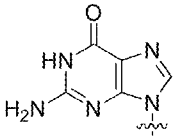 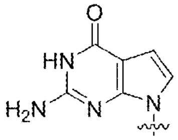 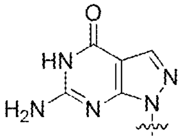 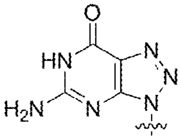 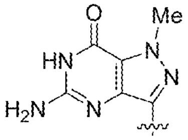
Guanine
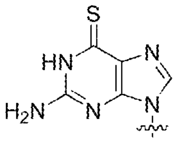 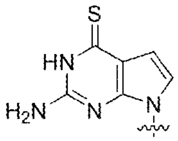 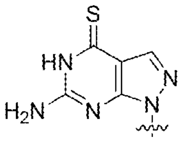 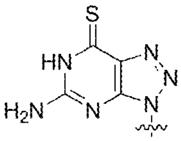 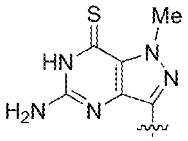
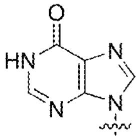 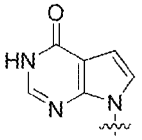 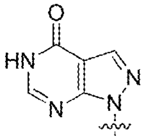 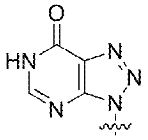 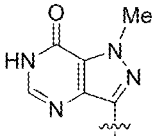
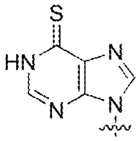 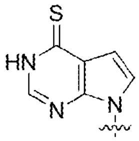 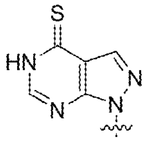 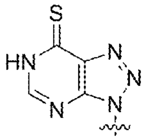 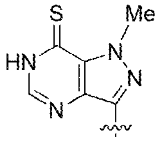 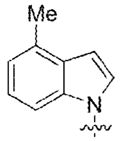
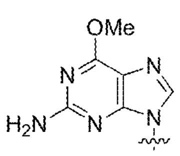 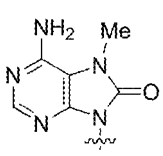 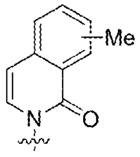 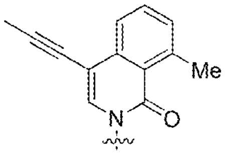 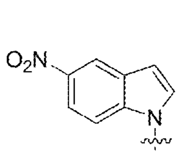
6-O-methylguanine

Figure 7
(continued from previous page)
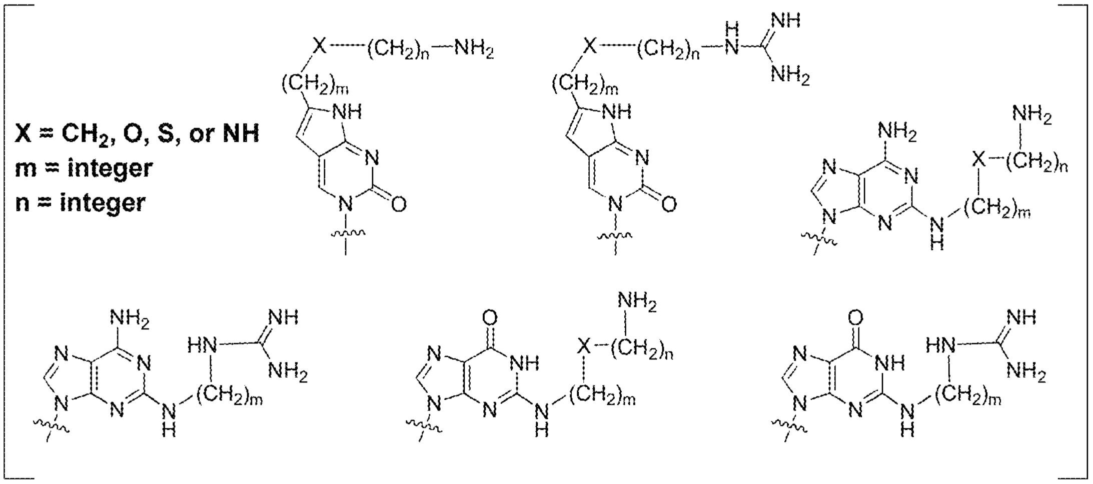
X = $CH_2$, O, S, or NH
m = integer
n = integer
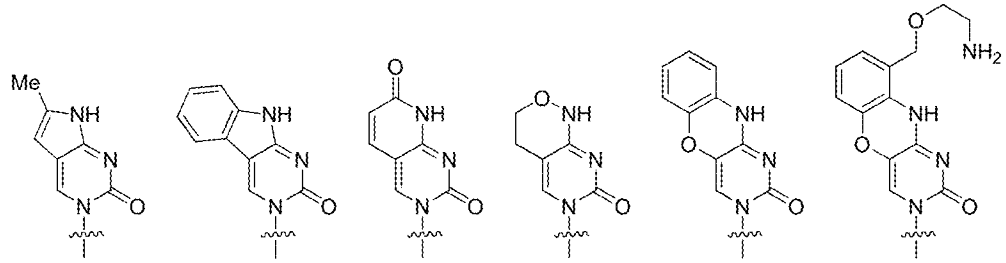

Examples of Non-substituted Alkyl Radical

Examples of Substituted Alkyl Radical

Examples of Non-substituted Alkylacyl Radical

Examples of Substituted Alkylacyl Radical

Examples of Substituted or Non-substituted Arylacyl Radical

Examples of Substituted Alkylamino or Arylamino Radical

Examples of Substituted or Non-substituted Aryl Radical

Examples of Substituted or Non-substituted Alkylsulfonyl or Arylsulfonyl Radical

Examples of Substituted or Non-substituted Alkyl- or Aryl-phosphonyl Radical

Examples of Substituted or Non-substituted Alkyloxycarbonyl Radical

Examples of Substituted or Non-substituted Aryloxycarbonyl Radical

Examples of Substituted or Non-substituted Alkylaminocarbonyl Radical

Examples of Substituted or Non-substituted Arylaminocarbonyl Radical

Examples of Substituted or Non-substituted Alkyloxythiocarbonyl Radical

Examples of Substituted or Non-substituted Alkylaminothiocarbonyl Radical

Examples of Substituted or Non-substituted Arylaminothiocarbonyl Radical

Examples of Substituted or Non-substituted Aryloxythiocarbonyl Radical

PNA Monomer

B : Nucleobase
p : Integer
q : Integer

Adenine

B =

Guanine

B =

Thymine

B =

Cytosine

B =

Modified Cytosine

C(pOq) : B =

Modified Adenine

A(p) : B =

A(pOq) :

B =

Modified Guanine

G(p) : B =

G(pOq) :

B =

Fmoc-

Fethoc-

Ac-

Benzoyl-

Piv-

Men-Propyl-

-Lys-

-Leu-

-Arg-

-Val-

-Gly-

Phenyl-

Benzyl-

-HEX-

FAM-

[N-(2-Phenylethyl)amino]carbonylp-Toluenesulfonyl-

H- Hydrido (H)

$-NH_2$ non-substituted amino

Fmoc-PNA Monomer

B : Nucleobase with protecting group(s)
X : methylene, oxygen, sulfur, or Boc-protected amino
m : Integer
n : Integer

Boc-

Modified Cytosine

C(mXn) : B =

Modified Adenine

A(mXn) :

B =

Modified Guanine

G(mXn) :

B =

EXON SKIPPING BY PEPTIDE NUCLEIC ACID DERIVATIVES

RELATED APPLICATIONS

This application is a national-stage filing under 35 U.S.C. § 371 of International Application No. PCT/IB2017/001725, filed Dec. 29, 2017, which claims the benefit of priority to U.S. Provisional Application No. 62/440,929, filed Dec. 30, 2016, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 21, 2019, is named OSH-00501_(32567-00501)_SL.txt and is 41,305 bytes in size.

BACKGROUND OF INVENTION

Oligonucleotides have been used for diverse biological purposes including antisense inhibition of gene expression, PCR (polymerase chain reaction), diagnostic analysis by gene chip, and so on. Since oligonucleotides interact with nucleic acid including DNA and RNA in a sequence specific manner, they are useful to predictably modulate biological processes involving DNA or RNA within cell. Oligonucleotides with good cell permeability are able to modulate such biological processes within cell in a sequence predictable manner.

Proteins as Drug Targets: Proteins mediate diverse cellular functions. It would not be not surprising to find that most of currently marketed drugs show therapeutic activity through modulating functions of protein(s). For example, non-steroidal anti-inflammatory drug aspirin inhibits enzymes called cyclooxygenases for its anti-inflammatory activity. Losartan binds to a trans-membrane receptor called angiotensin II receptor for its antihypertensive activity. Rosiglitazone selectively activates an intracellular receptor called peroxisome proliferator-activated receptor γ (PPARγ) to elicit its antidiabetic activity. Etanercept is a fusion protein which binds to a cytokine called tumor necrosis factor-α (TNF-α), and neutralizes the biological activity of TNF-α for its anti-rheumatic activity. Herceptin is a monoclonal antibody to treat breast cancer by selectively binding to erbB2 over-expressed in certain types of breast cancer cells.

Pre-mRNA: Genetic information is carried on DNA (2-deoxyribose nucleic acid), which is transcribed to produce pre-mRNA (pre-messenger ribonucleic acid) in the nucleus. Mammalian pre-mRNA usually consists of exons and introns, and exon and intron are inter-connected to each other. Exons and introns are numbered as illustrated in FIG. 1A.

Splicing of Pre-mRNA into mRNA: In the nucleus, pre-mRNA is processed into mRNA following deletion of introns and ligation of exons by a series of complex reactions collectively called "splicing" as schematically illustrated in FIG. 1B. [*Ann. Rev. Biochem.* 72(1), 291-336 (2003); *Nature Rev. Mol. Cell Biol.* 6(5), 386-398 (2005); *Nature Rev. Mol. Cell Biol.* 15(2), 108-121 (2014)]

Splicing is initiated by forming "splicesome E complex" (i.e. early splicesome complex) between pre-mRNA and splicing adapter factors. In "splicesome E complex", U1 binds to the junction of exon N and intron N, and U2AF[35] binds to the junction of intron N and exon (N+1). Thus the junction of exon/intron or intron/exon is critical to the formation of the early splicesome complex. "Splicesome E complex" evolves into "splicesome A complex" upon additional complexation with U2. "Splicesome A complex" then undergoes a series of complex reactions to delete or splice out the intron to adjoin the neighboring exons.

Alternative Splicing and Splice Variant: All the exons of pre-mRNA are not always retained to form the "full-length" mRNA during splicing. Certain exons are deleted, or spliced out to form variant mRNAs, i.e. "splice variants". Thus pre-mRNA can be "alternatively spliced" to yield multiple splice variants.

Alternative splicing in mammalian cells was first reported in 1981 with the gene encoding calcitonin. [*Nature* vol 290(5801), 63-65 (1981); *Proc. Natl. Acad. Sci. USA* vol 79(6), 1717-1721 (1982)] The gene consists of 6 exons, and the calcitonin mRNA is produced by the skipping of exon 5 and exon 6. In the meantime, the skipping of exon 4 yields an mRNA variant encoding calcitonin gene related peptide (CGRP).

Alternative splicing appears to be completely up to cells and conditions that cells are exposed to. Due to alternative splicing, multiple proteins are produced from a single gene. Alternative splicing allows animals to generate more diversities of proteins for their genome size. In humans, 95% of multi-exonic genes are estimated to be alternatively spliced. [*Nature Genetics* vol 40(12), 1413-1415 (2008)]

Splice Variants and Biological Functions: Splice variants are found as spontaneously occurring in a manner dependent on cell type or tissue, and encode proteins possessing biological profiles often different from the profiles of the full-length protein.

Androgen receptor (AR) would be a good example of genes yielding multiple splice variants. [*Int. J. Biol. Sci.* vol 7(6), 815-822 (2011)] The AR pre-mRNA consists of 8 exons plus 4 cryptic exons (cryptic exons are provided as shaded in the diagram below). There are at least seven splice variants of AR mRNA.

AR mRNA variant 1 is composed of exon 1 to exon 8 connected in series, and encodes the full length AR protein as illustrated in FIG. 2A. In case of AR mRNA variant 3, exon 4 to exon 8 are spliced out (i.e. deleted). Consequently AR mRNA variant 3 encodes a truncated AR protein (AR3) lacking the ligand binding domain (LBD) present in the full-length protein.

The full-length AR protein becomes functionally active upon complex formation with an androgen such as testosterone or dihydrotestosterone (DHT). In the meantime, the truncated AR3 protein is functionally active even in the absence of androgen. In prostate tumors resistant to androgen ablation therapy, the AR3 protein has been often found to be up-regulated. Thus the endogenous formation of the AR3 variant protein could be taken as a natural selection process for prostate cancer cells to evade the androgen ablation therapy.

Hypoxia-inducible factor 1α (HIF-1α) is a subunit of a transcription factor called hypoxia-inducible factor 1 (HIF-1), and is encoded by the HIF1A gene. HIF-1α is up-regulated in response to hypoxia (i.e., low oxygen level) and therefore may be regarded as the cellular oxygen sensor. [*Proc. Natl. Acad. Sci. USA*, vol 92, 5510-5514 (1995)] HIF-1α induces transcription of more than 60 genes including VEGF and EPO. HIF-1α promotes formation of new blood vessels via VEGF. [*Exp. Mol. Med.* vol 36, 1-12

(2004)] Solid tumors experience hypoxia due to limited blood supply, and up-regulate HIF-1α to survive under hypoxia.

HIF-1a protein consists of various domains for its functional activity as a transcription activator. It contains a basic helix-loop-helix (bHLH) and two PAS domains. [for PAS domain, cf. *Curr. Biol.* vol 7(11), R674-677 (1997); *Eur J. Biochem.* vol 271(6), 1198-1208 (2004)] HIF-1α possesses an oxygen-dependent degradation (ODD) domain which serves as the oxygen sensor and is well known to be critical to the stability of HIF-1α protein.

There are at least six variants of HIF-1α protein encoded by six HIF-1α mRNA splice variants as illustrated in FIG. 2B. [*Exp. Mol. Med.* vol 36, 1-12 (2004)] The full-length HIF-1α (HIF-1$\alpha^{FL}$) mRNA is similar to the wild type HIF-1α (HIF-1$\alpha^{WT}$) mRNA except for additional three bases (UAG) between exon 1 and exon 2 due to alternative splicing. Exon 14 is deleted or skipped in HIF-1$\alpha^{36}$. HIF-1$\alpha^{736}$ lacks C-terminal activation domain (CAD). Both HIF-1$\alpha^{FL}$ and HIF-1$\alpha^{736}$ are known to activate the VEGF promoter upon hypoxia. In the meantime, HIF-1$\alpha^{557}$ (HIF-1αZ) and HIF-1$\alpha^{516}$ function as a dominant negative isoform of HIF-1α. In breast cancer, HIF-1$\alpha^{FL}$ mRNA splice variant reflects a stage of cancer progression and is associated with poor prognosis. [*BMC Medicine* vol 8(44), 1-12 (2010)]

As exemplified by the androgen receptor and HIF-1α protein, splice variants play important roles in generating physiological diversities for a given mammalian gene. Nature spontaneously generates splice variants to maintain homeostasis as well as to respond to physiological dynamics.

Ribosomal Protein Synthesis: The introns of pre-mRNA are enzymatically spliced out to yield mRNA (messenger ribonucleic acid), which is then trans-located to the cytosolic compartment. In the cytosol, a complex of translational machinery called ribosome binds to the mRNA and carries out the protein synthesis as it scans the genetic information encoded along the mRNA. [*Biochemistry* vol 41, 4503-4510 (2002); *Cancer Res.* vol 48, 2659-2668 (1988)]

Codon: During the ribosomal protein synthesis, each amino acid is encoded by a triad of mRNA sequence. For example, "AUG", "UUA", "CCC" and "AGA" encode "methionine", "leucine", "proline", and "arginine", respectively. Such triads are called "codon". Given with 4 mRNA monomers of A, G, U, and C, there are 64 (4×4×4=64) possible codons. Certain codons correspond to the "stop" signal for ribosomal protein synthesis. "UGA", "UAA", and "UAG" are the codons for the "stop" signal. Ribosomal protein synthesis terminates when the ribosomal machinery recognizes a "stop" codon as it scans along the mRNA.

Antisense Oligonucleotide (ASO): An oligonucleotide binding to mRNA or pre-mRNA in a sequence specific manner (i.e. complementarily) is called "antisense oligonucleotide" (ASO). ASO tightly binding to mRNA can block ribosomal protein synthesis. Likewise, ASO tightly binding to pre-mRNA can interfere with the splicing process, and yield splice variants of mRNA.

Antisense Inhibition of Splicing: Pre-mRNA splicing begins after "splicesome E complex" (i.e., E-complex) is formed. As schematically described in FIG. 3, SR proteins (i.e. serine arginine rich proteins) bind to "exonic splicing enhancer" (ESE) regions and assist the recruiting of U1 and $U2AF^{35}$ for binding to "5' splice site" and "3' splice site", respectively. [*Biochem. Cell Biol.* vol 77(4), 277-291 (1999); *Curr Opin. Cell Biol.* vol 13(3), 302-309 (2001)]

In principle, ASO can sterically inhibit the formation of "splicesome E complex" by binding to a certain region of pre-mRNA which is critical to the formation of E-complex. The formation of E-complex is inhibited or blocked if ASO tightly binds to a "5' splice site", "3' splice site", or ESE region.

Since mRNA encodes protein according to its sequence, an mRNA splice variant encodes a protein different from the protein encoded by the "original" or "full-length" mRNA. Thus, antisense inhibition of splicing is an effective therapeutic option by encoding variant protein(s) showing biological properties different from those of the protein encoded by "original" or "full-length" mRNA.

Frame Shift Induced by Antisense Inhibition of Splicing: A part of "coding DNA sequence" (CDS) for the human HIF-1α mRNA [NCBI mRNA Code: NM_001530] is provided in FIG. 4A as an example to illustrate "frame shift" (i.e., out of frame) induced by antisense inhibition of splicing. The CDS (i.e., yellow bar) is displayed by codon and exon (i.e., green arrow). It should be noted that T (i.e., thymine) in the CDS should be replaced with U (i.e., uracil) in mRNA or pre-mRNA.

If exon 3 is deleted by antisense inhibition of splicing, the 3'-end of exon 2 is linked directly to the 5'-end of exon 4. Then the junction between exon 2 and exon 4 reads ". . . -GAT-GCT-(G-TTT)-GAA-CTA- . . . (SEQ ID NO: 1)" as provided in FIG. 4B (cf. left diagram). There are four nucleotides between the two neighboring codons of the full-length mRNA. The deletion of exon 3 puts the codons starting from exon 4 out of frame. Thus the deletion of exon 3 induces "frame shift" of codons.

If exon 3 and exon 4 are simultaneously deleted by antisense inhibition of splicing, the 3'-end of exon 2 adjoins to the 5'-end of exon 5. Then the junction between exon 2 and exon 5 reads ". . . -GAT-GCT-(G-GC)-CTT-GTG- . . . (SEQ ID NO: 2)" as shown in FIG. 4B (cf. right diagram). There are three nucleotides between the two neighboring codons of the full-length mRNA. The dual deletion of exon 3 and exon 4 puts the codons starting from exon 5 in frame, i.e., without frame shift.

Frame shift yields codons different from the "original" codons, and often generates a premature termination codon (PTC), as illustrated in FIG. 4C for the case of the exon 3 deletion in the HIF-1α mRNA. Exon skipping inducing frame shift is destined to yield a C-terminal-truncated protein fragment due to the premature termination of ribosomal protein synthesis. Such a protein fragment could show physiological properties different from the "original" or "full-length" protein. Thus, antisense inhibition of splicing may be an effective therapeutic option for a disease target gene.

Detection of Exon Skipping by Nested RT-PCR: A splice variant mRNA induced with an ASO is often detected by PCR (polymerase chain reaction). If an ASO induces the skipping of exon 4 of 150 bp length as illustrated in FIG. 5A, there are two possible mRNAs produced from the ASO's target pre-mRNA, i.e., the full-length mRNA and the mRNA splice variant lacking exon 4. In case the ASO induces the skipping of exon 4 completely (i.e., 100%), the cells treated with the ASO yield only the PCR product smaller than the PCR product of the full-length mRNA by 150 bp. The PCR product band for the exon skipping is sampled and subjected to sequencing in order to confirm that the PCR product band indeed came from the the mRNA splice variant.

Estimation of Exon Skipping Yield by PCR Method: In literatures, the exon skipping yield or efficiency has been estimated usually by comparing the gel band intensity of the PCR product for the splice variant mRNA with the intensity for the full-length mRNA. Such estimation is theoretically valid at large if only if the full-length mRNA and the splice variant mRNA possess comparable stability in cells as well as during the assay procedures adopted for the PCR detection. Considering that the stability of mRNA is the gross result of the evolution over a billion years, however, it is unlikely that mRNA splice variants should show the same stability as the full-length mRNA.

Likewise, it is fair to assume that the relative enrichment of the splice variant mRNA and the full-length mRNA may vary much depending on PCR primers, PCR conditions and PCR detection method. Recently digital qPCR was applied to estimate the exon skipping yield of the dystrophin mRNA in mdx mice treated with a dystrophin ASO of either morpholino or 2'-OMe PTO (phosphorothioate). The exon skipping yield by digital qPCR was considerably different from the yields by traditional methods such as nested qPCR. [*Lab. Investigation*, vol 90, 1396-1402 (2010)] A digital qPCR study for the exon skipping in myoblasts and fibroblasts from human DMD patients suggests that digital qPCR be the choice to reliably detect exon skipping products with high sensitivity. [*PLoS One* 0162467, September 9 (2016)]

Given that the apparent exon skipping yield tends to vary depending on the PCR assay method and condition, the exon skipping yield by PCR assay may need to be additionally validated by protein expression or functional assays for the target gene.

Feedback Upregulation of Transcription by EIciRNA: Intron lariat is formed as a byproduct during pre-mRNA splicing. Exon skipping yields not only splice variant mRNA but also exon intron circular RNA (EIciRNA) as illustrated in FIG. 5B, in which exon 3 and exon 4 are spliced out to yield the lariat composed of introns, exon 3 and exon 4. The lariat initially formed, i.e., EIciRNA ①, may undergo additional splicing to yield a secondary lariat definded as EIciRNA ②.

Those EIciRNA lariats retain the sequence of the 5' splice site of "exon 4", and are capable of recruiting "U1 small nuclear ribonuclear protein (U1 snRNP)". U1 snRNP then recruits RNA polymerase II, which may upregulate the transcription of the pre-mRNA. The transcription of a pre-mRNA may increase if EIciRNAs accumulate beyond a threshold level in the nucleus. Thus EIciRNAs may often function as a feedback regulator of transcription when exon skipping occurs excessively. [*Nature Struct. Mol. Biol.* vol 22(3), 256-264 (2015)]

Unnatural Oligonucleotides: DNA or RNA oligonucleotide is prone to degradation by endogenous nucleases, limiting their therapeutic utility. To date, a number of unnatural (i.e., naturally non-occurring) oligonucleotides have been developed and intensively investigated. [*Clin. Exp. Pharmacol. Physiol.* vol 33, 533-540 (2006)] Many of them show extended metabolic stability compared to DNA and RNA. Provided in FIG. 6A, are the chemical structures for some of representative unnatural oligonucleotides. Those oligonucleotides predictably bind to a complementary nucleic acid as DNA or RNA does.

Phosphorothioate Oligonucleotide (PTO): PTO is a DNA analog with one of the backbone phosphate oxygen atoms replaced with a sulfur atom per monomer. Such a small structural change made PTO comparatively resistant to degradation by nucleases. [*Ann. Rev. Biochem.* vol 54, 367-402 (1985)]

Reflecting the structural similarity of backbone between PTO and DNA, they both poorly penetrate the cell membrane in most mammalian cell types. For some types of cells abundantly expressing transporter(s) for DNA, however, DNA and PTO show comparably good cell permeability. Systemically administered PTOs are known to readily distribute to the liver and kidney owing to an abundant expression of transporters for DNA. [*Nucleic Acids Res.* vol 25, 3290-3296 (1997)]

In order to improve the PTO's cell permeability in vitro, lipofection has been popularly adopted. However, lipofection physically alters cell membrane, causes cytotoxicity, and therefore would not be ideal for long term therapeutic use.

Over the past 30 years, PTO and variants of PTO have been clinically evaluated to treat cancers, immunological disorders, metabolic diseases, and so on. [*Biochemistry* vol 41, 4503-4510 (2002); *Clin. Exp. Pharmacol. Physiol.* vol 33, 533-540 (2006)] Many of such antisense drug candidates have not been successfully developed partly due to PTO's poor cell permeability. In order to overcome the poor cell permeability, PTO needs to be administered at high dose for therapeutic activity. However, PTOs are known to elicit dose-limiting toxicity including increased coagulation time, complement activation, tubular nephropathy, Kupffer cell activation, and immune stimulation including splenomegaly, lymphoid hyperplasia, and mononuclear cell infiltration. [*Clin. Exp. Pharmacol. Physiol.* vol 33, 533-540 (2006)]

Many antisense PTOs have been found to show clinical activity for diseases with a significant contribution from the liver or kidneys. Mipomersen is a PTO analog which inhibits the synthesis of apoB-100, a protein involved in LDL cholesterol transport. Mipomersen manifested clinical activity in a certain population of atherosclerosis patients due to its preferential distribution to the liver. [*Circulation* vol 118(7), 743-753 (2008)] ISIS-113715 is a PTO analog inhibiting the synthesis of protein tyrosine phosphatase 1B (PTP1B), and was found to show therapeutic activity in type II diabetes patients. [*Curr Opin. Mol. Ther.* vol 6, 331-336 (2004)]

2'-O-Alkyl RNA: 2'-O-alkyl-RNA is an RNA analog having the 2'-hydroxy group on the ribose ring replaced with an alkyloxy group. 2'-O-alkyl RNA shows RNA affinity stronger than PTO or DNA. In addition, 2'-O-alkyl RNA shows improved metabolic stability for therapeutic purposes. However, 2'-O-alkyl-RNA shows poor membrane permeability, which limits the therapeutic scope.

Locked Nucleic Acid (LNA): In LNA, the backbone ribose ring of RNA is structurally constrained to increase the binding affinity for RNA or DNA. Thus, LNA may be regarded as a high affinity DNA or RNA analog. [*Biochemistry* vol 45, 7347-7355 (2006)] Nevertheless, LNA also shows poor cell permeability like DNA or RNA does.

Hybrid Oligonucleotide of DNA or RNA Backbone: PTO and 2'-O-alkyl RNA are often fused into a single oligonucleotide. Owing to the 2'-O-alkyl RNA part, such a hybrid oligonucleotide possesses an RNA binding affinity stronger than the PTO oligonucleotide of the same sequence. Similarly, LNA and PTO are often fused into a single oligonucleotide, and the hybrid oligonucleotide possesses an RNA binding affinity stronger than the PTO oligonucleotide of the same sequence. However, such hybrid oligonucleotides also show poor cell permeability.

Phosphorodiamidate Morpholino Oligonucleotide (PMO): In PMO, the DNA backbone modules of phosphate and 2-deoxyribose are replaced with phosphorodiamidate and morpholine, respectively. [*Appl. Microbiol. Biotechnol.* vol 71, 575-586 (2006)] Whilst the DNA backbone is negatively charged, the PMO backbone is not charged. Thus the binding between PMO and mRNA is free of the electrostatic repulsion between the backbones, and tends to be stronger than the binding between DNA and mRNA. Since PMO is markedly different from DNA in the backbone structure, PMO wouldn't be recognized by the hepatic transporter(s) recognizing DNA or RNA. However, PMO doesn't readily penetrate the cell membrane.

Peptide Nucleic Acid (PNA): PNA is a polypeptide with the unit backbone of N-(2-aminoethyl)glycine, and was discovered by Dr. Nielsen and colleagues. [*Science* vol 254, 1497-1500 (1991)] FIG. 6B illustrates the chemical structure and nomenclature for the prototype (i.e., unmodified) PNA.

Like DNA and RNA, PNA also selectively binds to a complementary nucleic acid. [*Nature* (*London*) vol 365, 566-568 (1992)] In binding to the complementary nucleic acid, the N-terminus of PNA is equivalent to the 5'-end of DNA or RNA, and the C-terminus of PNA is equivalent to the 3'-end of DNA or RNA.

Like PMO, the PNA backbone is not charged. Thus the binding between PNA and RNA tends to be stronger than the binding between DNA and RNA. Since PNA is markedly different from DNA in the chemical structure, PNA wouldn't be recognized by the hepatic transporter(s) recognizing DNA, and would show a tissue distribution profile different from that of DNA or PTO. However, PNA also poorly penetrates the mammalian cell membrane. [*Adv. Drug Delivery Rev*. vol 55, 267-280 (2003)]

Duchenne Muscular Dystrophy (DMD): DMD is a muscle-wasting disease that affects one per ca 3,500 newly-born male children. [*Lancet Neurol*. vol 9, 77-93 (2010)] DMD patients gradually lose their muscle function, and die from cardiac or respiratory failure before reaching their 30's. In many DMD patients, the dystrophin gene is mutated to yield the dystrophin mRNA with a premature termination codon (PTC), and expresses a truncated non-functional dystrophin lacking the C-terminal part. [*Human Mol. Genetics* vol 12(8), 907-914 (2003); and references therein]

A popular approach to treat DMD has been to skip the exon possessing a PTC in the dystrophin mRNA using an ASO, and encode a splice variant protein with the C-terminal which is often termed as the full-length dystrophin.

Exon 23 Skipping of Dystrophin mRNA in MDX Mice: Mdx mouse is a mutant with a PTC in exon 23 of the dystrophin pre-mRNA, and has been widely adopted as an animal model for human DMD. [*FEBS J*. vol 280(17), 4177-4186 (2013)] ASOs complementarily targeting the mouse dystrophin pre-mRNA have been evaluated for their ability to induce the skipping of exon 23. [*Artificial DNA: PNA & XNA* vol 2(1), 6-15 (2011)] In this regard, mdx mouse has served as a good model system to evaluate a class of oligonucleotide for its capability to induce exon skipping.

A 20-mer 2'-OMe PTO (2'-O-methyl phosphorothioate) ASO fully complementary to the junction of exon 23 and intron 23 (i.e. the 5' splice site of exon 23) was injected locally into a muscle of mdx mouse at ca 10 μg/Kg as formulated with an amphiphilic transfection agent F127, and increased the expression of the full-length dystrophin in the muscle tissue of the injection by immunohistochemistry (IHC) and western blot for the full-length dystrophin. These findings by IHC and western blot indicate that exon 23 was skipped by the local injection of the ASO. The ASO possesses an 18-mer complementary overlap with the 5'-end of intron 23 and a 2-mer complementary overlap with the 3'-end of exon 23. [*Nature Med*. vol 9(8), 1009-1014 (2003)]

Another 20-mer 2'-OMe PTO ASO fully complementary to the junction of exon 23 and intron 23 (i.e. the 5' splice site of exon 23) was evaluated for its ability to induce the skipping of exon 23. The 20-mer ASO complementarily targets the junction of exon 23 and intron 23, and possesses an 18-mer complementary overlap with the 5'-end of intron 23 and a 2-mer complementary overlap with the 3'-end of exon 23. A 96 hours incubation of mouse myoblasts with 2 or 4 μM ASO induced the skipping of exon 23 as confirmed by nested RT-PCR. The skipping of exon 23 was also identified by RT-PCR in mdx mice which received two intramuscular injections of 2.9 nmole of the ASO. Exon 23 skipping was detected in muscle tissues of mdx mice subcutaneously administered with the 2'-OMe PTO ASO at 50 mg/Kg. A 20-mer 2'-FPS (2'-fluoro-phosphorothioate) ASO processing the same sequence as the aforementioned 2'-OMe PTO ASO also induced the skipping of exon 23 in mouse myoblasts like the 2'-OMe PTO ASO. However, the 2'-FPS ASO failed to induce the skipping of exon 23 in mdx mice following intramuscular or subcutaneous injections. [*Mol. Ther Nucl. Acids* vol 4, e265 (2015)]

A 20-mer peptide nucleic acid (PNA) complementarily targeting the junction of exon 23 and intron 23 was evaluated for its ability to induce the skipping of exon 23 in mdx mice. The 20-mer PNA ASO possesses an 18-mer complementary overlap with the 5'-end of intron 23 and a 2-mer complementary overlap with the 3'-end of exon 23. The 20-mer PNA at 250 nM induced the deletion of exon 23 in $H_2K$ mdx cells as analyzed by nested RT-PCR. Following an intramuscular injection at 5 to 20 μg (ca 0.25 to 2 mg/Kg) in mdx mice, the 20-mer PNA induced exon 23 skipping in the muscle tissue of the injection site. The exon skipping efficiency of the 20-mer PNA was concluded to be superior to that of the afore-mentioned 2'-OMe PTO ASOs in mdx mice. The 20-mer PNA was covalently conjugated to various cell penetrating peptides (CPPs) to improve the cell permeability. Those PNA-CPP conjugates and the unmodified PNA comparably induced the skipping of exon 23 in cells as well as in the muscle tissue of the injection site. [*Mol. Ther* vol 16(1), 38-45 (2008)]

A 25-mer PMO ASO fully complementary to the junction of exon 23 and intron 23 (i.e., the 5' splice site of exon 23) was evaluated for its ability to induce the skipping of exon 23 in mdx mice. The 25-mer ASO possesses an 18-mer complementary overlap with intron 23 and a 7-mer complementary overlap with exon 23. The 25-mer PMO induced exon 23 skipping in mdx mice upon multiple intravenous injections at 2 mg per animal (ca 100 mg/Kg). [*Nat. Med*. vol 12(2), 175-177 (2006)] The 25-mer PMO was covalently conjugated to various cell penetrating peptides (CPPs) in order to improve the cell permeability. Those PMO-CPP conjugates induced the skipping of exon 23 in muscles upon a single intravenous injection at 3 mg/Kg. [*Human Mol. Genet*. vol 18(22), 4405-4414 (2009)]

Exon 46 Skipping of Dystrophin mRNA in Myoblasts from Human DMD Patient: 2'-OMe PTO ASOs were designed to complementarily target an exonic splicing enhancer (ESE) region within exon 46 in human dystrophin pre-mRNA, and were evaluated for the skipping efficiency of exon 46 in myoblast cells derived from a human DMD patient lacking exon 45 in the dystrophin mRNA. The cells were transfected with the ASO at 1 μM by lipofection, and incubated for 24 hours until the RNA extraction for nested RT-PCR to detect the skipping of exon 46. Several of the tested ASOs induced the skipping of exon 46. [*Human Mol. Genet*. vol 10(15), 1547-1554 (2001)]

Exon 51 Skipping of Dystrophin mRNA in DMD Patients: Drisapersen (PRO051 or GSK24022968) is a 20-mer 2'-OMe PTO designed to complementarily target an ESE region within exon 51 in the human dystrophin pre-mRNA, and was evaluated for therapeutic activity in human DMD patients. Upon biopsy evaluation of muscle tissues by nested PCR, drisapersen induced the skipping of exon 51 in DMD patients subcutaneously receiving 2 to 6 mg/Kg per week, although the exon skipping efficacy was not high. [*N. Engl. J. Med.* vol 364, 1513-1522 (2011)]

Eteplirsen (AVI-4658) is a 30-mer PMO designed to complementarily target an ESE within exon 51 in the human dystrophin pre-mRNA, and were evaluated for its therapeutic activity in DMD patients. Upon a biopsy evaluation of muscle tissues by IHC (immunohistochemistry) for the full-length dystrophin, eteplirsen induced the skipping of exon 51 in DMD patients receiving 2 to 20 mg/Kg per week by intravenous infusion. [*Lancet* vol 378(9791), 595-605 (2011)]

Exon 27 Skipping of APOB mRNA in HepG2 Cells: Apolipoprotein B (APOB) constitutes an integral part of lipoprotein particles. APOB mRNA consists of 29 exons. 2'-OMe RNAAPOB ASOs were designed to target the 3' splice site of exon 27, the 5' splice site of exon 27, or both the 3' splice site and 5' splice site. The 3' splice site ASO (3'-SS ASO) has a 15-mer overlap with intron 26 and a 5-mer overlap with exon 27. [*BMC Mol. Biol.* 2007, 8:3. published 17 Jan. 2007] The 5' splice site ASO (5'-SS ASO) possesses a 5-mer overlap with exon 27 and a 15-mer overlap with intron 27. A 40-mer 2'-OMe RNA ASO was designed by covalently fusing the 3'-SS ASO with 5'-SS ASO. Thus the 40-mer ASO is capable of interacting simultaneously with the 3' splice site as well as the 5' splice site.

The ASOs were evaluated for their ability to induce exon 27 skipping in HepG2 cells by lipofection. It is interesting to note that both the 3'-SS ASO and 5'-SS ASO failed to induce exon 27 skipping in HepG2 cells at 25 to 250 nM. In the meantime, the 40-mer ASO showed a marked level of exon 27 skipping in a dose dependent manner at 25 to 250 nM. It is likely that the 15-mer complementary overlap of the 2'-OME RNA with the intron part of a splice site alone would not be sufficient to effectively inhibit the formation of the early splicesome complex. Tighter binding to a splice site spanning exon 27 of APOB pre-mRNA would be desired to induce exon skipping by effectively inhibiting the formation of the early splicesome complex in HepG2 cells.

Alternative Splicing of Bcl-x Pre-mRNA: BCL2L1 (Bcl-x) is a human gene encoding Bcl-xL or Bcl-xS through alternative splicing. A 18-mer 2'-OMe PTO ASO was designed to target the 5' splice site of exon 2, and possesses a 16-mer complementary overlap with exon 2 and a 2-mer overlap with intron 2. By lipofection at 80 to 400 nM, the ASO promoted the cellular production of Bcl-xS through alternative splicing in a panel of cancer cells including MCF7, PC3, Du145, HeLa and MDA MB231. [*J. Biol. Chem.* vol 277(51), 49374-49382 (2002)]

Cell-Free In Vitro Splicing Correction in β-Globin Pre-mRNA: Thalassemia is inherited blood disorders caused by abnormal formation of hemoglobin. A rare mutation of $IVS2^{705}$ found in Mediterranean thalassemia patients carries a point mutation [T→G] at 705 nucleotide position in intron 2 of the human β-globin gene. The $IVS2^{705}$ mutation creates an additional 5' splice site and activates a cryptic 3' splice site at position 579 of the intron. The $IVS2^{705}$ mutation induces an alternative splicing to insert 127 nucleotides, i.e., nucleotide 579-705 of the intron between exon 2 and exon 3. [*J. Biol. Chem.* vol 260, 16332-16337 (1985)]

A 17-mer 2'-OMe RNA ASO fully complementary to the cryptic 5' splice site of the $IVS2^{705}$ mutant was evaluated for its ability to correct the aberrant splicing in a cell-free in vitro splicing system. The ASO possesses an 8-mer overlap with intron and 9-mer overlap with the cryptic exon. The ASO effectively corrected the aberrant splicing at 0.12 to 2 μM to yield the mRNA without the cryptic exon originating from intron 2. [*Proc. Natl. Acad. Sci. USA* vol 90, 8673-8677 (1993)] The in vitro splicing system is cell-free and therefore does not require any delivery agent to induce the exon skipping. The ASO induced the exon skipping at 120 nM in the cell free splicing system. If the ASO possessed stronger affinity for the 5' splice site, the exon skipping activity would be more potent. In order to improve the exon skipping potency, it is desired to use an ASO possessing a strong affinity for the 5' splice site.

Splicing Correction of Luciferase Pre-mRNA in HeLa pLuc/705 Cells by 2'-OMe RNA: pLuc/705 is a luciferase gene modified to have the intron 2 of the $IVS2^{705}$ mutant of the human β-globin inserted between nucleotides 1368 and 1369. HeLa pLuc/705 cells stably express the modified pLuc/705 luciferase gene. The modified HeLa cells express a luciferase mRNA with the cryptic exon between nucleotides 1368 and 1369, and therefore encode a nonfunctional luciferase variant protein.

A 17-mer 2'-OMe RNA oligonucleotide complementarily targeting the cryptic 5' splice site of the $IVS2^{705}$ mutant (possessing an 8-mer overlap with intron and 9-mer overlap with the cryptic exon) was evaluated for its ability to correct the aberrant splicing of the modified luciferase pre-mRNA in HeLa pLuc/705 cells. Upon lipofection at 20 to 500 nM, the 17-mer ASO restored the cellular luciferase activity in a dose dependent manner. The cryptic exon was found to be spliced out by the treatment with the ASO by RT-PCR analysis. The exon skipping activity was observed at 20 nM or higher concentration. [*Biochemistry* vol 37, 6235-6239 (1998)]

Splicing Correction of Luciferase Pre-mRNA in HeLa pLuc/705 Cells by PNA: 17-mer PNA derivatives complementarily targeting the cryptic 5' splice site of the $IVS2^{705}$ mutant (possessing an 8-mer overlap with intron and 9-mer overlap with the cryptic exon) were evaluated for its ability to correct the aberrant splicing of the modified luciferase pre-mRNA in HeLa pLuc/705 cells. Those PNA derivatives were designed to possess a varying number of phosphonate groups covalently conjugated to the N-terminus of the PNA sequence. [*Nucl. Acids Res.* vol 30(13), 4424-4432 (2008)] The covalent conjugation of phosphonate moieties to PNA was introduced to facilitate transfection into cell by lipofection.

Upon lipofection at 2.5 to 60 nM, the PNA ASOs restored the cellular luciferase activity in a dose dependent manner. The cryptic exon was found to be spliced out by the treatment with the ASO by RT-PCR. PNA ASOs with more phosphonate groups attached thereto showed higher potency and efficacy in splicing out the cryptic exon. A PNA ASO with 12 phosphonate groups showed an exon skipping efficacy of 81% at 2.5 nM.

The observed sub-nanomolar potency of the exon skipping by the PNA ASO is much stronger than the potency of the 17-mer 2'-OMe RNA ASO. [*Biochemistry* vol 37, 6235-6239 (1998)] PNA would be very useful to potently induce exon skipping, if properly modified for delivery into cell.

Exon Skipping of FOLH1 Pre-mRNA with 2'-OMe PTO: The prostate specific membrane antigen (PSMA) is a product of the folate hydrolase (FOLH1) gene, and is highly expressed in malignant prostate tissues. 2'-OMe PTO ASOs targeting the FOLH1 pre-mRNA were evaluated for their ability to induce exon skipping in LNCap prostate cancer cells following a transfection by lipofection. [*Oligonucleotides*, vol 16, 186-175 (2006)]

SSO1 is an 18-mer ASO targeting the 5' splice site of exon 1, and possesses a 16-mer complementary overlap with exon 1 and a 2-mer overlap with intron 1. SSO6 and SSO18 are 18-mer ASOs complementarily targeting exon 6 and exon 18, respectively.

SSO1 induced alternative splicing with an $IC_{50}$ of ca 400 nM. SSO6 induced the skipping of exon 6 with an $IC_{50}$ of ca 4 nM. SSO18 induced the skipping of exon 18 with an $IC_{50}$ of ca 4 nM.

It is interesting to note that SSO6 and SSO18 targeting an intra-exonic region (i.e., exonic splicing enhancer site) induced exon skipping far more potently than SSO1 targeting a 5' splice site. Targeting an ESE region with 2'-OMe PTO ASOs was found to be more effective than targeting a splice site in this specific example.

Alternative Splicing of IL-5Rα Pre-mRNA with 2'-O-MOE RNA: 2'-O-MOE RNA (2'-O-methoxyethyl RNA) ASOs complementarily targeting the murine IL-5Rα pre-mRNA were evaluated for their ability to induce alternative splicing (i.e., exon skipping) in BCL1 cells following a transfection by electroporation. [*Mol. Pharmacol.* vol 58, 380-387 (2000)]

ASOs were designed by complementarily scanning various regions of exon 9 and the splice sites flanking exon 9. A 20-mer ASO fully complementary to the 3' splice site (3' SS) of exon 9 with a 4-mer overlap with intron 8 induced the alternative splicing markedly at 10 μM. ASOs targeting intra-exonic regions of exon 9 induced the alternative splicing at 10 μM with an efficacy comparable to the 3' SS ASO. All the tested ASOs induced the alternative splicing, indicating that exon 9 and its splice sites are highly susceptible to the exon skipping. The 3' splice site was more susceptible than the 5' splice site.

20-mer ASOs were also designed to complementarily target the splice sites flanking exon 8 with a 4-mer overlap with intron. The ASOs induced the skipping of exon 8 at 10 μM, although the 3' SS ASO was more effective than the 5' SS ASO.

The micromolar exon skipping potency of the 2'-O-MOE RNA ASOs by electroporation is considered to be very poor compared to the nanomolar exon skipping potency of 2'-OMe PTO ASOs targeting the FOLH1 pre-mRNA by lipofection. [*Oligonucleotides*, vol 16, 186-175 (2006)] Lipofection would be more effective than electroporation for transfection of oligonucleotides with negatively charged backbone into cell.

Skipping of Exon 10 of Tau Pre-mRNA with 2'-O-MOE PTO: The 5' splice site of exon 10 in the tau pre-mRNA possesses an 18-mer sequence amenable to forming a stem loop, and would not be suited to the formation of splicesome E complex. Thus exon 10 of the tau pre-mRNA is highly prone to skipping.

2'-O-MOE PTO ASOs targeting either the 3' splice site or the 5' splice site of tau exon 10 were evaluated for their ability to enhance the skipping of exon 10. [*J. Biol. Chem.* vol 276(46), 42986-42993 (2001)] E10α is an 18-mer ASO complementarily targeting the 3' splice site. E10α possesses a 10-mer overlap with intron 9 and an 8-mer overlap with exon 10. E10β is a 21-mer ASO complementarily targeting the 5' splice site. E10β possesses an 8-mer overlap with exon 10 and a 13-mer overlap with intron 10.

Following a transfection into COS-1 cells by lipofection, E10α and E10β induced the skipping of exon 10 with an $IC_{50}$ of 2-5 nM. In PC12 cells transfected by electroporation, the ASOs induced exon 10 skipping with a micromolar $IC_{50}$.

Skipping of Exon 2 of MyD88 Pre-mRNA with 2'-O-MOE RNA ASO: MyD88 is an adapter protein involved in IL-1R and TLR-induced activation of NF-kB. 20-mer 2'-O-methoxyethyl (2'-O-MOE) RNA ASOs were designed to complementarily target either the 3' splice site or 5' splice site of exon 2 in the human MyD88 pre-mRNA. The 20-mer ASOs were designed to have a 0, 5, 10, 15 or 20-mer overlap with either the 5'-end of intron 1 (i.e., the 3' splice site of exon 2) or the 3'-end of intron 2 (i.e., the 5' splice site of exon 2). The ASOs were evaluated for their ability to induce exon 2 skipping in A549 cells following a transfection by lipofection. [*J. Immunol.* vol 176, 3652-3661 (2006)]

Of the ASOs, the ASO possessing a 20-mer overlap with intron 1 in the 3' splice site of exon 2 induced exon 2 skipping most potently and effectively. The observed $IC_{50}$ for exon 2 skipping was between 50 and 100 nM. The ASOs targeting the 5' splice site were not as effective as the ASOs targeting the 3' splice site. Among the ASOs targeting the 5' splice site, the most potent ASO was the ASO possessing a 20-mer overlap with the 3'-end of exon 2.

Among the 2'-O-MOE RNA ASOs designed likewise to complementarily target either the 3' splice site or 5' splice site of exon 2 in the mouse MyD88 pre-mRNA, the ASO possessing a 20-mer overlap with the 5'-end of exon 2 induced most potently the skipping of exon 2 in RAW 264.7 cells transfected by lipofection.

The most potent ASO in the murine cells was administered twice per week for 2 weeks at 50 mg/Kg. There were significant decreases in the MyD88 mRNA by 60 to 85% in the intestine, adipose tissue and liver. 50 mg/Kg is a large dose which could cause typical adverse effects of oligonucleotide therapeutics with phosphate ribose backbone. There is a strong necessity to markedly improve the exon skipping potency if 2'-O-MOE RNA ASOs should show therapeutic activity without incurring typical adverse effects.

Restoration of Exon 7 in SMN2 by Nusinersen: Spinal muscular atrophy (SMA) is a life-threatening rare disease caused by deletion or loss-of-function in the SMN1 (survival of motor neuron 1) gene. Humans have a paralogous SMN2 gene which has an identical coding sequence except for 11 nucleotides. An SNP (single nucleotide polymorphism) of C to T in SMN2 exon 7 induces the skipping of exon 7, and the resulting splice variant mRNA encodes an SMN2 variant protein metabolized rapidly. Thus the SMN2 mutant is unable to compensate the functional shortage of the SMN1 protein, which leads to an outbreak of SMA. [*Neurology* vol 86, 890-897 (2016)]

Nusinersen (Spiranza™) is an 18-mer 2'-O-MOE RNA ASO complementarily targeting a splicing silencer region in SMN2 intron 7. Since nusinersen sterically blocks the binding of a splicing silencing protein, exon 7 is retained or restored to yield the full-length SMN2 protein. Nusinersen restores the regular splicing process by binding to the splicing silencer region located in SMN2 intron 7.

Nusinersen was approved by the US FDA in 2016 to treat SMA. Nusinersen is intrathecally administered at 12 mg once per quarter or two quarters. Nusinersen stays in the spinal cord with a half-life of 135 to 177 days in cerebrospinal fluid (CSF). [Nusinersen US Label, FDA, December 2016]

Therapeutic Potency of Exon Skipping Oligonucleotide Therapeutics: As in the exemplary cases cited earlier in this document, oligonucleotides with phosphate backbone induce exon skipping with a nanomolar potency in cells transfected by lipofection, but with a micromolar potency in cells treated as "naked" oligonucleotide.

The micromolar exon skipping potency of the MyD88 pre-mRNA was translated into a therapeutic dose of 10 mg/Kg or higher upon systemic administration as "naked"

oligonucleotide in mice. [*J. Immunol.* vol 176, 3652-3661 (2006)] At such a high therapeutic dose, oligonucleotides with phosphate backbone are susceptible to immunological adverse events. Thus it would be very much desired to develop a method or formulation to markedly improve therapeutic dose.

Drisapersen, a 20-mer 2'-OMe PTO designed to induce the skipping of exon 51 in the human dystrophin pre-mRNA, induced the skipping of exon 51 in DMD patients subcutaneously receiving the ASO at 2 to 6 mg/Kg per week as naked oligonucleotide, although the exon skipping efficacy was not high. [*N. Engl. J. Med.* vol 364, 1513-1522 (2011)] There was a concern in increasing the therapeutic dose of drisapersen due to the dose-limiting toxicity.

PNA and PMO possess a neutral backbone, are not recognized by immune systems (especially toll-like receptors), and would be free of the immunological responses commonly observed with oligonucleotides with phosphate backbone.

Eteplirsen (AVI-4658), a 30-mer PMO developed to induce exon 51 skipping in the human dystrophin pre-mRNA, was well tolerated in DMD patients receiving the ASO by intravenous infusion 2 to 20 mg/Kg per week. [*Lancet* vol 378(9791), 595-605 (2011)] Recently, eteplirsen received an accelerated approval from the US FDA for use in DMD patients.

Even though nusinersen is an ASO of exon restoring capability instead of exon skipping, the approved therapeutic dose of 12 mg per quarter is quite attractive. The efficient neuronal uptake following an intrathecal injection is considered to be largely responsible for the nusinersen's potency.

Clinical development of oligonucleotide therapeutics with phosphate backbone have been critically hampered by dose-limiting toxicities including immunological toxicity through the activation of toll-like receptors or complement activation, tissue specific toxicity in the liver or kidney. By improving the in vivo therapeutic potency, such dose-limiting toxicities could be overcome.

Oligonucleotides are very expensive to manufacture. The current level of the human therapeutic dose of 100 mg to 2 g per week is translated into an API cost of 100 to 2,000 USD (US dollars) per week, if the API manufacturing cost is generously assumed to be 1,000 USD per gram. In reality, the API manufacturing cost of oligonucleotide therapeutics is well beyond 1,000 USD per gram. Thus there will be a strong demand from healthcare stakeholders to markedly improve the therapeutic potency in order to provide oligonucleotide therapeutics at affordable annual treatment cost for chronic use.

Good Cell Permeability of Oligonucleotide: The cell membrane is a lipid bilayer barrier evolved over a billion years. The cell membrane indeed functions as a big barrier to single stranded antisense oligonucleotides of 4 to 10K Da size. Cellular delivery of such ASOs by direct penetration of the cell membrane is practically impossible. There are other pathways of cellular uptake of single stranded oligonucleotides. To cite a few, transporter-mediated endocytosis in hepatocytes as seen with mipomersen targeting ApoB100, neuronal uptake (likely to be endocytosis) as observed with nusinersen, GalNac (N-acetylgalactosamine) mediated cellular uptake, and so on. However, such cellular uptake pathways are highly dependent on tissues and are hardly applicable generally to most of tissue types. [*Nature Biotechnol.* vol 35(3), 222-229 (2017)]

It would be possible to properly formulate an oligonucleotide with phosphate backbone to possess good cell permeability, and such formulated oligonucleotide would be predicted to show better in vivo therapeutic potency than "naked" (i.e., without formulation) oligonucleotide. Given that oligonucleotides with phosphate backbone have shown nanomolar exon skipping potency at most in cells if transfected by lipofection, the in vivo therapeutic potency for an oligonucleotide formulated to possess good cell permeability would be markedly improved as the nanomolar in vitro exon skipping potency would dictate. Thus good cell permeability would be critical to in vivo therapeutic potency of oligonucleotides inducing exon skipping. Nonetheless, development of a formulation eliciting good delivery into tissues has remained a huge technical challenge in the field of oligonucleotide therapeutics.

Modified Nucleobases of PNA for Good Cell Permeability and High Affinity: As cited earlier, PNA derivatives were designed to possess a varying number of phosphonate groups covalently conjugated to facilitate delivery into cell by lipofection. Such PNA ASOs were found to show sub-nanomolar exon skipping potency in HeLa cells upon lipofection. [*Nucl. Acids Res.* vol 30(13), 4424-4432 (2008)] The sub-nanomolar potency is considerably more potent than the exon skipping potency observed with ASOs with phosphate backbone. Thus PNA would be useful to potently induce exon skipping if properly delivered into cell.

PNA was made highly permeable to mammalian cell membrane by introducing modified nucleobases with a cationic lipid or its equivalent covalently attached thereto. The chemical structures of such modified nucleobases are exemplified in FIG. 6C. Such modified nucleobases of cytosine, adenine, and guanine were found to predictably hybridize with guanine, thymine, and cytosine, respectively. [PCT Appl. No. PCT/KR2009/001256; EP2268607; U.S. Pat. No. 8,680,253]

Incorporation of such modified nucleobases onto PNA simulates situations of lipofection. By lipofection, oligonucleotide molecules are wrapped or complexed with cationic lipid molecules such as lipofectamine, and such lipofectamine/oligonucleotide complexes tend to penetrate the cell membrane rather easily compared to naked oligonucleotide molecules.

In addition to good membrane permeability, those PNA derivatives were found to possess ultra-strong affinity for complementary nucleic acid. For example, incorporation of 4 to 5 modified nucleobases onto 11- to 13-mer PNA derivatives readily yielded a $T_m$ gain of 20° C. or higher in duplex formation with complementary DNA.

Such PNA derivatives were found to be highly sensitive to a single base mismatch. A single base mismatch resulted in a $T_m$ loss of 11 to 22° C. depending on the type of modified base as well as the PNA sequence.

Given with good membrane permeability and ultra-high affinity for nucleic acid, PNA derivatives with such modified nucleobases would be useful to potently induce exon skipping.

BRIEF DESCRIPTION OF FIGURES

FIG. 17C discloses from top to bottom three nucleic acid sequences which are identical and set forth in SEQ ID NO: 170.

FIG. 21A discloses from top to bottom three nucleic acid sequences which are identical and set forth in SEQ ID NO: 171.

FIG. 22A discloses three nucleic acid sequences which are set forth in SEQ ID NO: 172, SEQ ID NO: 173, and SEQ ID NO: 174, respectively, from top to bottom.

FIG. 23B discloses from top to bottom three nucleic acid sequences which are identical and set forth in SEQ ID NO: 175.

FIG. 27B discloses from top to bottom three nucleic acid sequences which are identical and set forth in SEQ ID NO: 176.

FIG. 28B discloses from top to bottom six nucleic acid sequences. The three nucleic acid sequences on the top are identical and set forth in SEQ ID NO: 177. The three nucleic acid sequences on the bottom are identical and set forth in SEQ ID NO: 178.

FIG. 31B discloses from top to bottom three nucleic acid sequences which are identical and set forth in SEQ ID NO: 179.

FIG. 37B discloses from top to bottom three nucleic acid sequences which are identical and set forth in SEQ ID NO: 180.

FIG. 38B discloses three nucleic acid sequences which are set forth in SEQ ID NO: 181, SEQ ID NO: 182, and SEQ ID NO: 181, respectively, from top to bottom.

FIG. 46A discloses from top to bottom three nucleic acid sequences which are identical and set forth in SEQ ID NO: 183.

FIG. 47B discloses six nucleic acid sequences. The three nucleic acid sequences on the left are identical and set forth in SEQ ID NO: 184. The three nucleic acid sequences on the right are identical and set forth in SEQ ID NO: 185.

FIG. 47C discloses three nucleic acid sequences which are set forth in SEQ ID NO: 186, SEQ ID NO: 187, and SEQ ID NO: 186, respectively, from top to bottom.

FIG. 48A discloses from top to bottom three nucleic acid sequences which are identical and set forth in SEQ ID NO: 188.

FIG. 52B discloses from top to bottom two nucleic acid sequences which are identical and set forth in SEQ ID NO: 189.

FIG. 54B discloses six nucleic acid sequences. The three nucleic acid sequences on the left are identical and set forth in SEQ ID NO: 190. The three nucleic acid sequences on the right are identical and set forth in SEQ ID NO: 191.

Figure 56A:
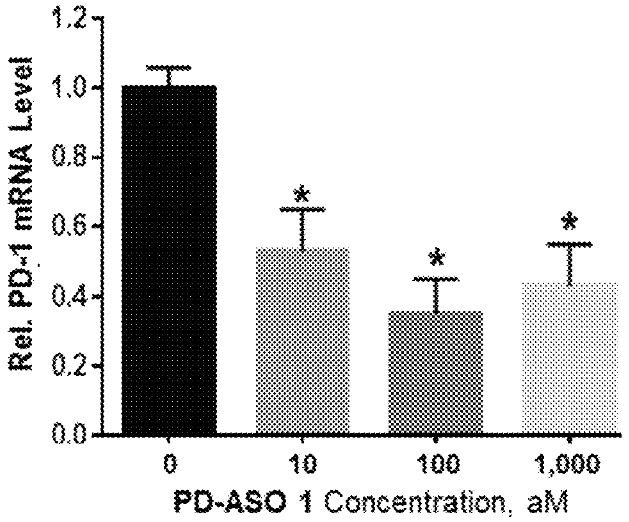
FIG. 56A. Changes in the human PD-1 mRNA level by nested qPCR in Jurkat cells treated with "PD-ASO 1" at 0 (negative control), 10, 100 or 1,000 aM. (error bar by standard error, and * for $p<0.05$)
Figure 56B:
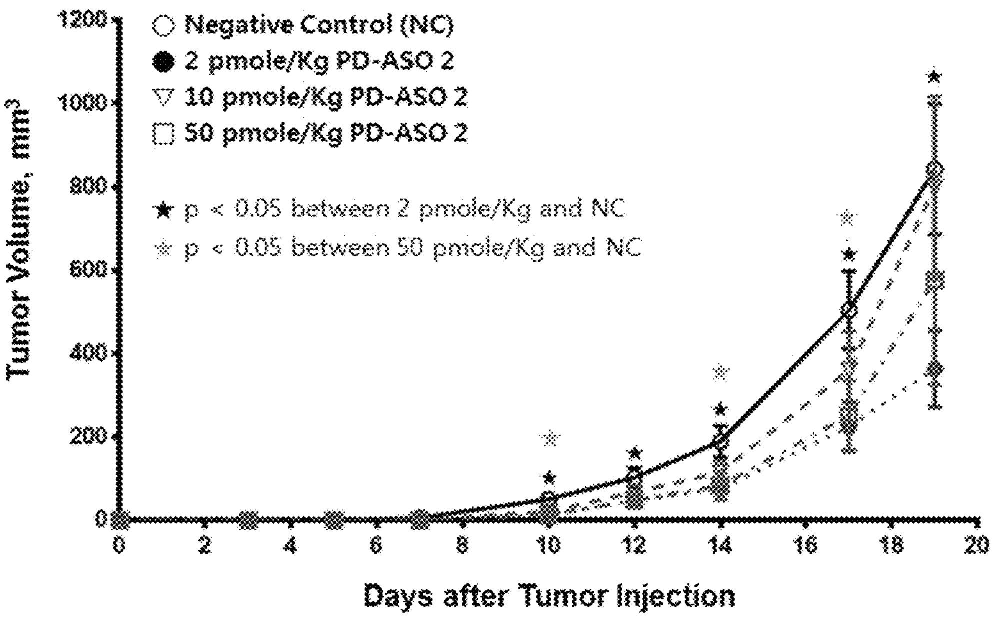

FIG. 56B. Inhibition of B16F10 melanoma growth in C57BL/6 mice subcutaneously administered with "PD-ASO 2" at 2, 10, or 50 pmole/Kg, 2× per week. (error bar by standard error, and * for $p<0.05$)

SUMMARY OF INVENTION

The present invention provides a peptide nucleic acid derivative represented by Formula I, or a pharmaceutically acceptable salt thereof:

Formula I

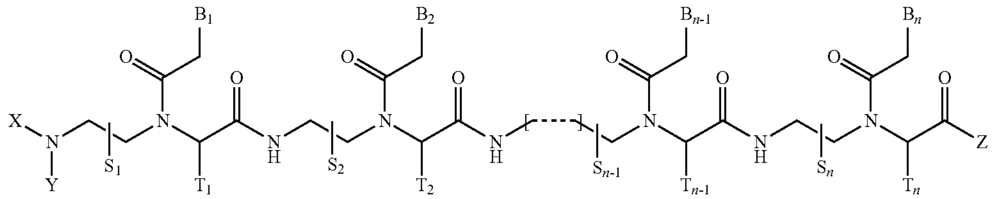

wherein, n is an integer between 10 and 25;

the compound of Formula I possesses at least a 10-mer complementary overlap with a 14-mer target splice site sequence consisting of 7-mer from intron and 7-mer from exon within a target pre-mRNA;

the compound of Formula I is fully complementary to the target pre-mRNA sequence, or partially complementary to the target pre-mRNA sequence with one or two mismatches;

$S_1, S_2, \ldots, S_{n-1}, S_n, T_1, T_2, \ldots, T_{n-1}$, and $T_n$ independently represent deuterido [D], hydrido [H], substituted or non-substituted alkyl, or substituted or non-substituted aryl radical;

X and Y independently represent hydrido, formyl [H—C(═O)—], aminocarbonyl [$NH_2$—C(═O)—], aminothiocarbonyl [$NH_2$—C(═S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl, or substituted or non-substituted arylphosphonyl radical;

Z represents hydrido, hydroxy, substituted or non-substituted alkyloxy, substituted or non-substituted aryloxy, non-substituted amino [—$NH_2$], substituted or non-substituted alkylamino, substituted or non-substituted arylamino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and at least four of $B_1, B_2, \ldots, B_{n-1}$, and $B_n$ are independently selected from unnatural nucleobases with a substituted or non-substituted amino radical covalently linked to the nucleobase moiety.

In some embodiments, the compound of Formula I possesses at least a 10-mer complementary overlap with a 14-mer target splice site sequence that consists of 7-mer from intron and 7-mer from exon within a target pre-mRNA, wherein the target splice site sequence is not [(5'→3') UUGCCUGGUAAGGA (SEQ ID NO: 3)] within the human androgen receptor pre-mRNA, [(5'→3') UUUUUGCGUAAGUA (SEQ ID NO: 4)] within the human SCN9A pre-mRNA, [(5'→3') UAAGUAGGAUAAGU (SEQ ID NO: 5)] within the human HIF-1α pre-mRNA, [(5'→3') AUCCCAGGGUAACA (SEQ ID NO: 6)] within the human SNAP25 pre-mRNA, [(5'→3') UGUUUAGGUACACU (SEQ ID NO: 7)] within the human SCN9A pre-mRNA, or

[(5'→3') UGUACAGAUUGUCU (SEQ ID NO: 8)] within the human tyrosinase pre-mRNA.

In some embodiments, the compound of Formula I possesses at least a 10-mer complementary overlap with a target splice site within a target pre-mRNA, wherein the target splice site sequence does not comprise [(5'→3') UUGCCUGGUAAGGA (SEQ ID NO: 3)] within the human androgen receptor pre-mRNA, [(5'→3') UUUUUGCGUAAGUA (SEQ ID NO: 4)] within the human SCN9A pre-mRNA, [(5'→3') UAAGUAGGAUAAGU (SEQ ID NO: 5)] within the human HIF-1α pre-mRNA, [(5'→3') AUCCCAGGGUAACA (SEQ ID NO: 6)] within the human SNAP25 pre-mRNA, [(5'→3') UGUUUAGGUACACU (SEQ ID NO: 7)] within the human SCN9A pre-mRNA, or [(5'→3') UGUACAGAUUGUCU (SEQ ID NO: 8)] within the human tyrosinase pre-mRNA.

The compound of Formula I potently induces the skipping of the target exon of the target pre-mRNA, yields mRNA splice variant(s) lacking the target exon, and therefore is useful to modulate the functional activity of the gene transcribing the target pre-mRNA.

DESCRIPTION OF INVENTION

The present invention provides a peptide nucleic acid derivative represented by Formula I, or a pharmaceutically acceptable salt thereof:

alkylsulfonyl, substituted or non-substituted arylsulfonyl, substituted or non-substituted alkylphosphonyl, or substituted or non-substituted arylphosphonyl radical;

Z represents hydrido, hydroxy, substituted or non-substituted alkyloxy, substituted or non-substituted aryloxy, non-substituted amino [—$NH_2$], substituted or non-substituted alkylamino, substituted or non-substituted arylamino, substituted or non-substituted alkyl, or substituted or non-substituted aryl radical;

$B_1$, $B_2$, . . . , $B_{n-1}$, and $B_n$ are independently selected from natural nucleobases including adenine, thymine, guanine, cytosine and uracil, and unnatural nucleobases; and at least four of $B_1$, $B_2$, . . . , $B_{n-1}$, and $B_n$ are independently selected from unnatural nucleobases with a substituted or non-substituted amino radical covalently linked to the nucleobase moiety.

In some embodiments, the compound of Formula I possesses at least a 10-mer complementary overlap with a 14-mer target splice site sequence that consists of 7-mer from intron and 7-mer from exon within a target pre-mRNA, wherein the target splice site sequence is not [(5'→3') UUGCCUGGUAAGGA (SEQ ID NO: 3)] within the human androgen receptor pre-mRNA, [(5'→3') UUUUUGCGUAAGUA (SEQ ID NO: 4)] within the human SCN9A pre-mRNA, [(5'→3') UAAGUAGGAUAAGU (SEQ ID NO: 5)]

Formula I

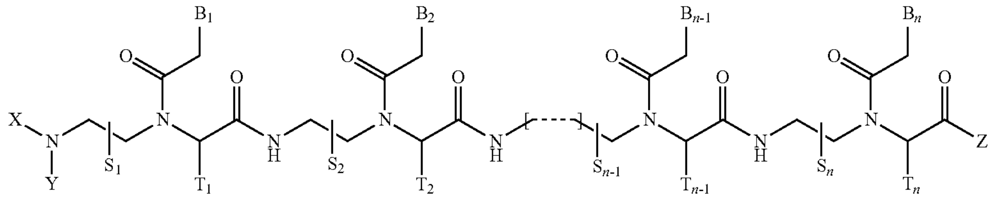

wherein, n is an integer between 10 and 25;

the compound of Formula I possesses at least a 10-mer complementary overlap with a 14-mer target splice site sequence consisting of 7-mer from intron and 7-mer from exon within a target pre-mRNA;

the compound of Formula I is fully complementary to the target pre-mRNA sequence, or partially complementary to the target pre-mRNA sequence with one or two mismatches;

$S_1$, $S_2$, . . . , $S_{n-1}$, $S_n$, $T_1$, $T_2$, . . . , $T_{n-1}$, and $T_n$ independently represent deuterido [D], hydrido [H], substituted or non-substituted alkyl, or substituted or non-substituted aryl radical;

X and Y independently represent hydrido, formyl [H—C(=O)—], aminocarbonyl [$NH_2$—C(=O)—], aminothiocarbonyl [$NH_2$—C(=S)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted within the human HIF-1α pre-mRNA, [(5'→3') AUCCCAGGGUAACA (SEQ ID NO: 6)] within the human SNAP25 pre-mRNA, [(5'→3') UGUUUAGGUACACU (SEQ ID NO: 7)] within the human SCN9A pre-mRNA, or [(5'→3') UGUACAGAUUGUCU (SEQ ID NO: 8)] within the human tyrosinase pre-mRNA.

In some embodiments, the compound of Formula I possesses at least a 10-mer complementary overlap with a target splice site within a target pre-mRNA, wherein the target splice site sequence does not comprise [(5'→3') UUGCCUGGUAAGGA (SEQ ID NO: 3)] within the human androgen receptor pre-mRNA, [(5'→3') UUUUUGCGUAAGUA (SEQ ID NO: 4)] within the human SCN9A pre-mRNA, [(5'→3') UAAGUAGGAUAAGU (SEQ ID NO: 5)] within the human HIF-1α pre-mRNA, [(5'→3') AUCCCAGGGUAACA (SEQ ID NO: 6)] within the human SNAP25 pre-mRNA, [(5'→3') UGUUUAGGUACACU (SEQ ID NO: 7)] within the human SCN9A pre-mRNA, or [(5'→3') UGUACAGAUUGUCU (SEQ ID NO: 8)] within the human tyrosinase pre-mRNA.

The compound of Formula I potently induces the skipping of the target exon of the target pre-mRNA, yields mRNA splice variant(s) lacking the target exon, and therefore is useful to modulate the functional activity of the gene transcribing the target pre-mRNA.

The condition adopted to describe the compound of Formula I that "n is an integer between 10 and 25" literally states that "n is an integer selected from 11, 12, 13, 14, 15, 16, 17, 18, 19, 20, 21, 22, 23, and 24".

It was estimated that there would be 26,564 genes in the whole human genome. [In *Silico Biol.* vol 4, 387-393 (2004)] Given that there are ca 8.8 exons and 7.8 introns per gene on average, there are 368,122 splice sites [{(8.2×2)−2}×25,564=368,122] possible in the human genome. Since there are 1,048,576 (i.e., $4^{10}$) possible sequences for 10-mer pre-mRNA, even 10-mer PNA derivatives would show a sufficient level of specificity for a target splice site. However, the 5'-end and 3'-end of each intron are highly conserved to possess the sequence starting with [(5'→3')|GU-] and the sequence ending with [(5'→3')-AG|], respectively, where "|" stands for the junction of intron-exon or exon-intron. Thus, the compound of Formula I with an oligomer length of 11-mer or longer (i.e., n is an integer larger than 10) is predicted to show a sufficient level of specificity for the target splice site.

The compound of Formula I tightly binds to complementary nucleic acid as exemplified in the prior art [PCT/KR2009/001256]. For example, incorporation of 4 to 5 modified (i.e., unnatural of naturally non-occurring) nucleobases onto 11- to 13-mer PNA derivatives of Formula I readily yields a $T_m$ gain of 20° C. or higher in duplex formation with complementary DNA. The compound of the present invention possesses strong affinity for complementary RNA as it does for complementary DNA. Thus it is preferred to have the compound of this invention as short as possible in order to avoid undesirable off-target effects originating from the binding of the said compound to other pre-mRNA sequences with a few number of mismatches. Thus the oligomer length of the said compound is limited to be shorter than 25-mer.

The compound of Formula I is highly sensitive to a single base mismatch as exemplified in the prior art [PCT/KR2009/001256]. For example, a single base mismatch resulted in a $T_m$ loss of 11 to 22° C. depending on the type of modified base as well as the PNA sequence. Owing to the strong affinity for RNA, however, the compound of this invention still tightly binds to the target splice site sequence possessing one or two mismatches, and potently induces the skipping of the target exon.

The compound of Formula I tightly binds to either a 3' splice site or a 5' splice site within a target pre-mRNA, depending on its sequence.

In case the compound binds to a 3' splice site, the said compound possesses at least a 10-mer complementary overlap with a 14-mer sequence in a target 3' splice site consisting of 7-mer from the target intron and 7-mer from the target exon. Thus the 3' splice site is unambiguously defined as the junction between the 3'-end of the target intron and the 5'-end of the target exon.

In case the compound binds to a 5' splice site, the said compound possesses at least a 10-mer complementary overlap with a 14-mer sequence in a target 5' splice site consisting of 7-mer from the target exon and 7-mer from the target intron. Thus the 5' splice site is unambiguously defined as the junction between the 3'-end of the target exon and the 5'-end of the target intron.

The 14-mer sequence describing the compound of Formula I targeting a 3' splice site is illustrated with the 3' splice site spanning the junction of intron 1 and exon 2 in the human HIF-1α (hypoxia-inducible factor 1 alpha) pre-mRNA read out from the human HIF1A gene [NCBI Reference Sequence: NG_029606.1]. A 40-mer sequence of the 3' splice site consisting of the 20-mer from intron 1 and the 20-mer from exon 2 reads [(5'-3') uucuuguuguuguuaaguag|GAUAAGUUCUGAACGUCGAA (SEQ ID NO: 9)], in which the intron and exon sequences are denoted by small and capital letters, respectively, and the junction between intron 1 and exon 2 is marked with "|". Thus the 14-mer sequence of the 3' splice site consisting of the 7-mer from HIF-1α intron 1 and the 7-mer from HIF-1α exon 2 reads [(5'→3') uaaguag|GAUAAGU (SEQ ID NO: 10)]. In this 3' splice site, the target intron and exon are HIF-1α intron 1 and exon 2, respectively.

The above 40-mer pre-mRNA sequence was provided to unequivocally identify the 3' splice site of exon 2 in the human HIF-1α pre-mRNA, since exon numbers often vary depending on mRNA transcripts. Throughout this invention, the target splice site of the said PNA compound is unequivocally identified wherever applicable by simultaneously specifying the target exon number and a pre-mRNA sequence comprising the target splice site.

The 14-mer sequence describing the compound of Formula I targeting a 5' splice site is illustrated with the 5' splice site spanning the junction of exon 2 and intron 2 in the human HIF-1α pre-mRNA. A 40-mer sequence of the 5' splice site consisting of the 20-mer from exon 2 and the 20-mer from intron 2 reads [(5'-3') GAGGAAACUUCUGGAUGCUG|gugaguuauuuuacaagggu (SEQ ID NO: 11)], in which the exon and intron sequences are denoted by capital and small letters, respectively, and the junction between exon 2 and intron 2 is marked with "|". Thus the 14-mer sequence of the 5' splice site consisting of the 7-mer from HIF-1α exon 2 and the 7-mer from HIF-1α intron 2 reads [(5'→3') GAUGCUG|gugaguu (SEQ ID NO: 12)]. In this 5' splice site, the target exon and intron are HIF-1α exon 2 and intron 2, respectively.

The compound of Formula I tightly binds to the target splice site within the target pre-mRNA, and interferes with the formation of "splicesome early complex" involving the compound's target splice site. The said compound tightly binds to either a 3' splice site or a 5' splice site within the target pre-mRNA depending on the nucleotide sequence of the said compound. Since the compound of this invention sterically inhibits the formation of "splicesome early complex", the target exon is spliced out to yield mRNA splice variant(s) lacking the target exon. Consequently the compound of the present invention potently induces the skipping of the target exon.

Figure 1A:
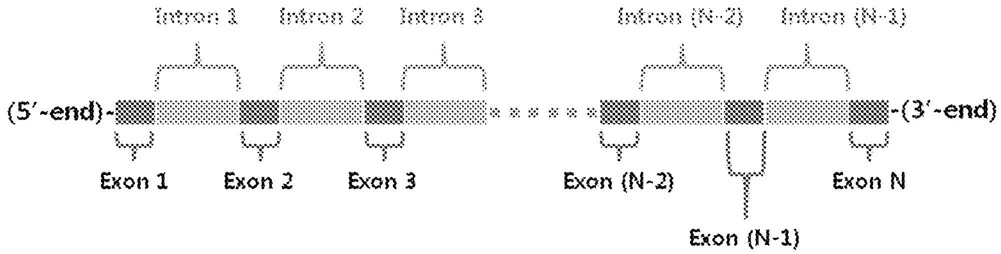
FIG. 1A. Illustration of the numbering for introns and exons in pre-mRNA.
Figure 1B:
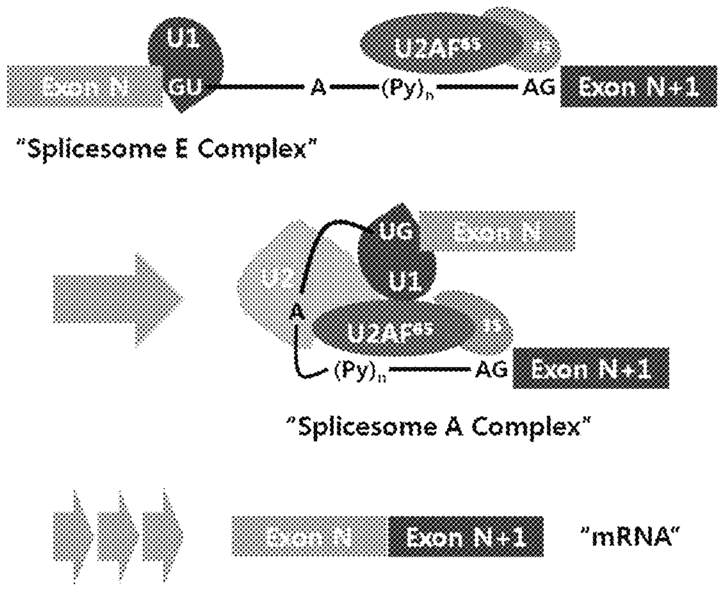
FIG. 1B. Brief schematic illustration of splicing process.
Figure 2A:
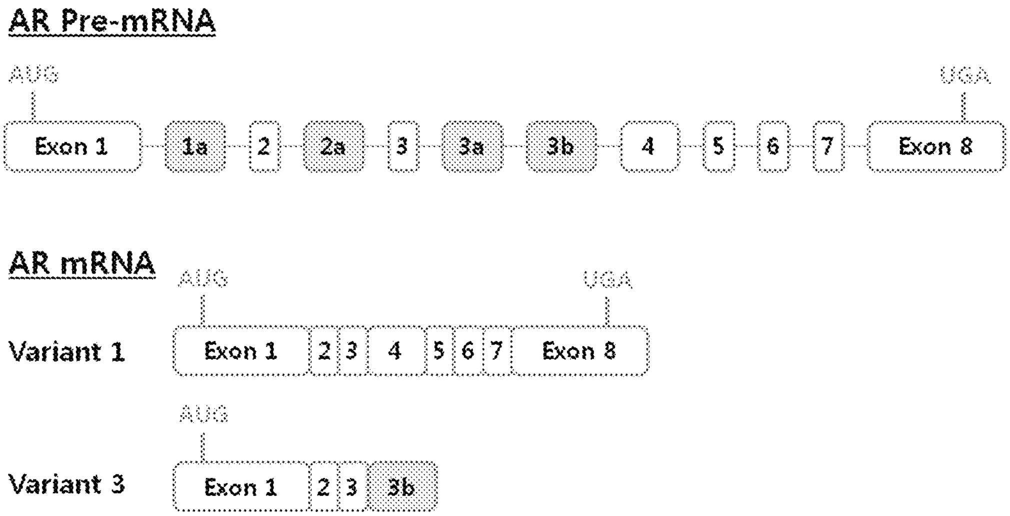
FIG. 2A. AR mRNA splice variants encoding variant AR proteins.
Figure 2B:
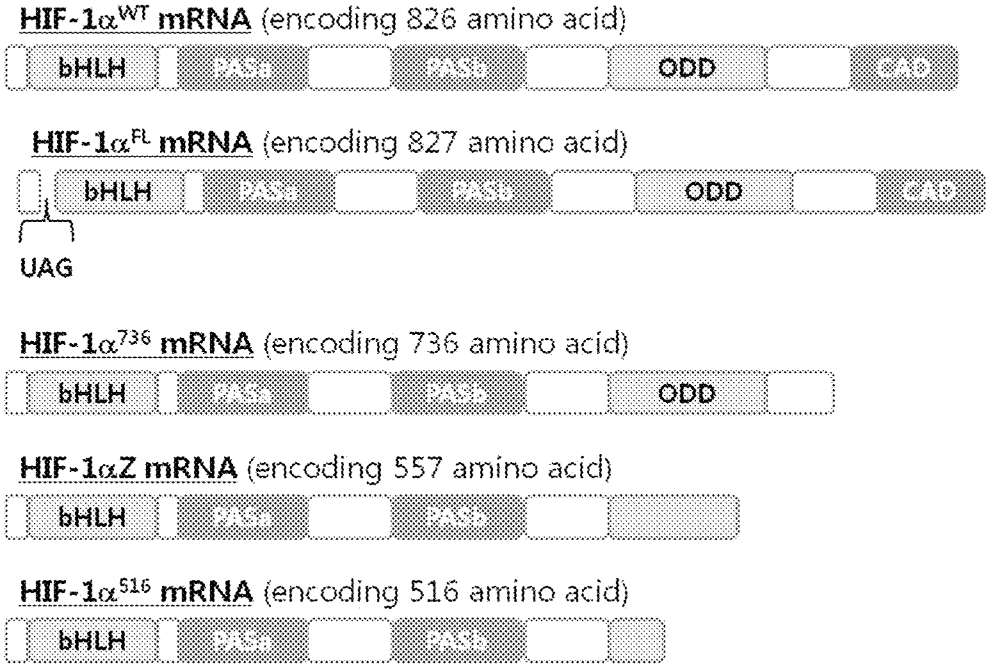
FIG. 2B. HIF-1α mRNA splice variants encoding variant HIF-1α proteins.
Figure 3:
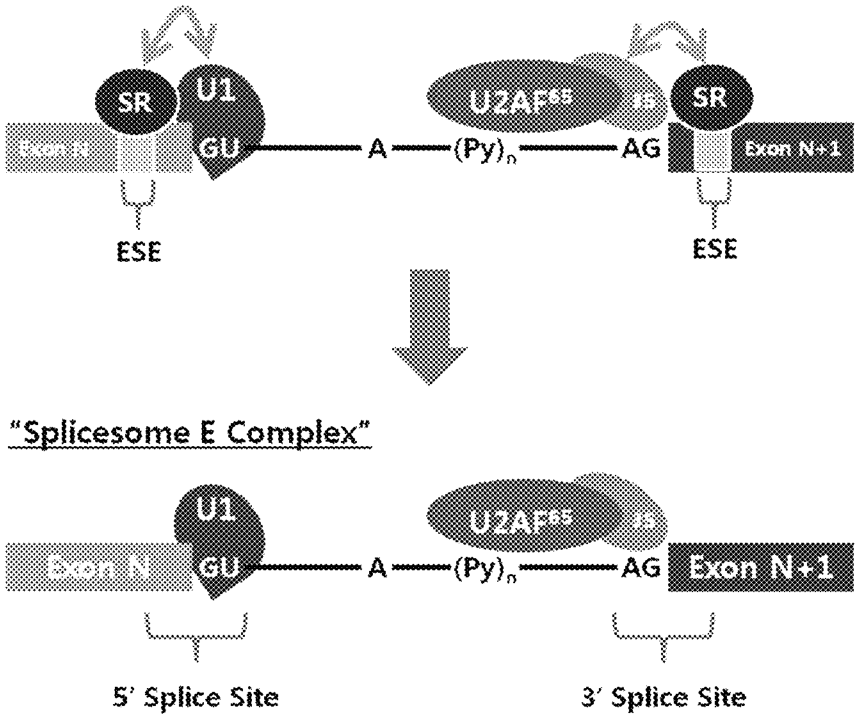
FIG. 3. Schematic illustration for the biological processes involved in the formation of splicesome early complex.
Figure 4A:
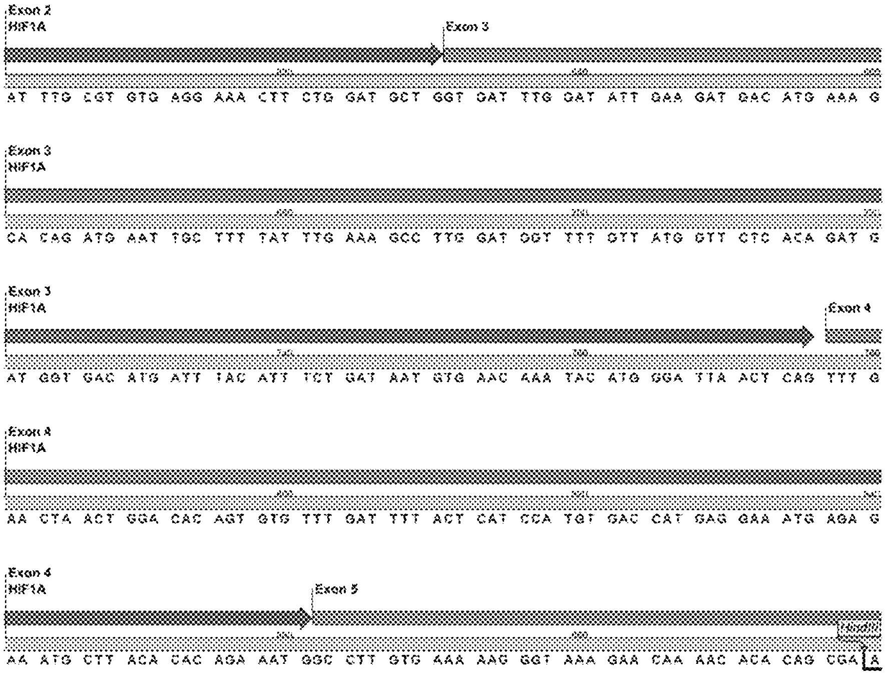
FIG. 4A. A part of CDS read out from the human HIF-1α mRNA (SEQ ID NO: 166).
Figure 4B:
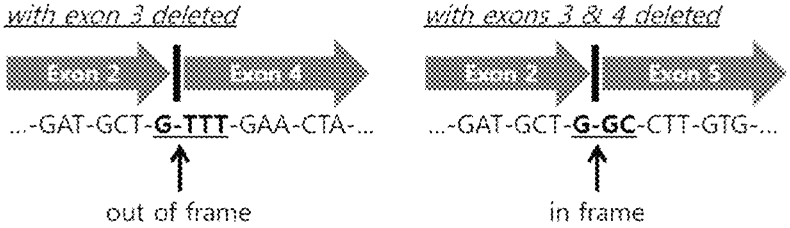
FIG. 4B. Exon-exon junction sequences of the HIF-1α splice variants lacking exon 3 (left; SEQ ID NO: 167) and exons 3-4 (right; SEQ ID NO: 168) illustrating frame shift (out of frame) and in frame, respectively.
Figure 4C:
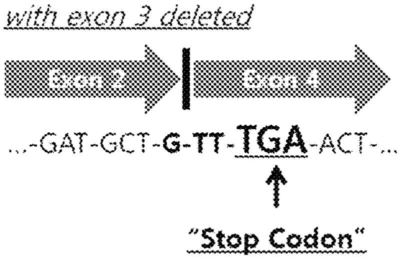
FIG. 4C. Exemplary frame shift yielding a PTC (SEQ ID NO: 169).
Figure 5A:
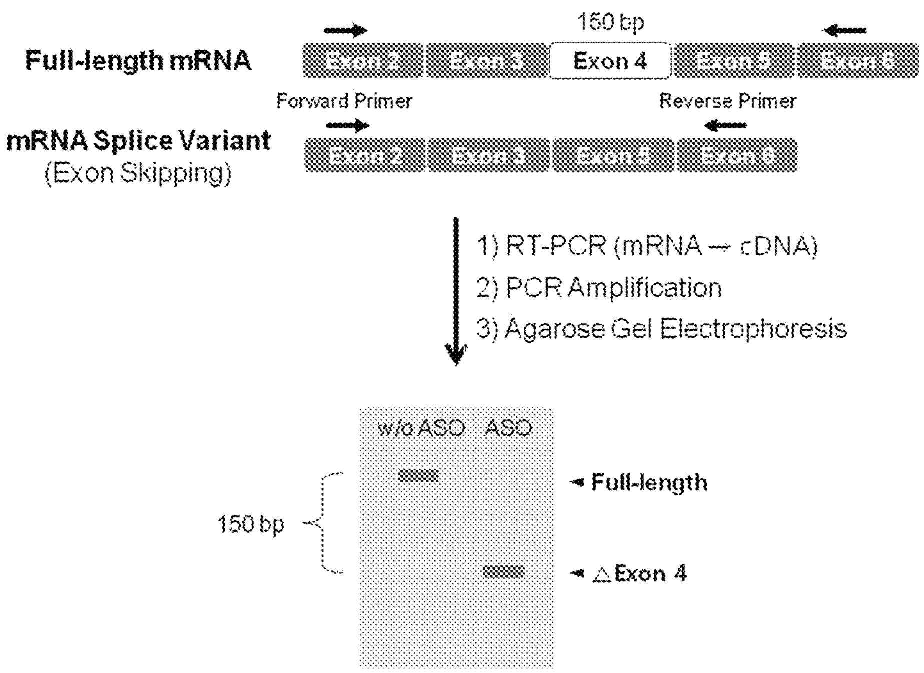
FIG. 5A. Schematic illustration for nested RT-PCR to detect exon skipping.
Figure 5B:
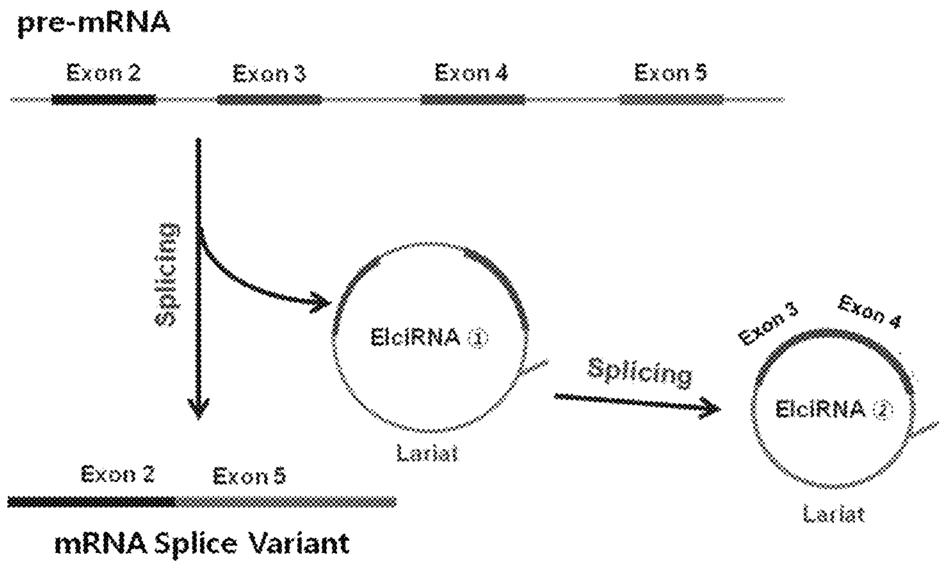
FIG. 5B. Schematic illustration of the formation of EIciRNAs during exon skipping.
Figure 6A:
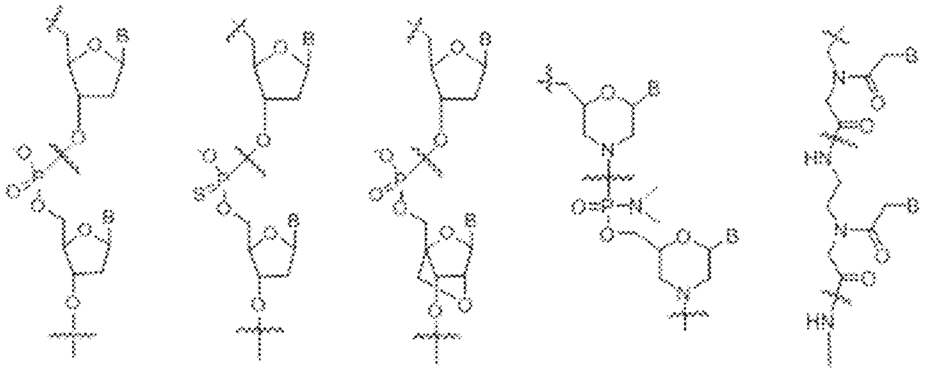
FIG. 6A. Chemical structures for representative unnatural oligonucleotides.
Figure 6B:
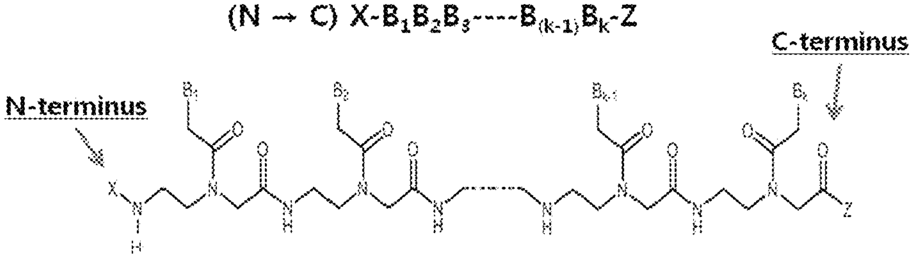
FIG. 6B. The chemical structure and abbreviated nomenclature of prototype PNA.
Figure 6C:
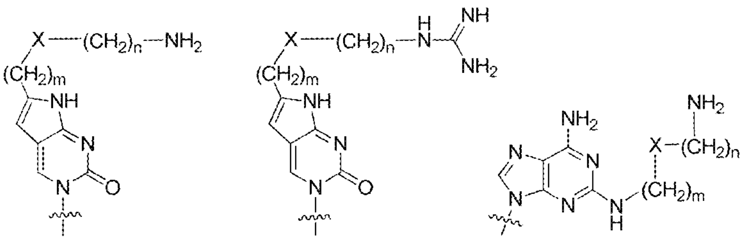
FIG. 6C. Modified nucleobases developed to improve the membrane permeability of PNA.
Figure 6C:
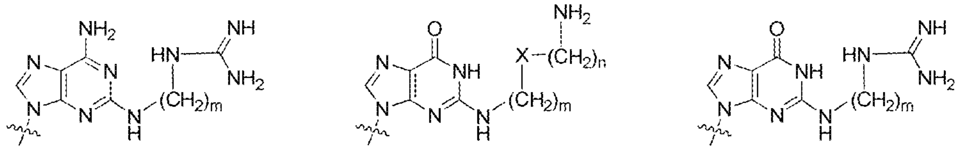
Figure 7:
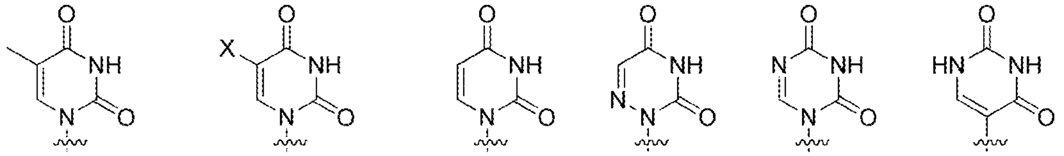
FIG. 7. Examples of natural or unnatural (modified) nucleobases selectable for the peptide nucleic acid derivative of Formula I.
Figure 7:
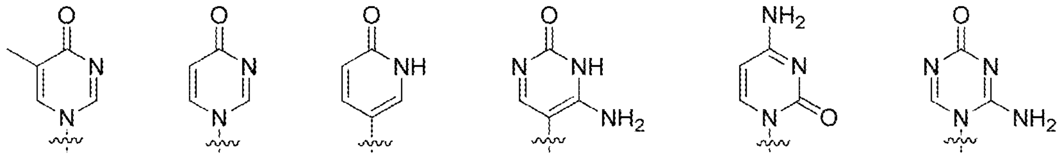
Figure 7:
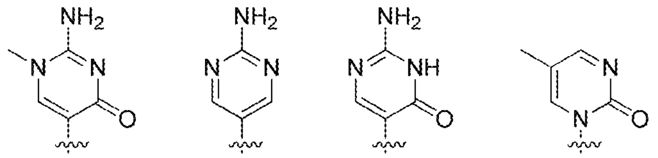
Figure 7:
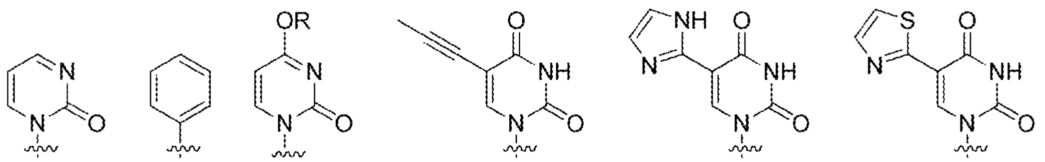
Figure 7:
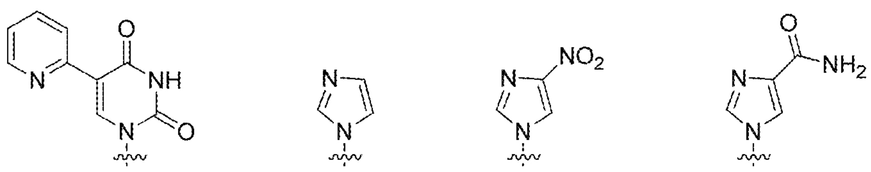

The chemical structures of natural (i.e., naturally occurring) or unnatural (i.e., naturally non-occurring) nucleobases adopted to describe the PNA derivative of Formula I are exemplified in FIG. 7. Natural or unnatural nucleobases of this invention comprise but are not limited to the nucleobases provided in FIG. 7. Provision of such natural or unnatural nucleobases is to illustrate the diversity of allowable nucleobases, and therefore should not be interpreted to limit the scope of the present invention to the nucleobases provided in FIG. 7. A skilled person in the field of oligonucleotide may easily figure out a natural nucleobase complementary to each of the unnatural nucleobases exemplified in FIG. 7. Therefore, the skilled person may unequivocally identify the complementarity between the compound of Formula I and the target pre-mRNA sequence.

Figure 8A:
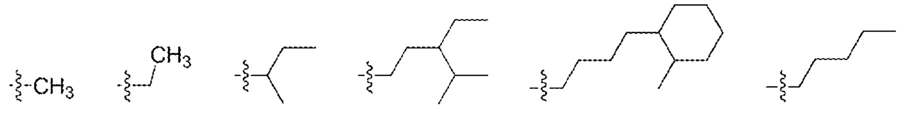
FIG. 8A. Examples for substituted or non-substituted alkyl radicals selectable for the compound of Formula I.
Figure 8A:
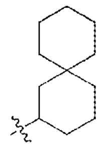
Figure 8A:
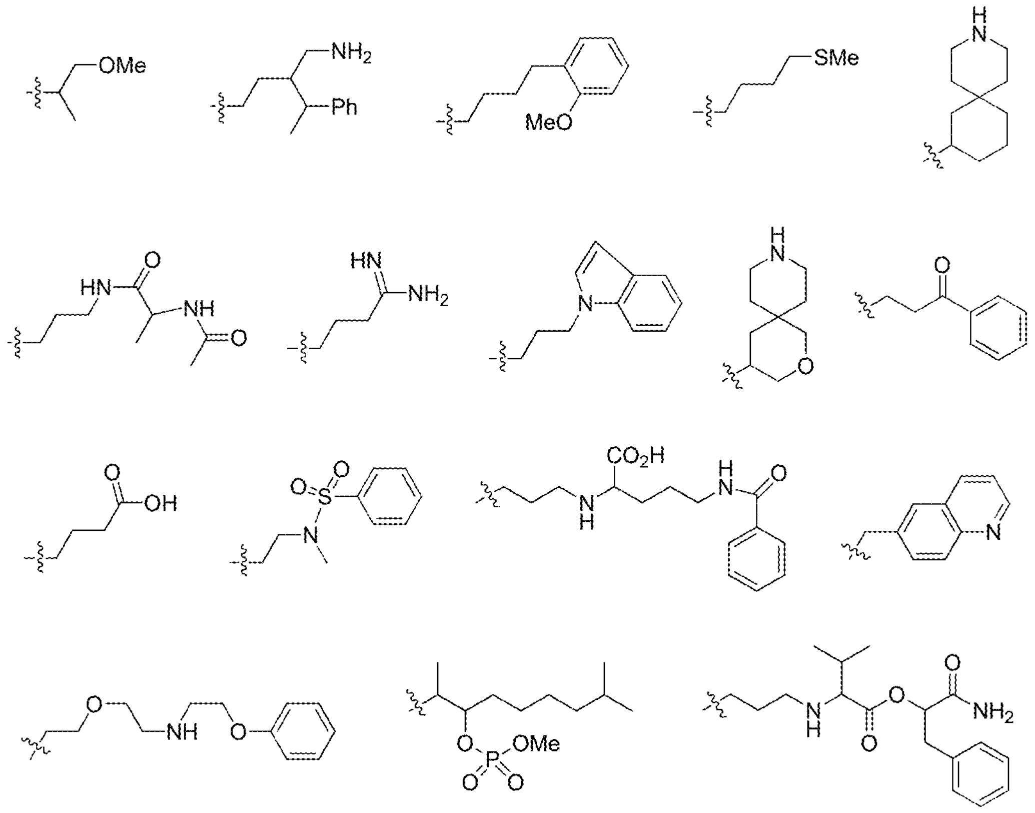
Figure 8B:
FIG. 8B. Examples for substituted or non-substituted alkylacyl, and substituted or non-substituted arylacyl radicals selectable for the compound of Formula I.
Figure 8B:
Figure 8B:
Figure 8B:
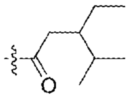
Figure 8B:
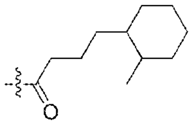
Figure 8B:
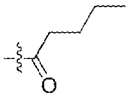
Figure 8B:
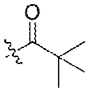
Figure 8B:
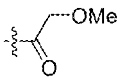
Figure 8B:
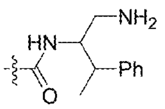
Figure 8B:
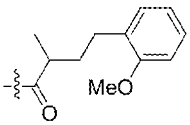
Figure 8B:
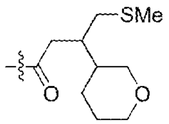
Figure 8B:
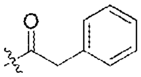
Figure 8B:
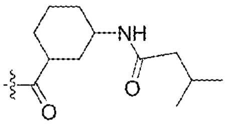
Figure 8B:
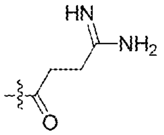
Figure 8B:
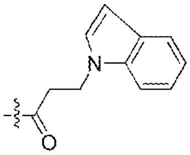
Figure 8B:
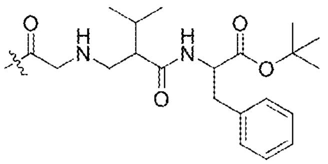
Figure 8B:
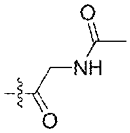
Figure 8B:
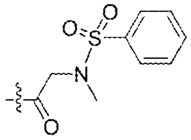
Figure 8B:
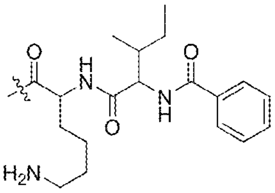
Figure 8B:
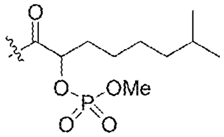
Figure 8B:
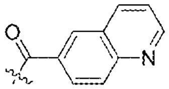
Figure 8B:
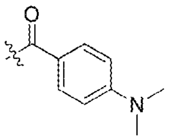
Figure 8B:
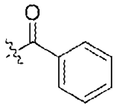
Figure 8B:
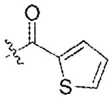
Figure 8B:
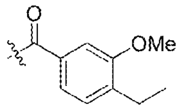
Figure 8B:
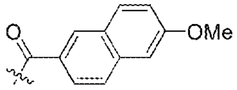
Figure 8B:
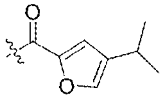
Figure 8B:
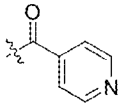
Figure 8B:
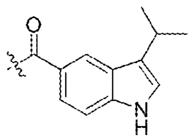
Figure 8C:
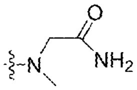
FIG. 8C. Examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals selectable for the compound of Formula I.
Figure 8C:
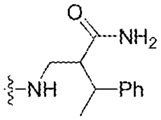
Figure 8C:
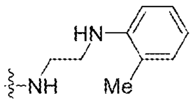
Figure 8C:
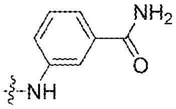
Figure 8C:
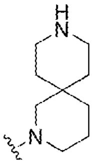
Figure 8C:
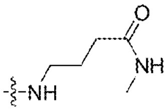
Figure 8C:
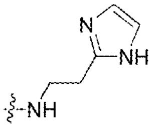
Figure 8C:
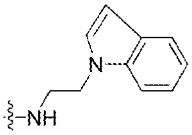
Figure 8C:
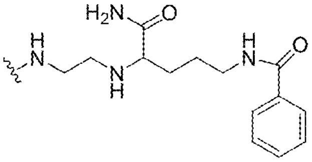
Figure 8C:
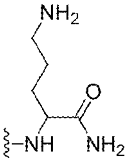
Figure 8C:
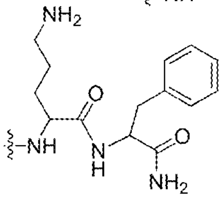
Figure 8C:
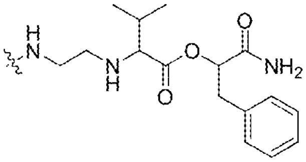
Figure 8C:
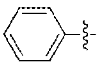
Figure 8C:
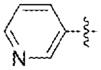
Figure 8C:
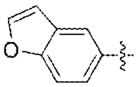
Figure 8C:
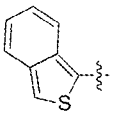
Figure 8C:
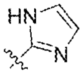
Figure 8C:
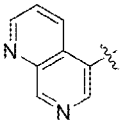
Figure 8C:
Figure 8C:
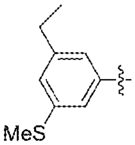
Figure 8C:
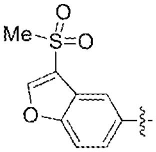
Figure 8C:
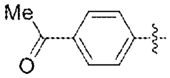
Figure 8C:
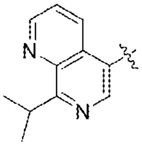
Figure 8C:
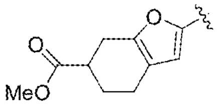
Figure 8C:
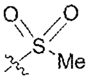
Figure 8C:
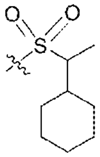
Figure 8C:
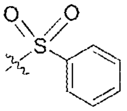
Figure 8C:
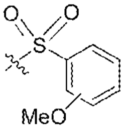
Figure 8C:
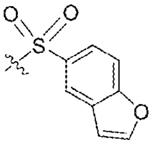
Figure 8C:
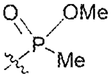
Figure 8C:
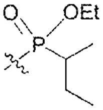
Figure 8C:
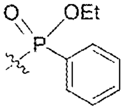
Figure 8C:
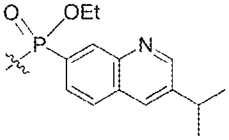
Figure 8C:
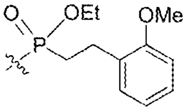
Figure 8D:
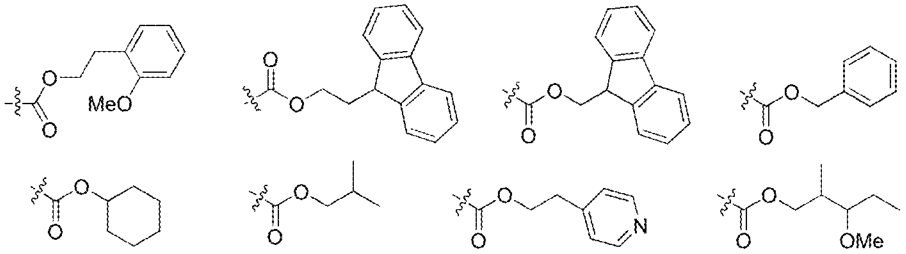
FIG. 8D. Examples for substituted or non-substituted alkyloxycarbonyl, substituted or non-substituted aryloxycarbonyl, substituted or non-substituted alkylaminocarbonyl, and substituted or non-substituted arylaminocarbonyl radicals selectable for the compound of Formula I.
Figure 8D:
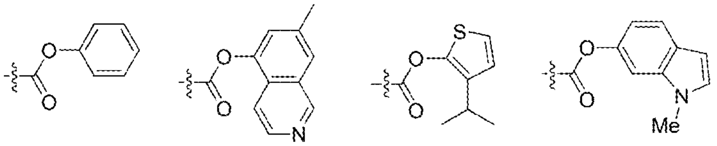
Figure 8D:
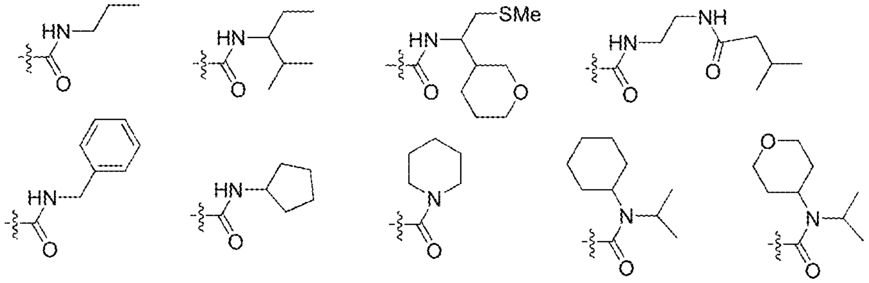
Figure 8D:
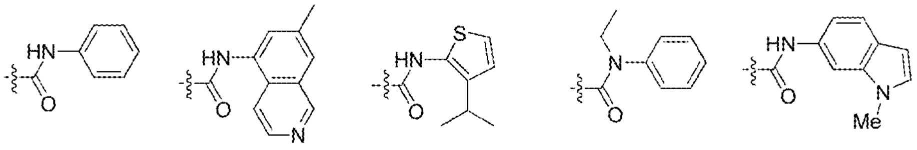
Figure 8E:
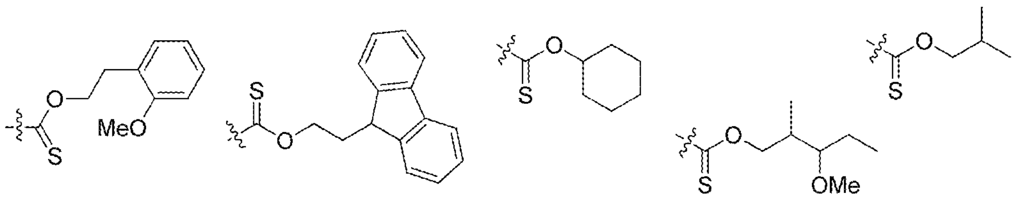
FIG. 8E. Examples for substituted or non-substituted alkyloxythiocarbonyl, substituted or non-substituted alkylaminothiocarbonyl, substituted or non-substituted arylaminothiocarbonyl, substituted or non-substituted alkyloxythiocarbonyl, and substituted or non-substituted aryloxythiocarbonyl radicals selectable for the compound of Formula I.
Figure 8E:
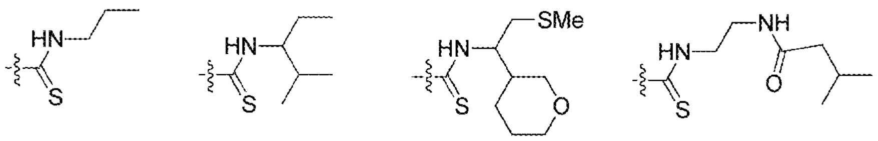
Figure 8E:
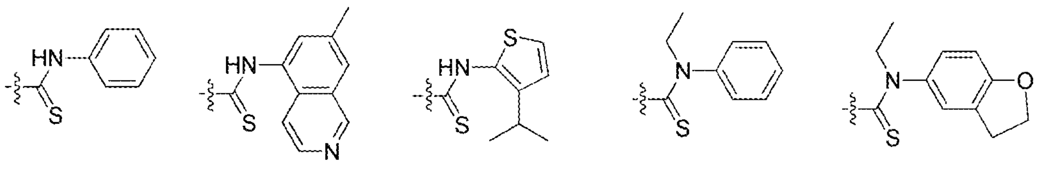
Figure 8E:
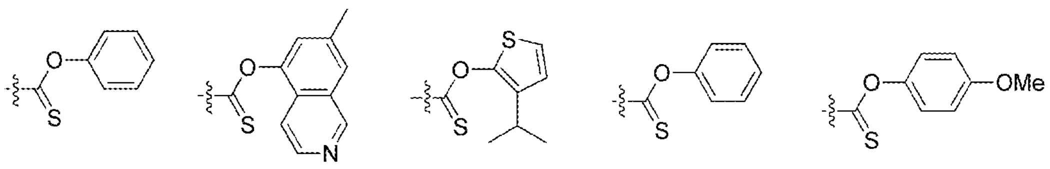

The substituents adopted to describe the PNA derivative of Formula I are exemplified in FIG. 8A to FIG. 8E. FIG. 8A provides examples for substituted or non-substituted alkyl radicals. Substituted or non-substituted alkylacyl, and substituted or non-substituted arylacyl radicals are exemplified in FIG. 8B. FIG. 8C illustrates examples for substituted alkylamino, substituted arylamino, substituted or non-substituted aryl, substituted or non-substituted alkylsulfonyl, substituted or non-substituted arylsulfonyl, substituted or non-substituted alkylphosphonyl, and substituted or non-substituted arylphosphonyl radicals. FIG. 8D provides examples for substituted or non-substituted alkyloxycarbonyl, substituted or non-substituted aryloxycarbonyl, substituted or non-substituted alkylaminocarbonyl, and substituted or non-substituted arylaminocarbonyl radicals. In FIG. 8E, are provided examples for substituted or non-substituted alkyloxythiocarbonyl, substituted or non-substituted alkylaminothiocarbonyl, substituted or non-substituted arylaminothiocarbonyl, substituted or non-substituted alkyloxythiocarbonyl, and substituted or non-substituted aryloxythiocarbonyl radicals. Provision of such exemplary substituents is to illustrate the diversity of allowable substituents, and therefore should not be interpreted to limit the scope of the present invention to the substituents exemplified in FIG. 8A to FIG. 8E. Since a skilled person in the field may easily figure out that oligonucleotide sequence is the overriding factor for sequence specific binding of oligonucleotide to the target pre-mRNA sequence over substituents in the N-terminus or C-terminus, there are more diverse substituents allowable for the said compound of this invention than those substituents exemplified in FIG. 8A to FIG. 8E.

The compound of Formula I possesses good cell permeability and can be readily delivered into cell as "naked" (i.e., without being formulated with adjuvant(s) to increase delivery into cell) oligonucleotide as exemplified in the prior art [PCT/KR2009/001256]. Thus the compound of this invention potently induces the skipping of the target exon in the target pre-mRNA to yield mRNA splice variant(s) lacking the target exon in cells treated with the compound of Formula I as "naked" oligonucleotide.

The compound of Formula I does not require any means or formulations for delivery into cell to potently induce the skipping of the target exon in cells. In this regard, the compound of the present invention is distinctively differentiated from other classes of oligonucleotide including DNA, RNA, PTO, 2'-OMe PTO, 2'-OMe RNA, 2'-OMOE RNA, LNA, PMO, PNA, and so on.

Given with the strong affinity for RNA and good cell permeability, the compound of Formula I readily induces the skipping of the target exon in cells with a sub-femtomolar antisense potency. To date, sub-femtomolar antisense exon skipping potency has never been reported or realized with other classes of oligonucleotide including DNA, RNA, PTO, 2'-OMe PTO, 2'-OMe RNA, 2'-OMOE RNA, LNA, PMO, PNA, and so on. Even sub-nanomolar antisense exon skipping potency has been rarely documented with other classes of oligonucleotide. Sub-nanomolar antisense exon skipping potency was reported with PNA ASOs designed to possess a varying number of phosphonate groups covalently conjugated to the N-terminus of the PNA sequence to facilitate lipofection for transfection into cell. [*Nucl. Acids Res.* vol 30(13), 4424-4432 (2008)] As cited earlier in this document, the in vitro potency of antisense exon skipping has been reported to be nanomolar to micromolar even under conditions of enforced delivery into cell such as lipofection, electroporation, and so on. In this regard, the compound of Formula I is distinctively differentiated from other classes of oligonucleotide including DNA, RNA, PTO, 2'-OMe PTO, 2'-OMe RNA, 2'-OMOE RNA, LNA, PMO, PNA, and so on.

In order for an oligonucleotide molecule to bind to its complementary sequence within a pre-mRNA, the molecule needs to be stretched out or unfolded for complementary binding to the target pre-mRNA sequence. Oligonucleotide molecules tend to aggregate or to remain folded (e.g., like hair-pin) due to their high propensity of forming intermolecular or intra-molecular hydrogen bondings between nucleobases. Thus there would be an additional energy barrier of unfolding against antisense exon skipping with popularly investigated oligonucleotides including DNA, RNA, PTO, 2'-OMe PTO, 2'-OMe RNA, 2'-OMOE RNA, LNA, PMO, PNA, and so on. Oligonucleotides have been conventionally quantified by UV absorption following an incubation at >90° C. in aqueous buffer to unfold oligonucleotide molecules as much as possible.

The PNA derivative of Formula I possesses multiple positive charges distributed over the whole oligonucleotide strand at physiological pH due to several basic amino groups covalently attached to the modified nucleobases therein. The multiple positive charges allow the compound of Formula I to remain unfolded or stretched-out due to electrostatic repulsion between neighboring positive charges on the same oligonucleotide strand. The derivative of Formula I has a low propensity to aggregate with other molecule(s) of Formula I. Thus the compound of Formula I tends to remain structurally ready (i.e., stretched out) for complementary binding to the target sequence within the target pre-mRNA. The structural readiness is also important for the oligonucleotide of Formula I to rapidly align with the target pre-mRNA sequence as the target pre-mRNA is being transcribed from the DNA. Thus, the structural readiness combined with the strong affinity is considered to add up to the strong binding affinity to yield the sub-femtomolar antisense exon skipping potency of the compound of Formula I. In these regards, the compound of Formula I is highly differentiated from other classes of oligonucleotide including DNA, RNA, PTO, 2'-OMe PTO, 2'-OMe RNA, 2'-OMOE RNA, LNA, PMO, PNA, and so on.

Owing to the good cell permeability, the PNA derivative of Formula I may be systemically administered as "naked" oligonucleotide to potently induce exon skipping in target tissue(s). The compound of Formula I does not require a formulation or an adjuvant to increase delivery into target tissue to elicit the desired therapeutic activity. The compound of Formula I is dissolved simply in PBS (phosphate buffered saline) or saline, and systemically administered to effortlessly elicit the therapeutic activity in target tissue(s).

Given with the sub-femtomolar potency of exon skipping in cells treated as "naked" oligonucleotide, the PNA derivative of the present invention shows in vivo therapeutic activity frequently at a systemic dose of 1 μg/Kg or less. Such a strong therapeutic potency has never been realized with other classes of oligonucleotide including DNA, RNA, PTO, 2'-OMe PTO, 2'-OMe RNA, 2'-OMOE RNA, LNA, PMO, PNA, and so on. Since the manufacturing cost of oligonucleotide is generally very high, the ultra strong potency is a big advantage for realizing an affordable treatment cost especially for patients with a chronic disease. In this regard, the compound of Formula I is highly differentiated from other classes of oligonucleotide including DNA, RNA, PTO, 2'-OMe PTO, 2'-OMe RNA, 2'-OMOE RNA, LNA, PMO, PNA, and so on.

Due to the good cell permeability, the PNA derivative of the current invention is readily delivered topically or transdermally to elicit the therapeutic activity at the administration site. The compound of this invention does not need to be heavily or invasively formulated to elicit the intended topical therapeutic activity. The PNA derivative of Formula I is readily delivered transdermally as "naked" oligonucleotide. Owing to the ultra strong exon skipping potency, the said compound shows therapeutic activity upon topical or transdermal administration of a sub-picomolar oligonucleotide solution. Topical or transdermal delivery as "naked" oligonucleotide has been extremely challenging with other classes of oligonucleotide including DNA, RNA, PTO, 2'-OMe PTO, 2'-OMe RNA, 2'-OMOE RNA, LNA, PMO, PNA, and so on. In this regard, the compound of Formula I is distinctively differentiated from other classes of oligonucleotide including DNA, RNA, PTO, 2'-OMe PTO, 2'-OMe RNA, 2'-OMOE RNA, LNA, PMO, PNA, and so on.

The compound of Formula I may be used as combined with a pharmaceutically acceptable acid or base including but not limited to sodium hydroxide, potassium hydroxide, hydrochloric acid, methanesulfonic acid, citric acid, trifluoroacetic acid, and so on.

The PNA derivative of Formula I or a pharmaceutically acceptable salt thereof may be administered to a subject in combination with a pharmaceutically acceptable adjuvant including but not limited to citric acid, hydrochloric acid, tartaric acid, stearic acid, polyethyleneglycol, polypropyleneglycol, ethanol, isopropanol, sodium bicarbonate, distilled water, preservative(s), and so on.

The compound of the present invention can be systemically administered to a subject at a therapeutically effective dose ranging from 1 fmole/Kg to higher than 1 nmole/Kg, which may vary depending on the dosing schedule, conditions or situations of subject, and so on. The compound of the current invention can be topically administered to a subject at a therapeutically effective concentration ranging from 1 aM to higher than 1 nM, which may vary depending on the dosing schedule, conditions or situations of subject, and so on.

Preferred is a PNA derivative of Formula I, or a pharmaceutically acceptable salt thereof:

wherein, n is an integer between 10 and 25;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence, or partially complementary to the target pre-mRNA sequence with one or two mismatches;

$S_1$, $S_2$, . . . , $S_{n-1}$, $S_n$, $T_1$, $T_2$, . . . , $T_{n-1}$, and $T_n$ independently represent deuterido, hydrido, substituted or non-substituted alkyl, or substituted or non-substituted aryl radical;

X and Y independently represent hydrido, formyl, aminocarbonyl, aminothiocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylaminothiocarbonyl, substituted or non-substituted arylaminothiocarbonyl, substituted or non-substituted alkyloxythiocarbonyl, substituted or non-substituted aryloxythiocarbonyl, substituted or non-substituted alkylsulfonyl, substituted or non-substituted arylsulfonyl, substituted or non-substituted alkylphosphonyl radical, or substituted or non-substituted arylphosphonyl radical;

Z represents hydrido, hydroxy, substituted or non-substituted alkyloxy, substituted or non-substituted aryloxy, non-substituted amino, substituted or non-substituted alkylamino, substituted or non-substituted arylamino, substituted or non-substituted alkyl, or substituted or non-substituted aryl radical;

$B_1$, $B_2$, . . . , $B_{n-1}$, and $B_n$ are independently selected from natural nucleobases including adenine, thymine, guanine, cytosine and uracil, and unnatural nucleobases;

at least four of $B_1$, $B_2$, . . . , $B_{n-1}$, and $B_n$ are independently selected from unnatural nucleobases represented by Formula II, Formula III, or Formula IV:

Formula II

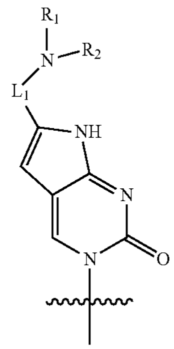

Formula III

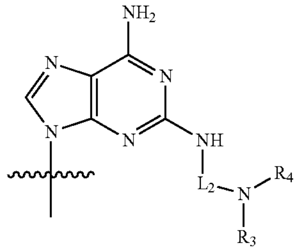

Formula IV

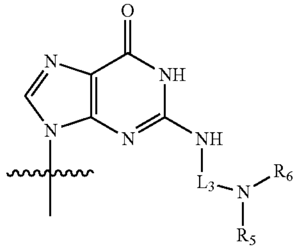

wherein, $R_1$, $R_2$, $R_3$, $R_4$, $R_5$ and $R_6$ are independently selected from hydrido, and substituted or non-substituted alkyl radical;

$L_1$, $L_2$ and $L_3$ are a covalent linker represented by Formula V covalently linking the basic amino group to the nucleobase moiety:

Formula V

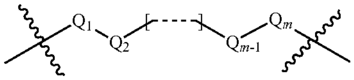

wherein, $Q_1$ and $Q_m$ are substituted or non-substituted methylene ($-CH_2-$) radical, and $Q_m$ is directly linked to the basic amino group;

$Q_2$, $Q_3$, . . . , and $Q_{m-1}$ are independently selected from substituted or non-substituted methylene, oxygen (—O—), sulfur (—S—), and substituted or non-substituted amino radical [—N(H)—, or —N(substituent)-]; and m is an integer between 1 and 15.

The unnatural nucleobases of Formula II, Formula III and Formula IV are equivalent to cytosine, adenine, and guanine, respectively, for complementary base pairing with pre-mRNA as illustrated in the prior art [PCT/KR2009/001256].

The condition adopted to describe Formula V that "m is an integer between 1 and 15" literally states that "n is an integer selected from 2, 3, 4, 5, 6, 7, 8, 9, 10, 11, 12, 13, and 14".

Of interest is a PNA oligomer of Formula I, or a pharmaceutically acceptable salt thereof:

wherein, n is an integer between 11 and 23;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence, or partially complementary to the target pre-mRNA sequence with one or two mismatches;

$S_1, S_2, \ldots, S_{n-1}, S_n, T_1, T_2, \ldots, T_{n-1}$, and $T_n$ are hydrido radical;

X and Y independently represent hydrido, aminocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, or substituted or non-substituted arylsulfonyl radical;

Z represents non-substituted amino, or substituted or non-substituted alkylamino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are substituted or non-substituted methylene radical, and $Q_m$ is directly linked to the basic amino group;

$Q_2, Q_3, \ldots$, and $Q_{m-1}$ are independently selected from substituted or non-substituted methylene, oxygen, and amino radical; and m is an integer between 1 and 11.

Of particular interest is a PNA derivative of Formula I, or a pharmaceutically acceptable salt thereof:

wherein, n is an integer between 11 and 21;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence, or partially complementary to the target pre-mRNA sequence with one or two mismatches;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, or substituted or non-substituted arylsulfonyl radical;

Z represents non-substituted amino, or substituted or non-substituted alkylamino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$ and $R_6$ are independently selected from hydrido, and substituted or non-substituted alkyl radical;

$Q_1$ and $Q_m$ are methylene radical, and $Q_m$ is directly linked to the basic amino group;

$Q_2, Q_3, \ldots$, and $Q_{m-1}$ are independently selected from methylene, oxygen, and amino radical; and m is an integer between 1 and 11.

Of high interest is a PNA oligomer of Formula I, or a pharmaceutically acceptable salt thereof:

wherein, n is an integer between 11 and 19;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence;

$S_1, S_2, \ldots, S_{n-1}, S_n, T_1, T_2, \ldots, T_{n-1}$, and $T_n$ are hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, or substituted or non-substituted arylsulfonyl radical;

Z represents non-substituted amino, or substituted or non-substituted alkylamino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1$, $R_3$, and $R_5$ are hydrido radical, and $R_2$, $R_4$, and $R_6$ independently represent hydrido, or substituted or non-substituted alkyl radical;

$Q_1$ and $Q_m$ are methylene radical, and $Q_m$ is directly linked to the basic amino group;

$Q_2, Q_3, \ldots$, and $Q_{m-1}$ are independently selected from methylene and oxygen radical; and m is an integer between 1 and 9.

Of higher interest is a PNA derivative of Formula I, or a pharmaceutically acceptable salt thereof:

wherein, n is an integer between 12 and 19;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence;

$S_1$, $S_2$, . . . , $S_{n-1}$, $S_n$, $T_1$, $T_2$, . . . , $T_{n-1}$, and $T_n$ are hydrido radical;

X and Y independently represent substituted or non-substituted alkylacyl, substituted or non-substituted arylacyl, or substituted or non-substituted alkyloxycarbonyl radical;

Z represents non-substituted amino, or substituted or non-substituted alkylamino radical;

$B_1$, $B_2$, . . . , $B_{n-1}$, and $B_n$ are independently selected from adenine, thymine, guanine, cytosine, and unnatural nucleobases;

at least five of $B_1$, $B_2$, . . . , $B_{n-1}$, and $B_n$ are independently selected from unnatural nucleobases represented by Formula II, Formula III, or Formula IV;

$R_1$, $R_2$, $R_3$, $R_4$, $R_5$, and $R_6$ are hydrido radical;

$Q_1$ and $Q_m$ are methylene radical, and $Q_m$ is directly linked to the basic amino group;

$Q_2$, $Q_3$, . . . , and $Q_{m-1}$ are independently selected from methylene and oxygen radical; and m is an integer between 1 and 9.

Of highest interest is a PNA derivative of Formula I, or a pharmaceutically acceptable salt thereof:

wherein, n is an integer between 12 and 18;

the compound of Formula I possesses at least a 10-mer complementary overlap with the 14-mer target splice site sequence consisting of 7-mer from intron and 7-mer from exon within the target pre-mRNA;

the compound of Formula I is fully complementary to the target pre-mRNA sequence;

$S_1$, $S_2$, . . . , $S_{n-1}$, $S_n$, $T_1$, $T_2$, . . . , $T_{n-1}$, and $T_n$ are hydrido radical;

X is hydrido radical;

Y represents substituted or non-substituted alkylacyl, substituted or non-substituted arylacyl, or substituted or non-substituted alkyloxycarbonyl radical;

Z represents non-substituted amino, or substituted or non-substituted alkylamino radical;

$B_1$, $B_2$, . . . , $B_{n-1}$, and $B_n$ are independently selected from adenine, thymine, guanine, cytosine, and unnatural nucleobases;

at least five of $B_1$, $B_2$, . . . , $B_{n-1}$, and $B_n$ are independently selected from unnatural nucleobases represented by Formula II, Formula III, or Formula IV;

$R_1$, $R_2$, $R_3$, $R_4$, $R_5$, and $R_6$ are hydrido radical;

$L_1$ represents $-(CH_2)_2-O-(CH_2)_2-$, $-CH_2-O-(CH_2)_2-$, $-CH_2-O-(CH_2)_3-$, $-CH_2-O-(CH_2)_4-$, $-CH_2-O-(CH_2)_5-$, $-CH_2-O-(CH_2)_6-$, or $-CH_2-O-(CH_2)_7-$ with the right end is directly linked to the basic amino group; and $L_2$ and $L_3$ are independently selected from $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_2-O-(CH_2)_2-$, $-(CH_2)_3-O-(CH_2)_2-$, and $-(CH_2)_2-O-(CH_2)_3-$ with the right end is directly linked to the basic amino group.

The compound of Formula I may be abbreviated as described in the prior art [PCT/KR2009/001256; EP2268607; U.S. Pat. No. 8,680,253]. Provided below are examples of such abbreviations used to describe the PNA derivatives of Formula I targeting the 3' splice site spanning the junction of intron 1 and exon 2 in the human HIF-1α pre-mRNA read out from the human HIF1A gene (NCBI Reference Sequence: NG_029606.1):

(N → C) Fethoc-CA(5)G-AA(5)C-TTA(5)-TCC(102)-TA(5)-$NH_2$;

(N → C) Fmoc-CA(5)G-AA(5)C-TTA(5)-TCC(102)-TA(5)-$NH_2$;

(N → C) H-CA(5)G-AA(5)C-TTA(5)-TCC(103)-TA(5)-$NH_2$;

(N → C) Ac-CA(5)G-AA(5)C-TTA(5)-TCC(102)-TA(5)-$NH_2$;

(N → C) Piv-CA(5)G-AA(5)C-TTA(5)-TCC(102)-TA(5)-$NH_2$;

(N → C) Benzoyl-CA(5)G(203)-AA(5)C-TTA(4)-TCC(102)-TA(5)-$NH_2$;

(N → C) n-Propyl-CA(5)G-AA(5)C-TTA(5)-TCC(202)-TA(5)-$NH_2$;

(N → C) Benzyl-CA(5)G-AA(5)C-TTA(5)-TCC(102)-TA(5)-$NH_2$;

(N → C) p-Toluenesulfonyl-CA(5)G-AA(5)C-TTA(202)-TCC(102)-TA(5)-$NH_2$;

(N → C) [N-(2-Phenylethyl)amino]carbonyl-CA(5)G(3)-AA(5)C-TTA(3)-TCC(102)-TA(5)-$NH_2$;

(N → C) Fethoc-Lys-Leu-CA(5)G(202)-AA(5)C-TTA(8)-TCC(102)-TA-Lys-$NH_2$;

(N → C) N-Phenyl-N-Me-CA(5)G-AA(5)C-TTA(5)-TCC(102)-TA(5)-Lys-$NH_2$;

(N → C) Piv-HEX-CA(5)G-AA(5)C-TTA(5)-TCC(102)-TA(5)-Lys-$NH_2$;

(N → C) FAM-HEX-CA(5)G-AA(5)C-TTA(5)-TCC(102)-TA(5)-Lys-$NH_2$;

(N → C) Fethoc-GA(5)A-C(102)TT-A(5)TC-CTA(5)-C(102)T-$NH_2$;

(N → C) Fethoc-Arg-GA(5)A-C(102)TT-A(5)TC-CTA(5)-C(102)T-Gly-$NH_2$;

(N → C) Fethoc-Val-GA(5)A-CTT-A(6)TC-CTA(5)-C(202)T-Gly-Lys-$NH_2$;

(N → C) Fethoc-C(105)TT-A(6)TC-CTA(6)-C(102)TT-AA(6)C-$NH_2$;

(N → C) Fmoc-Val-CTC(102)-A(5)TC-CTA(6)-C(103)TT-AA(202)C-$NH_2$;

and (N → C) Fethoc-TTC(105)-AG(5)A-A(4)CT-TA(5)T-CC(202)T-A(6)CT-TA(6)-$NH_2$:

wherein,

A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively:

Formula VI

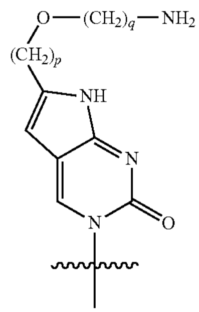

Formula VII

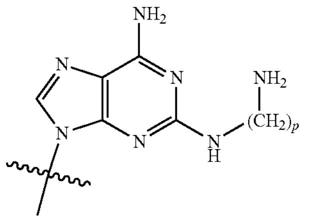

Formula VII

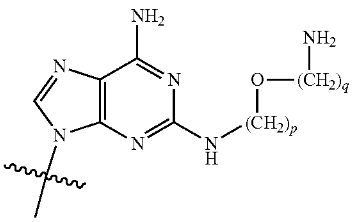

Formula IX

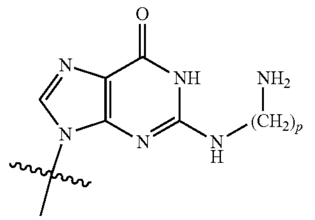

Formula X

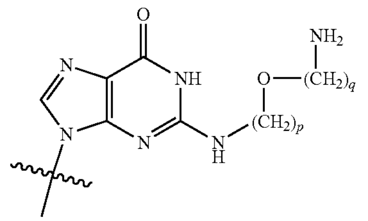

wherein, p and q are integers; and the abbreviations for the N- and C-terminus substituents are specifically defined as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "pivalyl-"; "n-Propyl-" for "1-(n-propyl)-"; "H-" for "hydrido-" group; "p-Toluenesulfonyl" for "(4-methylbenzene)-1-sulfonyl-"; "-Lys-" for amino acid residue "lysine"; "-Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-1-(2-phenylethyl)amino]carbonyl-"; "Benzyl-" for "1-(phenyl)methyl-"; "Phenyl-" for "phenyl-"; "Me-" for "methyl-"; "-HEX-" for "6-amino-1-hexanoyl-"; "FAM-" for "5, or 6-fluorescein-carbonyl- (isomeric mixture)"; and "—$NH_2$" for non-substituted "-amino" group.

Figure 9:
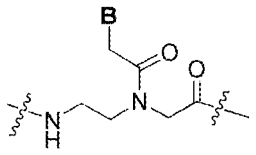
FIG. 9. Chemical structures of PNA monomers with natural or modified nucleobase.
Figure 9:
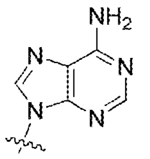
Figure 9:
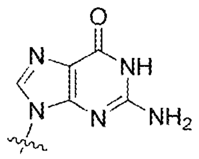
Figure 9:
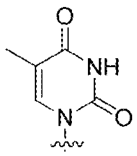
Figure 9:
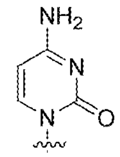
Figure 9:
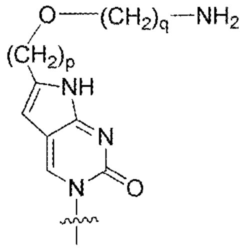
Figure 9:
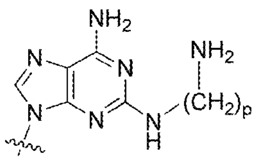
Figure 9:
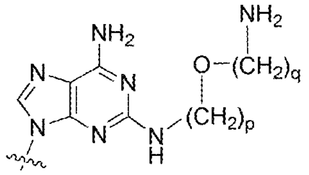
Figure 9:
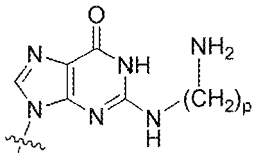
Figure 9:
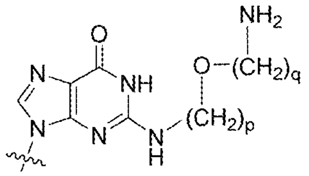

FIG. 9 collectively provides the chemical structures for the PNA monomers abbreviated as A, G, T, C, C(pOq), A(p), A(pOq), G(p), and G(pOq). As discussed in the prior art [PCT/KR2009/001256], C(pOq) is regarded as a modified PNA monomer equivalent to "cytosine" due to its preferred hybridization to "guanine". A(p) and A(pOq) are taken as modified PNA monomers acting as "adenine" for their tight affinity for "thymine". Likewise G(p) and G(pOq) are considered to be modified PNA monomers equivalent to "guanine" owing to their productive base pairing with "cytosine".

Figure 10:
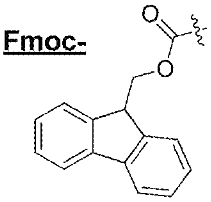
FIG. 10. Chemical structures for abbreviations of N-terminus or C-terminus substituents.
Figure 10:
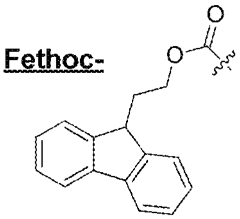
Figure 10:
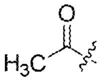
Figure 10:
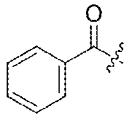
Figure 10:
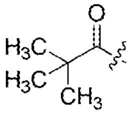
Figure 10:
Figure 10:
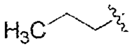
Figure 10:
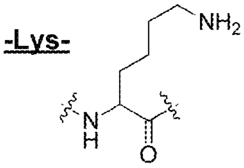
Figure 10:
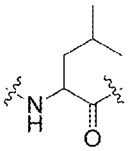
Figure 10:
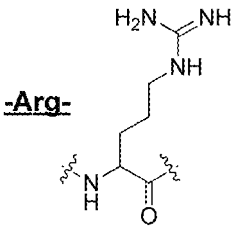
Figure 10:
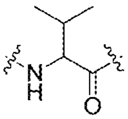
Figure 10:
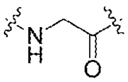
Figure 10:
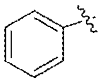
Figure 10:
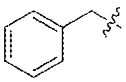
Figure 10:
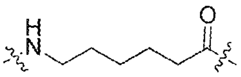
Figure 10:
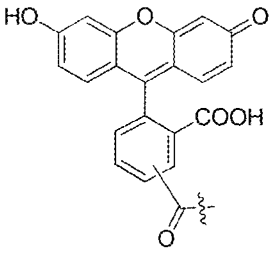
Figure 10:
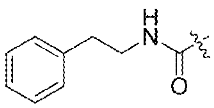
Figure 10:
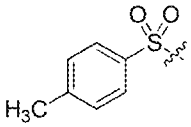

FIG. 10 unequivocally provides the chemical structures for a variety of abbreviations for substituents used to diversify the N-terminus or C-terminus of the PNA derivative of Formula I in this invention. Provision of the N-terminus or C-terminus groups in FIG. 10 as examples is to illustrate the diversity of allowable substituents for the the N-terminus or C-terminus of the PNA derivative of Formula I, and therefore should not be interpreted to limit the scope of the N-terminus or C-terminus groups for the compound of this invention. A skilled person in the art may easily figure out that the oligonucleotide sequence is the overriding contributor to the sequence specific interaction with the target pre-mRNA sequence.

Figure 11:
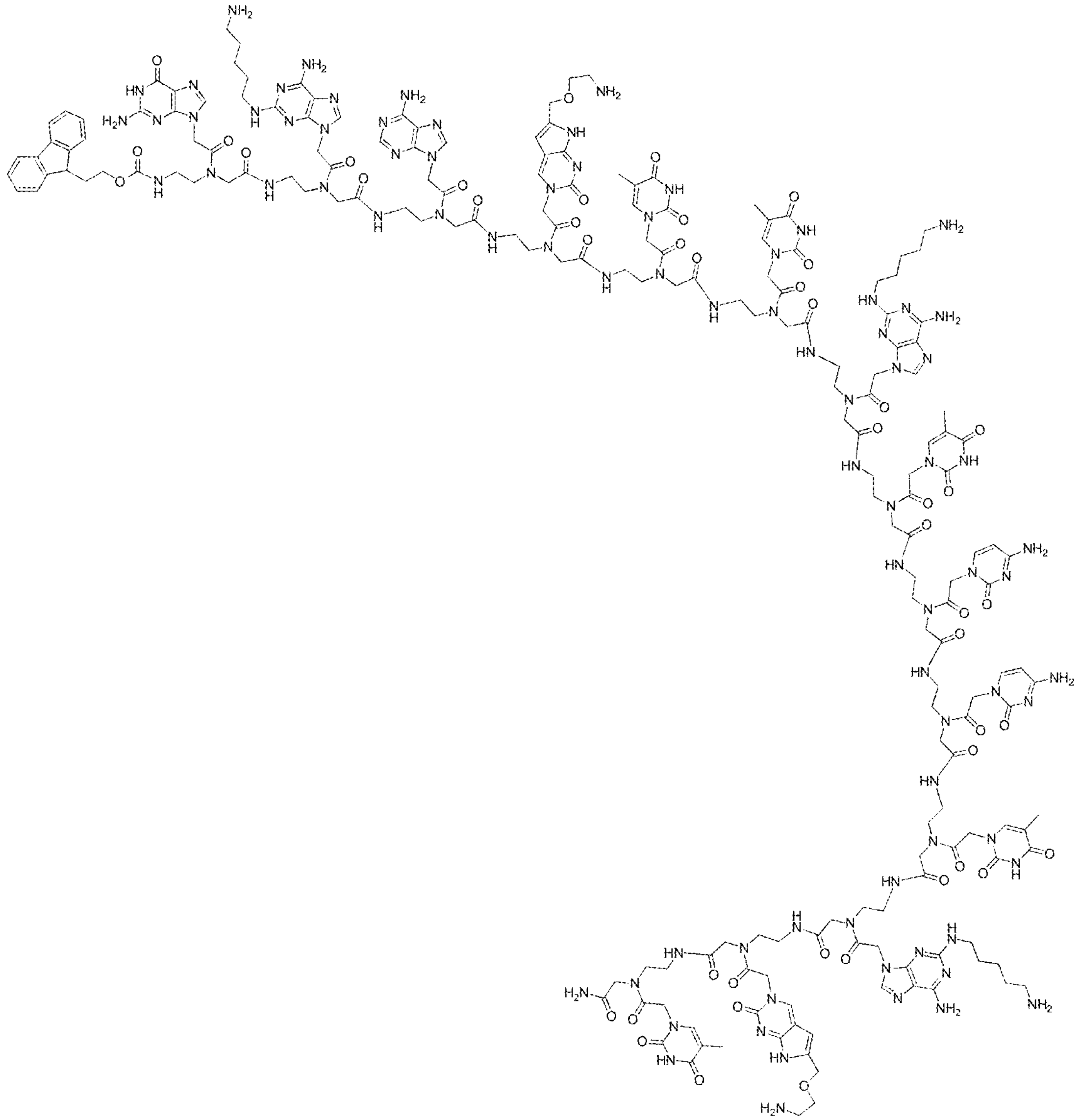
FIG. 11. Chemical structure for the 14-mer PNA derivative of (N→C) Fethoc-GA(5)A-C(1O2)TT-A(5)TC-CTA(5)-C(1O2)T-$NH_2$.

In order to illustrate the abbreviations adopted for such PNA derivatives, the chemical structure for a 14-mer PNA derivative abbreviated as "(N→C) Fethoc-GA(5)A-C(1O2)TT-A(5)TC-CTA(5)-C(1O2)T-$NH_2$" is provided in FIG. 11.

Figure 12:
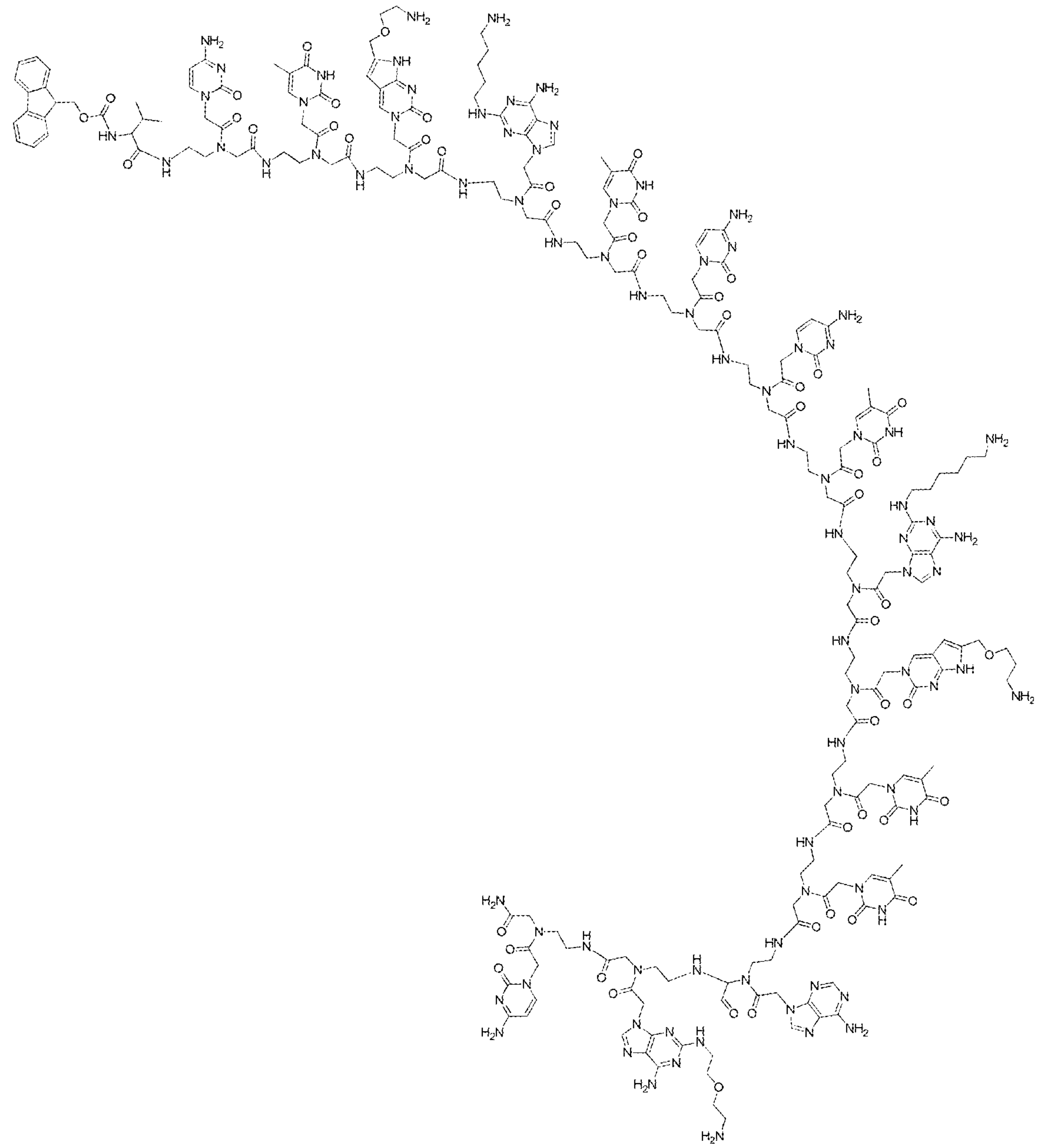
FIG. 12. Chemical structure for the 15-mer PNA derivative of (N→C) Fmoc-Val-CTC(1O2)-A(5)TC-CTA(6)-C(1O3)TT-AA(2O2)C—$NH_2$.

As another illustration, the chemical structure for a 15-mer PNA derivative abbreviated as "(N→C) Fmoc-Val-CTC(1O2)-A(5)TC-CTA(6)-C(1O3)TT-AA(2O2)C—$NH_2$" is provided in FIG. 12.

The compound of Formula I should meet the requirement to possess "at least a 10-mer complementary overlap with a 14-mer target splice site sequence consisting of 7-mer from intron and 7-mer from exon within a target pre-mRNA". If the compound of Formula I targets, for example, the 3' splice site spanning the junction of intron 1 and exon 2 in the human HIF-1α pre-mRNA, the 3' splice site is unequivocally defined by the 30-mer human HIF-1α pre-mRNA sequence of [(5'-3') guuguuguuaaguag|GAUAAGUUCUGAACG (SEQ ID NO: 13)]. Then the 14-mer sequence of the target HIF-1α 3' splice site reads [(5'-3') uaaguag|GAUAAGU (SEQ ID NO: 14)].

A 15-mer HIF-1α ASO with a sequence of "(N→C) Fethoc-CA(5)G-AA(5)C-TTA(5)-TCC(1O2)-TA(5)C—$NH_2$" is equivalent to the DNA sequence of "(5'→3') CAG-AAC-TTA-TCC-TAC (SEQ ID NO: 15)" for complementary binding to the human HIF-1α pre-mRNA. The 15-mer ASO has a 15-mer complementary overlap (i.e., fully complementary) with the 3' splice site spanning the junction of intron 1 and exon 2 in the HIF-1α pre-mRNA as marked “bold” and “underlined” in the 30-mer pre-mRNA sequence of

[(5' → 3') guuguuguuaaguag | GAUAAGUUCUGAACG (SEQ ID NO: 16)].

The PNA ASO possesses an 11-mer complementary overlap (i.e., 4-mer from intron 1 and 7-mer from exon 2) with the 14-mer HIF-1α pre-mRNA sequence of [(5'→3') uaaguag-|GAUAAGU (SEQ ID NO: 17)]. Thus the 15-mer HIF-1α PNA ASO meets the conditions of the complementary overlap required for the compound of Formula I.

Another 15-mer HIF-1α ASO with a sequence of “(N→C) Fethoc-CTC(1O2)-A(6)TC-CTA(6)-C(1O2)TT-AA(6)C—$NH_2$” is equivalent to the DNA sequence of “(5'→3') CTC-ATC-CTA-CTT-AAC (SEQ ID NO: 18)” for complementary binding to the HIF-1α pre-mRNA. The 15-mer PNA ASO possesses a single mismatch with the 3' splice site spanning the junction of intron 1 and exon 2 as marked “bold” and “underlined” in the 30-mer HIF-1α pre-mRNA sequence of

[(5' → 3') guuguuguuaaguag | GAU"A"AGUUCUGAACG (SEQ ID NO: 19)], in which the single mismatch is marked with a quote (“ ”) sign. The 15-mer PNA possesses a 12-mer complementary overlap with the 14-mer 3' splice site sequence adopted to describe the compound of Formula I as marked “bold” and “underlined” in

[(5' → 3') uaaguag | GAU"A"AGU (SEQ ID NO: 20)], in which the single mismatch is marked with a quote (“ ”) sign. Despite the single mismatch, the 15-mer HIF-1α ASO meets the conditions of the complementary overlap required for the compound of Formula I.

In case the compound of Formula I targets, for example, the 5' splice site spanning the junction of exon 4 and intron 4 in the human SCN9A pre-mRNA, the 5' splice site is unequivocally defined by the 30-mer human SCN9A pre-mRNA sequence of [(5'→3') CGUCAUU-GUUUUUGC|guaaguacuuucagc (SEQ ID NO: 21)] read out from the human SCN9A gene (accessed from NCBI Reference Sequence: NC_000002.12). Then the 14-mer sequence of the target SCN9A 5' splice site reads [(5'→3') UUUUUGC|guaagua (SEQ ID NO: 22)].

A 16-mer SCN9A ASO with a sequence of “(N→C) Fethoc-AC(1O2)T-TA(5)C-G(6)CA-A(5)AA(5)-AC(1O2) A-A(5)-$NH_2$” is equivalent to the DNA sequence of “(5'→3') ACT-TAC-GCA-AAA-ACA-A (SEQ ID NO: 23)” for complementary binding to the human SCN9A pre-mRNA. The 16-mer PNA possesses a 16-mer complementary (i.e., fully complementary) overlap with the 5' splice site spanning the junction of exon 4 and intron 4 in the human SCN9A pre-mRNA as marked “bold” and “underlined in the 30-mer SCN9A pre-mRNA sequence of

[(5' → 3') CGUCAUUGUUUUUGC | guaaguacuuucagc (SEQ ID NO: 24)].

The 16-mer SCN9A ASO possesses a 13-mer complementary overlap with the 14-mer 5' splice site sequence as marked “bold” and “underlined” in

[(5' → 3') UUUUUGC | guaagua (SEQ ID NO: 25)].

The 16-mer SCN9A ASO meets the conditions of the complementary overlap required for the compound of Formula I.

DETAILED DESCRIPTION OF INVENTION

General Procedures for Preparation of PNA Oligomers

PNA oligomers were synthesized by solid phase peptide synthesis (SPPS) based on Fmoc-chemistry according to the method described in the prior art [U.S. Pat. No. 6,133,444; WO 96/40685] or with minor modifications. The solid support used in this invention was H-Rink Amide-ChemMatrix purchased from PCAS BioMatrix Inc. (Quebec, Canada). Fmoc-PNA monomers with a modified nucleobase were synthesized as described in the prior art [PCT/KR 2009/001256] or with minor modifications.

Figure 13:
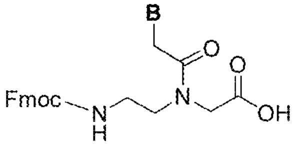
FIG. 13. Chemical structures for Fmoc-PNA monomers used to synthesize the PNA derivatives of this invention.
Figure 13:
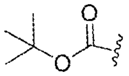
Figure 13:
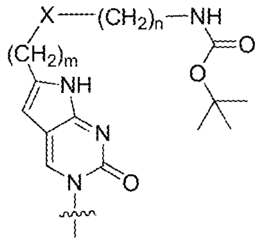
Figure 13:
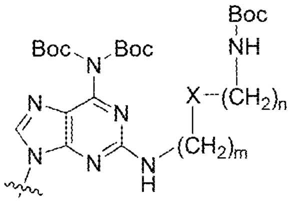
Figure 13:
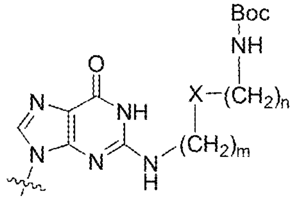

The chemical structures of Fmoc-PNA monomers with a modified nucleobase used in this invention are provided in FIG. 13. The Fmoc-PNA monomers provided in FIG. 13 should be taken as examples, and therefore should not be taken to limit the scope of the present invention. A skilled person in the field may easily figure out that a large number of variations in protecting groups, for example, are possible for such Fmoc-PNA monomers used to synthesize the PNA derivative of Formula I.

PNA oligomers were purified by Cis-reverse phase HPLC (water/acetonitrile or water/methanol with 0.1% TFA) and characterized by mass spectrometry including MALDI-TOF/MS and ESI-TOF/MS.

Figure 14:
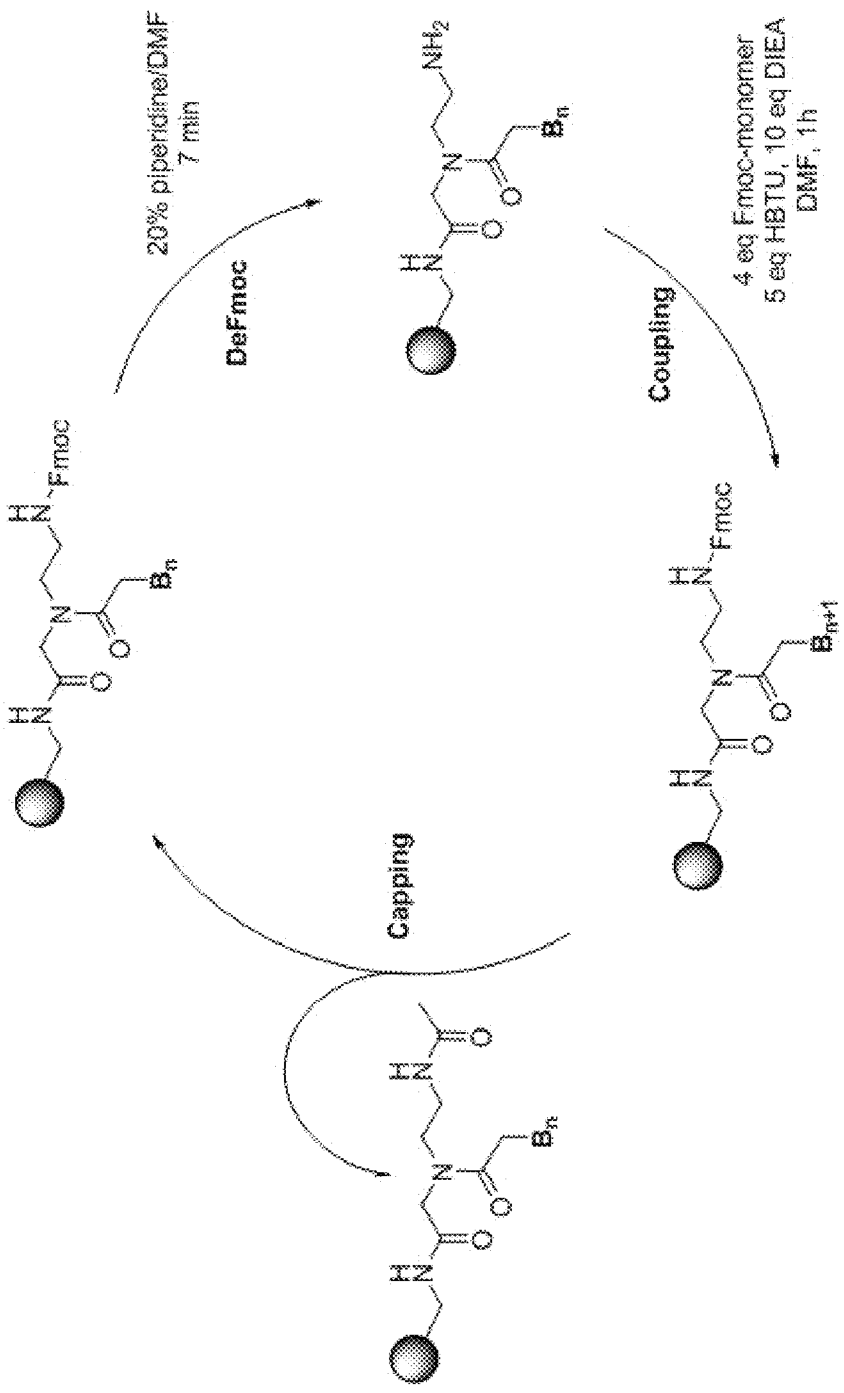
FIG. 14. Typical monomer elongation cycle adopted in the solid phase peptide synthesis FIG. 15A. $C_{18}$-reverse phase HPLC chromatogram for "HIF-ASO 1" before purification.

FIG. 14 provides a typical monomer elongation cycle adopted in the SPPS of this invention, and the synthetic details are provided as below. To a skilled person in the field, however, there should be lots of minor variations obviously possible to run such SPPS reactions on an automatic peptide synthesizer or manual peptide synthesizer. The involved reaction steps of the SPPS are provided below as exemplary reaction procedures.

[Activation of H-Rink-ChemMatrix Resin] 0.01 mmol (ca 20 mg resin) of the ChemMatrix resin in 1.5 mL 20% piperidine/dimethylformamide (DMF) was vortexed in a libra tube for 20 min, and the reaction solution was filtered off. The resin was washed for 30 sec each in series with 1.5 mL methylene chloride (MC), 1.5 mL DMF, 1.5 mL MC, 1.5 mL DMF, and 1.5 mL MC. The resulting free amines on the solid support were subjected to coupling either with an Fmoc-PNA monomer or with an Fmoc-protected amino acid derivative.

[DeFmoc] The resin was vortexed in 1.5 mL 20% piperidine/DMF for 7 min, and the DeFmoc solution was filtered off. The resin was washed for 30 sec each in series with 1.5 mL MC, 1.5 mL DMF, 1.5 mL MC, 1.5 mL DMF, and 1.5 mL MC. The resulting free amines on the solid support were immediately subjected to coupling with an Fmoc-PNA monomer.

[Coupling with Fmoc-PNA Monomer] The free amines on the solid support were coupled with an Fmoc-PNA monomer as follows. 0.04 mmol of an Fmoc-PNA monomer, 0.05 mmol HBTU [2-(1H-benzotriazol-1-yl)-1,1,3,3-tetramethyluronium hexafluoro-phosphate], and 10 mmol DIEA (N,N-diisopropylethylamine) were incubated for 2 min in 1 mL anhydrous DMF, and added to the resin with free amines. The resin solution was vortexed for 1 hour and the reaction medium was filtered off. Then the resin was washed for 30 sec each in series with 1.5 mL MC, 1.5 mL DMF, and 1.5 mL MC.

[Capping] Following the coupling reaction, the unreacted free amines were capped by shaking for 5 min in 1.5 mL capping solution (5% acetic anhydride and 6% 2,6-leutidine in DMF). Then the capping solution was filtered off and and the resin was washed for 30 sec each in series with 1.5 mL MC, 1.5 mL DMF, and 1.5 mL MC.

[Introduction of "Fethoc-" Radical in N-Terminus] "Fethoc-" radical was introduced to the N-terminus by reacting the free amines on the resin with "Fethoc-OSu" under usual basic coupling conditions. The chemical structure of "Fethoc-OSu" [CAS No. 179337-69-0, $C_{20}H_{17}NO_5$, MW 351.36] is provided as follows.

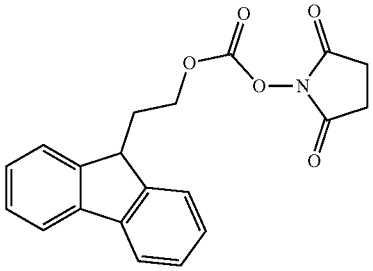

Fethoc-OSu

[Cleavage from Resin] PNA oligomers bound to the resin were cleaved off the resin by shaking the resin for 3 hours in 1.5 mL cleavage solution (2.5% tri-isopropylsilane and 2.5% water in trifluoroacetic acid). The resin was filtered off and the filtrate was concentrated under reduced pressure or by blowing nitrogen gas over the solution. The resulting residue was triturated with diethylether and the resulting precipitate was collected by filtration for purification by reverse phase HPLC.

Figure 15A:
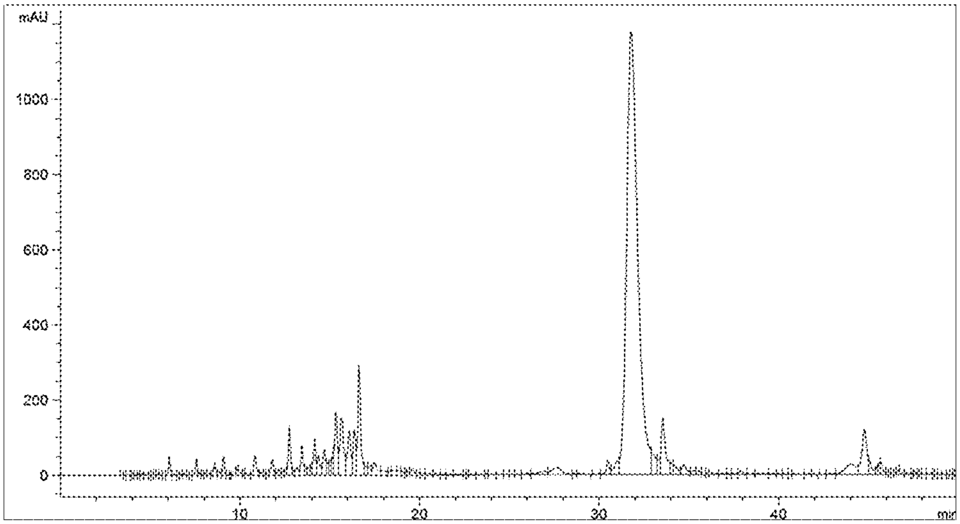
FIG. 15B. $C_{18}$-reverse phase HPLC chromatogram for "HIF-ASO 1" after HPLC purification.
Figure 15B:
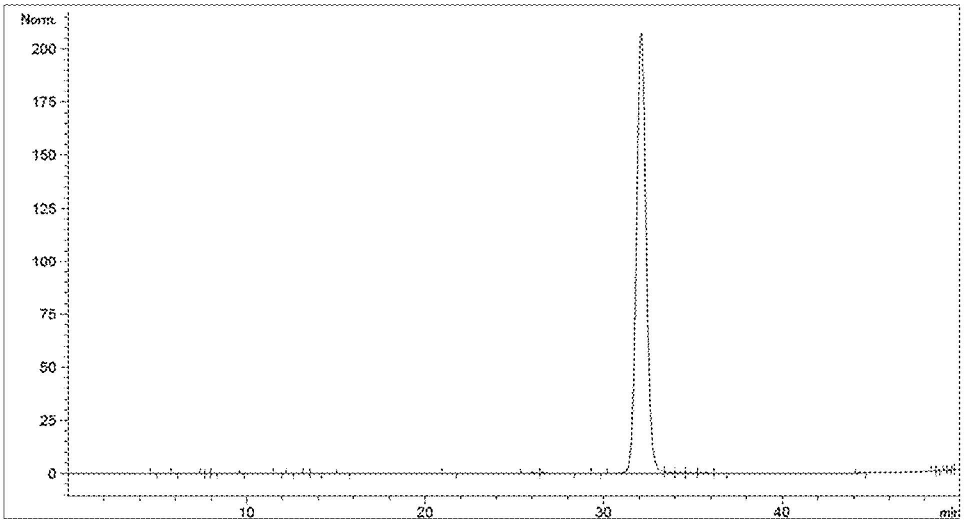

[HPLC Analysis and Purification] Following the cleavage off the resin, the PNA crude product was purified by Cis-reverse phase HPLC eluting water/acetonitrile or water/methanol (gradient method) containing 0.1% TFA. FIG. 15A and FIG. 15B are exemplary HPLC chromatograms for "HIF-ASO 1" before and after the HPLC purification, respectively. The oligomer sequence of "HIF-ASO 1" is provided in Table 1.

Synthetic Examples for PNA Derivatives of Formula I

PNA derivatives were prepared according to the above synthetic procedures with or without minor modifications. PNA derivatives of this invention were designed to target a splice site within a pre-mRNA including but not limited to the human or mouse HIF-1α pre-mRNA, the human or mouse androgen receptor (AR) pre-mRNA, the human or rat SCN9A pre-mRNA, the mouse dystrophin pre-mRNA, the human or mouse tyrosinase pre-mRNA, the human or mouse SNAP25 pre-mRNA, the human IDO1 pre-mRNA, the human or mouse PD-1 pre-mRNA, and so on. Provision of such PNA derivatives targeting a splice site for a number of pre-mRNAs is to exemplify the PNA derivatives of Formula I, and should not be interpreted to limit the scope of the present invention to those target splice sites cited as examples.

Table 1 provides PNA derivatives complementarily targeting the 3' splice site spanning the junction of intron 1 and exon 2 in the human HIF-1α pre-mRNA along with structural characterization data by mass spectrometry. Provision of the HIF-1α ASOs in Table 1 is to exemplify the PNA derivatives of Formula I, and should not be interpreted to limit the scope of the present invention to the PNA derivatives specified in Table 1.

TABLE 1

PNA derivatives complementarily targeting the 3' splice site spanning the junction of intron 1 and exon 2 in the human HIF-1α pre-mRNA along with structural characterization data by mass spectrometry.

| PNA | PNA Sequence (N → C) | Exact Mass, m/z Theor.[a] | Exact Mass, m/z Obs.[b] |
|---|---|---|---|
| HIF-ASO 1 | Fethoc-CA(5)G-AA(5)C-TTA(5)-TCC(102)-TA(5)-$NH_2$ | 4486.05 | 4486.04 |
| HIF-ASO 2 | Fethoc-GA(5)A-C(102)TT-A(5)TC-CTA(5)-C(102)T-$NH_2$ | 4473.99 | 4474.02 |
| HIF-ASO 3 | Fethoc-G(5)AA(5)-CTT-A(5)TC-CTA(5)-C(102)T-$NH_2$ | 4462.03 | 4462.07 |
| HIF-ASO 4 | Fethoc-GA(5)A-C(102)TT-A(5)TC-CTA(5)-CT-$NH_2$ | 4376.94 | 4376.99 |
| HIF-ASO 5 | Fethoc-G(5)AA(6)-CTT-A(6)TC-CTA(6)-C(102)T-$NH_2$ | 4504.07 | 4504.09 |
| HIF-ASO 6 | Fethoc-A(6)GA-A(6)CT-TA(6)T-CC(102)T-A(6)CT-TA(6)-$NH_2$ | 5393.47 | 5393.44 |
| HIF-ASO 7 | Fethoc-C(105)TT-A(6)TC-CTA(6)-C(102)TT-AA(6)C-$NH_2$ | 4784.18 | 4784.14 |
| HIF-ASO 8 | Fethoc-CTC(102)-A(6)TC-CTA(6)-C(102)TT-AA(6)C-$NH_2$ | 4727.13 | 4727.79 |
| HIF-ASO 9 | Piv-A(6)TC-CTA(6)-C(102)TT-A(5)AC-$NH_2$ | 3695.73 | 3695.74 |

TABLE 1-continued

PNA derivatives complementarily targeting the 3' splice site spanning the junction of intron 1 and exon 2 in the human HIF-1α pre-mRNA along with structural characterization data by mass spectrometry.

| PNA | PNA Sequence (N → C) | Exact Mass, m/z | |
|---|---|---|---|
| | | Theor.[a] | Obs.[b] |
| HIF-ASO 10 | Piv-Lys-AA(6)C-TTA(6)-TCC(102)-TA(6)C-TTA(5)-Val-$NH_2$ | 4844.33 | 4844.33 |
| HIF-ASO 11 | Fethoc-A(6)GA-A(6)CT-CA(6)T-CC(102)T-A(6)CT-TA(6)-$NH_2$ | 5448.54 | 5448.50 |
| HIF-ASO 12 | H-CA(5)G-AA(5)C-TTA(5)-TCC(103)-TA(5)-$NH_2$ | 4263.98 | 4263.99 |
| HIF-ASO 13 | Benzoyl-CA(5)G(203)-AA(5)C-TTA(4)-TCC(102)-TA(5)-$NH_2$ | 4441.06 | 4441.06 |
| HIF-ASO 14 | n-Propyl-CA(5)G-AA(5)C-TTA(5)-TCC(202)-TA(5)-$NH_2$ | 4306.03 | 4306.05 |
| HIF-ASO 15 | p-Toluenesulfonyl-CA(5)G-AA(5)C-TTA(202)-TCC(102)-TA(5)-NH2 | 4405.95 | 4405.90 |
| HIF-ASO 16 | [N-(2-Phenylethyl)amino]carbonyl-CA(5)G(3)-AA(5)C-TTA(3)-TCC(102)-TA(5)-NH2 | 4426.06 | 4426.08 |
| HIF-ASO 17 | Fethoc-Lys-Leu-CA(5)G(202)-AA(5)C-TTA(8)-TCC(102)-TA(5)-Lys-$NH_2$ | 4984.44 | 4984.46 |
| HIF-ASO 18 | N-Phenyl-N-Me-CA(5)G-AA(5)C-TTA(5)-TCC(102)-TA(5)-Lys-$NH_2$ | 4468.11 | 4468.14 |

[a])theoretical exact mass; [b])observed exact mass

Figure 16:
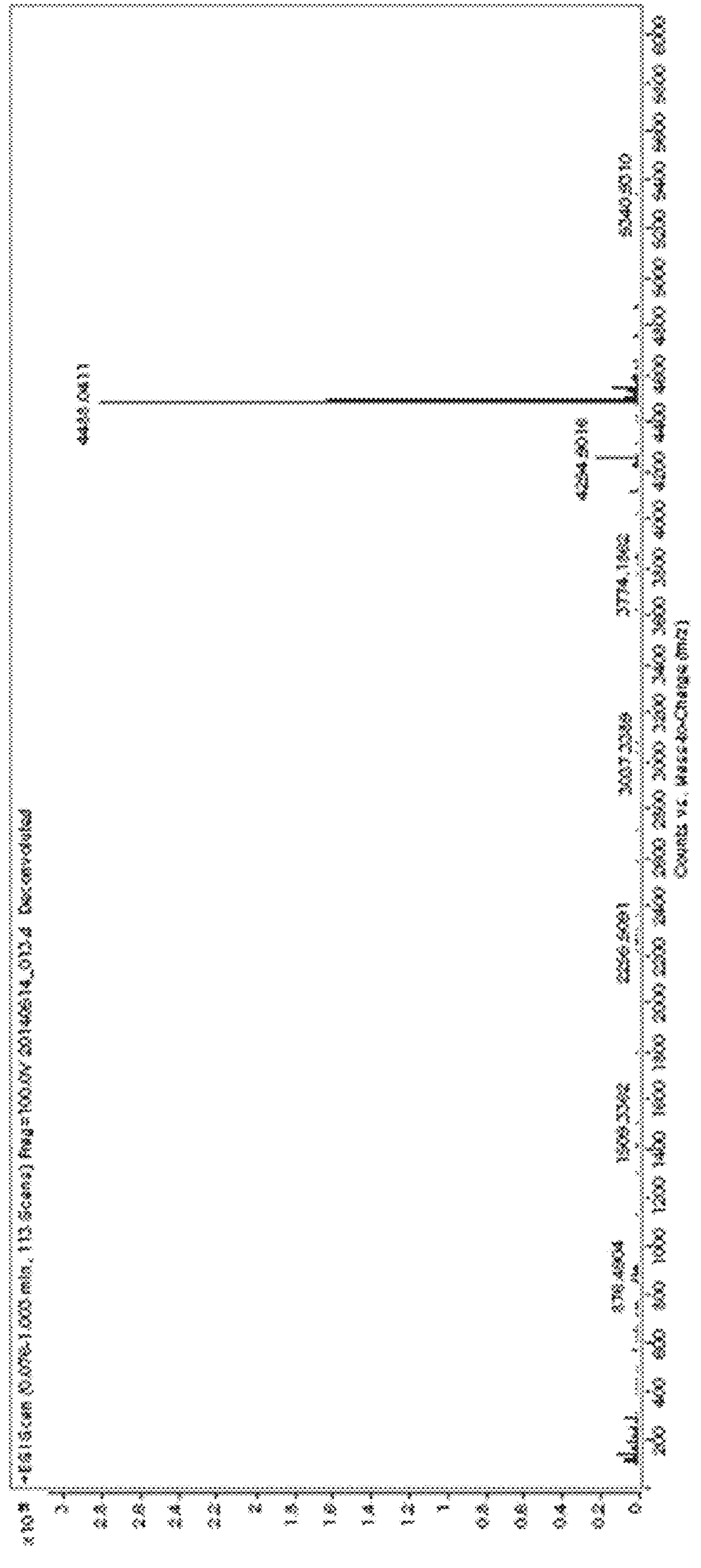
FIG. 16. ESI-TOF mass spectrum of "HIF-ASO 1" purified by $C_{18}$—RP prep HPLC.

FIG. 15A is a HPLC chromatogram obtained with a crude product of "HIF-ASO 1". The crude product was purified by $C_{18}$—RP preparatory HPLC. FIG. 15B is a HPLC chromatogram for a purified product of "HIF-ASO 1". The purity of "HIF-ASO 1" improved markedly following the preparatory HPLC purification. FIG. 16 provides an ESI-TOF/MS spectrum obtained with the purified product of "HIF-ASO 1". Provision of the analysis data for "HIF-ASO 1" is to illustrate how the PNA derivatives of Formula I were purified and identified in the present invention, and should not be interpreted to limit the scope of this invention.

Table 2 provides PNA derivatives complementarily targeting the 3' splice site spanning the junction of intron 3 and exon 4 in the human HIF-1α pre-mRNA along with structural characterization data by mass spectrometry. Provision of the HIF-1α ASOs in Table 2 is to exemplify the PNA derivatives of Formula I, and should not be interpreted to limit the scope of the present invention to the HIF-1α ASOs specified in Table 2.

TABLE 2

PNA derivatives complementarily targeting the 3' splice site spanning the junction of intron 3 and exon 4 in the human HIF-1α pre-mRNA along with structural characterization data by mass spectrometry.

| PNA | | Exact Mass, m/z | |
|---|---|---|---|
| Example | PNA Sequence (N → C) | theor.[a] | obs.[b] |
| HIF-ASO 19 | Fethoc-TA(5)G-TTC(102)-A(5)AA(5)-CTG(6)-TA(5)A-$NH_2$ | 4915.27 | 4915.26 |

TABLE 2-continued

PNA derivatives complementarily targeting the 3' splice site spanning the junction of intron 3 and exon 4 in the human HIF-1α pre-mRNA along with structural characterization data by mass spectrometry.

| PNA | | Exact Mass, m/z | |
|---|---|---|---|
| Example | PNA Sequence (N → C) | theor.[a] | obs.[b] |
| HIF-ASO 20 | Fethoc-TA(5)G-TTC(102)-A(5)AA(5)-CTG(6)-CA(5)A-$NH_2$ | 4900.27 | 4900.29 |

[a])theoretical exact mass; [b])observed exact mass

Table 3 provides PNA derivatives complementarily targeting the 5' splice site spanning the junction of exon 5 and intron 5 in the human androgen receptor (AR) pre-mRNA read out from the human AR gene (accessed from NCBI Reference Sequence: NC_000023.11) along with structural characterization data by mass spectrometry. Provision of the AR ASOs in Table 3 is to exemplify the PNA derivatives of Formula I, and should not be interpreted to limit the scope of the present invention to the AR ASOs specified in Table 3.

TABLE 3

PNA derivatives complementarily targeting the 5' splice site spanning
the junction of exon 5 and intron 5 in the human AR pre-mRNA along
with structural characterization data by mass spectrometry.

| PNA Example | PNA Sequence (N → C) | Exact Mass, m/z | |
|---|---|---|---|
| | | theor.[a] | obs.[b] |
| AR-ASO 1 | Fethoc-C(1O2)TT-A(5)CC-A(5)GG-C(1O2)AA(5)-G-NH$_2$ | 4257.90 | 4257.92 |
| AR-ASO 2 | Fethoc-TC(1O2)C-TTA(6)-CCA(6)-GGC(1O2)-AA(6)G-G(6)-NH$_2$ | 5207.37 | 5207.42 |
| AR-ASO 3 | Fethoc-TC(1O2)C-TTA(5)-CCA(5)-GGC(1O2)-AA(5)G-G(6)-NH$_2$ | 5165.32 | 5165.31 |
| AR-ASO 4 | Fethoc-TA(5)C-CAG(6)-GC(1O2)A-A(5)GG(6)-C-NH$_2$ | 4283.97 | 4283.96 |
| AR-ASO 5 | Fethoc-C(1O2)TT-A(5)CC-A(5)GG(6)-CA(5)A-NH$_2$ | 3968.85 | 3968.86 |
| AR-ASO 6 | Fethoc-C(1O2)TT-A(5)CC-A(6)GG(6)-CA(5)A-NH$_2$ | 3982.86 | 3982.88 |
| AR-ASO 7 | Ac-C(1O2)TT-A(5)CC-A(5)GG(6)-CA(5)A-NH$_2$ | 3774.77 | 3774.83 |
| AR-ASO 8 | Fethoc-C(1O2)TT-A(6)CC-A(6)GG(6)-CA(6)A-NH$_2$ | 4010.89 | 4010.93 |
| AR-ASO 9 | H-CTT-A(5)C(1O3)C-A(5)G(3)G-C(1O2)AA(5)-G-NH$_2$ | 4092.89 | 4092.90 |
| AR-ASO 10 | Benzoyl-CTT-A(5)C(1O5)C-A(5)G(2O2)G-C(1O2)AA(5)-G-NH$_2$ | 4254.96 | 4254.99 |
| AR-ASO 11 | n-Propyl-CTT-A(5)C(2O2)C-A(3)G(2O3)G-C(1O2)AA(5)-G-NH$_2$ | 4150.93 | 4150.93 |
| AR-ASO 12 | p-Toluenesulfonyl-CTT-A(5)C(1O2)C-A(8)G(5)G-C(1O2)AA(5)-G-NH$_2$ | 4302.96 | 4302.90 |
| AR-ASO 13 | Fethoc-Lys-Leu-CTT-A(5)C(1O2)C-A(2O2)GG-C(1O2)AA(5)-G-Lys-NH$_2$ | 4629.16 | 4629.16 |
| AR-ASO 14 | Fethoc-CTT-A(5)C(1O2)C-A(5)GT-C(1O2)TA(5)-G-NH$_2$ | 4223.88 | 4223.93 |
| AR-ASO 15 | N-Phenyl-N-Me-CTT-A(5)C(1O2)C-A(5)GG-C(1O2)AA(5)-G-Lys-NH$_2$ | 4239.96 | 4240.00 |

[a] theoretical exact mass;
[b] observed exact mass

Table 4 provides PNA derivatives complementarily targeting the 5' splice site spanning the junction of exon 4 and intron 4 in the human SCN9A (sodium channel subtype 9A) pre-mRNA read out from the human SCN9A gene (accessed from NCBI Reference Sequence: NC_000002.12) along with structural characterization data by mass spectrometry. Provision of the SCN9A ASOs in Table 4 is to exemplify the PNA derivatives of Formula I, and should not be interpreted to limit the scope of the present invention to the ASOs specified in Table 4.

TABLE 4

PNA derivatives complementarily targeting the 5' splice site spanning
the junction of exon 4 and intron 4 in the human SCN9A pre-mRNA
along with structual characterization data by mass spectrometry.

| PNA Example | PNA Sequence (N → C) | Exact Mass, m/z | |
|---|---|---|---|
| | | theor.[a] | obs.[b] |
| SCN-ASO 1 | Fmoc-TA(5)A-A(5)TA(5)-CGC(1O2)-AA(5)A-A(5)A-NH$_2$ | 4640.19 | 4640.88 |
| SCN-ASO 2 | FAM-HEX-TA(5)A-A(5)TA(5)-CGC(1O2)-AA(5)A-A(5)A-NH$_2$ | 4887.24 | 4887.40 |

TABLE 4-continued

PNA derivatives complementarily targeting the 5' splice site spanning the junction of exon 4 and intron 4 in the human SCN9A pre-mRNA along with structual characterization data by mass spectrometry.

| PNA Example | PNA Sequence (N → C) | Exact Mass, m/z theor.[a] | Exact Mass, m/z obs.[b] |
|---|---|---|---|
| SCN-ASO 3 | Fethoc-TA(5)A-A(5)TA(5)-CGC(102)-AA(5)A-A(5)A-$NH_2$ | 4652.20 | 4652.24 |
| SCN-ASO 4 | Fethoc-TG(6)T-TA(5)A-A(5)TA(5)-CGC(102)-AA(5)A-A(5)A-$NH_2$ | 5574.61 | 5574.57 |
| SCN-ASO 5 | Fethoc-TA(5)C-GC(102)A-A(5)AA(5)-ACA(5)-A-$NH_2$ | 4261.98 | 4262.00 |
| SCN-ASO 6 | Fethoc-TA(6)C-GC(102)A-A(6)AA(6)-ACA(6)-A-$NH_2$ | 4318.05 | 4318.17 |
| SCN-ASO 7 | Fethoc-AC(102)T-TA(5)C-G(6)CA-A(5)AA(5)-AC(102)A-A(5)-$NH_2$ | 5250.53 | 5250.46 |
| SCN-ASO 8 | Fmoc-TA(5)A-A(5)TA(5)-CGC(102)-AA(5)A-A(5)AC-A(5)A-$NH_2$ | 5539.61 | 5539.57 |
| SCN-ASO 9 | Piv-TA(5)A-A(5)TA(5)-CGC(102)-AA(5)A-A(5)A-$NH_2$ | 4500.17 | 4499.80 |
| SCN-ASO 10 | FAM-HEX-A(5)TA(5)-CGC(102)-AA(5)A-A(5)A-$NH_2$ | 3970.82 | 3974.17 |
| SCN-ASO 11 | Fmoc-TA(6)A-A(5)TA(6)-CGC(102)-AA(6)A-AA(6)C-A(6)-$NH_2$ | 5334.57 | 5335.59 |
| SCN-ASO 12 | Fethoc-CTT-A(5)CG(6)-C(102)AA(5)-AA(5)A-C(102)AA(5)-$NH_2$ | 4975.34 | 4975.34 |
| SCN-ASO 13 | H-CTT-A(5)CG(3)-C(102)AA(5)-AA(5)A-C(103)AA(5)-$NH_2$ | 4711.22 | 4711.25 |
| SCN-ASO 14 | Benzoyl-CTT-A(5)CG(202)-C(102)AA(5)-AA(5)A-C(105)AA(5)-$NH_2$ | 4873.30 | 4873.32 |
| SCN-ASO 15 | n-Propyl-CTT-A(5)CG(203)-C(102)AA(3)-AA(5)A-C(202)AA(5)-$NH_2$ | 4769.27 | 4769.30 |
| SCN-ASO 16 | p-Toluenesulfonyl-CTT-A(5)CG(6)-C(102)AA(8)-AA(5)A-C(102)AA(5)-$NH_2$ | 4935.32 | 4935.29 |
| SCN-ASO 17 | [N-(2-Phenylethyl)amino]carbonyl-CTT-A(5)CG(6)-C(102)AA(202)-AA(5)A-C(102)A A(5)-$NH_2$ | 4888.31 | 4888.32 |
| SCN-ASO 18 | Fethoc-CTT-A(5)CG(6)-C(102)TA(5)-AA(5)T-C(102)AA(5)-$NH_2$ | 4957.32 | 4957.32 |
| SCN-ASO 19 | Fethoc-Lys-Leu-CTT-A(5)CG(6)-C(102)AA(4)-AA(5)A-C(102)AA(5)-Lys-$NH_2$ | 5330.60 | 5330.60 |
| SCN-ASO 20 | N-Phenyl-N-Me-CTT-A(5)CG(6)-C(102)AA(5)-AA(5)A-C(102)AA(5)-Lys-$NH_2$ | 4957.40 | 4957.42 |

[a]) theoretical exact mass;
[b]) observed exact mass

Table 5 provides PNA derivatives complementarily targeting the 3' splice site spanning the junction of intron 3 and exon 4 in the human SCN9A pre-mRNA along with structural characterization data by mass spectrometry. Provision of the SCN9A ASOs in Table 5 is to exemplify the PNA derivatives of Formula I, and should not be interpreted to limit the scope of the present invention to the SCN9A ASOs provided in Table 5.

TABLE 5

PNA derivatives complementarily targeting the 3' splice site spanning
the junction of of intron 3 and exon 4 in the human SCN9A pre-mRNA
along with structural characterization data by mass spectrometry.

| PNA | | Exact Mass, m/z | |
|---|---|---|---|
| Example | PNA Sequence (N → C) | theor.[a] | obs.[b] |
| SCN-ASO 21 | Fethoc-TA(5)A-A(5)AG(6)-TG(6)T-A(5)CC(1O2)-TA(5)A-A(5)-NH$_2$ | 5398.60 | 5398.58 |
| SCN-ASO 22 | Fethoc-AA(5)G-TG(6)T-A(5)CC(1O2)-TAA(5)-A-NH$_2$ | 4282.97 | 4283.00 |
| SCN-ASO 23 | Fethoc-AA(5)G-TG(6)T-AC(1O2)C-TAA(5)-A-NH$_2$ | 4182.87 | 4182.89 |
| SCN-ASO 24 | Fethoc-A(5)AG-TG(6)T-A(5)CC(1O2)-TAA-A(5)-NH$_2$ | 4282.97 | 4283.00 |
| SCN-ASO 25 | Fethoc-AAG(6)-TG(6)T-A(5)CC(1O2)-TA(5)A-A-NH$_2$ | 4281.98 | 4282.05 |
| SCN-ASO 26 | Fethoc-AA(5)G-TG(5)T-A(5)CC(1O2)-TA(5)A-A(5)-NH$_2$ | 4369.06 | 4369.08 |
| SCN-ASO 27 | Fethoc-AA(5)G-TG(5)T-A(5)CC(1O2)-TA(5)A-A(5)C-NH$_2$ | 4620.16 | 4620.14 |
| SCN-ASO 28 | Fethoc-A(5)GT-G(5)TA(5)-CC(1O2)T-A(5)AA(5)-C-NH$_2$ | 4345.56 | 4345.08 |
| SCN-ASO 29 | Fethoc-AA(6)G-TG(5)T-A(6)CC(1O2)-TA(6)A-A(6)C-NH$_2$ | 4676.22 | 4676.25 |
| SCN-ASO 30 | Fethoc-AA(5)G-TG(5)T-A(5)CC(1O2)-TA(5)A-A(5)G-NH$_2$ | 4660.16 | 4660.15 |
| SCN-ASO 31 | Fethoc-AA(5)G-TG(5)T-A(5)CC(1O2)-TA(5)A-A(5)CA-NH$_2$ | 4895.27 | 4895.20 |
| SCN-ASO 32 | Fethoc-AA(5)G-TG(5)T-A(5)CC(1O2)-TA(5)A-A(5)GG-NH$_2$ | 4951.27 | 4951.26 |
| SCN-ASO 33 | Fethoc-AA(5)G-TG(5)T-ACC(1O2)-TA(5)A-A(5)CA(5)-C-NH$_2$ | 5146.37 | 5146.35 |

[a]theoretical exact mass;
[b]observed exact mass

Table 6 provides PNA derivatives complementarily targeting a specific splice site in the human or rat SCN9A pre-mRNA along with structural characterization data by mass spectrometry. Provision of the SCN9A ASOs in Table 6 is to exemplify the PNA derivatives of Formula I, and should not be interpreted to limit the scope of the present invention to the SCN9A ASOs specified in Table 6.

TABLE 6

PNA derivatives complementarily targeting a specific splice site (SS) in
the human or rat SCN9A pre-mRNA along with structural chacterization
data by mass spectrometry.

| PNA | | Target | | Exact Mass, m/z | |
|---|---|---|---|---|---|
| Example | Species | Site[a] | PNA Sequence (N → C) | theor.[b] | obs.[c] |
| SCN-ASO 34 | Human | 5' SS of Exon 2 | Fethoc-GA(5)T-A(5)TG-A(5)GT-G(6)TA(5)-C(1O2)TA(5)-A-NH$_2$ | 5346.49 | 5346.46 |
| SCN-ASO 35 | Rat | 5' SS of Exon 2 | Fethoc-GA(5)T-A(5)TG-A(5)GT-G(6)CA(5)-C(1O2)TA(5)-A-NH$_2$ | 5331.49 | 5331.52 |
| SCN-ASO 36 | Human & Rat | 5' SS of Exon 7 | Fethoc-A(5)TA(5)-CC(1O2)C-TG(6)A-A(5)TC-TG(6)T-NH$_2$ | 4866.26 | 4866.29 |

TABLE 6-continued

PNA derivatives complementarily targeting a specific splice site (SS) in the human or rat SCN9A pre-mRNA along with structural chacterization data by mass spectrometry.

| PNA Example | Species | Target Site[a] | PNA Sequence (N → C) | Exact Mass, m/z theor.[b] | Exact Mass, m/z obs.[c] |
|---|---|---|---|---|---|
| SCN-ASO 37 | Human & Rat | 3' SS or Exon 15 | Fethoc-AA(5)G-A(5)C(12)T-CG(6)G-A(5)GC(102)-TA(5)-$NH_2$ | 4772.23 | 4772.21 |

[a])SS denotes splice site;
[b])theoretical exact mass; and
[c])observed exact mass.

“SCN-ASO 34” is a 16-mer ASO fully complementary to the 5' splice site spanning the junction of exon 2 and intron 2 in the human SCN9A pre-mRNA. “SCN-ASO 34” possesses an 11-mer complementary overlap with exon 2 and a 5-mer complementary overlap with intron 2 as marked “bold” and “underlined” in the 25-mer human SCN9A pre-mRNA sequence of

[(5' → 3')GAUUUUAGUACACUC|auauccuuuu (SEQ ID NO: 26)].

“SCN-ASO 35” is a 16-mer ASO complementarily targeting the 5' splice site spanning the junction of exon 2 and intron 2 in the “rat” SCN9A pre-mRNA. “SCN-ASO 35” possesses an 11-mer complementary overlap with exon 2 and a 5-mer complementary overlap with intron 2 as marked “bold” and “underlined” in the 25-mer rat SCN9A pre-mRNA sequence of

[(5' → 3')GAUCUUAGUGCACUC|auauccuuuc (SEQ ID NO: 27)].

read out from the rat genomic DNA [accessed from NCBI Reference Sequence: NC_005102.3]. “SCN-ASO 35” possesses a single mismatch with the human SCN9A pre-mRNA as marked with a quote (“ ”) sign in the 25-mer pre-mRNA sequence of [(5'→3') GAUUUUAGU“A”CACUC|auauccuuuu (SEQ ID NO: 28)]

“SCN-ASO 36” is a 15-mer ASO complementarily targeting the 5' splice site spanning the junction of exon 7 and intron 7 in the human SCN9A pre-mRNA. “SCN-ASO 36” possesses an 11-mer complementary overlap with exon 7 and a 4-mer complementary overlap with intron 7 as marked “bold” and “underlined” in the 25-mer human SCN9A pre-mRNA sequence of

[(5' → 3')CAGCACAGAUUCAGG|guauguaaua (SEQ ID NO: 29)].

The target sequence of “SCN-ASO 43” is conserved in the rat SCN9A pre-mRNA.

“SCN-ASO 37” is a 14-mer ASO complementarily targeting the 3' splice site spanning the junction of intron 14 and exon 15 in the human SCN9A pre-mRNA. “SCN-ASO 37” possesses a 3-mer complementary overlap with intron 14 and an 11-mer complementary overlap with exon 15 as marked “bold” and “underlined” in the 25-mer human SCN9A pre-mRNA sequence of

[(5' → 3')uugcuuuuag|CUCCGAGUCUUCAAG (SEQ ID NO: 30)].

The ASO's target sequence is conserved in the rat SCN9A pre-mRNA, and marked “bold” and “underlined” in the rat 25-mer pre-mRNA sequence of

[(5' → 3')uuauuucuag|CUCCGAGUCUUCAAG (SEQ ID NO: 31)].

Table 7 provides PNA derivatives complementarily targeting either the 3' or the 5' splice site of exon 23 in the mouse dystrophin pre-mRNA read out from the mouse genomic DNA [accessed from NCBI Reference Sequence: NC_000086.7] along with structural characterization data by mass spectrometry. Provision of the dystrophin ASOs in Table 7 is to exemplify the PNA derivatives of Formula I, and should not be interpreted to limit the scope of the present invention the dystrophin ASOs specified in Table 7.

TABLE 7

PNA derivatives complementarily targeting either the 3' or the 5' splice site of exon 23 in the mouse dystrophin pre-mRNA along with stuctural characterization data by mass spectrometry.

| PNA Example | Target Site[a] | PNA Sequence (N → C) | Exact Mass, m/z theor.[b] | Exact Mass, m/z obs.[c] |
|---|---|---|---|---|
| DMD-ASO 1 | 3' SS | Fethoc-A(5)GA-G(6)CC(102)-TCA-A(5)AA(5)-T-$NH_2$ | 4267.97 | 4267.97 |
| DMD-ASO 2 | 3' SS | Fethoc-TTG(6)CA(5)G-AG(6)C-C(102)TC-AA(5)A-A(5)T-$NH_2$ | 5441.49 | 5441.54 |
| DMD-ASO 3 | 3' SS | Fethoc-TTG(6)-CA(6)G-AG(6)C-C(12)TC-AA(6)A-A(6)T-$NH_2$ | 5483.54 | 5483.55 |

TABLE 7-continued

PNA derivatives complementarily targeting either the 3' or the 5'
splice site of exon 23 in the mouse dystrophin pre-mRNA along with
stuctural characterization data by mass spectrometry.

| PNA Example | Target Site[a] | PNA Sequence (N → C) | Exact Mass, m/z theor.[b] | obs.[c] |
|---|---|---|---|---|
| DMD-ASO 4 | 3' SS | Fethoc-A(6)CT-TTG(6)-CA(6)G-A(6)GC(1O2)-CTC(1O2)-AA(6)-NH₂ | 5571.59 | 5571.59 |
| DMD-ASO 5 | 3' SS | Fethoc-TG(6)C-A(5)GA-G(6)CC(1O2)-TCA(5)-A-NH₂ | 4258.96 | 4258.98 |
| DMD-ASO 6 | 5' SS | Fethoc-C(12)TC-GG(6)C-TTA(6)-CC(1O2)T-GA(6)A-A(6)TT-NH₂ | 5672.52 | 5672.51 |
| DMD-ASO 7 | 5' SS | Fethoc-C(1O2)TT-A(5)CC(1O2)-TG(6)A-AA(5)T-TT-NH₂ | 4488.00 | 4488.00 |

[a] SS denotes splice site;
[b] theoretical exact mass; and
[c] observed exact mass.

Table 8 provides PNA derivatives complementarily targeting a splice site in the human or mouse indoleamine 2,3-dioxygenase (IDO1) pre-mRNA along with structural characterization data by mass spectrometry. The human and mouse IDO 1 pre-mRNA sequences were read out from the human genomic DNA [accessed from NCBI Reference Sequence: NC_000008.11] and the mouse genomic DNA [accessed from NCBI Reference Sequence: NC_000074], respectively. Provision of the IDO1 ASOs in Table 8 is to exemplify the PNA derivatives of Formula I, and should not be interpreted to limit the scope of the present invention to the IDO1 ASOs specified in Table 8.

Table 9 provides PNA derivatives complementarily targeting the 3' splice site of "exon 7" in the human SNAP25 pre-mRNA read out from the human SNAP25 gene [NCBI Reference Sequence: NG_029626.1] along with structural characterization data by mass spectrometry. Provision of the SNAP25 ASOs in Table 9 is to exemplify the PNA derivatives of Formula I, and should not be interpreted to limit the scope of the present invention to the SNAP25 ASOs specified in Table 9.

TABLE 8

PNA derivatives complementarily targeting a specific splice site (SS) in
the human or mouse IDO1 pre-mRNA along with structural characterization
data by mass spectrometry.

| PNA Example | Species | Target Site[a] | PNA Sequence (N → C) | Exact Mass, m/z theor.[b] | obs.[c] |
|---|---|---|---|---|---|
| IDO-ASO 1 | Human | 3' SS of Exon 7 | Fethoc-GG(6)A-A(5)TT-A(5)CC(1O2)-TAA(5)-A-NH₂ | 4282.97 | 4283.00 |
| IDO-ASO 2 | Human | 3' SS of Exon 7 | Fethoc-AA(5)T-TA(5)C-CTA(5)-AA(5)A-C(1O2)A-NH₂ | 4503.08 | 4503.09 |
| IDO-ASO 3 | Mouse | 3' SS of Exon 7 | Fethoc-GG(5)G-A(5)TT-G(5)CC(1O2)-TTT-A(5)AA(5)-NH₂ | 4918.24 | 4918.26 |
| IDO-ASO 4 | Mouse | 3' SS of Exon 7 | Fethoc-GG(5)G-A(5)TT-G(5)CC(1O2)-TTT-A(5)-NH₂ | 4267.91 | 4267.93 |
| IDO-ASO 5 | Human | 5' SS of Exon 3 | Fethoc-CA(5)A-A(5)CC(1O2)-TTA(5)-CGG(6)-A-NH₂ | 4243.96 | 4243.98 |
| IDO-ASO 6 | Human | 3' SS of Exon 4 | Fethoc-GG(6)C-AA(5)G-A(5)CC(1O2)-TGA(5)-T-NH₂ | 4299.96 | 4299.97 |

[a] SS denotes splice site;
[b] theoretical exact mass; and
[c] observed exact mass.

TABLE 9

PNA derivatives complementarily targeting the 3' splice site spanning the junction of intron 6 and exon 7 in the human SNAP25 pre-mRNA along with stuctural characterization data by mass spectrometry.

| PNA Example | PNA Sequence (N → C) | Exact Mass, m/z theor.[a] | Exact Mass, m/z obs.[b] |
|---|---|---|---|
| SNAP-ASO 1 | Fethoc-A(6)TT-TG(6)T-TA(6)C-CC(102)T-GG(6)G-A(6)-$NH_2$ | 5188.36 | 5188.38 |
| SNAP-ASO 2 | Fethoc-TG(5)T-TA(6)C-C(102)CT-GG(5)G-A(5)-$NH_2$ | 4266.93 | 4266.95 |
| SNAP-ASO 3 | Fethoc-TG(5)T-TA(6)C-C(102)CT-GG(5)G-A(5)T-$NH_2$ | 4533.03 | 4533.04 |
| SNAP-ASO 4 | Fethoc-TG(5)G-TA(5)C-C(102)CT-TG(5)G-A(5)T-$NH_2$ | 4519.01 | 4518.95 |
| SNAP-ASO 5 | Fethoc-TG(6)T-TA(3)C-CC(105)T-GG(6)G-A(3)T-$NH_2$ | 4533.03 | 4533.04 |
| SNAP-ASO 6 | Fethoc-G(5)TT-A(5)CC(102)-CTG-G(5)GA(5)-TC(102)-$NH_2$ | 4601.07 | 4601.08 |
| SNAP-ASO 7 | Fethoc-C(102)AT-TTG(6)-TTA(5)-CCC(102)-TG(6)-$NH_2$ | 4478.98 | 4478.99 |
| SNAP-ASO 8 | Fethoc-CA(6)T-TTG(5)-TTA(5)-CCC(102)-TG(5)-$NH_2$ | 4468.02 | 4468.04 |
| SNAP-ASO 9 | Fethoc-A(6)TT-TG(G)T-TA(5)C-C(102)CT-G(5)-$NH_2$ | 4216.91 | 4216.93 |
| SNAP-ASO 10 | Fethoc-CA(6)T-CA(6)T-TTG(5)-TTA(5)-CCC(102)-TG(5)-$NH_2$ | 5374.45 | 5374.44 |
| SNAP-ASO 11 | Fethoc-A(6)TT-TG(5)T-TA(6)C-C(102)CT-GG(5)G-A(5)-$NH_2$ | 5188.36 | 5188.35 |
| SNAP-ASO 12 | Fethoc-A(6)TT-TG(5)T-TA(6)C-C(102)CT-G(5)G-$NH_2$ | 4522.04 | 4522.05 |

[a])theoretical exact mass; and
[b])observed exact mass

Table 10 provides PNA derivatives complementarily targeting the 3' splice site spanning the junction of intron 1 and exon 2 in the human tyrosinase (TYR) pre-mRNA read out from the human TYR gene [NCBI Reference Sequence: NG_0008748], or the mouse TYR pre-mRNA read out from the mouse genomic DNA [accessed from NCBI Reference Sequence: NC_000073] Provision of the TYR ASOs in Table 10 is to exemplify the PNA derivatives of Formula I, and should not be interpreted to limit the scope of the present invention to the TYR ASOs specified in Table 10.

TABLE 10

PNA derivatives complementarily targeting the 3' splice site spanning the junction of intron 1 and exon 2 in the human or mouse TYR pre-mRNA along with structural characterization data by mass spectrometry.

| PNA Example | Species | PNA Sequence (N → C) | Exact Mass, m/z theor.[a] | Exact Mass, m/z obs.[b] |
|---|---|---|---|---|
| TYR-ASO 1 | Human | Fethoc-CA(5)G-ACA(5)-ATC(102)-TG(6)T-A(5)-$NH_2$ | 4258.96 | 4260.99 |
| TYR-ASO 2 | Human | Fethoc-AC(12)A-GA(5)C-AA(5)T-CTG(6)-TA(5)C(102)-AA(5)-$NH_2$ | 5532.55 | 5532.54 |
| TYR-ASO 3 | Human | Fethoc-AC(102)A(5)-GA(5)C-AA(5)T-CTG(6)-C(102)C-$NH_2$ | 4592.11 | 4592.11 |
| TYR-ASO 4 | Mouse | Fethoc-CA(5)A-A(5)TG-A(5)TC(102)-TG(6)T-G-$NH_2$ | 4289.95 | 4289.96 |

[a])theoretical exact mass; and
[b])observed exact mass

Table 11 provides PNA derivatives complementarily targeting either 3' or the 5' splice site of exon 2 in the human PD-1 pre-mRNA read out from the human PDCD1 gene [NCBI Reference Sequence: NG_012110], or the mouse PD-1 pre-mRNA read out from the mouse genomic DNA [accessed from NCBI Reference Sequence: NC_000067] Provision of the PD-1 ASOs in Table 11 is to exemplify the PNA derivatives of Formula I, and should not be interpreted to limit the scope of the present invention to the PD-1 ASOs specified in Table 11.

TABLE 11

PNA derivatives complementarily targeting either 3' splice site or the 5' splice site of exon 2 in the human or mouse PD-1 pre-mRNA along with structural characterization data by mass spectrometry.

| PNA | | | Exact Mass, m/z | |
|---|---|---|---|---|
| Example | Species | PNA Sequence (N → C) | theor.[a] | obs.[b] |
| PD-ASO 1 | Human | Fethoc-C(102)TG(6)-GG(6)G-AG(6)T-CTG-A(5)G-$NH_2$ | 4636.07 | 4636.08 |
| PD-ASO 2 | Mouse | Fethoc-CC(102)T-CA(5)C-CTG(5)-TTA(5)-C(102)CA(5)-C-$NH_2$ | 5022.27 | 5022.27 |
| PD-ASO 3 | Human | Fethoc-CG(6)C-A(5)CC-TG(6)T-CA(5)C-C(102)C-$NH_2$ | 4422.03 | 4422.05 |

[a] SS denotes splice site;
[b] theoretical exact mass; and
[c] observed exact mass.

Binding Affinity of Model PNA Derivatives for Complementary RNA or DNA 10-mer PNA derivatives possessing modified nucleobases were prepared as model compounds to exemplify the strong affinity of the PNA compounds of Formula I for RNA as well as DNA. These model PNA compounds were prepared according to the synthetic procedures provided in the present invention or with minor modifications. The 10-mer PNA derivatives are provided in Table 12 along with structural identification data by mass spectrometry.

TABLE 12

10-mer PNA derivatives as model compounds to exemplify the strong RNA or DNA affinity of the PNA compounds of Formula I.

| PNA Ex- | | Exact Mass, m/z | |
|---|---|---|---|
| ample | PNA Sequence (N → C) | theor.[a] | obs.[b] |
| PNA 10-1 | Fmoc-GTA-GAT-CAC-T-$NH_2$ | 2948.14 | 2949.05 |
| PNA 10-2 | Fmoc-GTA-GA(5)T-CAC-T-$NH_2$ | 3048.24 | 3050.41 |
| PNA 10-3 | Fmoc-GTA(5)-GAT-CA(5)C-T-$NH_2$ | 3148.34 | 3150.65 |
| PNA 10-4 | Fmoc-GTA(5)-GA(5)T-CA(5)C-T-$NH_2$ | 3248.44 | 3250.81 |
| PNA 10-5 | Fmoc-GTA-G(5)AT-CAC-T-$NH_2$ | 3032.25 | 3035.01 |

TABLE 12-continued 10-mer PNA derivatives as model compounds to exemplify the strong RNA or DNA affinity of the PNA compounds of Formula I.

| PNA Ex- | | Exact Mass, m/z | |
|---|---|---|---|
| ample | PNA Sequence (N → C) | theor.[a] | obs.[b] |
| PNA 10-6 | Fmoc-GTA-GAT-C(102)AC-T-$NH_2$ | 3044.21 | 3047.02 |

TABLE 12-continued 10-mer PNA derivatives as model compounds to exemplify the strong RNA or DNA affinity of the PNA compounds of Formula I.

| PNA Ex- | | Exact Mass, m/z | |
|---|---|---|---|
| ample | PNA Sequence (N → C) | theor.[a] | obs.[b] |
| PNA 10-7 | Fmoc-GTA(5)-GA(5)T-C(102)AC-T-$NH_2$ | 3245.39 | 3248.10 |

[a] theoretical exact mass; and
[b] observed exact mass

The 10-mer PNA oligomers in Table 12 were evaluated for their binding affinity for the complementary 10-mer RNA or DNA by measuring $T_m$ values as described below.

A mixed solution of 4 μM 10-mer PNA oligomer and 4 μM complementary 10-mer DNA or RNA in 4 mL aqueous buffer (pH 7.16, 10 mM sodium phosphate, 100 mM NaCl) in 15 mL polypropylene falcon tube was incubated at 90° C. for a minute and slowly cooled down to ambient temperature. Then the solution was transferred into a 4 mL quartz UV cuvette, and subjected to $T_m$ measurement at 260 nm on a UV/Visible spectrophotometer as described in the prior art [PCT/KR2009/001256] or with minor modifications. The DNA and RNA for $T_m$ measurement were purchased from Bioneer (www.bioneer.com, Dajeon, Republic of Korea) and used without further purification.

Table 13 provides $T_m$ values (as uncorrected) measured between the model PNA oligomers and the complementary DNA or RNA. "PNA 10-1", the reference PNA oligomer without modified nucleobase, yielded $T_m$ values of 51 and 55° C. against the complementary DNA and RNA, respectively. The model PNA oligomers possessing modified nucleobase(s) tended to show higher $T_m$ value with more incorporation of modified nucleobases. "PNA 10-7" showed a $T_m$ of 69° C. against the complementary DNA and RNA as well, suggesting that the model PNA oligomers bind to their complementary DNA and RNA with comparable binding affinity.

TABLE 13

$T_m$ values between 10-mer PNA and complementary DNA or RNA.

| PNA | Complementary DNA or RNA | $T_m$, °C. | $\Delta T_m$[a], °C. |
|---|---|---|---|
| PNA 10-1 | DNA (5'→3') AGT-GAT-CTA-C (SEQ ID | 51 | — |
| PNA 10-2 | NO: 192) | 55 | +4 |
| PNA 10-3 | | 61 | +10 |
| PNA 10-4 | | 66 | +15 |
| PNA 10-5 | | 53 | +2 |
| PNA 10-6 | | 59 | +8 |
| PNA 10-7 | | 69 | +18 |
| PNA 10-1 | RNA (5'→3') AGU-GAU-CUA-C (SEQ ID | 55 | — |
| PNA 10-4 | NO: 193) | 66 | +11 |
| PNA 10-7 | | 69 | +18 |

[a)] $T_m$ value-$T_m$ value of "PNA 10-1"

Binding Affinity of PNA Derivatives for 10-Mer Complementary DNA

PNA derivatives of Formula I were evaluated for their binding affinity for 10-mer DNAs complementarily targeting either the N-terminal or C-terminal. The binding affinity was assessed by the $T_m$ value for the duplex between PNA and 10-mer complementary DNA. The duplex between PNA derivatives and DNAs of full complementarity usually show $T_m$ values too high to be reliably determined in aqueous buffer solution. The aqueous buffer solution tends to boil off during $T_m$ measurement.

Observed $T_m$ values (as uncorrected) of the PNA derivatives of Formula I were very high for a complementary binding to 10-mer DNA, and are provided in Table 14. For example, "AR-ASO 1" showed a $T_m$ value of 86.1° C. for the duplex with the 10-mer complementary DNA targeting the N-terminal 10-mer within the PNA as marked "bold" and "underlined" in

[(N→C) Fethoc-C(102)TT-A(5)CC-A(5)GG-C(102)AA(5)-G-$NH_2$].

In the meantime, "AR-ASO 1" showed a $T_m$ value of 81.3° C. for the duplex with the 10-mer complementary DNA targeting the C-terminal 10-mer within the PNA as marked "bold" and "underlined" in

[N→C) Fethoc-C(102)TT-A(5)CC-A(5)GG-C(102)AA(5)-G-$NH_2$].

TABLE 14

$T_m$ values between PNAs and 10-mer complementary DNA targeting either the N-terminal or the C-terminal of PNA.

| PNA | $T_m$ Value, ° C. 10-mer DNA against N-Terminal | 10-mer DNA against C-Terminal |
|---|---|---|
| AR-ASO 1 | 86.1 | 81.3 |
| AR-ASO 4 | 84.3 | 84.5 |
| AR-ASO 5 | 84.4 | 78.4 |

TABLE 14-continued $T_m$ values between PNAs and 10-mer complementary DNA targeting either the N-terminal or the C-terminal of PNA.

| PNA | $T_m$ Value, ° C. 10-mer DNA against N-Terminal | 10-mer DNA against C-Terminal |
|---|---|---|
| HIF-ASO 1 | 66.0 | 60.0 |
| HIF-ASO 4 | 66.0 | 53.4 |
| HIF-ASO 5 | 62.0 | 58.0 |
| HIF-ASO 7 | 69.0 | 61.0 |
| HIF-ASO 8 | 73.0 | 61.0 |
| HIF-ASO 9 | 60.9 | 59.0 |
| HIF-ASO 10 | 61.0 | 60.0 |
| HIF-ASO 11 | 73.4 | 61.0 |
| SCN-ASO 4 | 63.5 | 71.6 |
| SCN-ASO 7 | 65.0 | 64.6 |
| SCN-ASO 8 | 74.0 | 68.6 |
| SCN-ASO 12 | 76.0 | 77.0 |
| SCN-ASO 22 | 74.0 | 65.0 |
| SCN-ASO 24 | 77.0 | 66.0 |
| SCN-ASO 25 | 78.0 | 66.0 |
| SCN-ASO 26 | 75.0 | 72.0 |
| SCN-ASO 27 | 77.0 | 69.0 |
| SCN-ASO 28 | 78.1 | 70.0 |
| SCN-ASO 30 | 79.0 | 74.0 |
| SNAP-ASO 2 | 76.0 | 87.6 |
| SNAP-ASO 3 | 77.3 | 88.7 |
| SNAP-ASO 8 | 58.0 | 68.0 |
| SNAP-ASO 9 | 62.0 | 76.0 |
| SNAP-ASO 10 | 61.0 | 68.0 |
| SNAP-ASO 12 | 62.0 | 74.0 |
| TYR-ASO 1 | 78.0 | 73.0 |
| TYR-ASO 4 | 72.0 | 72.0 |

Examples for In Vitro Activity of HIF-1α ASOs

PNA derivatives of Formula I complementarily targeting the 3' splice site of either exon 2 or exon 4 in the human HIF-1α (hypoxia-inducible factor 1α) pre-mRNA were evaluated for their HIF-1α antisense exon skipping activity in HeLa cells. Biological examples for these HIF-1α ASOs are provided as examples to illustrate that exon skipping is potently induced by the compound of Formula I targeting a splice site in a target pre-mRNA, and therefore should not be interpreted to limit the scope of the current invention to HIF-1α ASOs.

HIF-1α Example 1. Exon Skipping Induced by "HIF-ASO 2"

"HIF-ASO 2" specified in Table 1 is a 14-mer ASO fully complementary to a region in the 3' splice site of exon 2 in the human HIF-1α pre-mRNA as marked "bold" and "underlined" in the 20-mer pre-mRNA sequence of

[(5'→3') uguua<u>aguag</u>|<u>GAUAAGUUCU</u> (SEQ ID NO: 32)], where the symbol "|" stands for the intron-exon junction. "HIF-ASO 2" possesses a 5-mer complementary overlap with intron 1 and a 9-mer complementary overlap with exon 2.

"HIF-ASO 2" was evaluated by HIF-1α nested PCR for its ability to induce the skipping of exon 2 of the human HIF-1α mRNA in HeLa cells. The employed procedures are provided below.

[Cell Culture & ASO Treatment] HeLa cells (Cat. Number CCL-2, ATCC) were grown in 60 mm culture dish containing 5 mL of EMEM medium supplemented with 10% FBS (fetal bovine serum), 1% streptomycin/penicillin, 1% L-glutamine, and 1% sodium pyruvate under 5% $CO_2$ atmosphere at 37° C. The cells were treated with "HIF-ASO 2" at 0 (negative control), 10, 100 or 1,000 zM. The ASO was serially diluted to a proper concentration in DDW and aliquoted into culture dish.

[RNA Extraction] 5 hours later, total RNA was extracted using "Universal RNA Extraction Kit" (Cat. Number 9767, Takara) according to the manufacturer's instructions.

[cDNA Synthesis by One Step RT-PCR] 200 ng of RNA template was subjected to a 25 μL reverse transcription reaction using Super Script® One-Step RT-PCR kit with Platinum® Taq polymerase (Cat. Number 10928-042, Invitrogen) against a set of exon-specific primers [HIF-exon 1_forward: (5'→3') CTTGCCTTTCCTTCTCTTCT (SEQ ID NO: 33); HIF-exon 8_reverse: (5'→3') AACCCAGACATATCCACC (SEQ ID NO: 34)] according to the following cycle conditions: 50° C. for 30 min and 94° C. for 2 min, which was followed by 15 cycles of 30 sec at 94° C., 30 sec at 55° C., and 1 min at 72° C.

[Nested PCR Amplification] 1 μL of cDNA was subjected to a 20 μL nested PCR reaction (Cat. Number K2612, Bioneer) against a set of exon-primers [HIF-exon 1n_forward: (5'→3') TGAAGACATCGCGGGGAC (SEQ ID NO: 35); HIF-exon 5n_reverse: (5'→3') TTTTTCACAAGGCCATTTCT (SEQ ID NO: 36)] according to the following cycle conditions: 95° C. for 5 min followed by 39 cycles of 30 sec at 95° C., 40 sec at 50° C., and 50 sec at 72° C.

Figure 17A:
FIG. 17A. Target positions of the exon-specific primers employed in the HIF-1α nested PCR to detect the exon skipping induced by "HIF-ASO 2" in HeLa cells.

The sets of exon-specific primers for the one step RT-PCR and nested PCR amplification are schematically summarized in FIG. 17A.

Figure 17B:
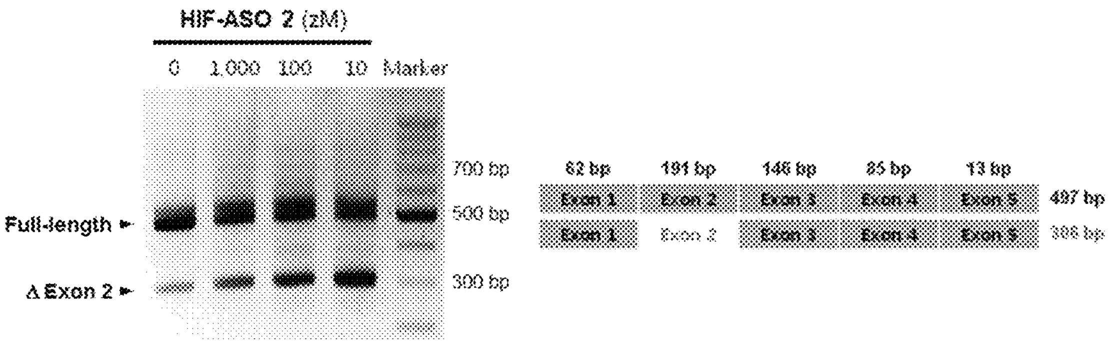
FIG. 17B. Electrophoresis data of HIF-1α nested PCR products in HeLa cells treated with "HIF-ASO 2" at 0 (negative control), 10, 100 or 1,000 zM.
Figure 17C:
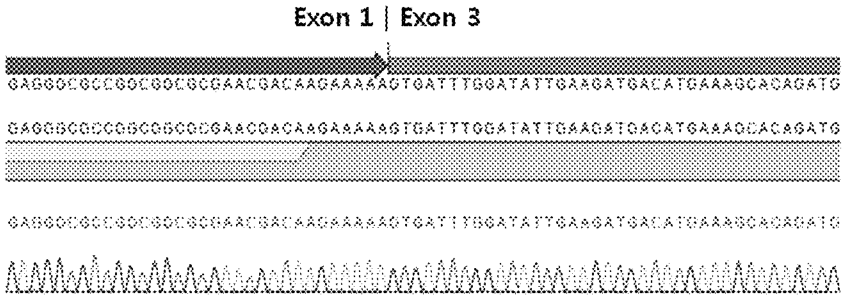
FIG. 17C. Sanger sequencing data for the PCR product band assigned to the skipping HIF-1α exon 2.

[Identification of "Exon 2 Skipping" Product] The PCR products were subjected to electrophoretic separation on a 2% agarose gel along with a size marker cocktail. The bands of target size were collected and analyzed by Sanger Sequencing. The observed PCR bands corresponded to the full-length mRNA (i.e., without exon skipping), and the splice variant lacking exon 2 as assigned in FIG. 17B. The cells treated with the ASO yielded a strong PCR band of a size assignable to the skipping of exon 2. The cells without the ASO treatment (i.e., negative control) also yielded the PCR product corresponding to the skipping of exon 2, suggesting that exon 2 is spontaneously deleted to a certain extent. However, the intensity of the exon skipping band was much stronger in the cells treated with the ASO than in the cells without ASO treatment. Thus "HIF-ASO 2" promoted the skipping of exon 2 in HeLa cells. The sequencing data for the exon skipping band is provided in FIG. 17C, which manifests the mRNA sequence for the junction of exon 1 and exon 3.

[Number of Cells Influenced by a Single ASO Molecule] "HIF-ASO 2" induced exon 2 skipping even at 10 zM. There are ca 30 ASO molecules at 10 zM (i.e., $10^{-21}$M) concentration in 5 mL of the culture medium in 60 mm culture dish. Given that ca 30 ASO molecules induced the skipping in ca 100,000 HeLa cells in 60 mm culture dish, each ASO molecule is estimated to have affected or controlled the exon skipping in ca 3,000 HeLa cells on average. Thus each ASO molecule is considered to have rapidly shuttled around a large number of cells to execute its destined role for the exon skipping.

HIF-1α Example 2. Inhibition of HIF-1α Protein Expression in HeLa Cells by "HIF-ASO 2"

"HIF-ASO 2" was evaluated for its ability to inhibit the expression of HIF-1α protein in HeLa cells as described below.

[Cell Culture & ASO Treatment] HeLa cells grown in 60 mm culture dish containing 5 mL culture medium were treated with "HIF-ASO 2" at 0 zM (negative control), 10 zM, 100 zM, 1 aM, or 10 aM.

[$CoCl_2$ Treatment and Cell Lysis] 24 hours after the ASO treatment, the culture dishes except for the one without ASO treatment were treated with 200 μM $CoCl_2$ for another 3 hours to upregulate the HIF-1α protein level by suppressing the activity of prolylhydroxylases (PHDs). Then the cells were washed 2× with 1 mL cold PBS, and subjected to lysis on ice with 200 μL 1×RIPA buffer (Cat. Number 9806, Cell Signaling Tech) supplemented with 1% SDS and 1× proteinase inhibitor cocktail (cOmplete Mini, Roche). Each lysate was collected in 1.5 mL e-tube, mixed with 100 μL 5× sample buffer, and boiled for 5 min at 100° C. The lysates were subjected to electrophoretic separation on an 8% SDS-PAGE gel, and transferred onto a 0.45 μm PVDF membrane. The membrane was probed with an anti-HIF-1α antibody (Cat. Number 610958, BD Biosciences) and an anti-β-actin antibody (Cat. Number sc4778, Santa Cruz).

Figure 18A:
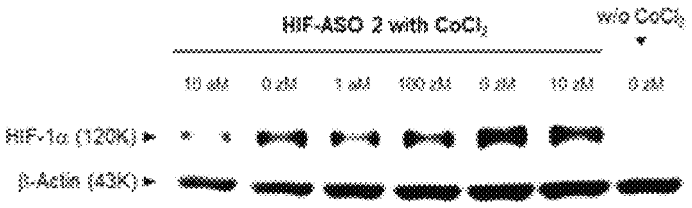
FIG. 18A. HIF-1α western blot data in HeLa cells treated with "HIF-ASO 2" at 0 zM (negative control), 10 zM, 100 zM, 1 aM or 10 aM for 24 hours.
Figure 18B:
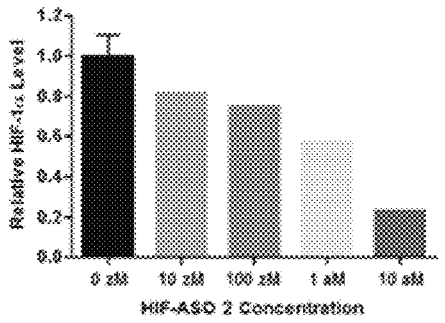
FIG. 18B. Relative HIF-1α protein expression levels normalized against β-actin in HeLa cells treated with "HIF-ASO 2" at 0 zM (negative control), 10 zM, 100 zM, 1 aM or 10 aM for 24 hours. (error bar by standard error)

[Inhibition of HIF-1α Protein Expression] FIG. 18A provides the HIF-1α western blot data obtained in HeLa cells treated with "HIF-ASO 2". Whilst there was no HIF-1α band detected with the lysate of the cells without $CoCl_2$ treatment, the lysates of the cells treated with $CoCl_2$ yielded a strong band for HIF-1α. FIG. 18B provides the individual HIF-1α band intensities normalized against each individual β-actin band intensity by densitometry. The HIF-1α expression gradually decreased as the "HIF-ASO 2" concentration was increased. The observed decrease was ca 75% at 10 aM "HIF-ASO 2".

HIF-1α Example 3. qPCR by SYBR Green for HIF-1α mRNA in HeLa Cells Treated with "HIF-ASO 2"

"HIF-ASO 2" was evaluated by nested qPCR for its ability to inhibit the expression of the full-length HIF-1α mRNA in HeLa cells as follows.

[Cell Culture & ASO Treatment] HeLa cells grown in 60 mm culture dish containing 5 mL medium were treated with "ASO 2" at 0 (negative control), 10, 100 or 1,000 zM (2 culture dishes per each ASO concentration).

[RNA Extraction] 3 hours after the ASO treatment, total RNA was extracted with "MiniBEST Universal RNA Extraction Kit" (Cat. Number 9767, Takara) according to the manufacturer's instructions.

[cDNA Synthesis by One Step RT-PCR] 200 ng of RNA template was subjected to a 25 μL reverse transcription reaction using Super Script® One-Step RT-PCR kit with Platinum® Taq polymerase (Cat. Number 10928-042, Invitrogen) against a set of exon-specific primers [HIF-exon 1_forward: (5'→3') CTTGCCTTTCCTTCTCTTCT (SEQ ID NO: 37); HIF-exon 8_reverse: (5'→3') AACCCAGACATATCCACC (SEQ ID NO: 38)] according to the following cycle conditions: 50° C. for 30 min and 94° C. for 2 min, which was followed by 15 cycles of 30 sec at 94° C., 30 sec at 55° C., and 1 min at 72° C.

[Nested qPCR] 1 μL of cDNA diluted by 100 times was subjected to a 20 μL Real-Time PCR reaction against the following sets of exon-specific primers: [HIF-exon 2n_forward (5'→3') CTTGCTCATCAGTTGCCACTTC (SEQ ID NO: 39); HIF-exon 2n_reverse (5'→3') AAGTTTCCTCACACGCAAATAG (SEQ ID NO: 40); HIF-exon 3n_forward (5'→3') GAAAGCACAGATGAATTGC (SEQ ID NO: 41); HIF-exon 3n_reverse (5'→3') TCATGTCACCATCATCTGT (SEQ ID NO: 42); HIF-exon 4n_forward (5'→3') CTAACTGGACACAGTGTGTTTG (SEQ ID NO: 43); HIF-exon 4n_reverse (5'→3') TCTGTGTGTAAGCATTTCTCTC (SEQ ID NO: 44); HIF-exon 5n_forward (5'→3') GCCTTGTGAAAAAGGGTAAAG (SEQ ID NO: 45); HIF-exon 5n_reverse (5'→3') CCATGTTGCAGACTTTATGT] (SEQ ID NO: 46). The PCR reactions were probed with SYBR Green (Takara, Japan) according to the following cycle conditions: 95° C. for 3 min followed by 40 cycles for 5 sec at 95° C. and 30 sec at 60° C.

Figure 18C:
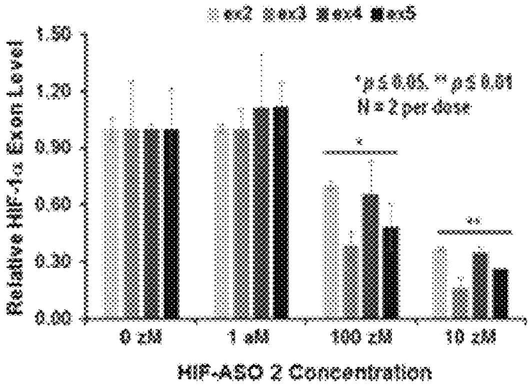
FIG. 18C. HIF-1α nested qPCR by SYBR Green in HeLa cells treated with "HIF-ASO 2" at 0 (negative control), 10, 100 or 1,000 zM. (error bar by standard error)

[Changes in HIF-1α mRNA Exon Levels] The individual exon levels of ASO treated samples were normalized against each individual exon level without ASO treatment. The observed relative individual exon levels are provided in FIG. 18C. All the individual exon levels significantly decreased by 60 to 80% and 50 to 70% in the cells treated with "HIF-ASO 2" at 10 zM and 100 zM, respectively. However, the individual exon levels obtained with the cells treated with "HIF-ASO 2" at 1,000 zM (i.e., 1 aM) were not different from the exon levels in the cells without ASO treatment. Although it remains to be elucidated why the exon levels increased back to the levels of negative control as the ASO concentration was increased to 1,000 zM. Nevertheless, the inverted dose response pattern in FIG. 18C is comparable to the inverted dose response pattern of the exon skipping in "HIF-1α Example 1". (cf. FIG. 17A)

HIF-1α Example 4. qPCR by TaqMan Probe for HIF-1α mRNA in HeLa Cells Treated with "HIF-ASO 2"

"HIF-ASO 2" was evaluated by nested qPCR for its ability to inhibit the expression of the full-length HIF-1α mRNA in HeLa cells as described in "HIF-1α Example 3" unless noted otherwise.

[cDNA Synthesis by One Step RT-PCR] 200 ng of RNA template subjected to a 25 μL reverse transcription reaction using Super Script® One-Step RT-PCR kit with Platinum® Taq polymerase (Cat. Number 10928-042, Invitrogen) against a set of exon-specific primers [HIF-exon 1_forward (2): (5'→3') CGCGAACGACAAGAAAAA (SEQ ID NO: 47); HIF-exon 8_reverse(2): (5'→3') CTGTGGTGACTTGTCCTTT (SEQ ID NO: 48)] according to the following cycle conditions: 50° C. for 30 min and 94° C. for 2 min, which was followed by 20 cycles of 30 sec at 94° C., 40 sec at 51° C., and 50 sec at 72° C.

[Nested qPCR] 1 μL of cDNA diluted by 100 times was subjected to a 20 μL Real-Time PCR reaction using a TaqMan probe (Hs00936371_m1, Thermo Fisher) designed to detect the junction of the human HIF-1α exon 1 and exon 2 according to the following cycle conditions: 95° C. for 3 min followed by 40 cycles 10 sec at 95° C., and 30 sec at 60° C.

Figure 18D:
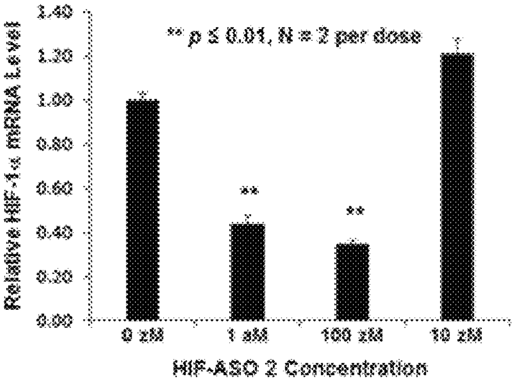
FIG. 18D. HIF-1α nested qPCR by TaqMan probe in HeLa cells treated with "HIF-ASO 2" at 0 (negative control), 10, 100 or 1,000 zM. (error bar by standard error)

[Changes in HIF-1α mRNA Level] The full-length mRNA level of ASO treated samples were normalized against the mRNA level without ASO treatment. The observed normalized mRNA levels are provided in FIG. 18D. The full-length HIF-1α mRNA level significantly (by student's t-test) decreased by 65% and 55% in the cells treated with "HIF-ASO 2" at 100 zM and 1,000 zM, respectively. The full-length mRNA level remained unchanged in the cells treated with "ASO 2" at 10 zM.

HIF-1α Example 5. Exon Skipping Induced by "HIF-ASO 6"

"HIF-ASO 6" specified in Table 1 is a 17-merASO fully complementary to the 3' splice site spanning the junction of intron 1 and exon 2 in the human HIF-1α pre-mRNA as marked "bold" and "underlined" in the 20-mer pre-mRNA sequence of

[(5'→3') ugu<u>uaaguag</u>|<u>GAUAAGUUCU</u> (SEQ ID NO: 49)],

"HIF-ASO 6" possesses a 7-mer complementary overlap with intron 1 and a 10-mer complementary overlap with exon 2.

"HIF-ASO 6" was evaluated by HIF-1α nested PCR for its ability to induce the skipping of exon 2 of the human HIF-1α mRNA in HeLa cells according to the procedures described in "HIF-1α Example 1" unless noted otherwise.

Figure 19A:
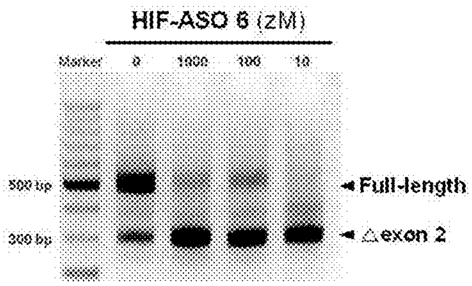
FIG. 19A. Electrophoresis data of HIF-1α nested PCR products in HeLa cells treated with "HIF-ASO 6" at 0 (negative control), 10, 100 or 1,000 zM.

The PCR products were subjected to electrophoretic separation on a 2% agarose gel, and the electrophoresis results are provided in FIG. 19A. The skipping of exon 2 was robust at all the treatment concentrations of "HIF-ASO 6". "HIF-ASO 6" induced the skipping of exon 2 more effectively than "HIF-ASO 2". The PCR band for the full-length HIF-1α mRNA disappeared almost completely at all the concentrations of "HIF-ASO 6". In the meantime, there was a significant level of the full-length HIF-1α mRNA remaining in the cells treated with "HIF-ASO 2" at 10 to 1,000 zM. [cf. FIG. 17A]

"HIF-ASO 6" possesses more complementary overlap with the 3' splice site of exon 2 than "HIF-ASO 2", which would be responsible for the higher exon skipping efficacy observed with "HIF-ASO 6". Tighter binding of ASO to the target splice site appears to induce more effectively the skipping of the target exon.

HIF-1α Example 6. Inhibition of HIF-1α Protein Expression in HeLa Cells by "HIF-ASO 6"

Figure 19B:
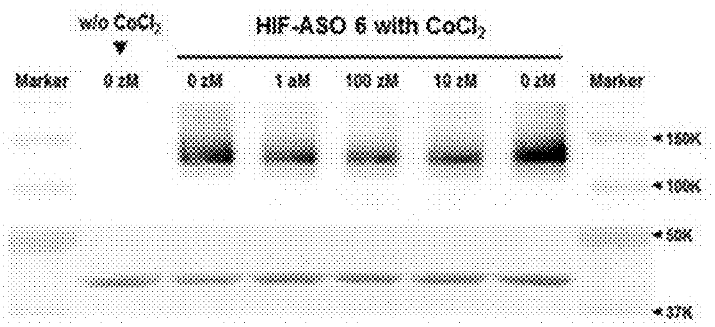
FIG. 19B. HIF-1α western blot data in HeLa cells treated with "HIF-ASO 6" at 0 zM (negative control), 10 zM, 100 zM, or 1 aM for 24 hours.
Figure 19C:
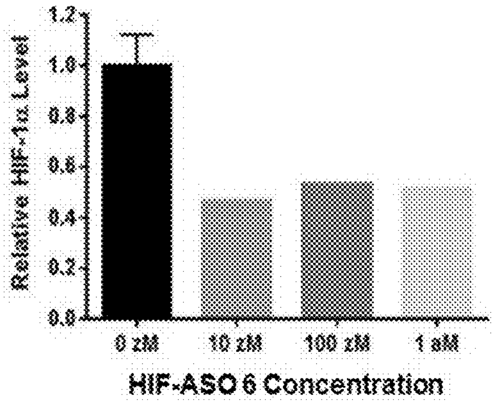
FIG. 19C. HIF-1α expression levels normalized against β-actin in HeLa cells treated with "HIF-ASO 6" at 0 zM (negative control), 10 zM, 100 zM, or 1 aM for 24 hours. (error bar by standard error)

"HIF-ASO 6" was evaluated for its ability to down-regulate the HIF-1α expression in HeLa cells according to the procedures described in "HIF-1α Example 2" unless noted otherwise. FIG. 19B is a western blot data obtained with HeLa cells treated with "HIF-ASO 6" at 0 (negative control), 10, 100 or 1,000 zM for 24 hours. FIG. 19C provides the individual HIF-1α band intensities normalized against each individual β-actin band intensity by densitometry. The expression of HIF-1α protein decreased by ca 45-55% in the cells treated with "HIF-ASO 6".

HIF-1α Example 7. qPCR by SYBR Green for HIF-1α mRNA in HeLa Cells Treated with "HIF-ASO 6"

"HIF-ASO 6" was evaluated for its ability to induce a change in HIF-1α mRNA in HeLa cells by nested qPCR according to the procedures in "HIF-1α Example 4" unless noted otherwise.

[cDNA Synthesis by One Step RT-PCR] 200 ng of RNA template was subjected to a 25 μL reverse transcription reaction using Super Script® One-Step RT-PCR kit with Platinum® Taq polymerase (Cat. Number 10928-042, Invitrogen) against a set of exon-specific primers [HIF-exon 1_forward(2): (5'→3') CGCGAACGACAAGAAAAA (SEQ ID NO: 50); HIF-exon 8(2) reverse: (5'→3') CTGTGGTGACTTGTCCTTT (SEQ ID NO: 51)] according to the following cycle conditions: 50° C. for 30 min and 94° C. for 2 min, which was followed by 15 cycles of 30 sec at 94° C., 40 sec at 51° C., and 50 sec at 72° C.

Figure 20A:
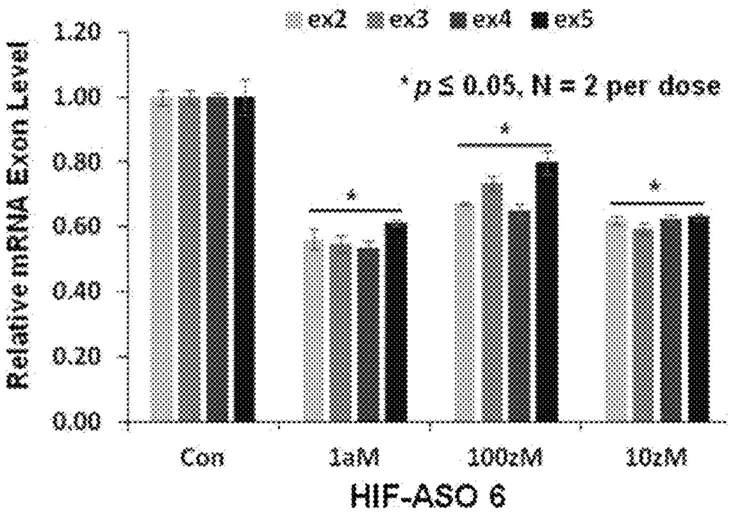
FIG. 20A. Nested qPCR data by SYBR Green in HeLa cells treated with "HIF-ASO 6" at 0 (negative control), 10, 100 or 1,000 zM. (error bar by standard error)

[Changes in HIF-1α mRNA Exon Levels] The individual exon levels normalized against the individual exon levels without ASO treatment are provided in FIG. 20(A). The exon levels significantly (student's t-test) decreased by 35%, ca 30%, and ca 45% in the cells treated with "HIF-ASO 6" at 10, 100, and 1,000 zM, respectively.

HIF-1α Example 8. qPCR by TaqMan Probe for HIF-1α mRNA in HeLa Cells Treated with "ASO 6"

"HIF ASO 6" was evaluated by nested qPCR for its ability to inhibit the expression of the full-length HIF-1α mRNA in HeLa cells as described in "HIF-1α Example 4" unless noted otherwise.

Figure 20B:
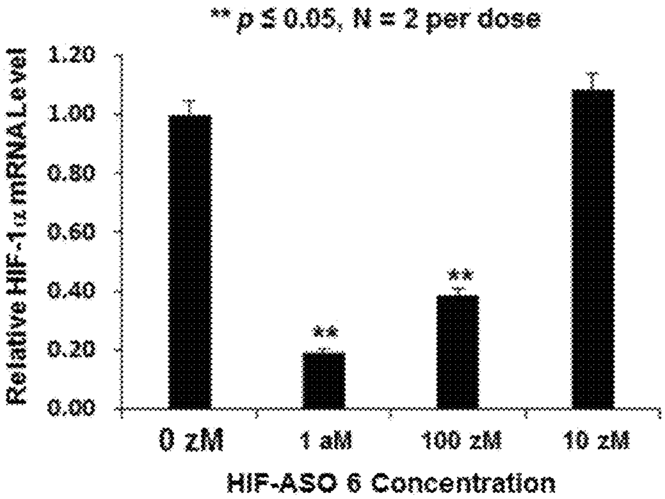
FIG. 20B. Nested qPCR data by TaqMan probe in HeLa cells treated with "HIF-ASO 6" at 0 (negative control), 10, 100 or 1,000 zM. (error bar by standard error)

[Changes in Full-length HIF-1α mRNA Level] The full-length mRNA level of ASO treated samples was normalized against the mRNA level without ASO treatment. The observed relative mRNA levels are provided in FIG. 20(B). The full-length HIF-1α mRNA level significantly (student's t-test) decreased by ca 60% and 80% in the cells treated with "HIF-ASO 6" at 100 zM and 1,000 zM (1 aM), respectively. However, the full-length mRNA level remained unchanged in the cells treated with "HIF-ASO 6" at 10 zM.

HIF-1α Example 9. Exon Skipping Induced by "HIF-ASO 1"

"HIF-ASO 1" is a 14-mer ASO fully complementary to a region in the 3' splice site spanning the junction of intron 1 and exon 2 in the human HIF-1α pre-mRNA as marked "bold" and "underlined" in the 23-mer pre-mRNA sequence of

[(5'→3') uguuaag<u>uag</u>|<u>GAUAAGUUCUG</u>AA (SEQ ID NO: 52)],

"HIF-ASO 1" possesses a 3-mer overlap with intron 1 and an 11-mer overlap with exon 2.

"HIF-ASO 1" was evaluated for its ability to induce exon skipping in the HIF-1α mRNA as described in "HIF-1α Example 1", unless nested otherwise. HeLa cells were treated with "HIF-ASO 1" at 0 (negative control), 1, 3, 10, 30 or 100 aM. 24 hours later, total RNA was extracted and subjected to HIF-1α nested PCR to detect exon skipping.

Figure 21A:
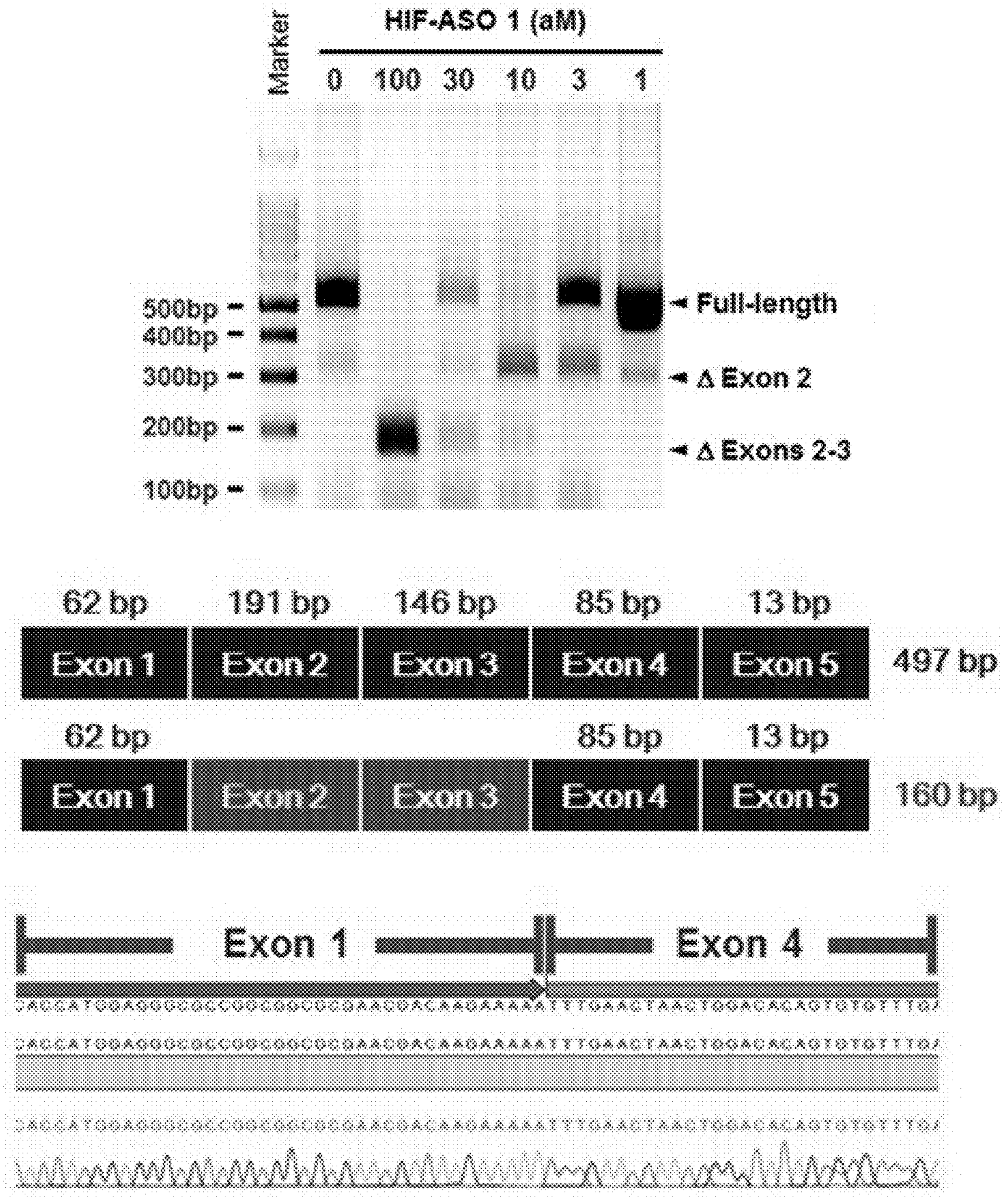
FIG. 21A. Electrophoresis data of HIF-1α nested PCR products in HeLa cells treated with "HIF-ASO 1" at 0 (negative control), 1, 3, 10, 30 or 100 aM (left); and Sanger sequencing data for the PCR product assignable to the skipping of exons 2-3 (right).

[Exon Skipping Data] FIG. 21A provides the electrophoresis data obtained with the nested PCR products along with the Sanger sequencing data for the PCR product assignable to the skipping of exons 2-3. The full-length mRNA level tended to decrease as the ASO concentration was increased from 1 aM to 100 aM. The skipping of exon 2 was predominant with "HIF-ASO 1" at 3 aM and 10 aM. However, the skipping of exons 2-3 became overring as the ASO concentration was increased to 100 aM. The PCR product for the skipping product of exons 2-3 was unequivocally confirmed by the Sanger sequencing. [cf. FIG. 21A right]

HIF-1α Example 10. Inhibition of HIF-1 Protein Expression in HeLa Cells by "HIF-ASO 1"

"HIF-ASO 1" was evaluated for its ability to inhibit the HIF-1α protein expression in HeLa cells according to the procedures described in "HIF-1α Example 2" unless noted otherwise. In this example, HeLa cells were treated with "HIF-ASO 1" at 0 zM (negative control), 100 zM, 300 zM, 1 aM, 3 aM, 10 aM, 30 aM, 100 aM or 300 aM for 72 hours prior to suppressing the activity of PHDs by an incubation with 200 μM $CoCl_2$ for 3 hours. There were 4 culture dishes of the negative control, i.e., 0 zM "HIF-ASO 1".

Figure 21B:
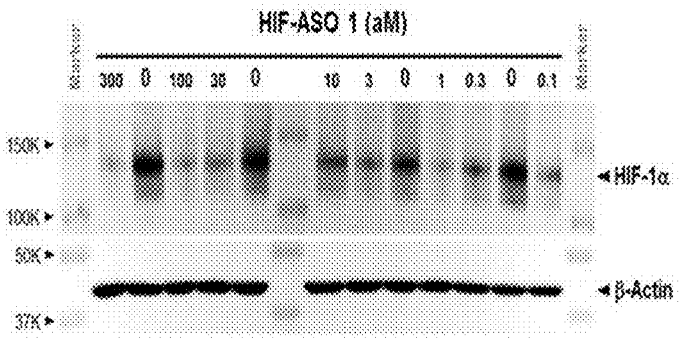
FIG. 21B. HIF-1α western blot data in HeLa cells treated with "HIF-ASO 1" for 72 hours at 0 zM (negative control), 100 zM, 300 zM, 1 aM, 3 aM, 10 aM, 30 aM, 100 aM or 300 aM.
Figure 21C:
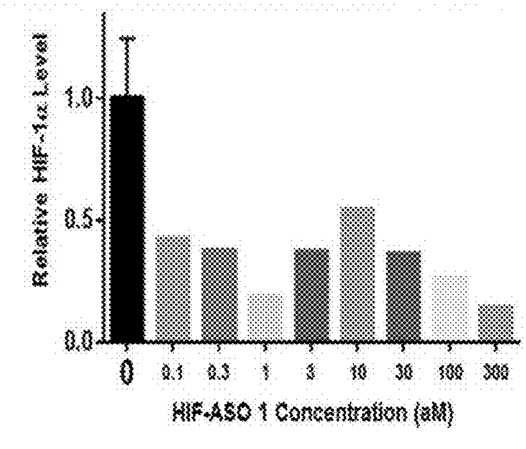
FIG. 21C. HIF-1α expression levels normalized against β-actin in HeLa cells treated with "HIF-ASO 1" for 72 hours at 0 zM (negative control), 100 zM, 300 zM, 1 aM, 3 aM, 10 aM, 30 aM, 100 aM or 300 aM.

FIG. 21B provides the HIF-1α western blot data obtained with the HeLa cell lysates. The HIF-1α protein level was considerably higher in the lysates of the negative control than all the lysates of the cells treated with "HIF-ASO 1". FIG. 21C provides the individual HIF-1α band intensities normalized against β-actin band intensity by densitometry. The HIF-1α expression in HeLa cells decreased by 40 to 80% by the 72 hour incubation with "HIF-ASO 1" at 0.1 to 300 aM.

HIF-1α Example 11. Exon Skipping Induced by "HIF-ASO 12"

"HIF-ASO 12" specified in Table 2 is a 15-mer ASO fully complementary to a region in the 3' splice site spanning the junction of intron 3 and exon 4 in the human HIF-1α pre-mRNA as marked "bold" and "underlined" in the 20-mer pre-mRNA sequence of

[(5'→3') ugu<u>uuacag</u>|<u>UUUGAACTA</u>AC (SEQ ID NO: 53)],

"HIF-ASO 12" possesses a 6-mer overlap with intron 3 and a 9-mer overlap with exon 4.

"HIF-ASO 12" was evaluated by HIF-1α nested PCR for its ability to induce the skipping of exon 4 of the human HIF-1α mRNA in HeLa. HeLa cells were incubated with "HIF-ASO 12" for 6 hours, and then subjected to total RNA extraction according to the protocol described in "HIF-1α Example 1", unless noted otherwise.

Figure 22A:
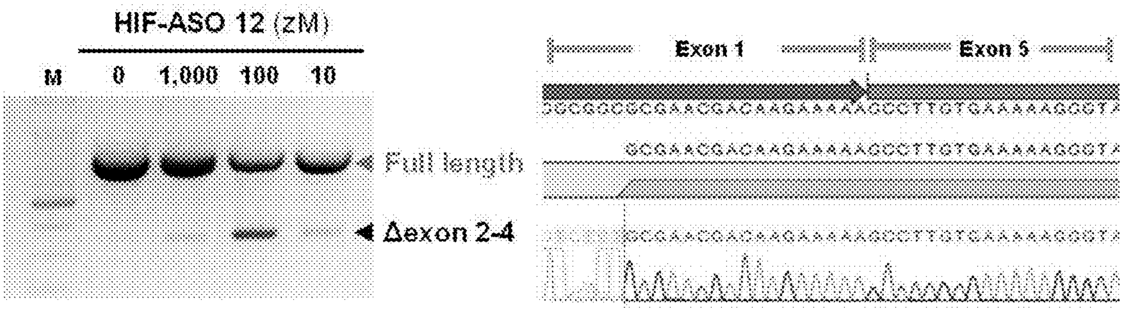
FIG. 22A. HIF-1α nested PCR data in HeLa cells treated with "HIF-ASO 12" at 0 (negative control), 10, 100 or 1,000 zM (left) along with the Sanger sequencing data of the exon skipping band (right).

FIG. 22A provides the HIF-1α nested PCR data in HeLa cells treated with "HIF-ASO 12". An exon skipping band assignable to the skipping of exons 2-4 was detected in all the PCR products of the ASO treated cells, whilst not in that of the non-treated cells. (cf. left diagram) The intensity of the exon skipping band was most intense at 100 zM "HIF- ASO 12". The intensity of the full-length mRNA band decreased most at 100 zM "HIF-ASO 12". The skipping of exons 2-4 was confirmed by Sanger sequencing as provided in the right diagram.

HIF-1α Example 12. Inhibition of HIF-1α Protein Expression in HeLa Cells by "HIF-ASO 12"

"HIF-ASO 12" was evaluated for its ability to inhibit the expression of HIF-1α in HeLa cells as described in "HIF-1α Example 2" unless noted otherwise.

[ASO Treatment] HeLa cells were treated with "HIF-ASO 12" at 0 zM (negative control), 10 zM, 100 zM or 1 aM. 3 culture dishes for the negative control. 21 hours later, cells were treated with 200 μM $CoCl_2$ except for one dish of the negative control. 3 hours later, all the cells were subjected to lysis on ice as follows. Cells were washed 2× with 1 mL cold PBS, and then subjected to lysis with 200 μL 2× Lammeli sample buffer (24 mM Tris-HCl, 20% glycerol, 0.8% SDS, 0.04% bromophenol blue, 2% β-mercaptoethanol) to minimize the degradation of HIF-1α. Each lysate was collected in 1.5 mL e-tube, and boiled for 5 min. Then the lysates were subjected to western blot on an 8% SDS-PAGE gel.

Figure 22B:
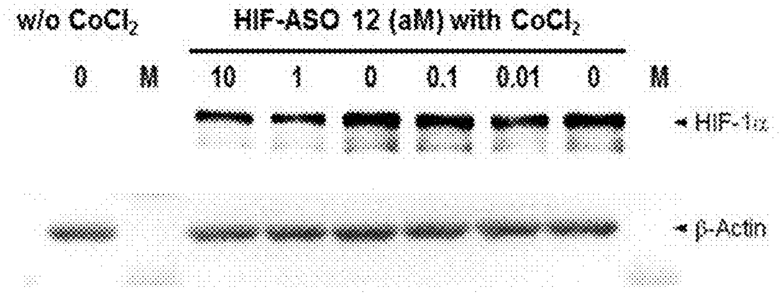
FIG. 22B. HIF-1α western blot data in HeLa cells treated with "HIF-ASO 12" at 0 (negative control), 0.01, 0.1, 1 or 10 aM.

FIG. 22B provides the western blot data showing that the HIF-1α band intensity clearly decreased in the cells treated with "HIF-ASO 12" at 1 and 10 aM.

HIF-1α Example 13. qPCR by SYBR Green for HIF-1α mRNA in HeLa Cells Treated with "HIF-ASO 12"

"HIF-ASO 12" was evaluated by HIF-1α nested qPCR for its ability to induce a change in the HIF-1a mRNA in HeLa cells as described in "HIF-1a Example 3", unless noted otherwise. HeLa cells were treated with "HIF-ASO 12" for 6 hours, and then subjected to total RNA extraction.

Figure 22C:
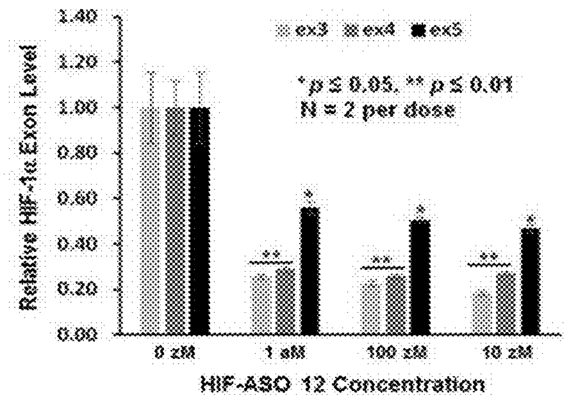
FIG. 22C. HIF-1α nested qPCR data obtained in HeLa cells treated with "HIF-ASO 12" at 0 (negative control), 10, 100 or 1,000 zM. (error bar by standard error)

FIG. 22C provides the qPCR data, in which the mRNA levels of exons 2 and 3 significantly decreased (student's t-test) by 70~80% in the cells treated with the ASO. The qPCR findings are consistent with the skipping of exons 2-4 induced by "HIF-ASO 12" (cf. "HIF-1α Example 11").

Examples for In Vitro & In Vivo Activity of AR ASOs

PNA derivatives of Formula I complementarily targeting the 5' splice site spanning the junction of exon 5 and intron 5 in the human androgen receptor (AR) pre-mRNA were evaluated for their AR antisense exon skipping activity in cells and in mice as well. Biological examples for these AR ASOs are provided as examples to illustrate that exon skipping is potently induced by the compound of Formula I targeting a splice site in a target pre-mRNA, and therefore should not be interpreted to limit the scope of the current invention to AR ASOs.

AR Example 1. Exon Skipping Induced by "AR-ASO 1"

"AR-ASO 1" specified in Table 3 is a 13-mer ASO fully complementary to a region in the 5' splice site spanning the junction of exon 5 and intron 5 in the human androgen receptor (AR) pre-mRNA. "AR-ASO 1" complementarily binds to the 13-mer sequence as marked "bold" and "underlined" in the 20-mer pre-mRNA sequence of

[(5'→3') GC<u>CUUGCCUG</u>|
<u>guaag</u>gaaaa (SEQ ID NO: 54)].

"AR-ASO 1" possesses an 8-mer overlap with exon 5 and a 5-mer overlap with intron 5.

"AR-ASO 1" was evaluated by AR nested PCR for its ability to induce the skipping of exon 5 of the human AR mRNA in MCF7 cells as follows.

[Cell Culture & ASO Treatment] MCF7 cells (Cat. Number: HTB-22, ATCC) were maintained in EMEM medium supplemented with 10% FBS, 1% streptomycin/penicillin, and 0.01 mg/mL bovine insulin under 5% $CO_2$ atmosphere at 37° C. Cells grown in 60 mm culture dish were treated with "AR-ASO 1" for 3 hours at 0 (negative control), 3, 30, 300 or 3,000 aM (i.e., 3 fM).

[RNA Extraction] Total RNA was extracted using "Universal RNA Extraction Kit" (Cat. No. 9767, Takara) according to the manufacturer's instructions [cDNA Synthesis by One Step RT-PCR] 100 ng of RNA template was used in a 25 μL reverse transcription reaction using Super Script® One-Step RT-PCR kit with Platinum® Taq polymerase (Cat. No. 10928-042, Invitrogen) and a set of exon-specific primers [AR-exon 3_forward: (5'→3') TGGGTGTCACTATGGAGC (SEQ ID NO: 55); and AR-exon 9_reverse: (5'→3') GGGT-GTGGAAATAGATGGG (SEQ ID NO: 56)] according to the following cycle conditions: 50° C. for 30 min and 94° C. for 2 min, which was followed by 39 cycles of 30 sec at 94° C., 30 sec at 55° C., and 1 min at 72° C.

[Nested PCR Amplification] Throughout the amplification process, was used a unique amplification technique (touch up as increasing annealing temperature per cycle) that worked efficiently and specifically over a temperature range, rather than at one specific annealing temperature (i.e., conventional PCR method). 1 μL of cDNA was further amplified in a 20 μL nested PCR reaction using a set of exon-specific primers [AR-exon 3_forward: (5'→3') TGGGTGTCACTATGGAGC (SEQ ID NO: 57); and AR-exon 7n_reverse: (5'→3') GGGGTGATTTGGAGC-CAT (SEQ ID NO: 58)] according to the following cycle conditions: initial 10 cycles [94° C. for 30 sec, 47° C. for 40 sec (+0.5° C. every cycle), 72° C. for 40 sec], followed by 20 cycles [94° C. for 30 sec, 50° C. for 30 sec, and 72° C. for 40 sec].

Figure 23A:
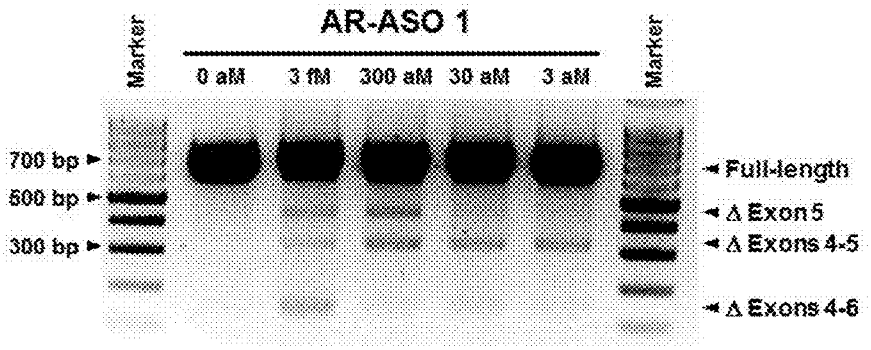
FIG. 23A. Electrophoretic analysis of the AR nested PCR products in MCF7 cells treated with "AR-ASO 1" for 3 hours at 0 (negative control), 3, 30, 300 or 3,000 aM.
Figure 23B:
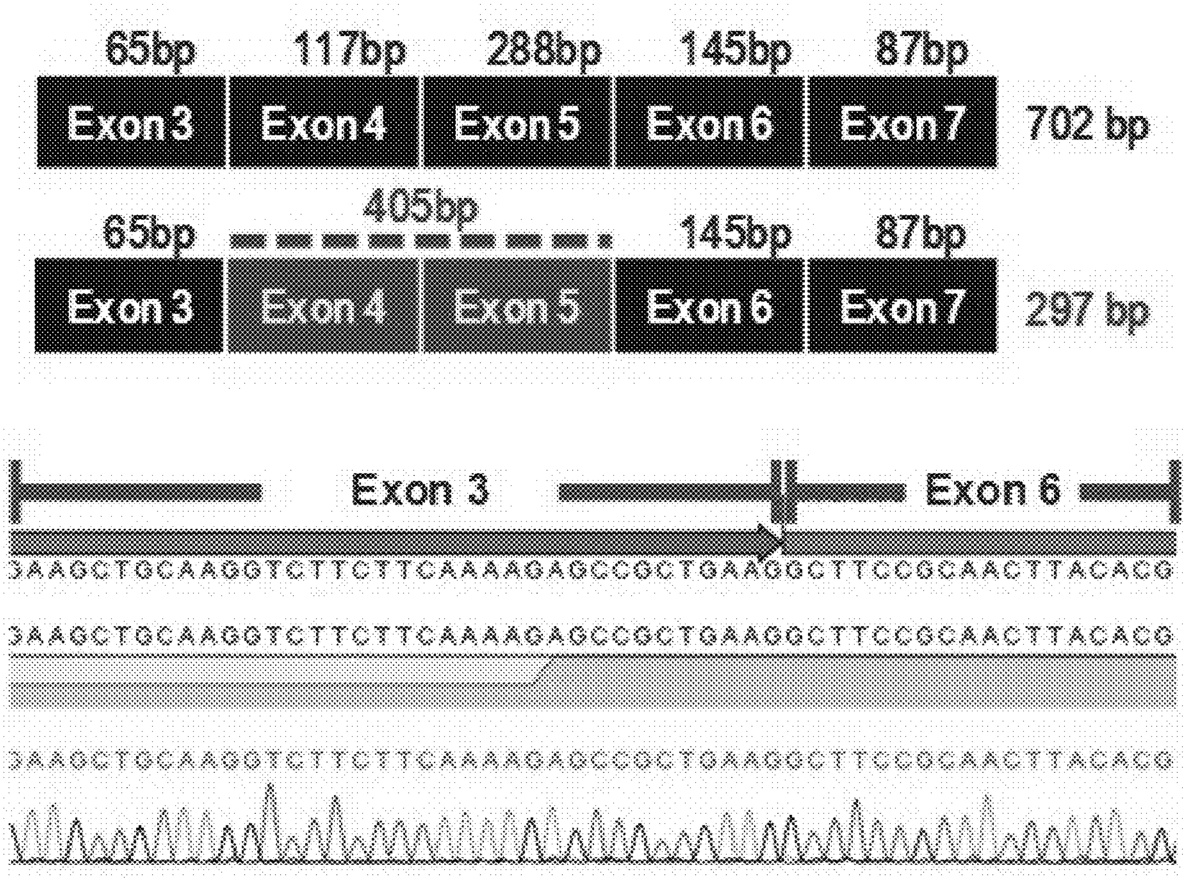
FIG. 23B. Sanger sequencing data for the PCR product band assigned to the skipping of exons 4-5.

[Identification of Exon Skipping Products] The PCR products were subjected to electrophoretic separation on a 2% agarose gel. The bands of target size were collected and analyzed by Sanger Sequencing. In FIG. 23A, there are three treatment-related PCR product bands assignable to AR mRNA splice variants lacking exon 5. "AR-ASO 1" was found to induce the skipping of exon 5, exons 4-5, and exons 4-6, although the ratio of the skipping products appeared to depend on the ASO concentration. FIG. 23B provides the actual sequencing data for the skipping band of exons 4-5 in FIG. 23A.

AR Example 2. Inhibition of AR Protein Expression in MCF7 Cells by "AR-ASO 1"

Figure 23C:
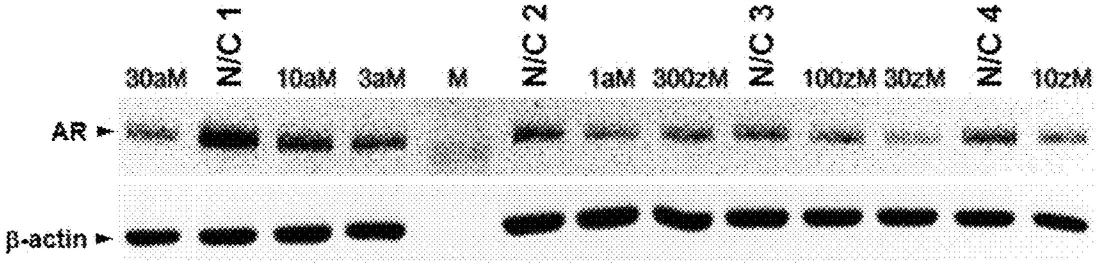
FIG. 23C. AR western blot data in MCF7 cells treated with "AR-ASO 1" for 48 hours at 0 zM (negative control, i.e., N/C), 10 zM, 30 zM, 100 zM, 300 zM, 1 aM, 3 aM, 10 aM or 30 aM.

MCF7 cells in 60 mm culture dish containing 5 mL culture medium were treated with "AR-ASO 1" at 0 zM (negative control) or 10 zM to 30 aM. 4 culture dishes for the negative control. 48 hours later, cells were washed 2× with cold PBS, and then subjected to lysis with 200 μL 1× cell lysis buffer (Cat. No. 9803, Cell Signaling Tech) supplemented with 1× protease inhibitors (Cat. No. P8340, Sigma). The lysates were collected in 1.5 mL e-tube. 200 μL of each lysate was mixed with 100 μL 3× sample buffer, and boiled for 5 min. 20 μL of each lysate (4 negative controls and 8 ASO treatment samples) was subjected to electrophoretic separation on a 8% SDS-PAGE gel, and transferred onto a PVDF membrane. The membrane was probed with an anti-AR antibody (Cat. Number 5153, Cell Signaling Tech) and an anti-3-actin antibody (Cat. Number sc4778, Santa Cruz). FIG. 23C provides the AR western blot data obtained in MCF7 cells treated with "AR-ASO 1" at 0 zM (4 negative controls) to 30 aM. The AR band (120K size) intensity of the lysates treated with the ASO was weaker than the intensity of their neighboring lysates the negative control.

AR Example 3. qPCR by SYBR Green for AR mRNA in MCF7 Cells Treated with "AR-ASO 1"

[ASO Treatment and RNA Extraction] MCF7 cells in 5 mL culture medium were treated with "AR-ASO 1" at 0 zM (negative control) or 1 zM to 1 aM. (2 culture dishes per concentration) 5 hours later, total RNA was extracted using "MiniBEST Universal RNA Extraction Kit" according to the manufacturer's instructions (Cat. Number 9767, Takara).

[cDNA Synthesis with OligodT] 500 ng of RNA template was subjected to a cDNA synthesis against "oligo-dT" according to the manufacturer's instructions (Cat. Number 6110A, Takara).

[First PCR] cDNA was then subjected to the 1st PCR against a set of exon-specific primers [AR-exon 3_forward: (5'→3') TGGGTGTCACTATGGAGC (SEQ ID NO: 59); and AR-exon 9 reverse: (5'→3') GGGTGTGGAAATA-GATGGG (SEQ ID NO: 60)] according to the following cycle conditions: 94° C. for 2 min followed by 15 cycles of 15 sec at 94° C., 30 sec at 55° C., and 2 min at 72° C.

Figure 24A:
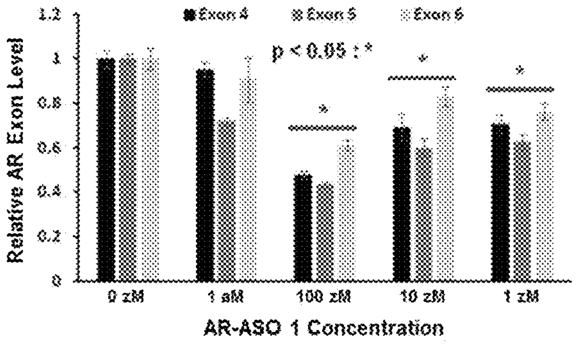
FIG. 24A. qPCR data by SYBR Green for AR exon 4-6 levels in MCF7 cells treated with "AR-ASO 1" for 5 hours at 0 (negative control), 1, 10, 100 or 1,000 zM. (error bar by standard error)

[Nested PCR] The 1st PCR products were diluted by 2,000 times, and 1 μL of each diluted PCR product was subjected to a 20 μL Real-Time PCR reaction against sets of exon-specific primers [AR-exon 4_forward(q): (5'→3') GAC-CATGTTTTGCCCATTG (SEQ ID NO: 61); AR-exon 4_reverse(q): (5'→3') GGCTCTTTTGAAGAAGACC (SEQ ID NO: 62); AR-exon 5_forward(q): (5'→3') GAAACAGAAGTACCTGTGC (SEQ ID NO: 63); AR-exon 5_reverse(q): (5'→3') GTCATCCCTGCTTC-ATAAC (SEQ ID NO: 64); AR-exon 6_forward(q): (5'→3') CGGAAGCTGAAGAAACTTG (SEQ ID NO: 65); AR-exon 6_reverse(q): (5'→3') CACTTGACCACGTGTA-CAAG (SEQ ID NO: 66)]. The PCR reactions were probed by SYBR Green (Takara, Japan). Cycle Conditions: 95° C. for 3 min followed by 40 cycles for 5 sec at 95° C., and 30 sec at 60° C. The exon levels gradually but significantly decreased as the dose was increased from 1 zM to 100 zM. The decreases were 40-50% in the cells treated with "AR-ASO 1" at 100 zM. [cf. FIG. 24A] However, the exon levels rebounded close toward the negative control levels in the cells treated with "AR-ASO 1" at 1 aM.

AR Example 4. qPCR by SYBR Green for AR mRNA in MCF7 Cells Treated with "AR-ASO 5"

"AR-ASO 5" specified in Table 3 is a 12-mer ASO fully complementary to a region in the 5' splice site spanning the junction of exon 5 and intron 5 in the human AR pre-mRNA. "AR-ASO 5" complementarily binds to the 12-mer sequence as marked "bold" and "underlined" in the 20-mer pre-mRNA sequence of

[(5'→3') GCCUUGCCUG|guaaggaaaa (SEQ ID NO: 67)].

"AR-ASO 5" possesses a 7-mer overlap with exon 5 and a 5-mer overlap with intron 5.

Figure 24B:
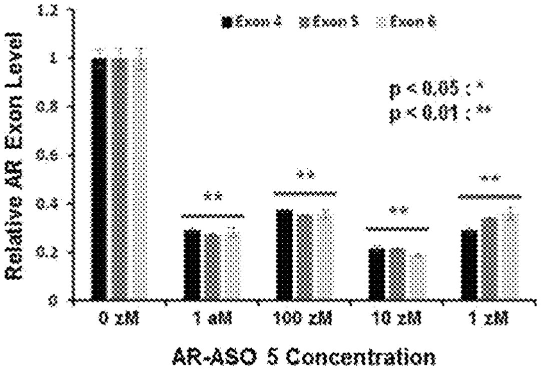
FIG. 24B. qPCR data by SYBR Green for AR exon 4-6 levels in MCF7 cells treated with "AR-ASO 5" for 5 hours at 0 (negative control), 1, 10, 100 or 1,000 zM. (error bar by standard error)

"AR-ASO 5" was evaluated for its ability to induce changes in the AR mRNA exon levels by qPCR according to the methods described in "AR Example 3". As provided in FIG. 24B, the AR exon levels significantly (student's t-test) decreased by ca 60-80% in the cells treated with "AR-ASO 5" at 1 to 1,000 zM.

Unlike the case of "AR-ASO 1" (cf. "AR Example 3"), there was no rebound in the exon message levels at 1,000 zM "AR-ASO 5".

AR Example 5. qPCR by TaqMan Probe for AR mRNA in MCF7 Cells Treated with "AR-ASO 5"

"AR-ASO 5" was evaluated for its ability to down-regulate the human AR mRNA by qPCR adopting a TaqMan probe.

MCF7 cells were treated with "AR-ASO 5" at 0 zM (negative control) to 1 aM. (2 dishes per concentration) 24 hours later, total RNA was extracted by "MiniBEST Universal RNA Extraction Kit" according to the manufacturer's instructions (Cat. No. 9767, Takara).

400 ng of RNA template was subjected to a cDNA synthesis with One-Step RT-PCR kit (Invitrogen) against a set of exon-specific primers [AR-exon 3_forward: (5'→3') TGGGT-GTCACTATGGAGC (SEQ ID NO: 68); and AR-exon 9_reverse: (5'→3') GGGTGTGGAAATAGATGGG (SEQ ID NO: 69)] according to the following cycle conditions: 50° C. for 30 min and 94° C. for 2 min, which was followed by 15 cycles of 30 sec at 94° C., 30 sec at 50° C., and 1 min at 72° C.

1 μL of each cDNA solution diluted by 50× was subjected to a 20 μL Real-Time PCR reaction against a set of exon-specific primers of [AR-exon 4_forward(q2): (5'→3') TTGTCCATCTTGTCGTCTT (SEQ ID NO: 70); and AR-exon 5_reverse(q2): (5'→3') CCTCTCCTTCCTC-CTGTA (SEQ ID NO: 71)] according to the following cycle conditions: 95° C. for 3 min followed by 40 cycles 15 sec at 95° C., and 30 sec at 60° C. The qPCR reaction was monitored with a TaqMan probe of [(5'→3') TTTCTTCAG-ZEN-CTTCCGGGCTC-3IABkFQ (SEQ ID NO: 72)]. The TaqMan probe was designed to probe the junction of exon 4 and exon 5 in the full-length AR mRNA.

Figure 24C:
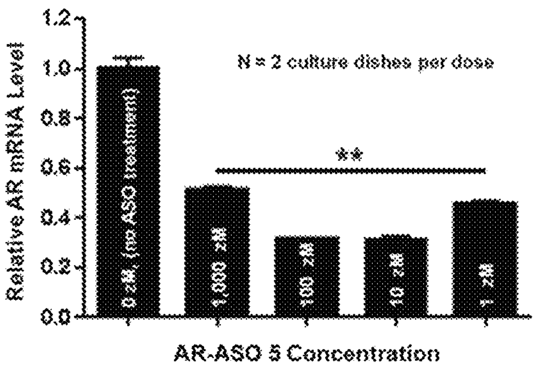
FIG. 24C. qPCR data by TaqMan assay for AR mRNA in MCF7 cells treated with "AR-ASO 5" for 24 hours at 0 (negative control), 1, 10, 100, or 1,000 zM. (error bar by standard error)

FIG. 24C provides the qPCR data by the TaqMan probe. The relative expression of the full-length AR mRNA significantly (student's t-test) decreased by ca 50 to 70% in the cells treated with "AR-ASO 5" at 1 zM to 1 aM.

AR Example 6. Inhibition of AR Protein Expression in Skin of Mice Subcutaneously Treated with "AR-ASO-5"

"AR-ASO 5" targets the AR pre-mRNA sequence conserved in humans and mice. "AR-ASO 5" was evaluated for its ability to inhibit the AR protein expression in the skin of mice following a single subcutaneous administration as follows.

[Hair Removal and Grouping] In Day 0, 7 weeks old male C57BL/6 mice were anesthetized with zoletil/rompun, and the hair in the back was cut with a clipper and removed by carbo-waxing. In Day 5, mice with flawless (i.e., spotless) hair removal were selected and randomly assigned into five groups of 0 pmole/Kg (vehicle only, negative control), 1 pmole/Kg, 10 pmole/Kg, 100 pmole/Kg, and 1,000 pmole/Kg "AR-ASO 5". (6 animals per group).

[ASO Injection Solution & Administration] An aqueous mother stock solution of "AR-ASO 5" was serially diluted in PBS supplemented with 0.1% Tween 80 to prepare "AR-ASO 5" solutions of 0 nM (vehicle only, negative control), 0.5 nM, 5 nM, 50 nM, or 500 nM. In Day 5, individual mice in each dose group were subcutaneously administered in the nape (i.e., near neck) with a single injection of the test article at 2 mL/Kg.

[Extraction of Skin Samples] In Day 10, the animals were sacrificed to obtain skin samples from the injection site and the hip as a non-injection site. The skin samples were frozen in liquid nitrogen immediately after the sampling. Each skin sample was micronized while maintaining the sample frozen with liquid nitrogen. The micronized samples were subjected to lysis with RIPA buffer supplemented with 1% SDS. The lysates were mixed with 5× sample buffer and boiled for 5 min.

[AR Western Blot] The lysates were subjected to AR western blot on a PVDF membrane. A total of 10 lysates were loaded on each 10% PAGE gel with two individual lysates from each group. AR protein (120K daltons) was probed with a polyclonal AR antibody (N-20, sc-816, Santa Cruz).

[Quantification of AR Protein Expression] Each AR band on a single PVDF membrane was normalized against individual β-actin band. The average AR band intensity (normalized against β-actin) of the two samples of the negative control group (i.e., no ASO treatment) was used to normalize the AR band intensities of the other 8 samples on the same PVDF membrane. Such double normalization was applied to the other two PVDF membranes to quantify the AR protein expression of individual samples by densitometry. All the AR expression levels after the double normalization of individual samples were pooled for statistical analysis by student's t-test against the expression level without the ASO treatment.

Figure 25A:
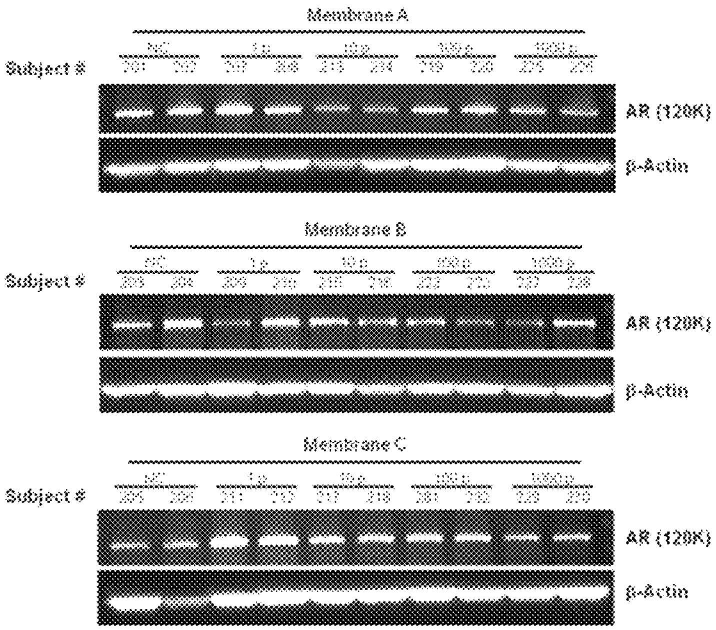
FIG. 25A. Raw western blot data obtained with the skin of the injection site. NC, 1p, 10p, 100p and 1,000p refer to the negative control group, 1, 10, 100 and 1,000 pmole/Kg ASO treatment group, respectively.
Figure 25B:
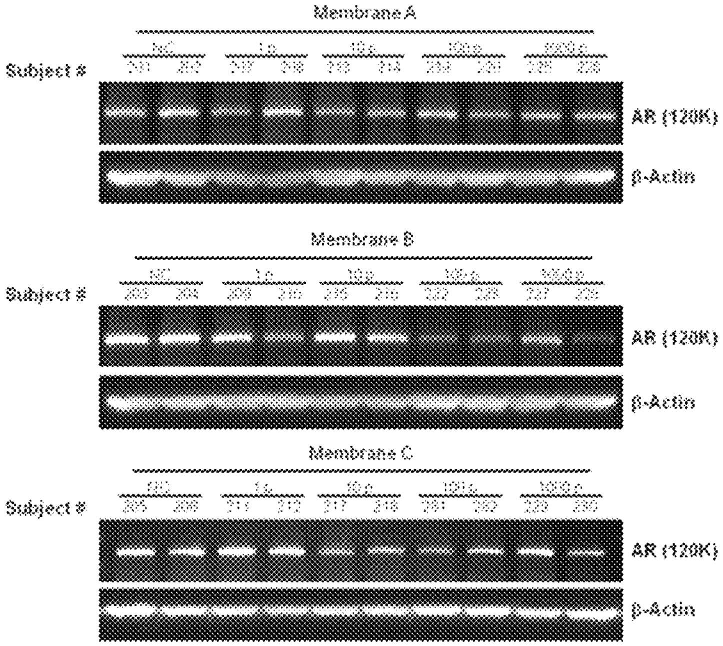
FIG. 25B. Raw western blot data obtained with the skin of the non-injection site. NC, 1p, 10p, 100p and 1,000p refer to the negative control group, 1, 10, 100 and 1,000 pmole/Kg ASO treatment group, respectively.

[Inhibition of AR Protein Expression] FIGS. 25A and 25B are the AR western blot data obtained with the skin samples from the injection site and the non-injection site, respectively.

Figure 26A:
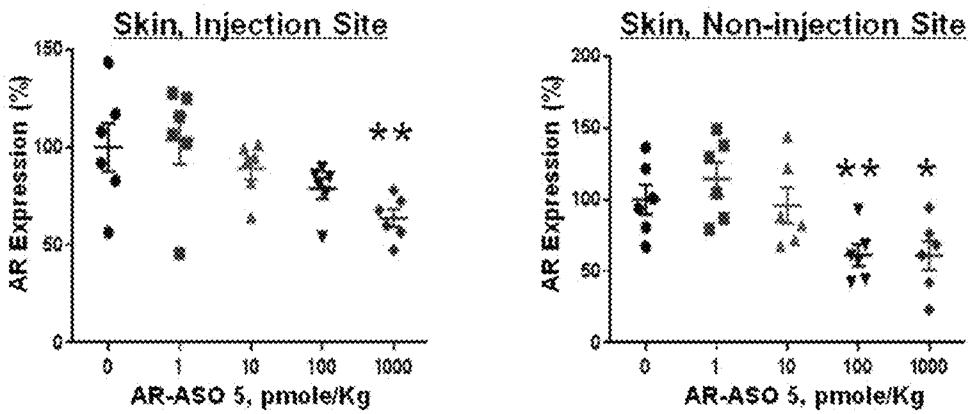
FIG. 26A. AR protein expression level by group as well as by subject in the injection site (left) and the non-injection site (right). (** for $p<0.01$, and * for $p<0.05$)

FIG. 26A provides the AR protein expression level by group as well as by subject. There was a large degree of inter-subject variability in the AR protein expression both in the injection site and in the non-injection site. However, the AR expression tended to decrease as the ASO dose was increased.

Figure 26B:
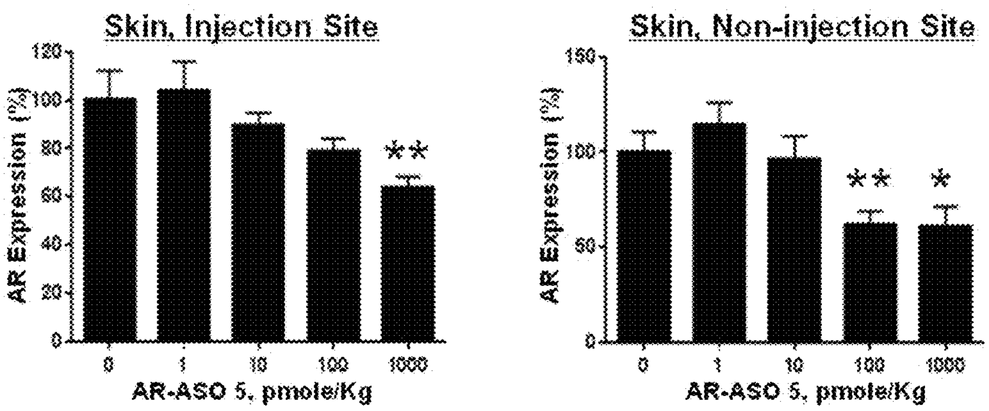
FIG. 26B. Average AR protein expression level by group in the injection site (left) and the non-injection site (right). (** for $p<0.01$, and * for $p<0.05$)

FIG. 26B provides the average AR expression level by group as normalized against the negative control group. In the injection site, the AR protein expression significantly decreased by ca 35% in the 1,000 pmole/Kg "AR-ASO 5" group. In the non-injection site, the AR protein expression significantly decreased by ca 40% in the treatment groups of 100 and 1,000 pmole/Kg.

The inhibition of AR protein expression observed in the skin distal to the injection site demonstrates that the ASO may readily distribute to tissues distal to the administration site through the systemic circulation following a subcutaneous injection. The ex vivo findings were provided to illustrate the systemic target engagement following a subcutaneous injection of the PNA derivative of Formula I, and therefore should not be interpreted to limit the scope of the present invention.

AR Example 7. Exon Skipping Induced by "AR-ASO 1" (2)

Depending on passage, cell density and culture conditions, the morphology of MCF7 cells varied. MCF cells at early passages tended to grow relatively fast and show colonies of cumulus shape. MCF7 cells at later passages are likely to grow slow and form flat epithelial colonies. However, maintaining MCF7 cells to show the morphology of cumulus shape was challenging.

"AR-ASO 1" was evaluated for its exon skipping ability in MCF7 cells grossly showing the morphology of cumulus shape as described in "AR Example 1", unless noted otherwise.

[ASO Treatment] MCF7 cells were treated with "AR-ASO 1" for 3 hours at 0 (negative control), 30, 100 or 1,000 aM (i.e., 1 fM). (2 culture dishes per ASO concentration)

[RNA Extraction] Total RNA was extracted using RNeasy mini prep kit (Cat. Number 74104, Qiagen) according to the manufacturer's instructions. 500 ng of RNA template was subjected to a 25 μL reverse transcription reaction.

Figure 27A:
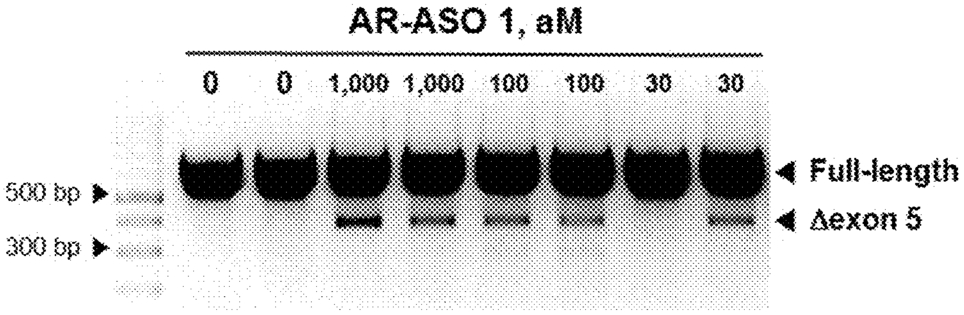
FIG. 27A. Electrophoretic analysis of the AR nested PCR products in MCF7 cells treated with "AR-ASO 1" for 3 hours at 0 (negative control), 30, 100 or 1,000 aM.
Figure 27B:
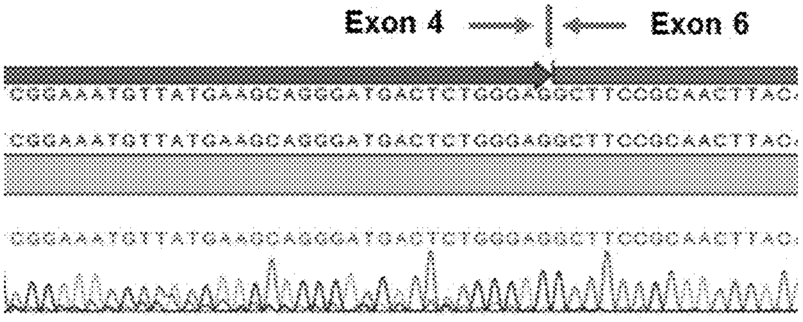
FIG. 27B. Sanger sequencing data for the PCR product band assigned to the skipping of exons 5.

[Exon Skipping Results] FIG. 27A provides the electrophoresis data obtained with the nested RT-PCR products. The skipping of exon 5 (confirmed by Sanger sequencing: cf. FIG. 27B) was distinctively predominant in the cells treated with the ASO, which would be contrasted with the case of "AR Example 1" (cf. FIG. 23A).

Examples for In Vitro & In Vivo Activity of SCN9A ASOs

PNA derivatives of Formula I complementarily targeting multiple splice sites in the human SCN9A (sodium channel subtype 9A) pre-mRNA were evaluated for their SCN9A antisense and exon skipping activity in cells and animals as well. Biological examples for these SCN9A ASOs are provided as examples to illustrate that exon skipping is potently induced by the compound of Formula I targeting a splice site in a target pre-mRNA, and therefore should not be interpreted to limit the scope of the current invention to SCN9A ASOs.

SCN9A Example 1. Exon Skipping Induced by "SCN-ASO 7"

"SCN-ASO 7" specified in Table 4 is a 16-mer ASO fully complementary to a region in the 5' splice site spanning the junction of exon 4 and intron 4 in the human SCN9A pre-mRNA read out from the human SCN9A gene (accessed from NCBI Reference Sequence: NC_000002.12). "SCN-ASO 7" complementarily binds to the 16-mer sequence as marked "bold" and "underlined" in the 20-mer pre-mRNA sequence of

[(5'→3') UUGUUUUUGC|
guaaguacuu (SEQ ID NO: 73)].

"SCN-ASO 7" possesses a 10-mer overlap with exon 4 and a 6-mer overlap with intron 4.

Given that PC3 cells are known to abundantly express the human SCN9A pre-mRNA [*Br. J. Pharmacol.* vol 156, 420-431 (2009)], "SCN-ASO 7" was evaluated by SCN9A nested PCR for its ability to induce the skipping of exon 4 in the human SCN9A pre-mRNA in PC3 cells as follows.

[Cell Culture & ASO Treatment] PC3 cells (Cat. No. CRL-1435, ATCC) were maintained in Ham's F-12K medium supplemented with 10% FBS, 1% streptomycin/ penicillin, 1% L-glutamine, and 1% sodium pyruvate under 5% $CO_2$ atmosphere at 37° C.

PC3 cells grown in 60 mm culture dish containing 5 mL medium were treated with "SCN-ASO 7" at 0 (negative control), 10, 100 or 1,000 zM.

[RNA Extraction] Following an 18 hour incubation, the PC3 cells were treated with 100 µg/mL cycloheximide for another 6 hours in order to freeze the ribosomal translation. Then total RNA was extracted from cells using "Universal RNA Extraction Kit" (Cat. Number 9767, Takara) according to the manufacturer's instructions.

[cDNA Synthesis by One Step RT-PCR] 200 ng of RNA template was used for a 25 µL reverse transcription reaction using Super Script® One-Step RT-PCR kit with Platinum® Taq polymerase (Cat. Number 10928-042, Invitrogen) and a set of exon-specific primers [SCN-exon 2_forward: (5'→3') CTTTCTCCTTTCAGTCCTCT (SEQ ID NO: 74), and SCN-exon 9_reverse: (5'→3') CGTCTGTTGGTAAA-GGTTTT (SEQ ID NO: 75)] according to the following cycle conditions: 50° C. for 30 min and 94° C. for 2 min, which was followed by 40 cycles of 30 sec at 94° C., 30 sec at 55° C., and 2 min at 72° C.

[Nested PCR Amplification] 1 µL of cDNA solution (diluted by 100×) was subjected to a 20 µl PCR amplification by nested PCR (Cat. Number K2612, Bioneer) against a set of exon-specific primers [SCN-exon 3n_forward: (5'→3') GGACCA-AAAATGTCGAGTATTT (SEQ ID NO: 76); and SCN-exon 8_reverse: (5'→3') GCTAAGAAGG-CCCAGC-TGAA (SEQ ID NO: 77)] according to the following cycle conditions: 95° C. for 5 min followed by 35 cycles of 30 sec at 95° C., 30 sec at 50° C., and 1 min at 72° C.

It is noted that the primer of "SCN-exon 3n_forward" targets the junction of exon 3 and exon 5 to effectively probe the deletion of exon 4, although the 22-mer primer still possesses an 18-mer complementary overlap with the junction of exon 3 and exon 4. Thus "SCN-exon 3n_forward" recognizes "the junction of exon 3 and exon 5" more selectively than "the junction of exon 3 and exon 4" found in the full length SCN9A mRNA. The primer sequence was designed to detect SCN9A splice variants lacking exon 4 more sensitively than the full length SCN9A mRNA. Such an exon skipping primer would be useful to detect mRNA splice variants having poor metabolic stability, since the full-length mRNA tends to show good metabolic stability gained through the evolution over billions years.

Figure 28A:
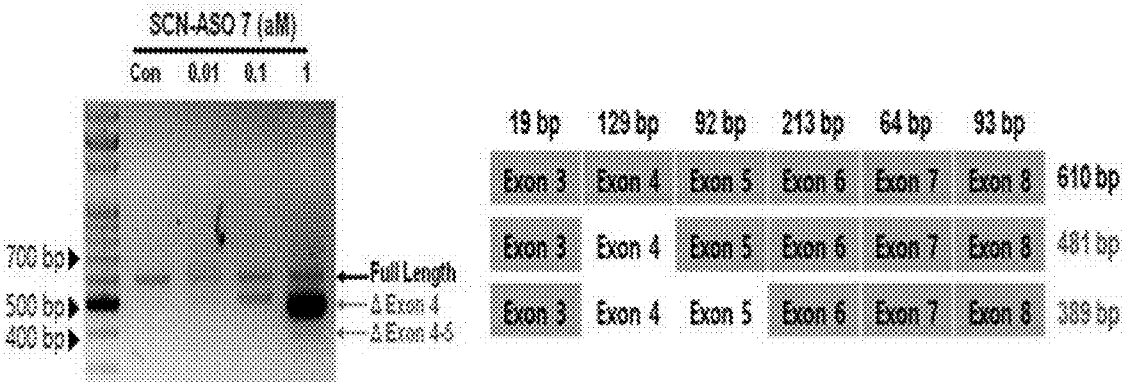
FIG. 28A. Electrophoretic analysis of the SCN9A nested PCR products in PC3 cells treated with "SCN-ASO 7" for 24 hours at 0 (negative control), 10, 100 or 1,000 zM.
Figure 28B:
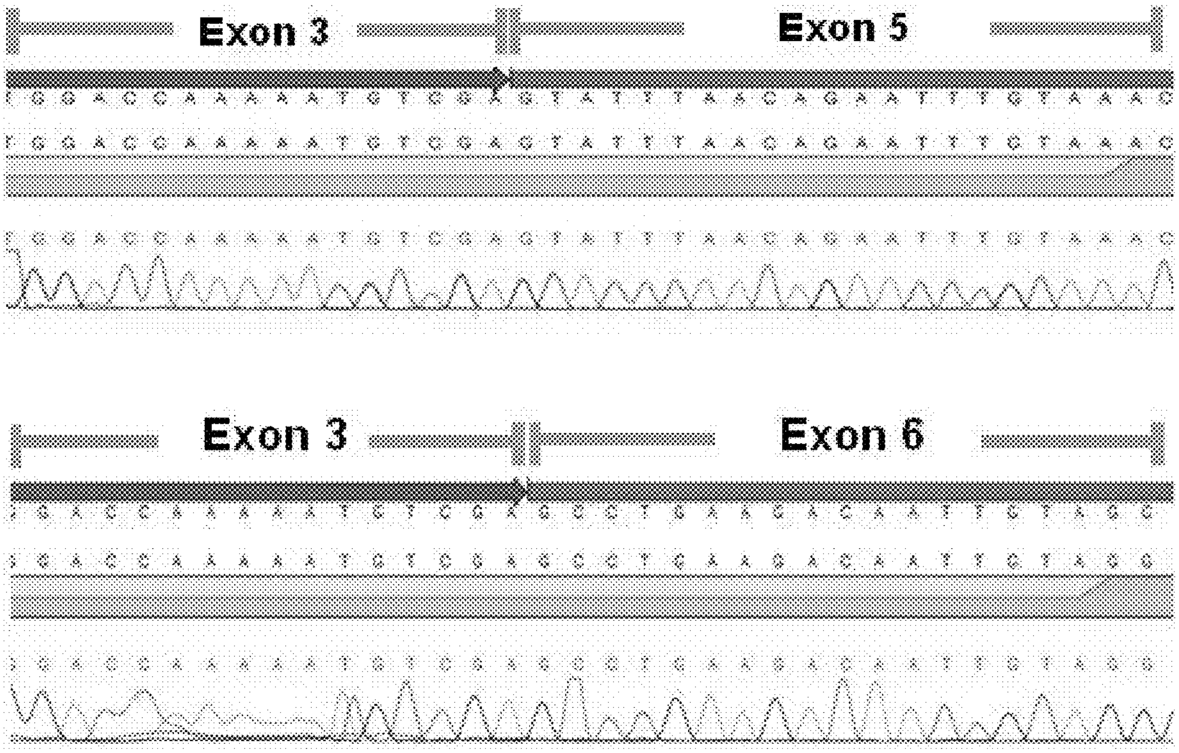
FIG. 28B. Sanger sequencing data for the nested PCR products assigned to the skipping of exon 4 (top) and exons 4-5 (bottom), respectively.

[Identification of Exon Skipping Products] The nested PCR products were subjected to electrophoretic separation on a 2% agarose gel. The bands of target size were collected and analyzed by Sanger sequencing. The skipping of exon 4 was conspicuously strong in PC3 cells treated with 1 aM "SCN ASO 7", although the skipping of exon 4 was visible too at 10 and 100 zM as shown in FIG. 28A. The exon skipping band was unequivocally confirmed by Sanger sequencing as provided in FIG. 28B.

SCN9A Example 2. qPCR by SYBR Green for SCN9A mRNA in PC3 Cells Treated with "SCN-ASO 7"

"SCN-ASO 7" was evaluated for its ability to inhibit the expression of the human SCN9A mRNA in PC3 cells by qPCR against a set of exon-specific primers as follows.

[Cell Culture & ASO Treatment] PC3 cells grown in 60 mm culture dish containing 5 mL culture medium were incubated with "SCN-ASO 7" for 24 hours at 0 (negative control), 10, 100 or 1,000 zM. (2 culture dishes per concentration)

[RNA Extraction] Total RNA was extracted using "MiniBEST Universal RNA Extraction Kit" (Cat. Number 9767, Takara) according to the manufacturer's instructions.

[cDNA Synthesis by One Step RT-PCR] 200 ng of RNA template was subjected to a 20 µL reverse transcription reaction using Super Script® One-Step RT-PCR kit with Platinum® Taq polymerase (Cat. Number 10928-042, Invitrogen) and against a set of exon-specific primers [SCN-exon 2_forward: (5'→3') CTTTCTCCTTTCAGTCCTCT (SEQ ID NO: 78); and SCN-exon 9_reverse: (5'→3') TTGCCTGGTTCTGTTCTT (SEQ ID NO: 79)]. Cycle Conditions: 50° C. for 30 min and 94° C. for 2 min, which was followed by 15 cycles of 15 sec at 94° C., 30 sec at 55° C., and 2 min at 72° C.

[Nested qPCR Amplification] 1 µL of each cDNA solution diluted by 50× was subjected to a 20 µL Real-Time PCR reaction against a set of exon specific primers sets [SCN-exon 4_forward: (5'→3') GTACACTTTTACTG-GAATATATAC (SEQ ID NO: 80); SCN-exon 4_reverse: (5'→3') AATGACGACAAAATCCAGC (SEQ ID NO: 81); SCN-exon 5_forward: (5'→3') GTATTTAACAGAAT-TTGTAAACCT (SEQ ID NO: 82); SCN-exon 5_reverse: (5'→3') CTGGGATTA-CAGAAATAGTTTTCA (SEQ ID NO: 83); SCN-exon 6_forward: (5'→3') GAAGACAAT-TGTAGGGGC (SEQ ID NO: 84); SCN-exon 6_reverse: (5'→3') GTCTTCTTCACTCTCTAGGG (SEQ ID NO: 85)]. The PCR reactions were probed with SYBR Green (Takara, Japan). Cycle conditions: 95° C. for 30 sec followed by 40 cycles 5 sec at 95° C., and 30 sec at 60° C.

Figure 29A:
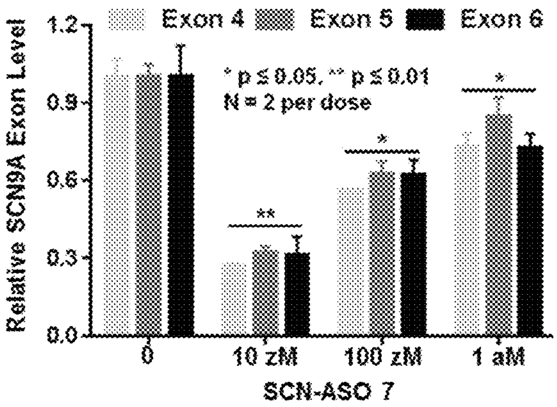
FIG. 29A. SCN9A nested qPCR data in PC3 cells treated with "SCN-ASO 7" for 24 hours at 0 (negative control), 10, 100 or 1,000 zM. (error bar by standard error)

[qPCR Results] Individual exon level of the ASO treated cells was normalized against the exon level of the negative control cells (i.e., without ASO treatment). FIG. 29(A) summarizes the qPCR results. The expression levels of exons 4-6 significantly decreased by ca 70%, 40% and 20-30% at 10, 100 and 1,000 zM, respectively.

SCN9A Example 3. qPCR by SYBR Green for SCN9A mRNA in PC3 Cells Treated with "SCN-ASO 3"

"SCN-ASO 3" specified in Table 4 is a 14-mer ASO targeting the 5' splice site spanning the junction of exon 4 and intron 4 in the human SCN9A pre-mRNA. "SCN-ASO 3" complementarily binds to the 12-mer sequence marked "bold" and "underlined" in the 20-mer pre-mRNA sequence of

[(5'→3') UUGUUUUUGC|gua"ag"uacuu (SEQ ID NO: 86)], in which the two mismatches are marked with a quote (" ") sign. "SCN-ASO 3" possesses a 7-mer complementary overlap with exon 4 and a 5-mer complementary overlap with intron 4.

"SCN-ASO 3" was evaluated for its ability to inhibit the expression of the full-length SCN9A mRNA in PC3 cells according to the protocol described in "SCN9A Example 2", unless noted otherwise.

Figure 29B:
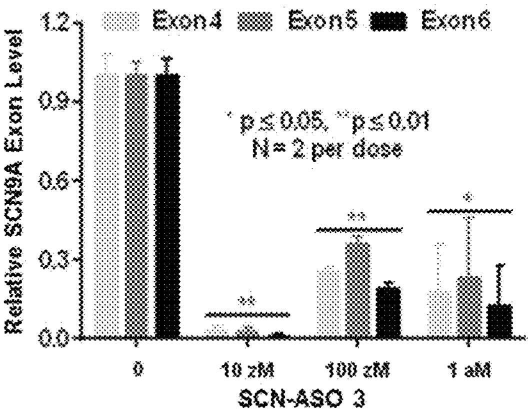
FIG. 29B. SCN9A nested qPCR data in PC3 cells treated with "SCN-ASO 3" for 24 hours at 0 (negative control), 10, 100 or 1,000 zM. (error bar by standard error)

The qPCR results are provided as summarized in FIG. 29B. The expression levels of exons 4-6 significantly decreased by >90%, ca 70% and ca 80% at 10, 100 and 1,000 zM, respectively. Like in the case of "SCN-ASO 7", 10 zM manifested the strongest inhibition of the full length SCN9A mRNA.

SCN9A Example 4. qPCR by SYBR Green for SCN9A mRNA in PC3 Cells Treated with "SCN-ASO 8"

"SCN-ASO 8" specified in Table 4 is a 17-mer ASO targeting a region in the 5' splice site spanning the junction of exon 4 and intron 4 in the human SCN9A pre-mRNA. "SCN-ASO 8" complementarily binds to the 15-mer sequence marked "bold" and "underlined" in the 20-mer pre-mRNA sequence of

[(5'→3') UUGUUUUUGC|gua"ag"uacuu (SEQ ID NO: 87)], in which the mismatch is marked with a quote sign (" "). "SCN-ASO 8" possesses a 10-mer complementary overlap with exon 4 and a 5-mer complementary overlap with intron 4 in the human SCN9A pre-mRNA.

"SCN-ASO 8" was evaluated for its ability to inhibit the expression of the full-length SCN9A mRNA in PC3 cells according to the protocol described in "SCN9A Example 2", unless noted otherwise.

Figure 29C:
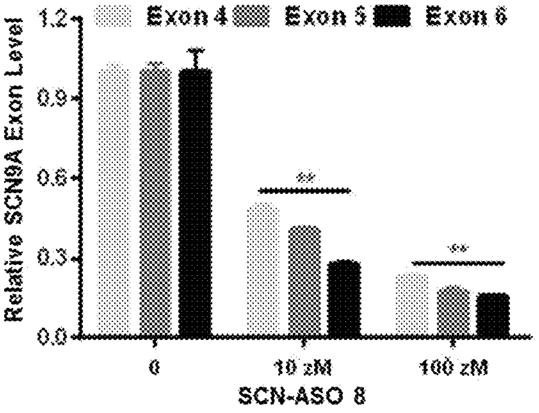
FIG. 29C. SCN9A nested qPCR data in PC3 cells treated with "SCN-ASO 8" for 24 hours at 0 (negative control), 10 or 100 zM. (error bar by standard error)

The qPCR results are provided as summarized in FIG. 29C. The expression levels of exons 4-6 significantly decreased by 50-70% and 70-80% at 10 and 100 zM, respectively.

SCN9A Example 5. Inhibition of Sodium Current by CoroNa Assay in PC3 Cells Treated with "SCN-ASO 7"

Cellular sodium current is measured by patch clamp. As sodium ions enter cell, the intra-cellular sodium ion level increases. The intra-cellular sodium level can be probed using a sodium ion sensitive dye. "CoroNa Green" is a dye with a sodium ion chelator of crown ether type. Upon chelation with a sodium ion, "CoroNa Green" emits green fluorescence. "CoroNa Green" has been used to indirectly measure the intra-cellular sodium level. The sodium level measured by "CoroNa Green" was found to correlate well with the sodium ion current measured by sodium ion patch clamp. [*Proc. Natl. Acad. Sci. USA* vol 106(38), 16145-16150 (2009)]

PC3 cells are known to abundantly express the human SCN9A mRNA, although there are other SCN subtypes concomitantly expressed. [*Br J. Pharmacol*. vol 156, 420-431 (2009)] Thus an inhibition of SCN9A mRNA expression may lead to a considerable reduction of the sodium current in PC3 cells, if the sodium ion current by the $Na_v1.7$ sodium channel subtype occupies a marked portion of the total sodium ion current in PC3 cells. It is note that the SCN9A mRNA encodes the $Na_v1.7$ sodium channel subtype.

"SCN-ASO 7" was evaluated for its ability to inhibit the sodium ion current in PC3 cells using "CoroNa Green" as follows.

[ASO Treatment] PC3 cells grown in 35 mm culture dish containing 2 mL F-12K medium were treated with "SCN-ASO 7" at 0 zM (negative control), 100 zM or 1 aM.

Figure 30A:
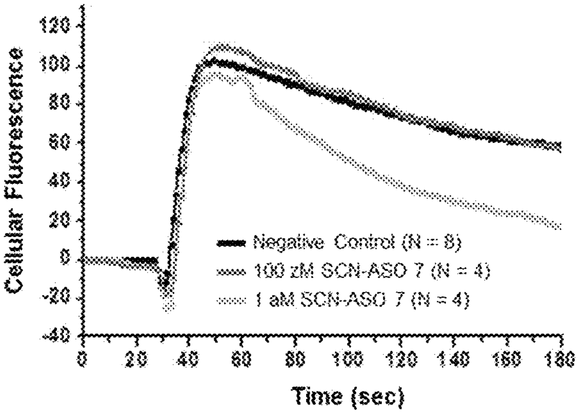
FIG. 30A. CoroNa assay results in PC3 cells treated with "SCN-ASO 7" for 30 hours at 0 (negative control), 100 or 1,000 zM.

[CoroNa Assay] 30 hours later, the cells were washed with 2 mL HBSS (Hank's Balanced Salt Solution, Cat. Number 14025-092, Life Technologies), and then charged with 2 mL fresh HBSS. Then the cells were treated with 5 μM "CoroNa Green" (Cat. Number C36676, Life Technologies) at 37° C. 30 min later, the cells were washed 2× with 2 mL HBSS, and charged with 2 mL fresh HBSS. The culture dish was mounted on an Olympus fluorescence microscope equipped with a digital video camera to continuously capture the green fluorescence images of the cells. The cells were acutely treated with 100 mM NaCl, and then the changes in fluorescence cellular images were digitally recorded over a period of 3 min. There were about 4 cells per frame on average. The fluorescence intensities from each individual cell were traced at the resolution of a second. The traces of the intracellular fluorescence intensities from individual cells were overlaid and averaged at each time point. The average of the traces from the individual cells of each ASO concentration were plotted as provided in FIG. 30A using ImageJ program (version 1.50i, NIH). The average fluorescence intensity trace was taken as the individual intracellular sodium concentration trace for the cells treated with "SCN-ASO 7" at 0 (negative control), 100 or 1,000 zM.

[CoroNa Assay Results] The observed traces of intracellular fluorescence intensity are summarized in FIG. 29B. The fluorescence intensity trace for the cells treated with 1,000 zM "SCN-ASO 7" runs lower than the trace for the cells without ASO treatment. The average fluorescence intensity of the cells without ASO treatment was 81.86 (arbitrary unit) at 100 sec. In the meantime, the average fluorescence intensity of the cells treated with 1,000 zM "SCN-ASO 7" was 51.47 (arbitrary unit) at 100 sec. Thus, the 30 hour incubation with 1,000 zM "SCN-ASO 7" induced a significant reduction of the sodium channel activity by 37% ($p<0.05$ by student's t-test) in PC3 cells. Considering that PC3 cells express various subtypes of voltage-gated sodium channel (VGSC), the 37% decrease is taken as marked for the inhibition of $Na_v1.7$ expression by "SCN-ASO 7". There was no notable decrease in the sodium current in the cells treated with 100 zM "SCN-ASO 7".

SCN9A Example 6. Inhibition of Sodium Current by Corona Assay in PC3 Cells Treated with "SCN-ASO 3"

"SCN-ASO 3" was evaluated for its ability to inhibit the sodium current in PC3 cells using "CoroNa Green" according to the protocol described in "SCN9A Example 5", unless noted otherwise.

Figure 30B:
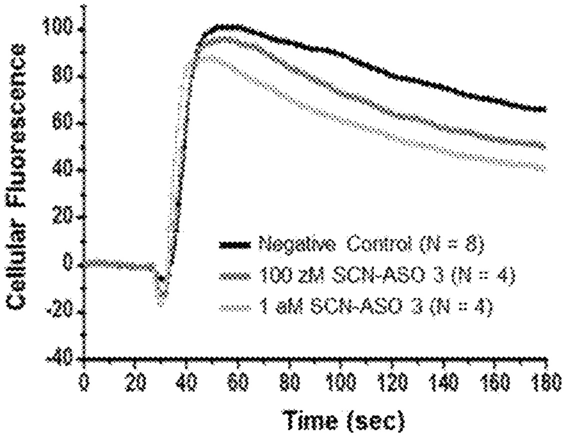
FIG. 30B. CoroNa assay results in PC3 cells treated with "SCN-ASO 3" for 30 hours at 0 (negative control), 100 or 1,000 zM.

The observed traces of cellular fluorescence intensity are provided in FIG. 30B. The average trace of the fluorescence intensity runs lower in the cells treated with "SCN-ASO 3" than in the cells without ASO treatment. The average cellular fluorescence intensity of the cells without ASO treatment was 89.32 (arbitrary unit) at 100 sec. In the meantime, the average cellular fluorescence intensity of the cells treated with 1,000 zM "SCN-ASO 3" was 61.36 (arbitrary unit) at 100 sec. Thus 1,000 zM "SCN-ASO 3" significantly ($p<0.01$) decreased the sodium current by 31% in PC3 cells. The decrease induced by 100 zM "SCN-ASO 3" was 18% although without significance.

SCN9A Example 7. Inhibition of Sodium Current in PC3 Cells Treated with "SCN-ASO 8"

"SCN-ASO 8" was evaluated for its ability to inhibit the sodium current in PC3 cells using "CoroNa Green" according to the protocol described in "SCN9A Example 3", unless noted otherwise.

Figure 30C:
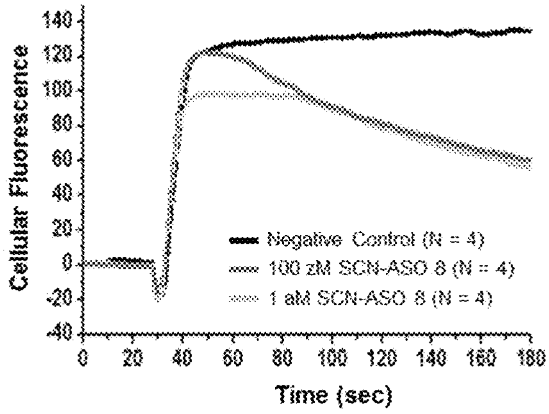
FIG. 30C. CoroNa assay results in PC3 cells treated with "SCN-ASO 8" for 30 hours at 0 (negative control), 100 or 1,000 zM.

The observed traces of cellular fluorescence intensity are provided in FIG. 30C. The average trace of the fluorescence intensity runs lower in the cells treated with "SCN-ASO 8"

than in the cells without ASO treatment. The average cellular fluorescence intensity of the cells without ASO treatment was 130.32 (arbitrary unit) at 100 sec. In the meantime, the average cellular fluorescence intensity of the cells treated with 1,000 zM "SCN-ASO 8" was 89.7 (arbitrary unit) at 100 sec. Thus 1,000 zM "SCN-ASO 8" significantly (p<0.001) decreased the sodium current by 31% in PC3 cells. The decrease induced by 100 zM "SCN-ASO 8" was 30% (p<0.001).

SCN9A Example 8. Exon Skipping Induced by "SCN-ASO 27" in PC3 Cells (A)

"SCN-ASO 27" specified in Table 5 is a 14-mer ASO fully complementary to the 3' splice site spanning the junction of "intron 3" and "exon 4" in the human SCN9A pre-mRNA. The 14-mer target sequence within the 3' splice site is marked "bold" and "underlined" in the 20-mer SCN9A pre-mRNA sequence of

[(5'→3') uuguguuuag|GUACACUUUU (SEQ ID NO: 88)].

"SCN-ASO 27" possesses a 6-mer overlap with "intron 3", and an 8-mer overlap with "exon 4".

"SCN-ASO 27" was evaluated for its ability to induce the skipping of "exon 4" in PC3 cells as described in "SCN9A Example 1", unless noted otherwise.

[Cell Culture & ASO Treatment] PC3 cells grown in 60 mm culture dish containing 5 mL culture medium were treated with "SCN-ASO 27" at 0 (negative control), 1, 10 or 100 zM.

[Nested PCR Amplification] 1 μL of cDNA was further amplified in a 20 μL nested PCR reaction (Cat. Number K2612, Bioneer) against a set of exon-specific primers of [SCN-exon 2n_forward: (5'→3') CCACCGGACTGGACCAAAAA (SEQ ID NO: 89); and SCN-exon 9n_reverse: (5'→3') GCTAAGAAGGCCCAGCTGAA (SEQ ID NO: 90)] according to the following cycle conditions: 95° C. for 2 min followed by 34 cycles of 30 sec at 95° C., 30 sec at 55° C., and 1 min at 72° C.

Figure 31A:
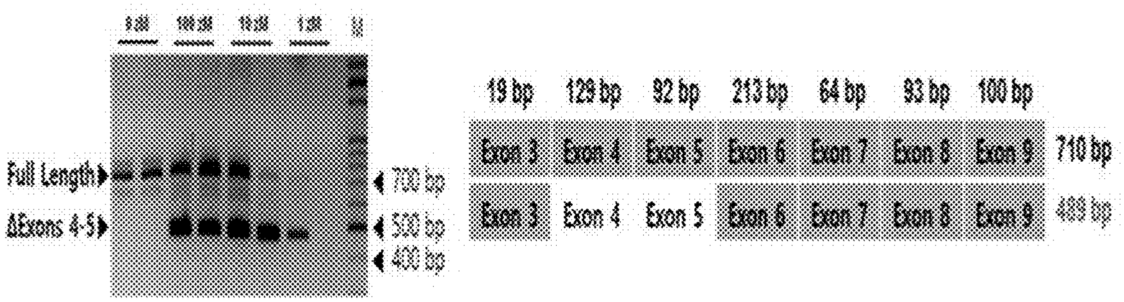
FIG. 31A. Electrophoresis data of SCN9A nested RT-PCR products in PC3 cells treated with "ASO 27" for 24 hours at 0 (negative control), 10, or 100 zM.
Figure 31B:
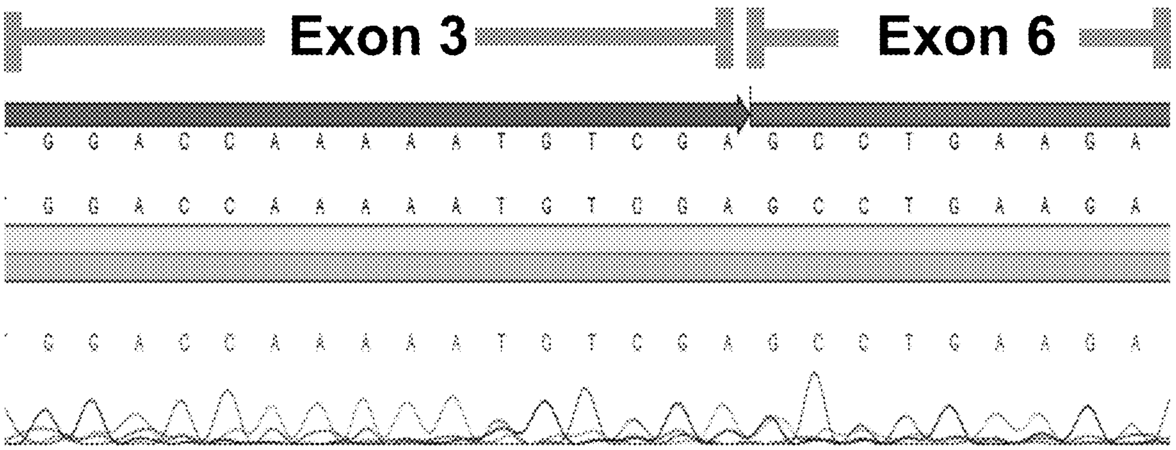
FIG. 31B. Sanger sequencing data for the PCR product band assigned to the skipping of exons 4-5.

[Identification of Exon Skipping Products] FIG. 31A provides the electrophoresis data of the nested PCR products, in which the cells treated with "SCN-ASO 27" yielded a strong PCR band assignable to the skipping of exons 4-5. However, the PCR band intensity for the full-length SCN9A mRNA was stronger in treatment samples of 10 zM and 100 zM ASO than in the samples of the negative control. The strange dose response pattern in the nested PCR could be due to a transcription upregulation induced by the "exon intron circular RNA (EIciRNA)" accumulated during the exon skipping by "SCN-ASO 27". [*Nature Struc. Mol. Biol.* vol 22(3), 256-264 (2015)] The exon skipping PCR product was confirmed by Sanger sequencing to correspond to the skipping of exons 4-5. (cf. FIG. 31B)

SCN9A Example 9. Exon Skipping Induced by "SCN-ASO 27" in PC3 Cells (B)

"SCN-ASO 27" was evaluated for its ability to induce the skipping of "exon 4" in PC3 cells as described in "SCN9A Example 8", unless noted otherwise. In this experiment, PC3 cells were treated with "SCN-ASO 27" at 0 (negative control), 1, 10, 100 and 1,000 aM for 24 hours.

[Nested PCR Amplification] The nested PCR reaction was carried out against a set of primers of [SCN-exon 3/6_forward: (5'→3') GGACCAAAAATGTCGAGCCT (SEQ ID NO: 91); and SCN-exon 9n_reverse: (5'→3') GCTAAGAAGGCCCAGCTGAA (SEQ ID NO: 92)] designed to selectively amplify the product possessing the junction sequence of exon 3 and exon 6.

It is noted that the primer sequence of "SCN-exon 3/6_forward" targets the junction of exon 3 and exon 6 to probe the skipping of exons 4-5, although the 20-mer primer still retains a 17-mer complementary overlap with the junction of exon 3 and exon 4. Thus the primer sequence of "SCN-exon 3/6_forward" recognizes "the junction of exon 3 and exon 6" more selectively than "the junction of exon 3 and exon 4" found in the full length SCN9A mRNA. The primer sequence was designed to detect the SCN9A splice variant lacking exons 4-5 more sensitively than the full length SCN9A mRNA. Such an exon skipping primer would be useful to detect mRNA splice variants with poor metabolic stability, since full-length mRNAs tend to show good metabolic stability gained through the evolution over billions years.

Figure 31C:
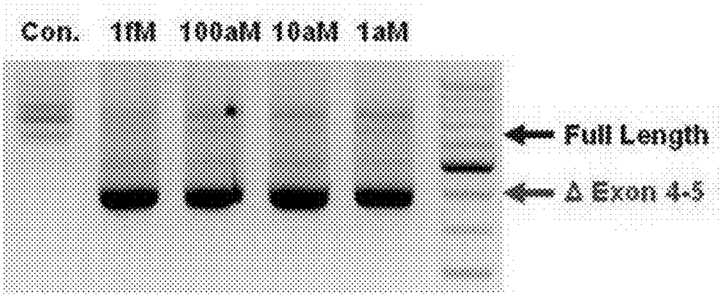
FIG. 31C. Electrophoresis data of SCN9A nested RT-PCR products in PC3 cells treated with "ASO 27" at 0 (negative control), 1, 10, 100 or 1,000 aM.

FIG. 31C provides the electrophoresis data of the nested PCR products, in which the cells treated with "SCN-ASO 27" yielded a strong PCR band assignable to the skipping of exons 4-5, which was confirmed by Sanger sequencing.

SCN9A Example 10. qPCR by One Step cDNA Synthesis for SCN9A mRNA in PC3 Cells Treated with "SCN-ASO 27"

"SCN-ASO 27" was evaluated by SCN9A nested qPCR for its ability to induce changes in the human SCN9A mRNA level in PC3 cells as described in "SCN9A Example 2" unless noted otherwise.

[ASO Treatment] PC3 cells were treated with "SCN-ASO 27" at 0 (negative control), 0.1, 1 or 10 aM for 24 hours. (2 culture dishes per ASO concentration)

[cDNA Synthesis by One-step PCR] 200 ng of RNA template was subjected to a 25 μL reverse transcription reaction using One Step RT-PCR kit (Invitrogen, USA) against a set of exon-specific primers of [SCN-exon 2_forward: (5'→3') CTTTCTCCTTTCAGTCCTCT (SEQ ID NO: 93); and SCN-exon 8/9_reverse: (5'→3') CGTCTGTTGGTAAAGGTTTT (SEQ ID NO: 94)] according to the following cycle conditions: 50° C. for 30 min and 94° C. for 2 min, which was followed by 15 cycles of 30 sec at 94° C., 30 sec at 55° C., and 2 min at 72° C.

[Nested qPCR Amplification] 1 μL of each cDNA solution diluted by 100× was subjected to a 20 μL Real-Time PCR reaction against a set of exon-specific primers of [SCN-exon 3_forward: (5'→3') TGACCATGAATAACCCAC (SEQ ID NO: 95); and SCN-exon 4_reverse(2): (5'→3') GCAAGGATTTTTACAAGT (SEQ ID NO: 96)] according to the following cycle conditions: 95° C. for 30 sec followed by 40 cycles 5 sec at 95° C., and 30 sec at 60° C. The qPCR reaction was monitored with a TaqMan probe of [(5'→3') 5,6-FAM-GGACCAAAA-Zen-ATGTCGAGTACAC-3IABkFQ (SEQ ID NO: 97)] targeting the junction of exon 3 and exon 4 in the full-length SCN9A mRNA.

Figure 32A:
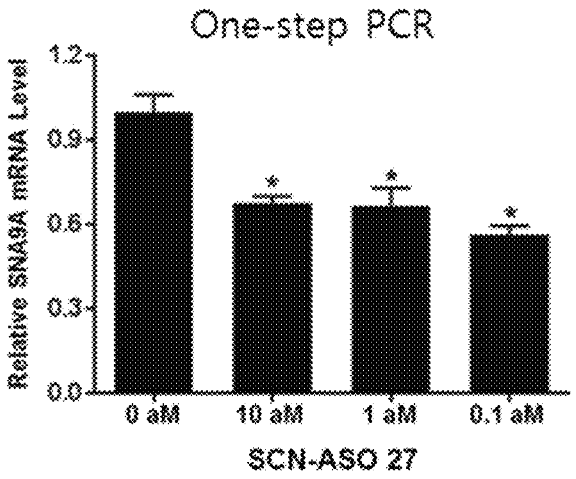
FIG. 32A. SCN9A qPCR data by one-step cDNA synthesis in PC3 cells treated with "SCN-ASO 27" at 0 (negative control), 0.1, 1 or 10 aM for 24 hours. (error bar by standard error)

The full-length SCN9A mRNA level significantly decreased (by student's t-test) in the cells treated with "SCN-ASO 27" by ca 35 to 45% as provided in FIG. 32A.

SCN9A Example 11. qPCR by cDNA Synthesis with Random Hexamers for SCN9A mRNA in PC3 Cells Treated with "SCN-ASO 27"

"SCN-ASO 27" was evaluated by SCN9A qPCR for its ability to induce changes in the human SCN9A mRNA level in PC3 cells as described in "SCN9A Example 10", unless noted otherwise. cDNA was synthesized using random hexamers, and subjected to SCN9A qPCR reaction using the TaqMan probe.

Figure 32B:
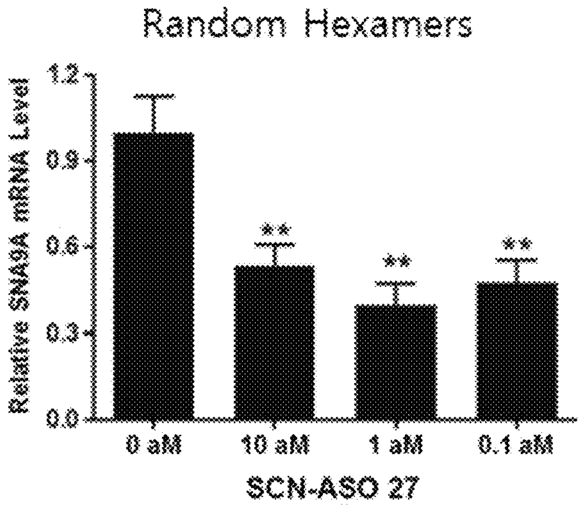
FIG. 32B. SCN9A qPCR data by cDNA synthesis with random hexamer in PC3 cells treated with "SCN-ASO 27" at 0 (negative control), 0.1, 1 or 10 aM for 24 hours. (error bar by standard error)

The full-length SCN9A mRNA level significantly decreased (student's t-test) in the cells treated with "SCN-ASO 27" by ca 50 to 60% as provided in FIG. 32B.

SCN9A Example 12. Inhibition of Sodium Current by CoroNa Assay in SNL-Activated Rat L5 DRG Cells by "SCN-ASO 27"

"SCN-ASO 27" is a 14-mer SCN9A ASO fully complementary to the human SCN9A pre-mRNA, but possesses a single mismatch the rat SCN9A pre-mRNA read out from the rat genomic DNA [NCBI Reference Sequence: NC_000002.12]. "SCN-ASO 27" possesses a 13-mer complementary overlap and a single mismatch with the rat SCN9A pre-mRNA as marked "bold" and "underlined" in the 20-mer rat pre-mRNA sequence of

[(5'→3') uuuc"c"uuuag|GUACACUUUU (SEQ ID NO: 98)], in which the single mismatch is marked with a quote (" ") sign.

"SCN-ASO 27" was evaluated for its ability to inhibit the sodium ion current in rat DRG (dorsal root ganglion) cells using "CoroNa Green" as follows.

[Spinal Nerve Ligation] Spinal nerve ligation (SNL) induces neuropathy in the dorsal root ganglia (DRG) and spinal cord, and has been widely used as a model for neuropathic pains. [*Pain* vol 50(3), 355-363 (1992)] Depending on how spinal nerve(s) is ligated, however, there can be several variations of SNL. The degree and duration of neuropathy in DRG appears to vary depending on how spinal nerve(s) is ligated. [*Pain* vol 43(2), 205-218 (1990)] The dual ligation of the L5 and L6 spinal nerve (i.e., "L5/L6 ligation") induces neuropathy more severe and persisting longer than the ligation of the L5 spinal nerve alone (i.e., "L5 ligation").

[SNL Surgery by L5/L6 Ligation] In Day 0, 6 weeks old male SD rats were anesthetized with zoletil/rompun. Then the L5 and L6 spinal nerve (left side) were exposed and tightly ligated. The muscle and skin were closed and clipped by due aseptic procedures. The rats were sporadically sensitized by von Frey scoring over a period of 4 weeks.

[Preparation of DRG Neuronal Cells] In Day 31, a rat showing a low von Frey score was sacrificed to extract both the left (ligated side) and the right (non-ligated side) DRG. The DRGs were immersed in 0.5 mL PBS immediately after the extraction. DRG cells were prepared as follows according to the procedures disclosed in the literature. [*Methods Mol Biol.* vol 846, 179-187 (2012); *PLOS One* vol 8(4); e60558 (2013)]

① DRG was immersed in a 1.5 mL e-tube containing 0.2 mL 0.125% collagenase (Collagenase Type IV, Cat. No. C5138-100MG, Sigma) in HBSS (Hank's Balanced Salt Solution, Cat. Number 14025-092, Life Technologies), chopped with scissors into small pieces, and incubated for 20 min in a $CO_2$ incubator at 37° C. under 5% $CO_2$ and 95% RH; ② 50 μL 0.25% trypsin/EDTA was added to the e-tube, which was kept in the incubator for another 10 min; ③ the e-tube was charged with 1 mL complete DMEM medium, and subjected to centrifugal sedimentation at 600 g for 5 min; ④ the resulting pellet was suspended in 4 mL Neurobasal-A medium (Neurobasal® Medium, Cat. No. 21103-049, Gibco) supplemented with 2× B-27 (B-27® Serum-Free Supplement, Cat. No. 17504-044, Gibco), 1× penicillin-streptomycin, 1× L-glutamine, and 1 mL of the cell suspension was carefully seeded onto a laminin-coated cover glass (Cat. No. GG-25-1.5-laminin, Neuvitro) placed in a 35 mm culture dish; ⑤ one day after the seeding, the dish was carefully charged with another 1 mL fresh Neurobasal-A medium; ⑥ two days after the seeding, the medium was replaced with 2 mL fresh Neurobasal-A medium supplemented with 1 aM Ara-C(Cat. No. C1768-100MG, Sigma) to selectively suppress the growth of cells other than DRG neuronal cells; ⑦ four days after the seeding, the medium was replaced again with 2 mL fresh Neurobasal-A medium supplemented with 1 μM Ara-C; and ⑧ five or six days after the seeding, DRG neuronal cells were treated with "SCN-ASO 27".

Figure 33A:
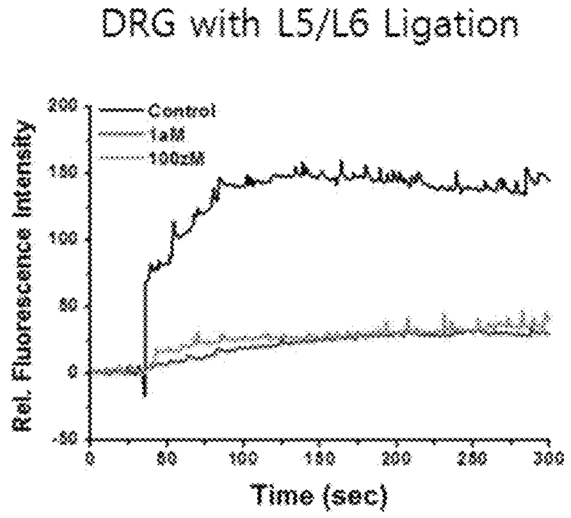
FIG. 33A. Average traces of the cellular fluorescence intensity in rat L5 DRG cells (stimulated with L5/L6 ligation) treated with "SCN-ASO 27" at 0 (negative control), 100 or 1,000 zM.
Figure 33B:
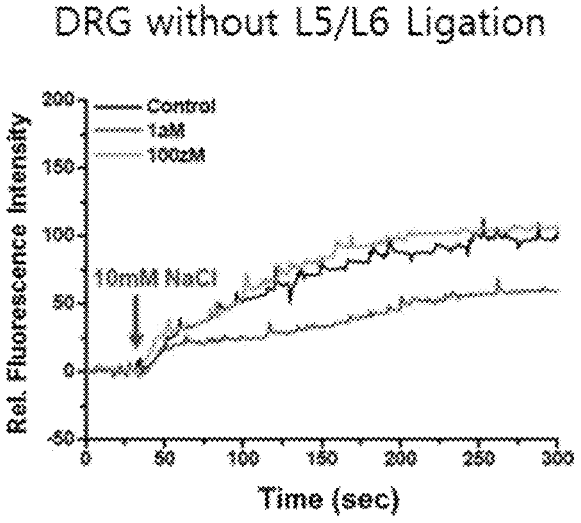
FIG. 33B. Average traces of the cellular fluorescence intensity in rat L5 DRG cells (without L5/L6 ligation treated with "SCN-ASO 27" at 0 (negative control), 100 or 1,000 zM.

[ASO Treatment & CoroNa Assay] L5 DRG neuronal cells either with L5/L6 ligation or without L5/L6 ligation were treated with "SCN-ASO 27" at 0 (negative control), 100 or 1,000 zM. 30 hours later, the cells were washed with 2 mL HBSS, and then charged with 2 mL fresh HBSS. Then the cells were treated with 5 μM "CoroNa Green" at 37° C. 30 min later, the cells were washed 2× with 2 mL HBSS, and charged with 2 mL fresh HBSS. The culture dish was mounted on a fluorescence microscope equipped with a CCD camera to continuously capture the green fluorescent images of the cells. The cells were acutely treated with 10 mM NaCl, and then the changes in the cellular fluorescent intensity were digitally recorded over a period of 300 sec. There were 4 to 5 cells per frame for image capturing. The fluorescence intensities from each individual cell were traced at a resolution of a second. The traces of the intracellular fluorescence intensities from individual cells were averaged using ImageJ program (version 1.50i, NIH), and the average traces are provided in FIGS. 33A and 33B for the cells with "L5/L6 ligation" and without "L5/L6 ligation", respectively. The average fluorescence intensity trace was taken as the individual intra-cellular sodium concentration trace for the cells treated with "SCN-ASO 27" at 0 (negative control), 100 or 1,000 zM.

[CoroNa Assay Results] In the cells stimulated with L5/L6 ligation (cf. FIG. 33A), the 30 hrs treatment with "SCN-ASO 27" at 100 zM or 1 aM yielded a significant decrease (by student's t-test) in the average cellular fluorescence intensity by 80 to 85% at the time point of 150 sec.

In the cells without L5/L6 ligation (cf. FIG. 33B), the 30 hrs treatment with "SCN-ASO 27" at 1 aM yielded a decrease of ca 50% in the fluorescence intensity. In case of the non-stimulated cells treated with "SCN-ASO 27" at 100 zM, there was no decrease in the fluorescence intensity. The fluorescence intensity of the cells without L5/L6 ligation was considerably smaller than that of the cells stimulated with L5/L6 ligation, which would suggest that L5/L6 induce a marked upregulation of the $Na_v1.7$ sodium channel activity.

DRG neuronal cells without neuropathic stimulation are known to express various subtypes of VGSC including $Na_v1.7$, $Na_v1.8$, $Na_v1.2$ and so on. $Na_v1.7$ subtype shows a limited contribution to the whole sodium current in DRG neuronal cells without stimulation. [*Nature Comm.* vol 3, Article Number 791: DOI:10.1038/ncomms1795 (2012)] The DRG neuronal cells without L5/L6 ligation may show a limited contribution of the sodium current from $Na_v1.7$ subtype.

In the meantime, neuronal cells are known to upregulate $Na_v1.7$ expression in response to persisting neuropathy. [*J*

*Biol Chem*. vol 279(28), 29341-29350 (2004); *J Neurosci*. vol 28(26), 6652-6658 (2008)] "SCN-ASO 27" at both 100 zM and 1 aM inhibited the sodium current by 80 to 85% in the neuronal cells stimulated by "L5/L6 ligation". The higher inhibition of the sodium current by "SCN-ASO 27" in the DRG cells with "L5/L6 ligation" is consistent with the upregulation of $Na_v1.7$ in neuronal cells due to chronic neuropathy.

SCN9A Example 13. Inhibition of $Na_v1.7$ Protein Expression in L5 DRG Neuronal Cells by "SCN-ASO 30"

"SCN-ASO 30" is a 14-mer ASO fully complementary to the rat SCN9A pre-mRNA, whilst "SCN-ASO 27" is a 14-mer ASO fully complementary to the human SCN9A pre-mRNA. "SCN-ASO 30" possesses a single mismatch with "SCN-ASO 27" in the C-terminal end. "SCN-ASO 30" against the rat SCN9A pre-mRNA may serve as a good model ASO for "SCN-ASO 27" against the human SCN9A pre-mRNA.

"SCN-ASO 30" was evaluated for its ability to inhibit the expression of $Na_v1.7$ protein in rat DRG neuronal cells as described below.

[Preparation of DRG Neuronal Cells] Male SD rats (7 weeks old) were subjected to tight "L5/L6 ligation". 7 days later, 4 rats were anesthetized with zoletil/rompun to sample the L5 DRG of the ligated side. The DRGs were pooled and processed to prepare DRG neuronal cells as described in "SCN9A Example 12".

[ASO Treatment] DRG neuronal cells were treated with "SCN-ASO 30" at 0 (negative control), 10, 100 or 1,000 zM for 24 hours, and then subjected to lysis for western blot against a $Na_v1.7$ antibody (Cat. No. ab85015, Abcam) probing the C-terminal of the $Na_v1.7$ protein. β-actin was probed for reference.

Figure 34A:
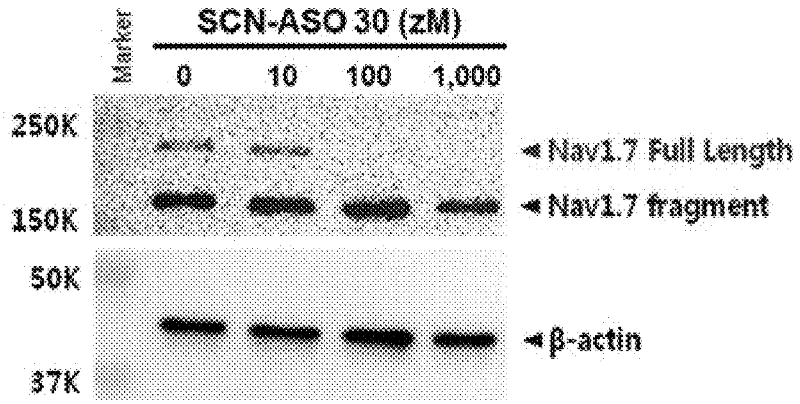
FIG. 34A. Western blot data for Nav1.7 protein expression in DRG neuronal cells (stimulated with L5/L6 ligation) treated with "SCN-ASO 30" for 24 hours at 0 (i.e., negative control), 10, 100 or 1,000 zM.

[Inhibition of $Na_v1.7$ Expression] FIG. 34A provides the western blot data obtained in the DRG neuronal cells treated with "SCN-ASO 30" at 0 (negative control), 10, 100 or 1,000 zM. All the lysates yielded a strong band at 170K, which would be assignable to a fragment or metabolite of the full-length $Na_v1.7$ protein. The full-length $Na_v1.7$ protein band was detected at 220-240K only with the lysates of the negative control and 10 zM "SCN-ASO 30". Thus $Na_v1.7$ expression was markedly inhibited in rat DRG neuronal cells following a 24 hour incubation with "SCN-ASO 30" at 100 and 1,000 zM.

SCN9A Example 14. Inhibition of Sodium Current in Rat L5 DRG Neuronal Cells by "SCN-ASO 30"

"SCN-ASO 30" was evaluated for its ability to inhibit the sodium current in rat L5 DRG neuronal cells stimulated with L5/L6 ligation as provided below.

[Preparation of DRG Neuronal Cells] Male SD rats (6 weeks old) were subjected to tight "L5/L6 ligation". 7 days later, rats were anesthetized with zoletil/rompun for the extraction of L5 DRG of the ligated side. L5 DRG neuronal cells were prepared as follows: ① DRG was immersed in a 1.5 mL e-tube containing 0.2 mL 0.125% collagenase in HBSS, chopped with scissors into small pieces, and incubated for 20 min in a $CO_2$ incubator at 37° C. under 5% $CO_2$ and 95% RH; ② 50 μL 0.25% trypsin/EDTA was added to the e-tube and the e-tube was kept in the incubator for another 10 min; ③ the e-tube was charged with 1 mL complete DMEM medium, and subjected to centrifugal sedimentation at 600 g for 5 min; ④ then the resulting pellet was suspended in 4 mL Neurobasal-A medium (Neurobasal® Medium, Cat. No. 21103-049, Gibco) supplemented with 2× B-27 (B-27® Serum-Free Supplement, Cat. No. 17504-044, Gibco), 1× penicillin-streptomycin, 1× L-glutamine; ⑤ the suspension of DRG cells was transported for about an hour as sealed in a 15 mL falcon tube containing ca 15 mL Neurobasal-A medium; ⑥ 0.5 mL of the cell suspension was carefully seeded onto a laminin-coated cover glass placed in a well of 24-well plate culture dish; ⑦ the cells seeded in the culture plate were incubated in a $CO_2$ incubator at 37° C. for 2 hours to attach cells onto the cover glass, and then treated with "SCN-ASO 30" at 0 (negative control) or 100 zM for 4 hours in the incubator; and ⑧ the DRG neuronal cells were subjected to sodium current measurement by manual patch clamp assay on a sodium patch clamp apparatus (Axopatch 200B Amplifier, Axon Instruments).

Figure 34B:
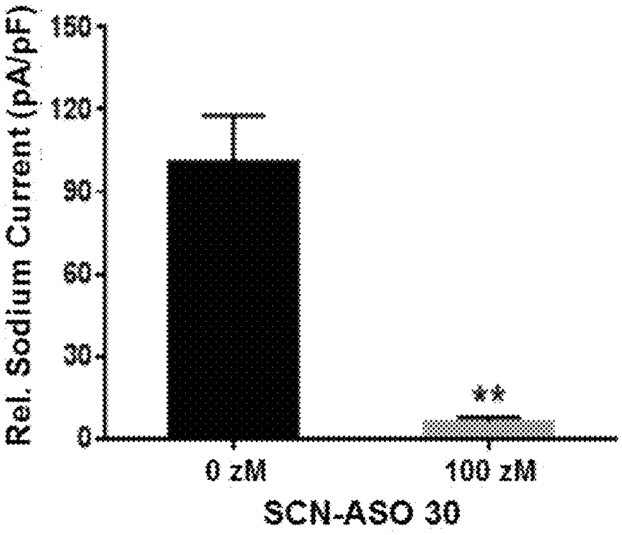
FIG. 34B. Sodium current by manual patch clamp assay in DRG neuronal cells (stimulated with L5/L6 ligation) treated with "SCN-ASO 30" for 4 hours at 0 (negative control) and 100 zM. (error bar by standard error)

[Patch Clamp Assay Results] FIG. 34B provides the sodium current data normalized against the cell size. Upon an incubation with 100 zM "SCN-ASO 30" for 4 hours, the sodium current significantly ($p<0.01$ by student's t-test) decreased by ca 90% in DRG neuronal cells expressing tetrodotoxin sensitive sodium channels, i.e. neuronal cells of small size. (N=4 cells per group)

SCN9A Example 15. qPCR by One Step cDNA Synthesis for SCN9A mRNA in Rat DRG Cells Treated with "SCN-ASO 30"

"SCN-ASO 30" was evaluated by SCN9A nested qPCR for its ability to inhibit the expression of the SCN9A mRNA in rat DRG cells as follows.

[Preparation of L5 DRG Cells] A 4 weeks old male SD rat was anesthetized with zoletil/rompun to extract the L5 DRGs. The DRG samples were pooled and processed to prepare L5 DRG cells as described in "SCN9A Example 12".

[ASO Treatment] Rat DRG cells were treated with "SCN-ASO 30" at 0 (negative control), 10, 30, 100, 300, or 1,000 zM. (1 culture dish per ASO concentration)

[RNA Extraction & cDNA Synthesis by One Step PCR] 24 hours later, total RNA was extracted from cells using "Universal RNA Extraction Kit" (Cat. Number 9767, Takara) according to the manufacturer's instructions. 200 ng of RNA template was used for a 25 μL reverse transcription reaction using One Step RT-PCR kit (Invitrogen, USA) against a set of exon-specific primers [SCN-exon 2(3)_forward: (5'→3') CAATCTTCCGTTTCAACGCC (SEQ ID NO: 99); and SCN-exon 10_reverse: (5'→3') ACCACAGCCAGGATCAAGTT (SEQ ID NO: 100)] according to the following cycle conditions: 50° C. for 30 min and 94° C. for 2 min, which was followed by 15 cycles of 30 sec at 94° C., 30 sec at 55° C., and 2 min at 72° C.

[Nested qPCR Amplification] 1 μL of each cDNA solution (duplicate per concentration) diluted by 100× was subjected to a 20 μL Real-Time PCR reaction with a TaqMan probe (Cat. No. Rn01514993_mH, ThermoFisher) targeting the junction of SCN9A exon 3 and exon 4 according to the following cycle conditions: 95° C. for 30 sec followed by 40 cycles 5 sec at 95° C., and 30 sec at 60° C.

Figure 35A:
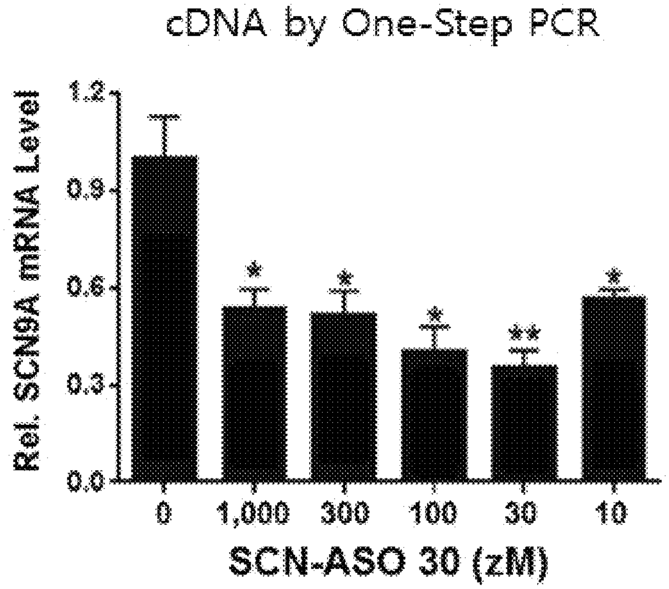
FIG. 35A. SCN9A qPCR data by one-step cDNA synthesis in rat L5 DRG neuronal cells treated with "SCN-ASO 30" for 24 hours at 0 (negative control), 10, 30, 100 or 300 zM. (error bar by standard error)

FIG. 35A provides the qPCR data. The full-length SCN9A mRNA expression level significantly decreased (by student's t-test) in the cells treated with "SCN-ASO 30" by ca 45~60%, although there was a single culture dish per each ASO concentration.

SCN9A Example 16. qPCR by cDNA Synthesis Random Hexamers for SCN9A mRNA in Rat DRG Cells Treated with "SCN-ASO 30"

"SCN-ASO 30" was evaluated by SCN9A qPCR for its ability to inhibit the expression of the SCN9A mRNA in rat L5 DRG cells. Total RNA was prepared as described in "SCN9A Example 15", and subjected to cDNA synthesis using random hexamers. The cDNA solutions (duplicate per ASO concentration) were diluted by 100 times, and 1 μL of each diluted PCR product was subjected to a 20 μL Real-Time PCR reaction with the TaqMan probe targeting the junction of SCN9A exon 3 and exon 4 according to the following cycle conditions: 95° C. for 30 sec followed by 40 cycles 5 sec at 95° C., and 30 sec at 60° C.

The cDNA solutions were also subjected to qPCR amplification for the GAPDH mRNA. The Ct values of the SCN9A mRNA were normalized against the Ct values of GAPDH mRNA.

Figure 35B:
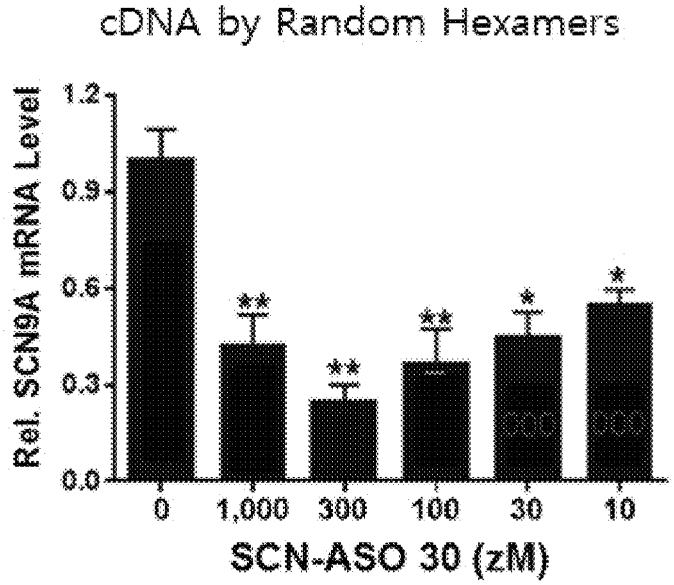
FIG. 35B. SCN9A qPCR data by cDNA synthesis with random hexamer in rat L5 DRG neuronal cells treated with "SCN-ASO 30" for 24 hours at 0 (negative control), 10, 30, 100 or 300 zM. (error bar by standard error)

FIG. 35B provides the SCN9A qPCR data normalized against GAPDH. The full-length SCN9A mRNA expression level significantly decreased (student's t-test) in the cells treated with "SCN-ASO 30" by ca 45-75%.

SCN9A Example 17. Reversal of Allodynia by SCN9A ASOs in Rats with Diabetes-Induced Peripheral Neuropathic Pain The SCN9A gene encodes the α-subunit of VGSC subtype $Na_v1.7$. There are an extremely small number of individuals who do not feel severe pains but are normal in other sensory functions. Such individuals were found to have the SCN9A gene mutated to encode nonfunctional $Na_v1.7$ subtype. [*Nature* vol 444, 894-898 (2006)] This has been termed as "SCN9A channelopathy". The behavioral phenotypes of human SCN9A channelopathy were reproduced fairly much in SCN9A knockout mice. [*PLOS One* 9(9): e105895 (2014)] Thus the SCN9A ASOs of Formula I may show analgesic activity in animal pain models accompanying $Na_v1.7$ upregulation.

"SCN-ASO 7", "SCN-ASO 8", "SCN-ASO 21", "SCN-ASO 35", "SCN-ASO 36" and "SCN-ASO 37" were evaluated for their ability to reverse the allodynia in rats with diabetes-induced peripheral neuropathic pain (DPNP). In this example, the six SCN9A ASOs targeting a total of five splice sites were evaluated for their ability to reverse the allodynia induced by diabetic neuropathy in rats.

[Induction of DPNP and Grouping] Diabetes was induced in rats by an intraperitoneal injection of streptozotocin at 60 mg/Kg in Day 0. In Day 10, rats with DPNP were randomly assigned to 6 groups of negative control (vehicle only), "SCN-ASO 7" 100 pmole/Kg, "SCN-ASO 8" 100 pmole/Kg, "SCN-ASO 21" 100 pmole/Kg, "SCN-ASO 35" 100 pmole/Kg, "SCN-ASO 36" 100 pmole/Kg, and "SCN-ASO 37" 100 pmole/Kg. The animals were grouped based on the von Frey scores of individual animals in Day 10. (N=8-9 per group) Allodynia was scored using a set of microfilaments (Touch Test®) according to the "Up & Down" method. [*J Neurosci. Methods* vol 53(1), 55-63 (1994)]

[ASO Treatment and von Frey Scoring] ASO solutions for injection were prepared by serially diluting aqueous mother stock solutions of the SCN9A ASOs to 100 nM in PBS (phosphate buffered saline). Animals were subcutaneously administered with ASO at 1 mL/Kg in Days 11, 13, 15, 17 and 19. Von Frey scoring was carried out 2 hours post dose in Days 11, 13, 15, 17 and 19. Von Frey scoring was additionally performed in Days 21 and 23 in order to assess the duration of the therapeutic activity after the final dosing. Daily von Frey scores were evaluated for statistical significance by student's t-test against the negative control group (vehicle only, i.e., PBS).

Figure 36:
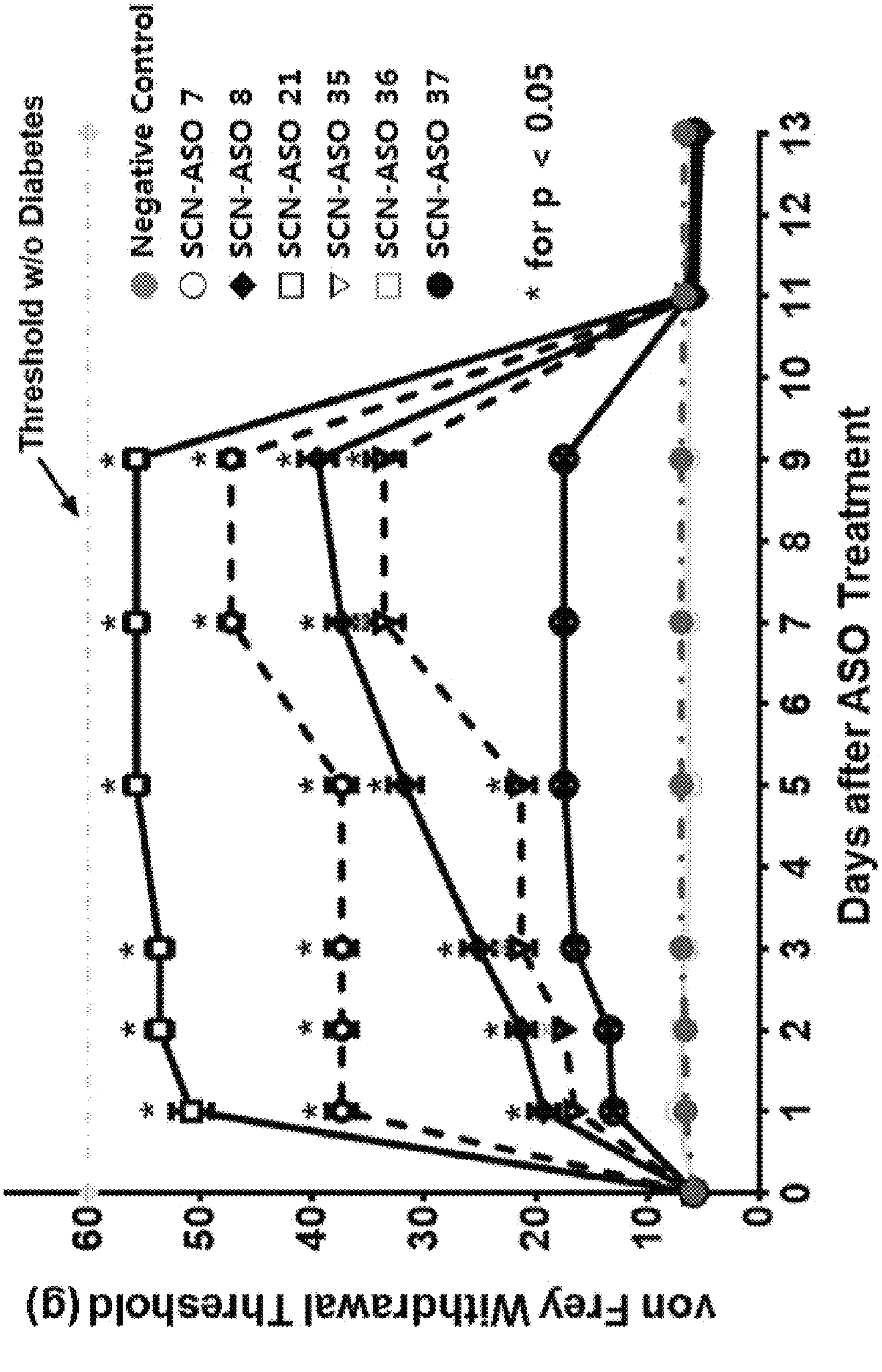
FIG. 36. Reversal of the allodynia induced by DPNP in rats subcutaneously administered with vehicle (PBS, negative control), "SCN-ASO 7" 100 pmole/Kg, "SCN-ASO 8" 100 pmole/Kg, "SCN-ASO 21" 100 pmole/Kg, "SCN-ASO 35" 100 pmole/Kg, "SCN-ASO 36" 100 pmole/Kg, or "SCN-ASO 37" 100 pmole/Kg. (error bar by standard error)

[Therapeutic Activity] The observed von Frey scores are summarized in FIG. 36. The allodynia was significantly reversed by all the ASOs except for "SCN-ASO 36" and "SCN-ASO 37", although "SCN-ASO 37" showed a clear trend of therapeutic activity (p-value=0.057 in Day 19). The therapeutic activity tended to gradually increase as the dosing was repeated. The maximum therapeutic efficacy based on the von Frey scores in Day 19 was ca 76% (significant), 61% (significant), 93% (significant), 52% (significant), 0% and 22% (non-significant, p-value=0.05×) for "SCN-ASO 7", "SCN-ASO 8", "SCN-ASO 21", "SCN-ASO 35", "SCN-ASO 36" and "SCN-ASO 37", respectively.

"SCN-ASO 7", "SCN-ASO 8", "SCN-ASO 21" and "SCN-ASO 35" possess a 5-mer complementary overlap with their target intron. In the meantime, "SCN-ASO 36" and "SCN-ASO 37" possess a 4-mer and 3-mer complementary overlap with their target intron, respectively. Although there are a number of factors affecting the therapeutic efficacy, the number of the complementary overlap with the target intron appears to affect the therapeutic efficacy.

In this example, the in vivo antisense activity was observed with SCN9A ASOs targeting 4 out of 5 splice sites. The hit ratio of 80% is considered to be very high, given that in vivo therapeutic activity depends on various factors including cellular antisense activity, the enrichment of drug molecules in the target tissue, pharmacokinetic half-life, and so on. Thus the compound of Formula I predictably modulates the expression of its target gene.

Given with the molecular weight of "SCN-ASO 7" (cf. Table 4), 100 pmole/Kg is translated into a therapeutic dose of ca 0.53 μg/Kg. The sub-attomolar in vitro exon skipping potency of "SCN-ASO 7" is considered to be largely responsible for the ultra-strong in vivo therapeutic potency of ca 0.53 μg/Kg in rats with diabetic neuropathy. Even more surprisingly, the ASO was administered as "naked" oligonucleotide. Such a strong in vivo therapeutic potency has never been realized with other classes of oligonucleotide including DNA, RNA, PTO, 2'-OMe PTO, 2'-OMe RNA, 2'-OMOE RNA, LNA, PMO, PNA, and so on.

Examples for In Vivo & Ex Vivo Activity of DMD ASOs

Duchenne muscular dystrophy (DMD) is a life-threatening mono-genic rare disease with muscular degeneration. DMD patients do not encode the full-length dystrophin protein due to a PTC (premature termination codon) resulting from a point mutation or deletion of exon(s).

Mdx mouse (C57BL/10ScSn-$Dmd^{mdx}$/J, Jackson Lab) is a mutant mouse with a point mutation in exon 23 of the dystrophin gene, which yields a PTC. Mdx mice encode a truncated form of dystrophin lacking the C-terminal portion. Since the C-terminal portion binds to the extracellular matrix (ECM), the truncated form loses its destined role to tightly link muscle fibers to the ECM. Consequently, mdx mice gradually lose the muscular integrity and strength with age.

Mdx mice have been widely adopted as an animal model for human DMD. Dystrophin ASOs targeting the mouse dystrophin exon 23 have been investigated to eliminate the PTC through the skipping of exon 23.

PNA derivatives of Formula I complementarily targeting either the 3' or the 5' splice site of exon 23 in the mouse dystrophin pre-mRNA were evaluated for their ability to induce the skipping of dystrophin exon 23 in mdx mice. Biological examples provided herein are to illustrate the exon skipping capability of dystrophin ASOs as examples for the compound of Formula I, and therefore should not be interpreted to limit the scope of the current invention to dystrophin ASOs.

DMD Example 1. Exon Skipping Induced by "DMD-ASO 1" and "DMD-ASO 4" in Mdx Mice (Nested PCR Method A)

"DMD-ASO 1" specified in Table 7 is a 13-mer ASO fully complementary to a region in the 3' splice site spanning the junction of intron 22 and exon 23 in the mouse dystrophin pre-mRNA. "DMD-ASO 1" complementarily binds to the 13-mer sequence as marked "bold" and "underlined" in the 25-mer sequence of

[(5'→3') uaauuuugag|GCUCUGCAAAGTTCT (SEQ ID NO: 101)].

"DMD-ASO 1" possesses an 8-mer overlap with intron 22 and a 5-mer overlap with exon 23.

"DMD-ASO 4" specified in Table 7 is a 17-mer ASO fully complementary to a region in the 3' splice spanning the junction of intron 22 and exon 23 in the mouse dystrophin pre-mRNA. "DMD-ASO 4" complementarily binds to the 17-mer sequence as marked "bold" and "underlined" in the 25-mer sequence of

[(5'→3') uaauuuugag|GCUCUGCAAAGTTCT (SEQ ID NO: 102)].

"DMD-ASO 4" possesses a 5-mer overlap with intron 22 and a 12-mer overlap with exon 23.

"DMD-ASO 1" and "DMD-ASO 4" were evaluated for their ability to induce exon skipping in muscles of mdx mice by subcutaneous administration as follows.

[ASO Treatment & Sampling Muscle Tissues] The injection solutions were prepared by diluting an aqueous mother stock solution of "DMD-ASO 1" or "DMD-ASO 4" in PBS to 500 nM. Male mdx mice were subcutaneously administered with vehicle only (negative control), "DMD-ASO 1" or "DMD-ASO 4" at 2 mL/Kg, 2× per day (BID) for 3 days. One day after the final dose, the animals were anesthetized with zoletil/rompun, and sacrificed to sample muscle tissues including the heart, diaphragm, gatrocnemius, quadriceps, and triceps.

[RNA Extraction] Muscle samples were homogenized by grinding in a tube kept on ice, and subjected to total RNA extraction with 1 mL trizol reagent (Invitrogen) per ca 100 mg muscle tissue.

[cDNA Synthesis by One-Step RT-PCR] 500 ng of RNA template was used in a 25 μL reverse transcription reaction using Super Script® One-Step RT-PCR kit with Platinum® Taq polymerase (Cat. Number 10928-042, Invitrogen) and a set of exon-specific primers [DMD-exon 21_forward: (5'→3') CAAAGAGAAAGAGCTACAGACA (SEQ ID NO: 103); and DMD-exon 25_reverse: (5'→3') CTGGGCT-GAATTGTTTGAAT (SEQ ID NO: 104)] according to the following cycle conditions: 50° C. for 30 min and 94° C. for 2 min, which was followed by 40 cycles of 30 sec at 94° C., 1 min at 58° C., and 2 min at 72° C.

[Nested PCR Amplification] 1 μL of cDNA was further amplified in a 20 μL nested PCR (Cat. Number K2612, Bioneer) reaction against a set of primers [DMD-exon 22n_forward: (5'→3') ATCCAGCAGTCAGAAAGCAAA (SEQ ID NO: 105); and DMD-exon 25n_reverse: (5'→3') ACTAAAAGTCTGCATTGT (SEQ ID NO: 106)] according to the following cycle conditions: 95° C. for 5 min followed by 39 cycles of 30 sec at 95° C., 40 sec at 50° C., and 50 sec at 72° C.

Figure 37A:
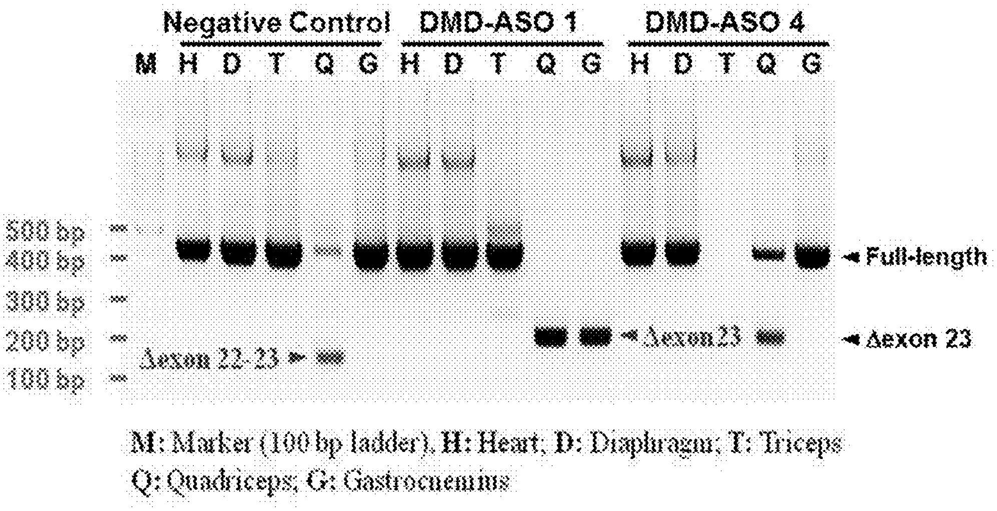
FIG. 37A. Electrophoresis data for the nested PCR (Method A) products obtained with muscle tissues of mdx mice subcutaneously administered with vehicle only (negative control), 1,000 pmole/Kg "DMD-ASO 1", or 1,000 pmole/Kg "DMD-ASO 4", BID for 3 days.

[Identification of Exon Skipping Product] The PCR products were subjected to electrophoretic separation on a 2% agarose gel as provided in FIG. 37A. The skipping of exon 23 was detected only in the animals treated with "DMD-ASO 1" and "DMD-ASO 4". Although the skipping of exon 23 was detected only in the quadriceps and gastrocnemius, "DMD-ASO 1" appears to be more effective than "DMD-ASO 4".

The subject of the negative control (i.e., no ASO treatment) yielded a PCR band assigned to the skipping of exons 22-23 in the quadriceps. The skipping of exons 22-23 yields a frame shift, and the dystrophin mRNA splice variant lacking exons 22-23 is doomed to encode a truncated dystrophin with the C-terminal portion missing.

Figure 37B:
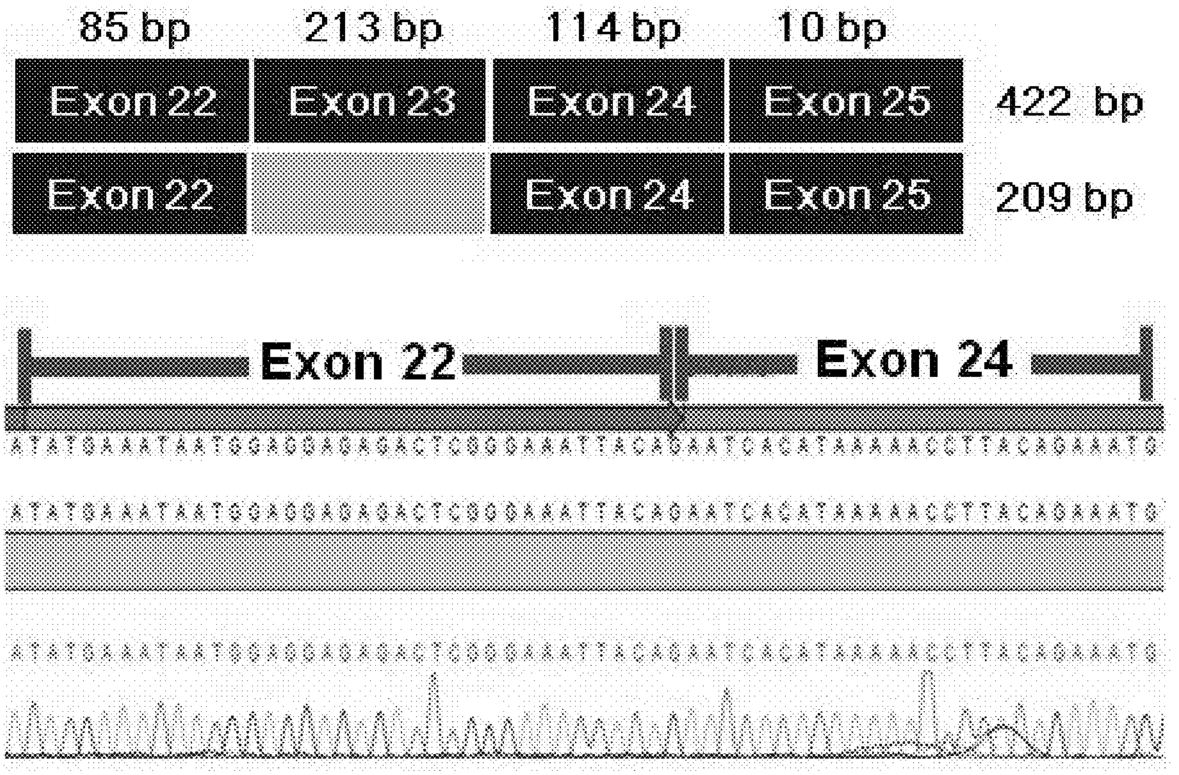
FIG. 37B. Sanger sequencing data for the PCR product band assigned to the skipping of exon 23.

The bands of target size were collected and analyzed by Sanger Sequencing, and confirmed the skipping of exon 23 induced by "DMD-ASO 1" and "DMD-ASO 4". (cf. FIG. 37B) The PCR bands for the full-length (i.e., without skipping) and the skipping of exons 22-23 were confirmed by sequencing, although the sequencing data for the skipping of exons 22-23 was not provided.

DMD Example 2. Exon Skipping Induced by "DMD-ASO 1" and "DMD-ASO 4" in Mdx Mice (Nested PCR Method B)

The RNA samples obtained in "DMD Example 1" were subjected to a one-step cDNA synthesis using a set of exon-specific primers of [DMD-exon 20_forward: (5'→3') CAGAATTCTGCCAATTGCTGAG (SEQ ID NO: 107); and DMD-exon 26_reverse: (5'→3') TTCTTCAGCTT-GTGTCATCC (SEQ ID NO: 108)]. The cDNA samples were then analyzed by nested PCR against another set of exon-specific primers of [DMD-exon 20n_forward: (5'→3') CCCAGTCTACCACCCTAT-CAGAGC (SEQ ID NO: 109); and DMD-exon 26n_reverse: (5'→3') CCTGCCTT-TAAGGCTTCCTT (SEQ ID NO: 110)].

Figure 38A:
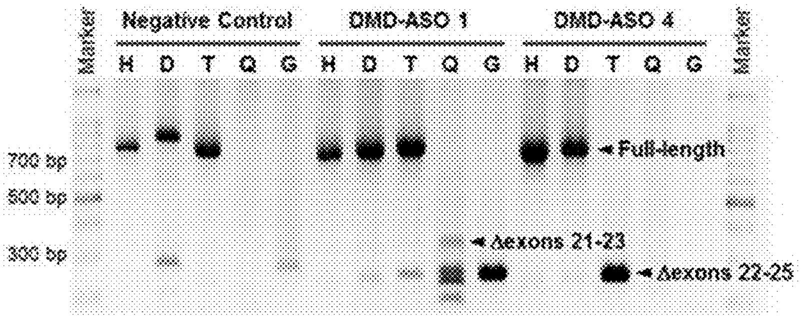
FIG. 38A. Electrophoresis data for the nested PCR (Method B) products obtained with muscle tissues of mdx mice subcutaneously administered with vehicle only (negative control), 1,000 pmole/Kg "DMD-ASO 1", or 1,000 pmole/Kg "DMD-ASO 4", BID for 3 days.
Figure 38B:
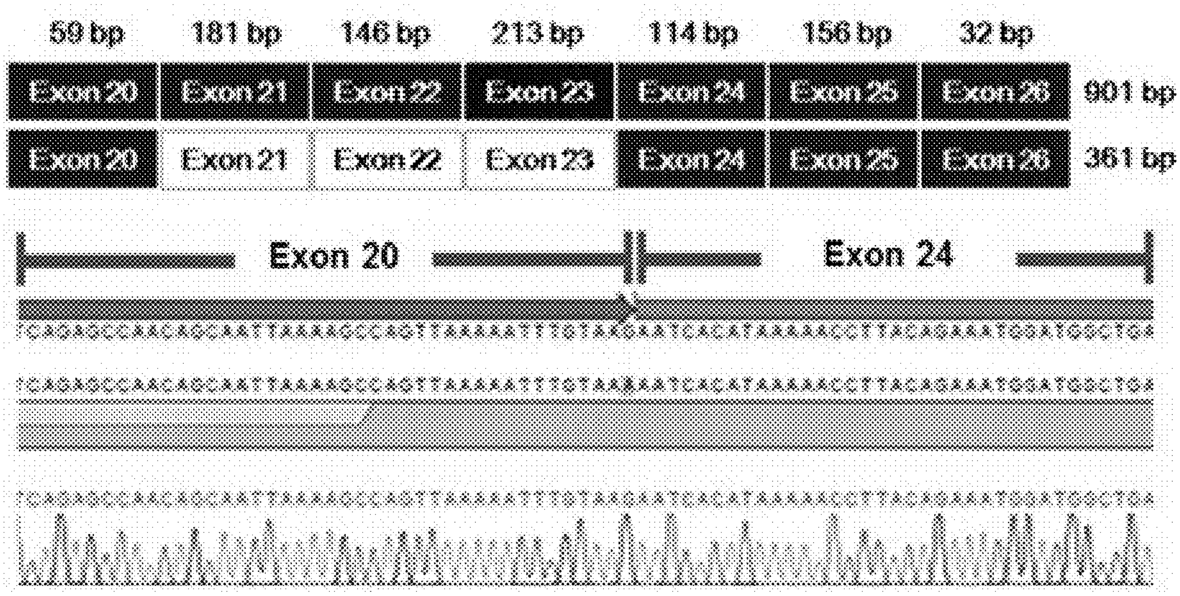
FIG. 38B. Sanger sequencing data for the PCR product band assigned to the skipping of exons 21-23.

The nested RT-PCR outcomes are provided as summarized in FIG. 38A and FIG. 38B. In the ASO treated animals (N=2 per group), the skippings of exons 21-23 and exons 22-25 were detected. While the skipping of exons 21-23 is in frame (i.e., without frame shift), the skipping of exons 22-25 is out of frame. The PCR band assigned to the skipping of exons 21-23 was unambiguously confirmed by Sanger sequencing. (cf. FIG. 38B)

The exon skipping profiles varied depending on the PCR method as provided above. Thus exon skipping profiles should be interpreted with discretion.

DMD Example 3. Exon Skipping Induced by "DMD-ASO 1" in Mdx Mice (Nested PCR Method A)

Mdx mice subcutaneously received "DMD-ASO 1" at 0 (negative control) or 10 pmole/Kg, 2× per day for 5 days. (2 animals per group) One day after the final dose, the animals were sacrificed for tissue sampling. The triceps samples were evaluated for the skipping of exon 23 according to the nested RT-PCR method described in "DMD Example 1".

Figure 38C:
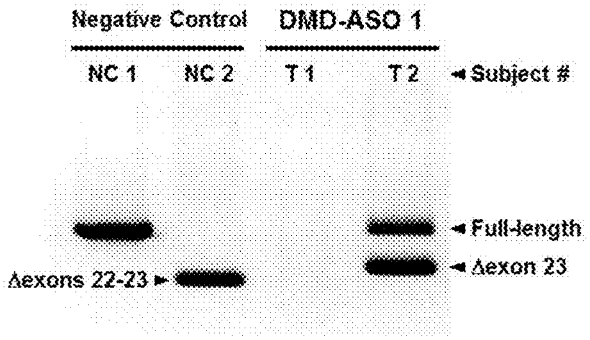
FIG. 38C. Electrophoresis data for the nested PCR (Method A) products obtained with the triceps samples in mdx mice subcutaneously administered with "DMD-ASO 1" at 0 (negative control) or 10 pmole/Kg, BID for 5 days.

The nested RT-PCR outcomes are summarized in FIG. 38C. Although one animal in the negative control group yielded the PCR band for the skipping of exons 22-23, the mRNA splice variant lacking exons 22-23 is out of frame. The PCR band for the skipping of exon 23 was detected only in one animal in the ASO treatment group. Thus DMD-ASO 1 induced the skipping of exon 23 as it was designed to.

DMD Example 4. Improvement of Muscle Function by Rotarod Test in Mdx Mice Subcutaneously Administered with "DMD-ASO 1"

Exon 23 skipping in mdx mice removes the PTC in exon 23, and the mRNA splice variant lacking exon 23 is in frame and therefore encodes a variant protein with the C-terminal portion binding to the ECM. Thus, the full-length variant dystrophin protein partially restores the physiological functions of the original or wild type full-length dystrophin.

Given with the exon skipping potential, "DMD-ASO 1" was evaluated in mdx mice for its ability to improve muscle function by rotarod test as described below.

[Grouping] 6 weeks old male mdx mice were trained for rotarod test over a period of 2 weeks, and then randomly assigned into 3 groups of 0 (negative control), 100 and 1,000 pmole/Kg "DMD-ASO 1" based on individual scores by rotarod test in Day 0, i.e., the day of grouping. (N=10 per group)

[ASO Treatment] The injection solutions were prepared by serially diluting the ASO to 20 nM and 200 nM in PBS. Animals were subcutaneously administered with vehicle (PBS, negative control), 20 nM "DMD-ASO 1" (100 pmole/Kg), or 200 nM "DMD-ASO 1" (1,000 pmole/Kg) at 5 mL/Kg, 3× per week over a period of Day 0 to Day 21.

[Rotarod Test and Statistical Analysis] Mice were subjected to rotarod test on a rotarod apparatus (Model #47650, Ugo Basile) with an acceleration schedule of 4 rpm to 45 rpm over 60 seconds. The latency to fall (i.e., the duration that animal remained on the rotarod) was scored for each individual animal. Statistical significance was evaluated by student's t-test against the negative control group.

Figure 39A:
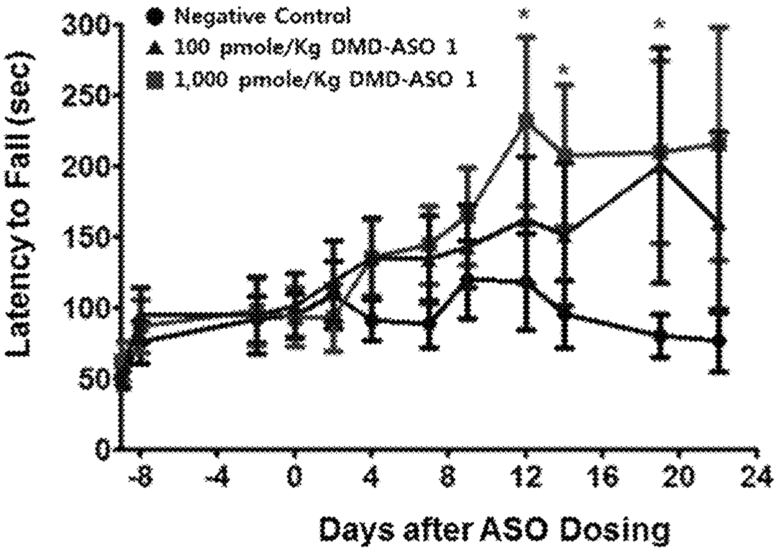
FIG. 39A. Rotarod scores in mdx mice treated with vehicle (negative control), 100 pmole/Kg "DMD-ASO 1" or 1,000 pmole/Kg "DMD-ASO 1". (error bar by standard error and * for $p<0.05$)

[Improvement of Muscle Function] FIG. 39A summarises the rotarod scores by group. The rotarod scores (i.e., latency to fall) remained stagnant at ca 70 to 120 sec on average in the negative control group. In the meantime, the muscle function of the 1,000 pmole/Kg group gradually and markedly improved till Day 12, and then remained stable afterwards at rotarod scores of 210 to 230 sec on average. The muscle function was significantly improved in Days 12, 14 and 19 by the ASO treatment at 1,000 pmole/Kg. The muscle function of the 100 pmole/Kg group showed a strong propensity of improvement, but was not significant.

DMD Example 5. Improvement of Muscle Function by Grip Test and Muscular Integrity in Mdx Mice Chronically Administered with "DMD-ASO 1"

"DMD-ASO 1" was evaluated by chronically administering to mdx mice for its ability to improve muscle function by grip test, to induce exon skipping, to upregulate the expression of the full-length dystrophin (i.e., dystrophin protein with the C-terminus encoded) by IHC, and to improve the muscular integrity by histopathology with H&E staining as described below.

[Grouping & ASO Treatment] Male mdx mice (7 weeks old) were randomly assigned to 4 groups of 0 (mdx negative control), 10, 50, and 200 pmole/Kg "DMD-ASO 1" based on individual grip strength scores by grip test. (N=12 per group) A satellite group of 12 male C57BL/6 mice (7 weeks old) was included in this study as the wild type negative control group for the full-length dystrophin expression level.

The 50 and 200 pmole/Kg group subcutaneously received "DMD-ASO 1" as dissolved in PBS, 2× per week until the final sacrifice in Week 43. In the meantime, the 10 pmole/Kg group subcutaneously received "DMD-ASO 1" initially 2× per week during Week 0 to 8, and 3× per week afterwards to increase the ASO exposure.

[Muscle Function by Grip Test] Muscle function was evaluated on a weekly basis by grip strength on a grip strength-meter (Cat. Number 47,200, Ugo Basile) according to the literature. [*J. Appl. Physiol.* vol 106(4), 1311-1324 (2009)] The grip strength scores by group were evaluated for statistical significance by student's t-test against the mdx negative control group.

Figure 39B:
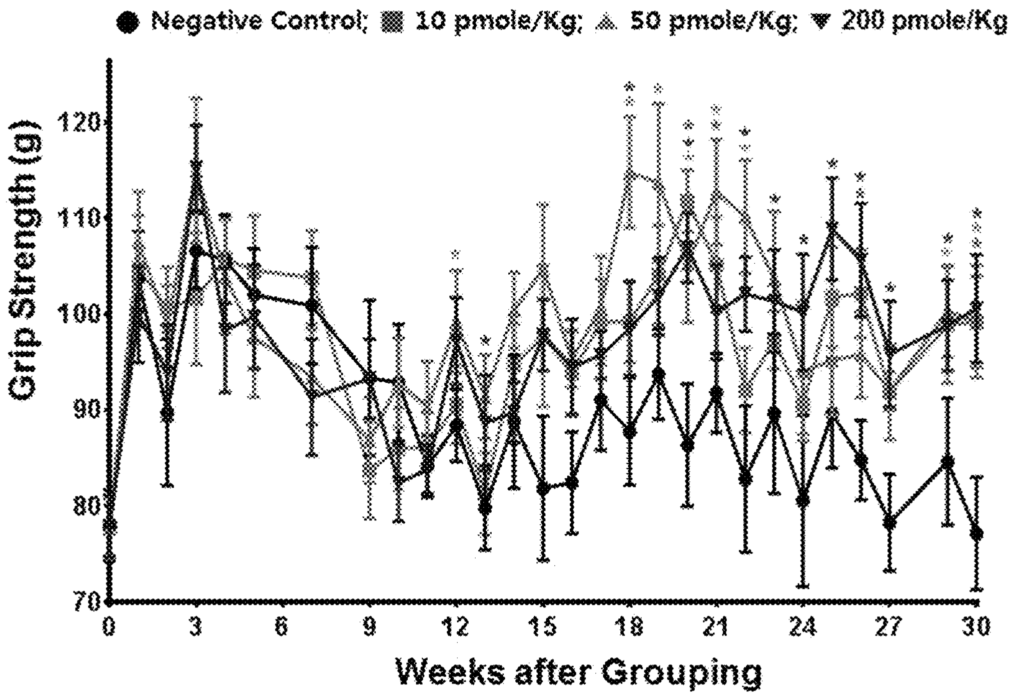
FIG. 39B. Grip strength scores in mdx mice chronically administered with "DMD-ASO 1" at 0 (negative control), 10, 50 or 200 pmole/Kg. (error bar by standard error and * for $p<0.05$)

FIG. 39B summarizes the observed grip strength scores by group during Week 0 to 30. During the first 11 weeks post the first dose, there were no marked changes in the grip strength between the ASO treatment groups and the negative control group. The grip strength of the mdx negative control group hit the maximum of ca 107 g in Week 3, gradually decayed over several weeks, and then remained relatively stable at ca 75 to 95 g. The grip strength of the ASO treatment groups began to gradually improve from Week 10 or so. In the treatment groups, the grip strength tended to increase by 30-50% compared to the mdx negative control group.

It is noted that 2 to 3 animals per group were randomly selected and sacrificed in Weeks 7, 13, 21 and 30 for IHC or nested PCR evaluation. (see below)

[IHC Evaluation of Skeletal Muscles against Full-length Dystrophin] In Weeks 7, 13 and 21, two animals per group were randomly selected and sacrificed to extract muscle tissues. In Week 30, 3 animals were sacrificed per group.

The muscle tissues sampled in Week 7 were subjected to IHC against the full-length dystrophin by cryosection. The muscle tissues sampled in Weeks 13, 21 and 30 were immunostained by paraffin block. IHC by paraffin block yielded images of better quality than IHC by cryosection.

Muscle samples were subjected to immunostaining in series with a primary antibody targeting the C-terminal of mouse dystrophin (Cat. Number sc-816, Santa Cruz) at 1:100 dilution, with a secondary anti-IgG antibody (Cat Number BA-1100, Vector) at 1:200 dilution, and then with Dylight 594-streptavidin (Cat Number SA-5594, Vector, CA, USA) at 1:200 dilution for red fluorescence tagging. The IHC images were captured on a Zeiss slide scanner (in Weeks 13, 21 and 30) or an Olympus fluorescence microscope (in Week 7). DAPI staining was additionally carried out.

Figure 40:
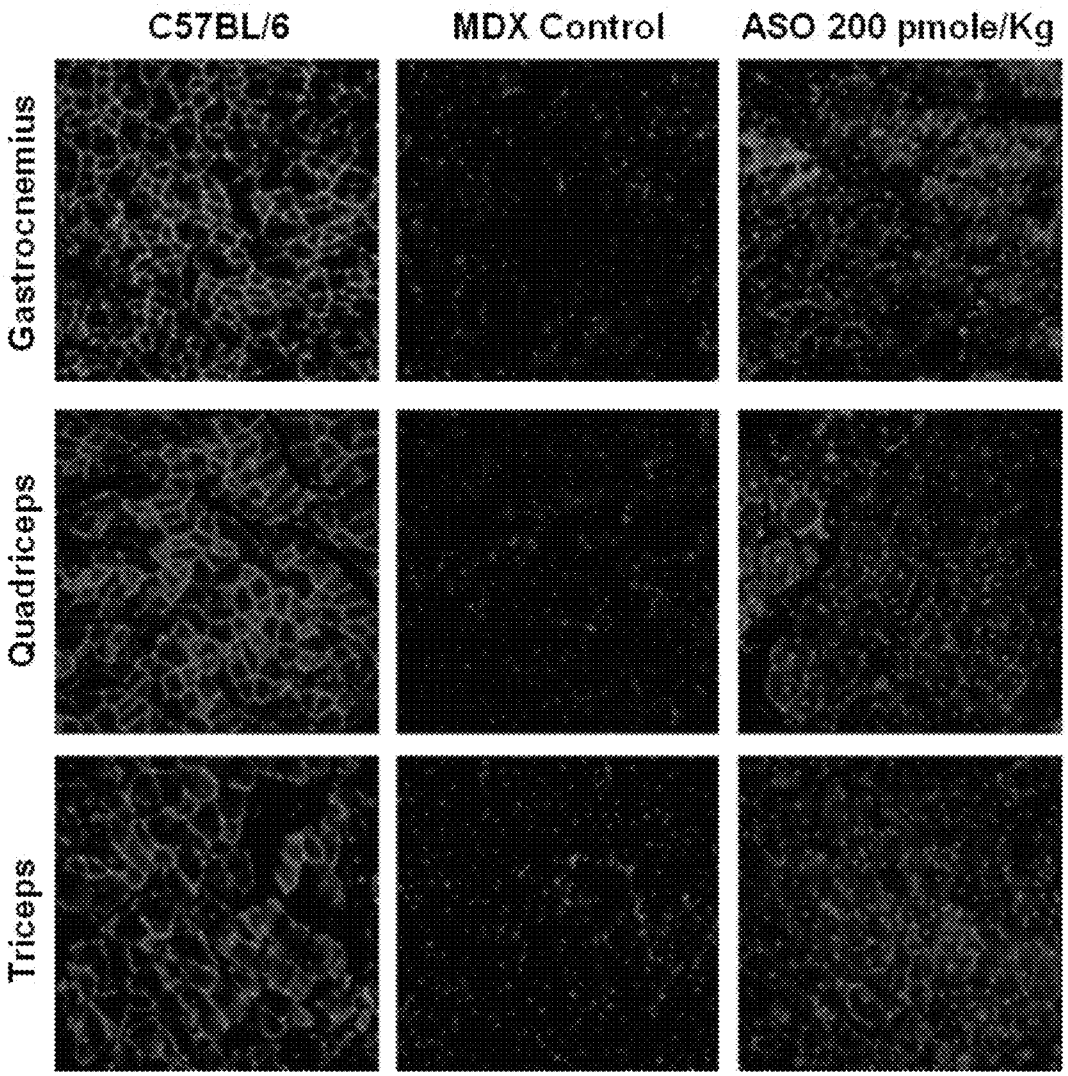
FIG. 40. Full-length dystrophin IHC images merged with DAPI staining in muscle tissues of mdx mice administered with "DMD-ASO 1" at 0 (negative control) or 200 pmole/Kg, 2× per week for 30 weeks.

FIG. 40 is a representative set of full-length dystrophin IHC images by group for the muscle samples extracted in week 30. The wild type (WT) negative control group yielded distinctive and angular patterns of dystrophin expression reflecting the natural structure of muscle fiber bundles. In the mdx mice negative control group, there was not much of the full-length dystrophin staining. In the meantime, strong and angular patterns of dystrophin staining were observed in the skeletal muscles of the 200 pmole/Kg treatment group. Although the muscle fiber bundle structures were blurry in mdx mice compared to the WT mice, the full-length dystrophin expression markedly increased in the animals treated with the ASO.

The dystrophin IHC images were subjected to quantification for the full-length dystrophin expression by digitally scoring the intensity of red fluorescence in each individual IHC image using the "ImageJ" program (NIH). Individual fluorescence scores were combined by group and muscle type for statistical evaluation against the wild type negative control group.

Figure 41:
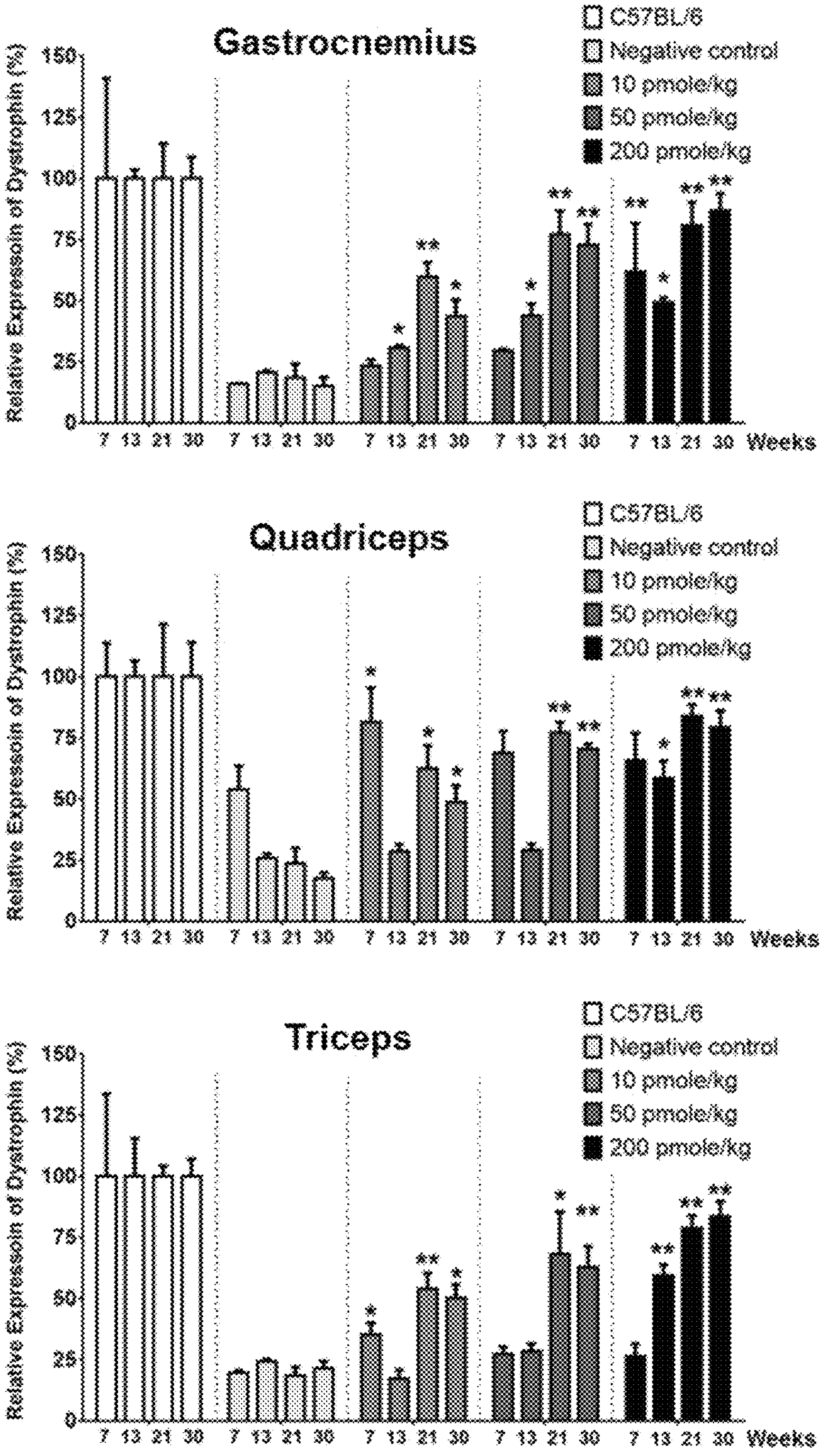
FIG. 41. Relative expression levels of the full-length dystrophin protein in skeletal muscles of mdx mice chronically administered with "DMD-ASO 1" at 0 (negative control), 10, 50 or 200 pmole/Kg. The expression level is as normalized against the expression level in WT mice. (error bar by standard error, * for $p<0.05$ and ** $p<0.01$)

FIG. 41 summarizes the changes in the relative expression level of the full length dystrophin protein in mdx mice. The expression of the full-length dystrophin tended to increase more at higher ASO dose and longer treatment duration. In Week 30, the full-length dystrophin expression in the 200 pmole/Kg group reached >80% of the WT negative control group, whilst the expression in the mdx negative control was less than 20% of the wild type negative control group.

[Nested PCR for Exon Skipping (Method B)] Muscle samples were homogenized by grinding in a tube kept on ice, and subjected to total RNA extraction with 1 mL trizol reagent (Invitrogen) per ca 100 mg muscle tissue. The total RNAs were evaluated for exon skipping by nested PCR as described in "DMD Example 2".

Figure 42:
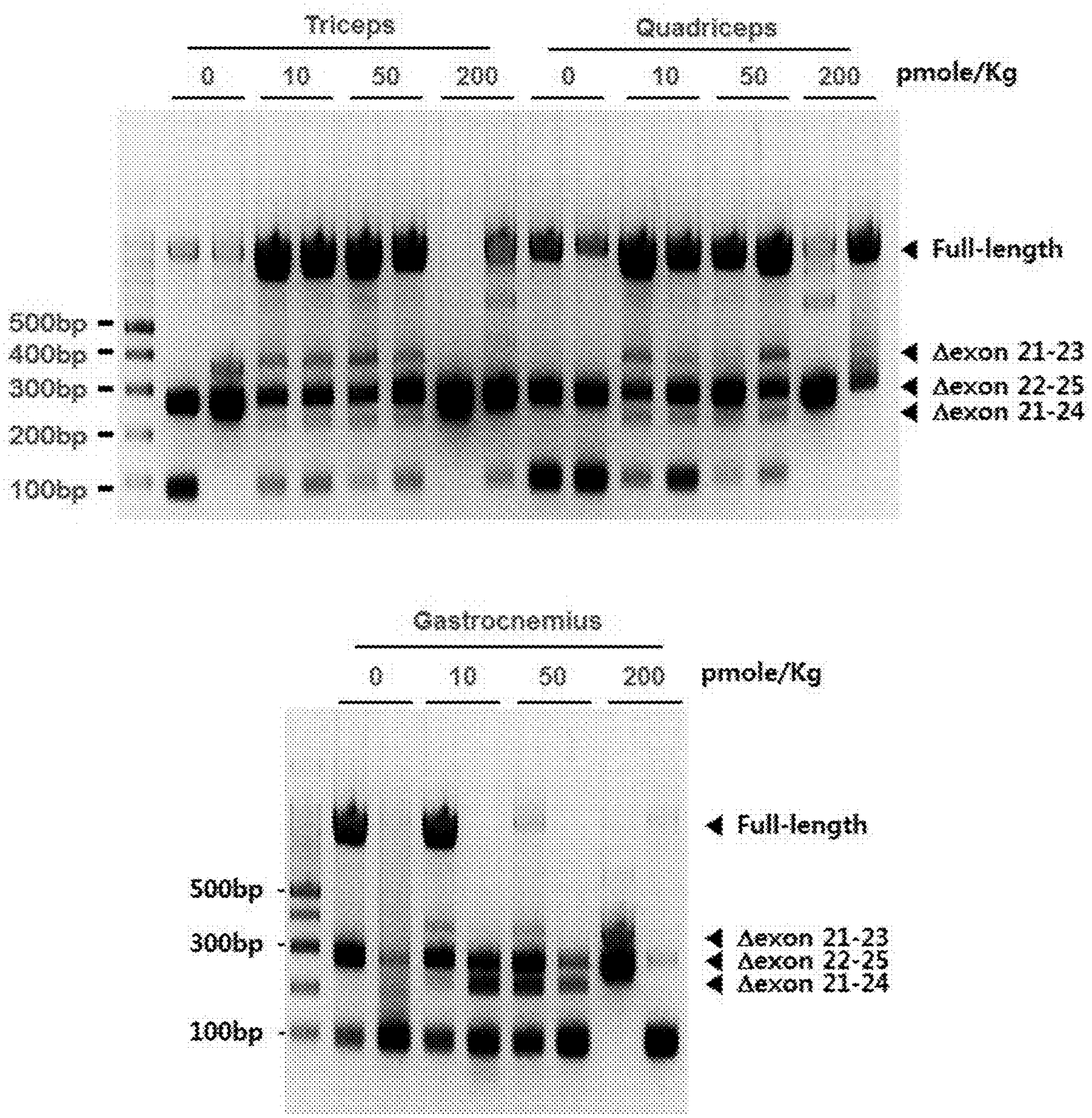
FIG. 42. Electrophoresis data of the nested PCR products obtained with the skeletal muscles sampled from the mdx mice in Week 7.

FIG. 42 provides the electrophoresis data of the nested PCR products obtained with skeletal muscles sampled in Week 7. The in-frame PCR products of Δexons 21-23 and Δexons 21-24 were detected in muscle samples of the ASO treatment groups, but not at all in those of the mdx negative control group.

Figure 43:
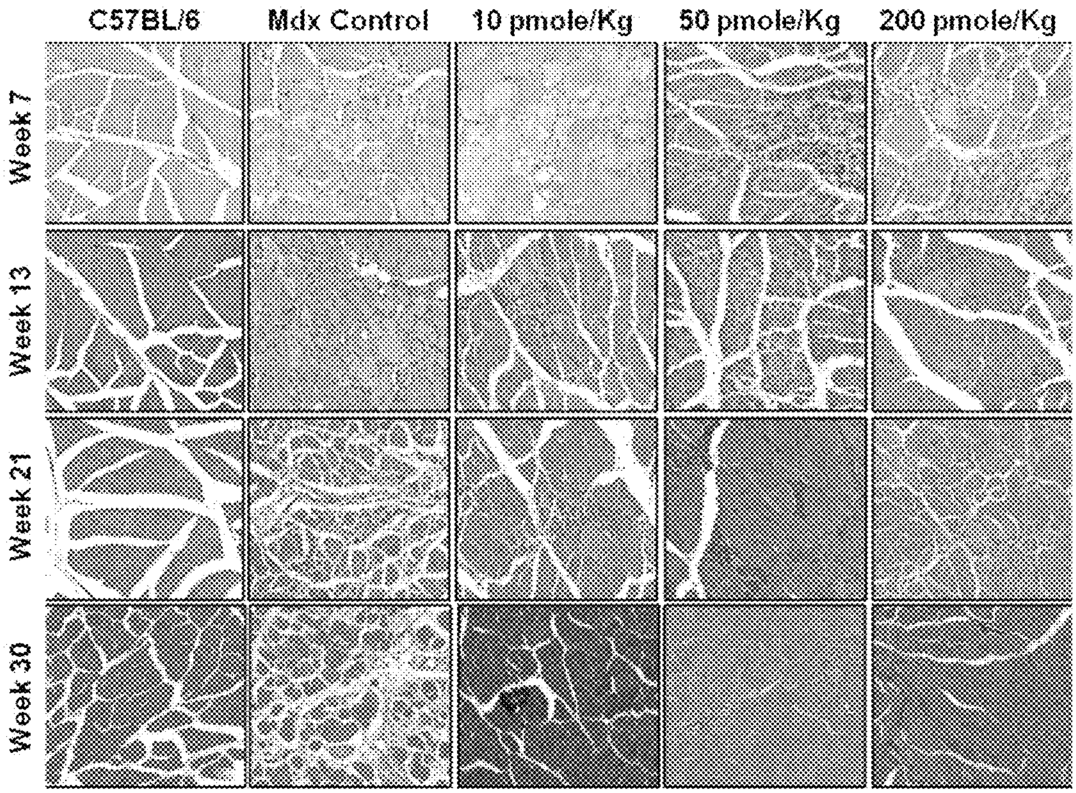
FIG. 43. Histopathologic changes by H&E staining of the triceps of C57BL/6 mice (WT negative control) and mdx mice chronically administered with "DMD-ASO 1" at 0 (mdx negative control), 10, 50 or 200 pmole/Kg.

[Histopathology by H&E Staining] Muscular inflammation and degeneration are the hallmark of DMD symptoms. Skeletal muscle samples were subjected to histopathology evaluation by H&E staining. FIG. 43 provides a representative set of H&E staining images for the triceps by group and sampling time point.

In the WT negative control group, the muscle structure was dense at all the time points of sampling. There were no suggestions of muscular inflammation in the muscles of the wild type mice at all the time points.

In the mdx negative control, the muscle structure showed a clear pattern of gradual degeneration with age. Most notably in Week 30, muscle bundles were not inter-connected and tended to degenerate to round shape. Also there was massive infiltration of inflammatory cells as suggested by blue dot stains, most notably in Weeks 13 and 21.

In the 200 pmole/Kg group, the loose muscle structure in Week 7 gradually recovered to a dense structure. The marked infiltration of inflammatory cells in Week 7 gradually disappeared with age. Thus muscular degeneration and inflammation in mdx mice were reversed upon chronic administrations of the ASO at 200 pmole/Kg, which would be consistent with the upregulation of the full-length dystrophin in the 200 pmole/Kg group.

The severity of the histopathology findings in the 10 and 50 pmole/Kg groups was weaker than the severity in the mdx negative control, but stronger than that in the 200 pmole/Kg group. Thus the upregulation of the full-length dystrophin induced by the ASO exposure is largely consistent with the histopathological findings.

[Miscellaneous Findings] There were three cases of unscheduled sacrifice or death (Weeks 26, 39 and 43) in the mdx negative control group due to a large mass of muscular lymphoma developed most likely by chronic muscular inflammation. There were no cases of lymphoma in all the ASO treatment groups.

[Comparison with Other Dystrophin ASO] Eteplirsen (exondys 51) is a PMO antisense oligonucleotide designed to induce the skipping of exon 51 in the human dystrophin pre-mRNA. Recently, the US FDA issued an accelerated approval of eteplirsen for use in a population of DMD patients requiring the skipping of exon 51. The recommended dose of eteplirsen is an intravenous injection of 30 mg/Kg per week.

The subcutaneous dose of 200 pmole/Kg "DMD-ASO 1" corresponds to ca 1 μg/Kg. The dystrophin ASO of Formula I is more potent than the PMO ASO by ca 30,000 times, although there are differences in species and exon between the two types of ASO. The unprecedentedly ultra-strong exon skipping potency of the PNA derivative of Formula I was translated again into an ultra-strong in vivo therapeutic potency for this hard-to-treat rare disease.

DMD Example 6. Improvement of Muscle Function by Walking Distance in MDX Mice Chronically Administered with "DMD-ASO 2"

"DMD ASO 2" specified in Table 7 is a 17-mer ASO fully complementary to a region in the 3' splice site spanning the junction of intron 22 and exon 23 in the mouse dystrophin pre-mRNA. "DMD-ASO 2" complementarily binds to the 17-mer sequence marked "bold" and "underlined" as in the 20-mer mouse dystrophin pre-mRNA sequence of

[(5'→3') uaauuuugag|GCUCUGCAAA (SEQ ID NO: 111)].

"DMD-ASO 2" possesses an 8-mer overlap with intron 22 and a 9-mer complementary overlap with exon 23.

"DMD-ASO 2" was chronically administered to mdx mice to evaluate its ability to improve muscle function by the walking distance on tread mill, and to inhibit the muscle degradation by the serum levels of creatine kinase (CK) and myoglobin.

[Animals & Grouping] Male mdx mice (6 weeks old) were randomly assigned to three groups of the mdx negative control (no ASO treatment), "DMD-ASO 2" 10 pmole/Kg, and "DMD-ASO 2" 30 mg/Kg based on the body weight. (N=16 per group) 12 male C57BL/6 mice (6 weeks old) were adopted as the wild type (WT) negative control group.

[Injection Solutions & ASO Treatment] An aqueous mother stock solution of "DMD-ASO 2" was diluted either in PBS or in PBS supplemented with 0.1% Tween 80 to prepare injection solutions of 20 and 60 nM "DMD-ASO 2" for 10 pmole/Kg and 30 pmole/Kg "DMD-ASO 2", respectively. Supplementation of PBS injection solution with 0.1% Tween 80 was considered to be necessary to prevent the ASO molecules from sticking to plastic injection vials, pipette tips, and syringes.

[Walking Distance on Tread Mill] During the first 30 weeks post grouping, the animals were administered with the injection solutions without Tween 80 2× per week at 2 mL/Kg. Starting from Week 7, the animals were subjected to walking on a tread mill (Model #LE8710, PanLab) on a weekly basis. During the first 30 weeks, however, the ASO treatment groups failed to show any significant improvements in the walking distance compared to the mdx negative control group.

In order to effectively increase the ASO dose, animals were administered with the injection solutions supplemented with Tween 80, 2× per week from Week 36. There was a washout (i.e., no ASO dosing) period of 5 weeks in between.

Figure 44A:
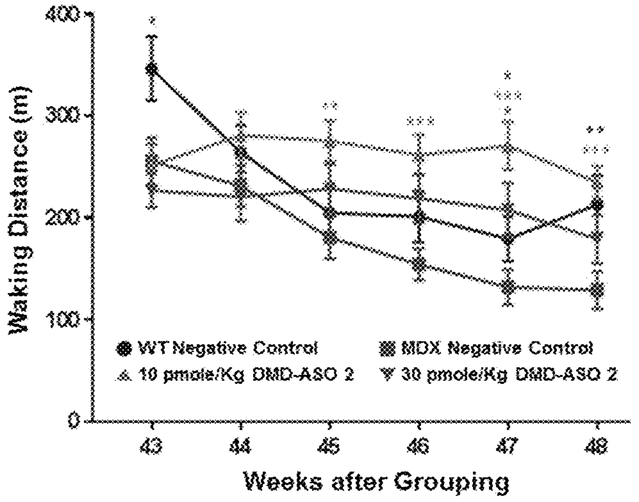
FIG. 44A. Walking distances on tread mill in C57BL/6 mice (WT negative control) and mdx mice chronically exposed to "DMD ASO2" at 0 (mdx negative control), 10 pmole/Kg or 30 pmole/Kg. (error bar by standard error, * for $p<0.05$,  for $p<0.01$ and * for $p<0.001$)

FIG. 44A summarizes the walking distances on tread mill by group during Weeks 43 to 48. The average walking distance of the mdx negative control group gradually but rapidly decreased from ca 250 meters in Week 43 to 130 meters in Week 48. The average walking distance of the ASO treatment groups were markedly longer than the distance of the mdx negative control group.

During Weeks 46 to 48, the 10 pmole/Kg group showed the average walking distances of 240 to 280 meters, which were significantly longer than the distances of the mdx negative control group. In the meantime, the 30 pmole/Kg group showed walking distances of ca 180 to 230 meters during Weeks 46 to 48. There was a tendency of longer walking distance with the 10 pmole/Kg group than the 30 pmole/Kg group. The inverted dose response of the walking distance would suggest natural a selection of different exon(s) at higher ASO dose as observed in "HIF-1α Example 9". Interestingly, the WT negative control group and the 30 pmole/Kg group showed comparable walking distances during Weeks 44 to 47.

[Terminal Sacrifice] In Week 48, the animals were subjected to terminal sacrifice for blood sampling. The blood samples were analyzed for the serum level of CK (Creatine Kinase Activity Assay Kit, Cat. Number ab155901, Abcam) and myoglobin (Myoglobin ELISA Kit, Cat. Number ab210965, Abcam) to assess the degree of muscle degradation according to the manufacturer's instructions. Muscle tissues were analyzed by western blot for the full-length dystrophin.

Figure 44B:
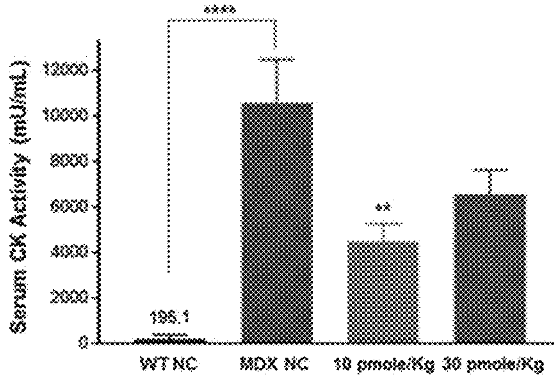
FIG. 44B. Serum creatine kinase levels in C57BL/6 mice (WT negative control) and mdx mice chronically exposed to "DMD ASO2" at 0 (mdx negative control), 10 pmole/Kg or 30 pmole/Kg. (error bar by standard error,  for $p<0.01$, and ** for $p<0.0001$)

[Serum Levels of CK and Myoglobin] FIG. 44B provides the observed serum CK levels by group. Reflecting the muscular fragility of mdx mice, all the mdx mice groups yielded serum CK activities significantly far higher than the WT negative control group. For example, the serum CK level of the mdx negative control group was ca 54 times higher than the level of the WT negative control group. The serum CK levels of the 10 and 30 pmole/Kg group were smaller than the level of the mdx negative control group by 58% and 38%, respectively. The difference in the serum CK levels between the 10 pmole/Kg and the mdx negative control group was significant.

Figure 44C:
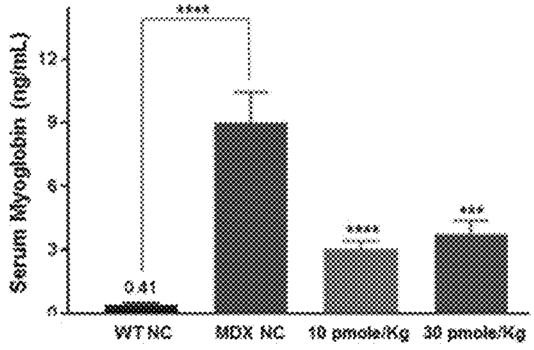
FIG. 44C. Serum myoglobin levels in C57BL/6 mice (WT negative control) and mdx mice chronically exposed to "DMD ASO2" at 0 (mdx negative control), 10 pmole/Kg or 30 pmole/Kg. (error bar by standard error, * for $p<0.001$, and ** for $p<0.0001$)

FIG. 44C provides the observed serum myoglobin levels by group. Reflecting the muscular fragility of mdx mice, all the mdx mice groups yielded serum myoglobin levels far higher than the level of the WT negative control group. For example, the serum myoglobin level of the mdx negative control group was ca 22 times higher than the level of the WT negative control group. The serum myoglobin levels of the 10 and 30 pmole/Kg group were significantly smaller than the level of the mdx negative control group by 67% and 58%, respectively.

The observed data of the serum biomarkers for muscular degradation are grossly consistent with the dose dependency of the walking distance provided in FIG. 44A.

[Full-length Dystrophin Expression in Triceps by Western Blot] Following homogenization at liquid nitrogen temperature, muscle (triceps) samples were subjected to lysis in RIPA buffer supplemented with 1% SDS. The protein concentration in each lysate was quantified by BCA assay against the BSA standard. 50 mg of protein of each lysate was subjected to electrophoretic separation on an 8% PAGE gel. Then the PVDF membrane was probed with a C-terminal targeting dystrophin antibody (Cat. Number ab154168, Abcam).

Figure 45A:
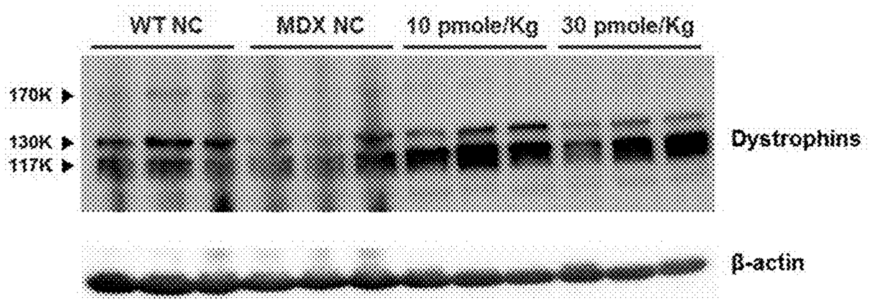
FIG. 45A. Western blot data probed for full-length dystrophins in skeletal muscle samples from wild type mice (WT negative control) or mdx mice chronically exposed to "DMD-ASO 2" at 0 (mdx negative control), 10, or 30 pmole/Kg.

FIG. 45A provides the observed western blot data. The full-length dystrophin of 427K size was not detected in all the samples. Instead the WT muscle samples yielded smaller dystrophin proteins of 170K, 130K and 117K size, among which the 130K size band was the most enriched.

In case of the mdx groups, the three dystrophin bands were detected. The 10 and 30 pmole/Kg treatment groups yielded the 117K band markedly stronger than the mdx negative control group as well as the WT control group. The 130K band intensity was considerably stronger in the 10 pmole/Kg group than in the mdx negative control group, too.

DMD Example 7. Long Term Evaluation of MDX Mice Administered with "DMD-ASO 1", "DMD-ASO 2" or "DMD-ASO 6"

"DMD ASO 6" specified in Table 7 is an 18-mer ASO fully complementary to a region in the 5' splice site spanning the junction of exon 23 and intron 23 in the mouse dystrophin pre-mRNA. "DMD-ASO 6" complementarily overlaps with the 18-mer sequence as marked "bold" and "underlined" in the 25-mer mouse dystrophin pre-mRNA sequence of

[(5'→3') AAAAUUUCAG|guaagccgagguuug (SEQ ID NO: 112)].

"DMD-ASO 6" possesses an 8-mer overlap with exon 23 and a 10-mer overlap with intron 23.

"DMD-ASO 1", "DMD-ASO 2" and "DMD-ASO 6" were evaluated for their physiological effects in male mdx mice by long term subcutaneous administration. In this evaluation the animals were not subjected to physical tests requiring muscular stress in order to keep the transcription of the dystrophin gene undisturbed by excessive muscular stimulation.

[Animals & Grouping] Male mdx mice (6 weeks old) were randomly assigned to 4 groups of the mdx negative control (no ASO treatment), "DMD-ASO 1" 50 pmole/Kg, "DMD-ASO 2" 10 mg/Kg, and "DMD-ASO 6" 10 mg/Kg based on the body weight. (N=12-13 per group) 12 male C57BL/6 mice (6 weeks old) were adopted as the wild type (WT) negative control group.

[Injection Solutions & ASO Treatment] Aqueous mother stock solutions of the ASOs were serially diluted in PBS to prepare the injection solutions of 25 nM "DMD-ASO 1" for 50 pmole/Kg "DMD-ASO 1", 5 nM "DMD-ASO 2" for "DMD-ASO 2" 10 pmole/Kg, and 5 nM "DMD-ASO 6" for "DMD-ASO 6" 10 pmole/Kg. The animals were subcutaneously administered with the injection solutions at 2 mL/Kg, 2× per week.

[Unscheduled Death or Sacrifice] The mdx mice treated with the ASOs tended to show longer life spans than the mdx negative control group, suggesting the therapeutic activity of the ASOs.

In the mdx negative control group, there were three cases of unscheduled death or sacrifice: one at a time in Weeks 42, 58 and 61. The "DMD-ASO 1" treatment group showed two premature deaths, one in Week 38 and another in Week 61. In case of the "DMD-ASO 2" treatment group, one death in Week 56 and another in Week 62. There were three premature deaths in the "DMD-ASO 6" treatment group: one at a time in Weeks 55, 65 and 66.

[Terminal Sacrifice] All the survived animals were sacrificed for blood sampling in Week 66 post the grouping. The blood samples were subjected to ELISA assays for serum creatine kinase (CK) and serum myoglobin as described in "DMD Example 6".

Figure 45B:
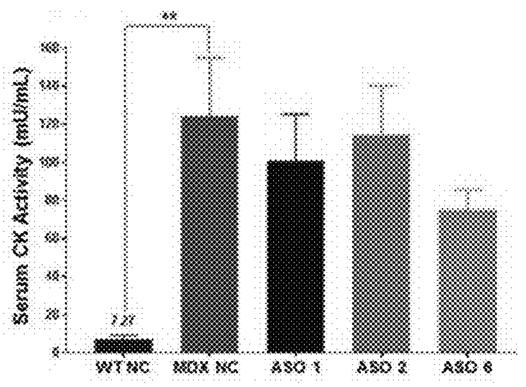
FIG. 45B. Serum creatine kinase levels in WT mice (WT negative control), mdx mice without ASO treatment, and mdx mice subcutaneously administered with 50 pmole/Kg "DMD-ASO 1", 10 pmole/Kg "DMD-ASO 2", or 10 pmole/Kg "DMD-ASO 6", 2× per week for 66 weeks. (error bar by standard error and ** for $p<0.01$)

[Serum Levels of CK and Myoglobin] FIG. 45B provides the observed serum CK levels by group. Reflecting the muscular fragility of mdx mice, all the mdx mice groups yielded serum CK activities significantly far higher than the WT negative control group. For example, the serum CK level of the MDX negative control group was ca 17 times higher than the level of the WT negative control group. The serum CK levels of the ASO treatment groups tended to be smaller than the level of the MDX negative control group, suggesting the therapeutic activity by the ASOs. However, the differences were not significant.

Figure 45C:
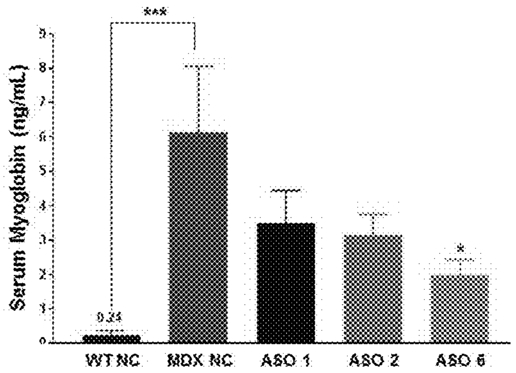
FIG. 45C. Serum myoglobin levels in WT mice (WT negative control), mdx mice without ASO treatment, and mdx mice subcutaneously administered with 50 pmole/Kg "DMD-ASO 1", 10 pmole/Kg "DMD-ASO 2", or 10 pmole/Kg "DMD-ASO 6", 2× per week for 66 weeks. (error bar by standard error, * for $p<0.05$, and *** for $p<0.001$)

FIG. 45C provides the observed serum myoglobin levels by group. Reflecting the muscular fragility of mdx mice, all the mdx mice groups yielded serum myoglobin significantly far higher than the WT negative control group. For example, the serum myoglobin level of the mdx negative control group was ca 26 times higher than the level of the WT negative control group. The serum myoglobin levels of the treatment groups of "DMD-ASO 1", "DMD-ASO 2" and "DMD-ASO 6" were smaller than the level of the mdx negative control group by 43%, 49% and 68%, respectively. The difference between the MDX negative control and "DMD-ASO 6" group was significant. The serum biomarkers for the muscular integrity indirectly support that "DMD-ASO 6" induces the skipping of dystrophin exon 23 and yields functionally active full-length dystrophin(s) in mdx mice.

Examples for In Vitro Activities of IDO1 ASOs

PNA derivatives of Formula I in Table 8 were designed to complementarily target various splice sites in the human IDO1 pre-mRNA. IDO1 ASOs were evaluated for the exon skipping activity in SKOV3 cells. Given that IDO1 catalyzes the degradation of L-tryptophan to N-formylkynurenine, IDO1 ASOs were evaluated for their functional ability to inhibit the production of kynurenine. Biological examples provided herein are to illustrate the exon skipping activity of the IDO1 ASOs as examples for the compound of Formula I, and therefore should not be interpreted to limit the scope of the current invention to IDO1 ASOs.

IDO1 Example 1. Exon Skipping Induced by "IDO-ASO 1"

"IDO-ASO 1" specified in Table 8 is a 13-mer ASO fully complementary to a region in the 3' splice site spanning the junction of intron 6 and exon 7 in the human IDO1 pre-mRNA. "IDO-ASO 1" complementarily targets the 13-mer sequence as marked "bold" and "underlined" in the 20-mer human IDO1 pre-mRNA sequence of

[(5'→3') uuuguuuuag|GUAAUUCCUA (SEQ ID NO: 113)].

"IDO-ASO 1" possesses a 5-mer overlap with intron 6 and an 8-mer overlap with exon 7.

"IDO-ASO 1" was evaluated for its ability to induce exon skipping in SKOV3 cells (Cat. Number HTB-77, ATCC) by IDO1 nested PCR as follows.

[Cell Culture & ASO Treatment] SKOV3 (human ovary adenocarcinoma) cells were subcultured in 60 mm culture dish containing 5 mL McCoy's 5A modified medium supplemented with 10% FBS, 1% streptomycin/penicillin, 1% L-glutamine, and 1% sodium pyruvate under 5% $CO_2$ at 37° C., and treated with "IDO-ASO 1" for 48 hours at 0 zM (negative control), 10 zM, 100 zM or 1 aM.

[RNA Extraction & cDNA Synthesis by One-Step RT-PCR] Total RNA was extracted from the cells using "Universal RNA Extraction Kit" (Cat. Number 9767, Takara) according to the manufacturer's instructions. 200 ng of RNA template was subjected to a 25 μL reverse transcription reaction using Super Script® One-Step RT-PCR kit with Platinum® Taq polymerase (Cat. Number 10928-042, Invitrogen) against a set of exon-specific primers [IDO-exon 2_forward: (5'→3') TTCATTGCTAAACATCTGCC (SEQ ID NO: 114); and IDO-exon 10_reverse: (5'→3') TGAAAGGACAAACTCACGGA (SEQ ID NO: 115)] according to the following cycle conditions: 50° C. for 30 min and 94° C. for 2 min, which was followed by 40 cycles of 30 sec at 94° C., 30 sec at 50° C., and 1 min at 72° C.

[Nested PCR Amplification] 1 μL of cDNA was further amplified in a 20 μL nested PCR reaction (Cat. No. K2612, Bioneer) against a set of exon-specific primers [IDO-exon 4_forward: (5'→3') CCTTACTGCCAACTCTCC (SEQ ID NO: 116); and IDO-exon 9_reverse: (5'→3') CTGCTTTGGCCTGCACTG (SEQ ID NO: 117)] according to the following cycle conditions: 95° C. for 5 min followed by 30 cycles of 30 sec at 95° C., 30 sec at 50° C., and 1 min at 72° C.

[Identification of Exon Skipping Product] The PCR products were subjected to electrophoretic separation on a 2% agarose gel. The bands of target size were collected and analyzed by Sanger sequencing.

Figure 46A:
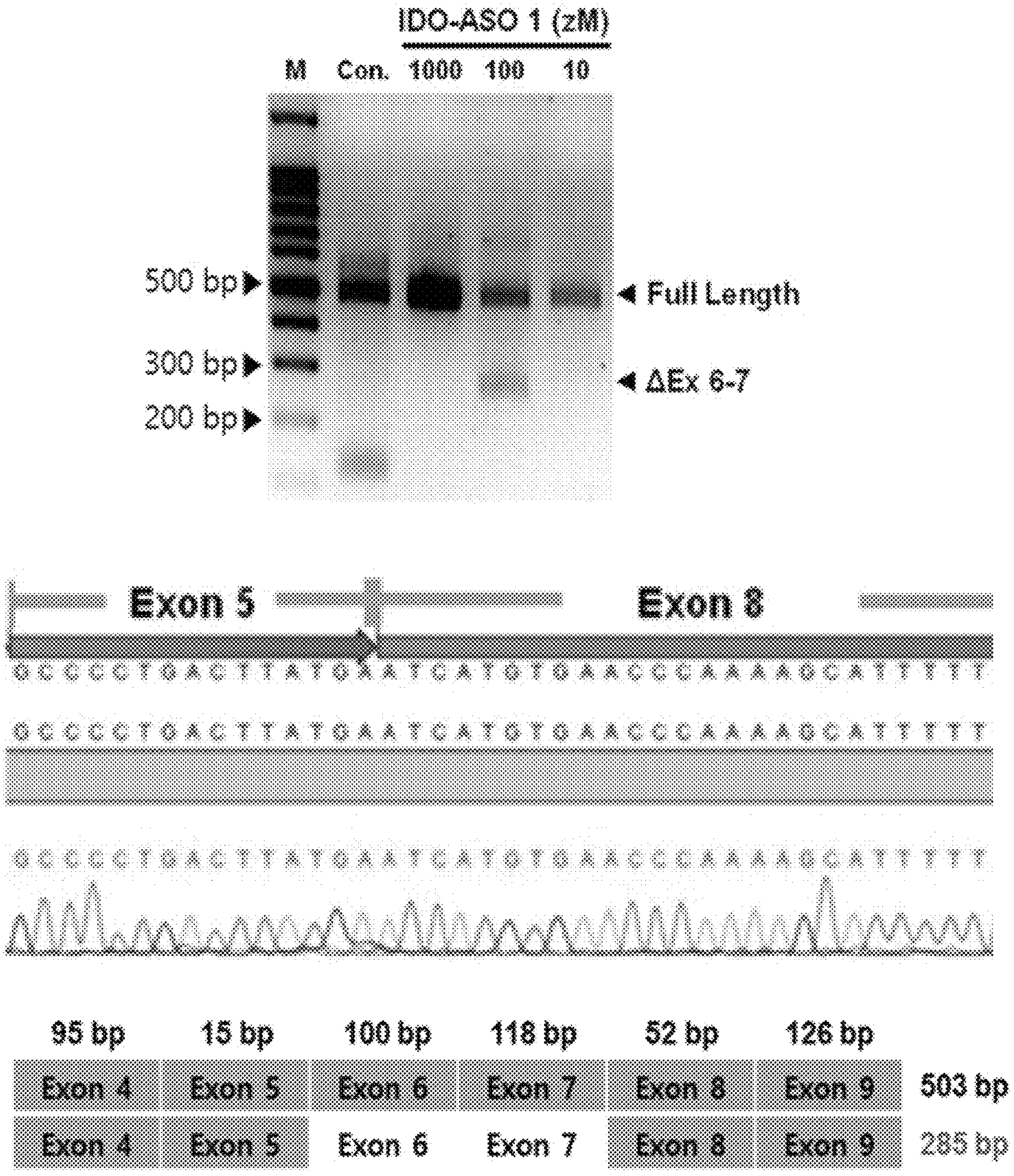
FIG. 46A. Electrophoresis data for the IDO-1 nested PCR products in SKOV3 cells treated with "IDO-ASO 1" at 0 (negative control), 10, 100 or 1,000 zM (left diagram), and the Sanger sequencing data for the exon skipping PCR band (right diagram).

FIG. 46A provides the electrophoresis data of the nested PCR products (left diagram) and the Sanger sequencing data for the PCR band assigned to the skipping of exons 6-7 (right). The skipping of exons 6-7 was detected in the RNA extract of the cells treated with 100 zM "IDO-ASO 1". The exon skipping band was not detected in the RNA extracts of the cells treated with the ASO at 10 zM or 1 aM most likely due to poor stability of the IDO1 mRNA splice variant lacking exons 6-7. Although the intensity of the full-length IDO-1 mRNA decreased in the cells treated with the ASO at 10 or 100 zM, the intensity of the full-length mRNA PCR increased in the cells treated with the ASO at 1 aM treatment. The observed increase of the full-length mRNA level at 1 aM has yet to be elucidated. It could be an artifact during the PCR reactions, or could be due to a (transient) transcription upregulation by the "exon intron circular RNA (EIciRNA)" accumulated during the exon skipping by "IDO-ASO 1". [*Nature Struct. Mol. Biol*. vol 22(3), 256-264 (2015)] The Sanger sequencing data (right diagram) unequivocally demonstrated the skipping of exons 6-7 induced by "IDO-ASO 1" in SKOV3 cells.

IDO1 Example 2. Antisense Functional Activity of "IDO-ASO 1"

The functional activity of "IDO-ASO 1" was evaluated for its ability to inhibit the secretion of kynurenine in SKOV3 cells as follows.

[Kynurenine Secretion Assay] SKOV3 cells grown in 60 mm culture dish containing 5 mL culture medium were treated with "IDO-ASO 1" at 0 zM (negative control) or 10 zM to 1 fM. (3 dishes per concentration) Cells were treated with the ASO along with 10 ng/mL γ-interferon to increase the kynurenine secretion. 24 hours later, 200 μL of the culture medium was sampled from each culture dish and mixed with 100 μL 30% trichloroacetic acid. The mixture was vortexed and subjected to centrifugation at 8,000 g for 5 min. 75 μL of the resulting supernatant was mixed with 75 μL Ehrlich reagent (0.8% p-dimethylamino-benzaldehyde in acetic acid), and the mixture was subjected to a quantification for kynurenine at 490 nm on an ELISA reader. [*PLOS One* 5(8): e63301 (2013)]

Figure 46B:
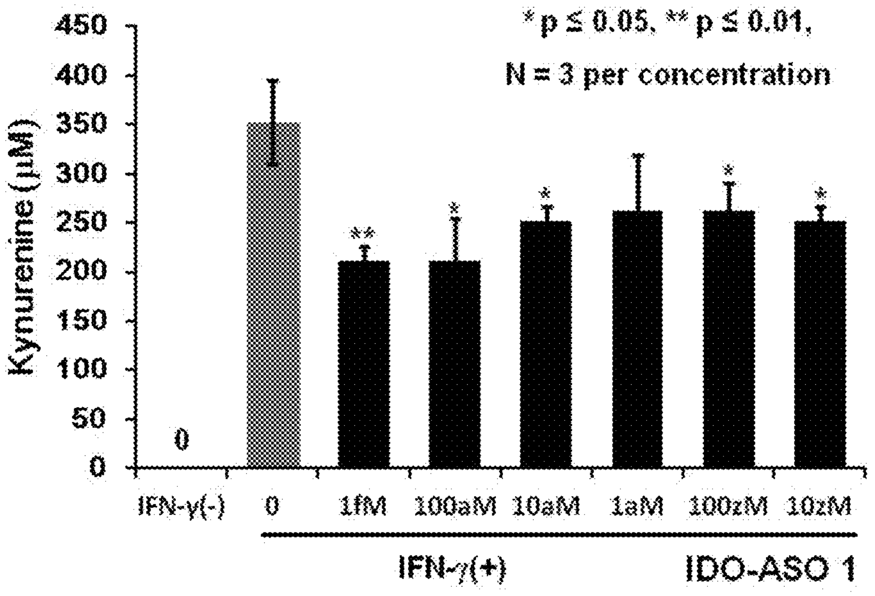
FIG. 46B. Kynurenine secretion assay results in SKOV3 cells treated with "IDO-ASO 1" at 0 zM (negative control) or 10 zM to 1 fM. (error bar by standard error, and * for $p<0.05$)

FIG. 46B provides the kynurenine assay results. Except for the cells treated with 1 aM "IDO-ASO 1", the secretion of kynurenine significantly (student's t-test) decreased in the cells treated with the ASO at 10 zM to 1 fM. Kynurenine secretion decreased by ca 40% in the cells treated with 1 fM "IDO-ASO 1".

IDO1 Example 3. Exon Skipping Induced by "IDO-ASO 5"

"IDO-ASO 5" specified in Table 8 is a 13-mer ASO fully complementary to a region in the 5' splice site spanning the junction of exon 3 and intron 3 in the human IDO1 pre-mRNA. "IDO-ASO 5" complementarily overlaps with the 13-mer sequence as marked "bold" and "underlined" in the 20-mer human IDO1 pre-mRNA sequence of

[(5'→3') UGUCCGUAAG|guuuggagau (SEQ ID NO: 118)].

"IDO-ASO 5" has an 8-mer complementary overlap with exon 3 and a 5-mer complementary overlap with intron 3.

"IDO-ASO 5" was evaluated for its ability to induce exon skipping in SKOV3 cells by IDO1 nested RT-PCR as described in "IDO1 Example 1" unless noted otherwise.

[ASO Treatment] SKOV3 cells grown in 60 mm culture dish were treated with "IDO-ASO 5" at 0 (negative control), 1, 3, 10, 30 or 100 aM for 48 hours.

[cDNA Synthesis by One-step PCR] 200 ng of RNA template was subjected to a 25 μl reverse transcription reaction using Super Script® One-Step RT-PCR kit with Platinum® Taq polymerase (Cat. No. 10928-042, Invitrogen) against a set of exon-specific primers [IDO-exon 1_forward: (5'→3') AAAACTCCTGGACAATCAGT (SEQ ID NO: 119); and IDO-exon 8_reverse: (5'→3') ACTTGAAGGGCTTTCTCC (SEQ ID NO: 120)] according to the following cycle conditions: 50° C. for 30 min and 94° C. for 2 min, which was followed by 40 cycles of 30 sec at 94° C., 30 sec at 52° C., and 40 sec at 72° C.

[Nested PCR Amplification] 1 μL of cDNA was further amplified in a 20 μL nested PCR (Cat. No. K2612, Bioneer) reaction using a set of exon-specific primers [IDO-exon 1n_forward: (5'→3') TATTGATGAAGAAGTGGG (SEQ ID NO: 121); and IDO-exon 8n_reverse: (5'→3') GTTCACATGATCGTGGATTTG (SEQ ID NO: 122)] according to the following cycle conditions: 95° C. for 5 min followed by 30 cycles of 30 sec at 95° C., 40 sec at 52° C., and 40 sec at 72° C.

Figure 47A:
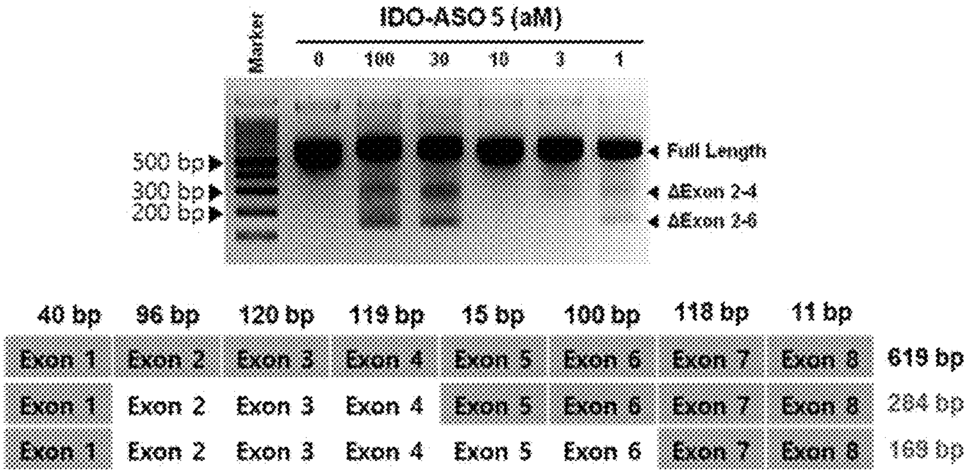
FIG. 47A. Electrophoresis data for the IDO-1 nested PCR products in SKOV3 cells treated with "IDO-ASO 5" at 0 (negative control), 1, 3, 10, 30 or 100 aM.
Figure 47B:
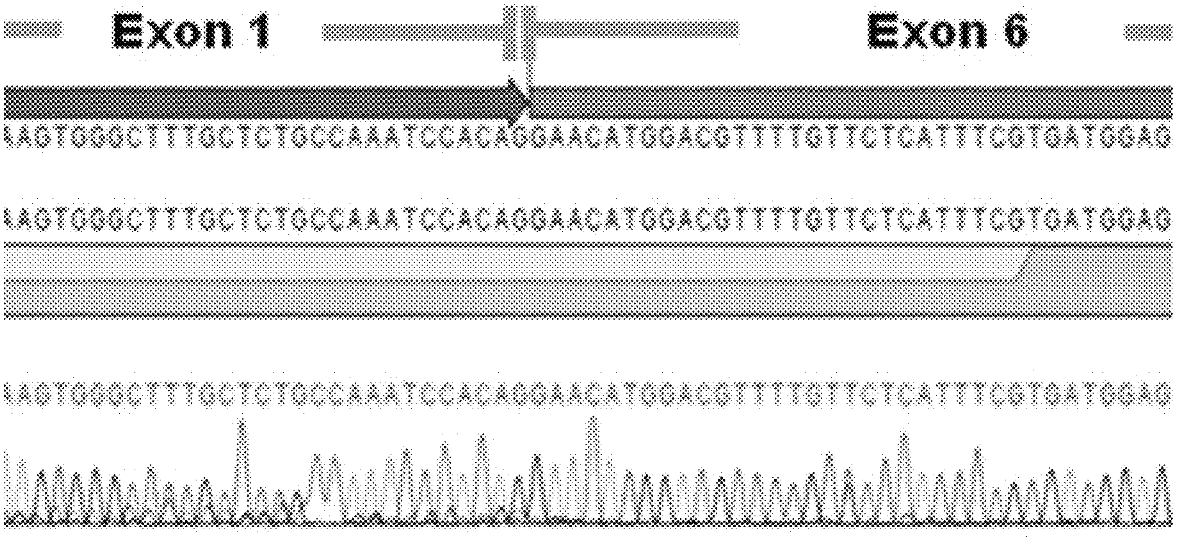
FIG. 47B. Sanger sequencing data for the PCR bands assigned to the skipping of exons 2-4 and exons 2-6.
Figure 47B:
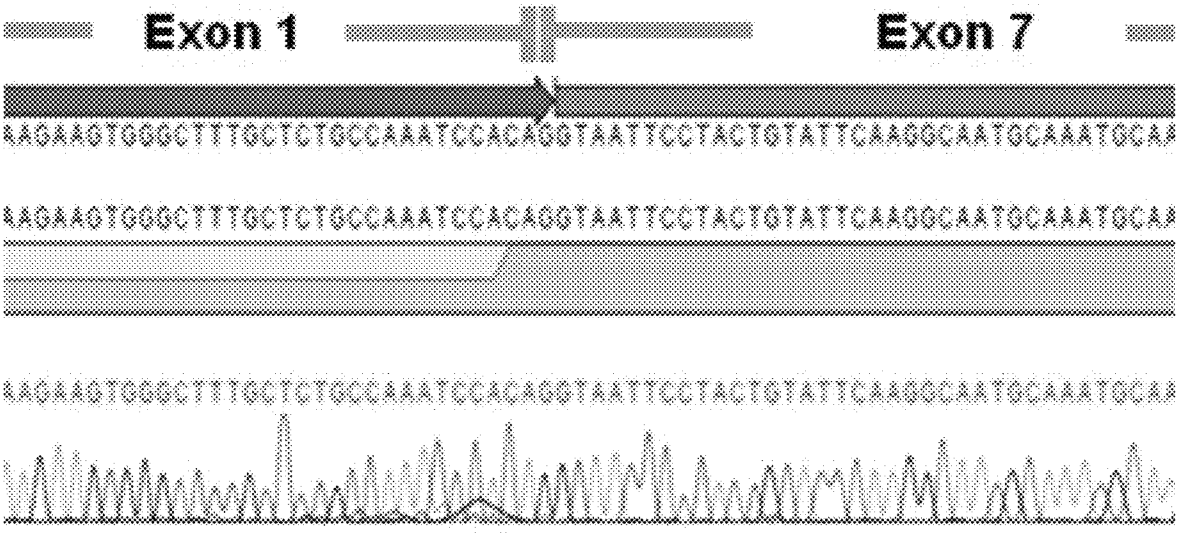

[Nested PCR Products Data] FIG. 47A provides the electrophoresis data of the nested PCR products. The cells treated with "IDO-ASO 5" at 30 and 100 aM clearly yielded the mRNA splice variants lacking exons 2-4 and exons 2-6. The intensity of the full-length mRNA decreased in the ASO treated cells, although the intensity slightly bumped up in the cells treated with the ASO at 10 aM. FIG. 47B provides the Sanger sequencing data for the mRNA splice variants lacking exons 2-4 and exons 2-6.

IDO1 Example 4. Exon Skipping Induced by "IDO-ASO 6"

"IDO-ASO 6" specified in Table 8 is a 13-mer ASO fully complementary to a region in the 3' splice site spanning the junction of intron 3 and exon 4 in the human IDO1 pre-mRNA. "IDO-ASO 6" complementarily targets the 13-mer sequence as marked "bold" and "underlined" in the 20-mer human IDO1 pre-mRNA sequence of

[(5'→3') uuuuaaucag|GUCUUGCCAA (SEQ ID NO: 123)].

"IDO-ASO 6" possesses a 5-mer complementary overlap with intron 3 and 8-mer complementary overlap with exon 4.

"IDO-ASO 6" was evaluated for its ability to induce exon skipping in SKOV3 cells by IDO1 nested PCR as described in "IDO1 Example 3" unless noted otherwise.

Figure 47C:
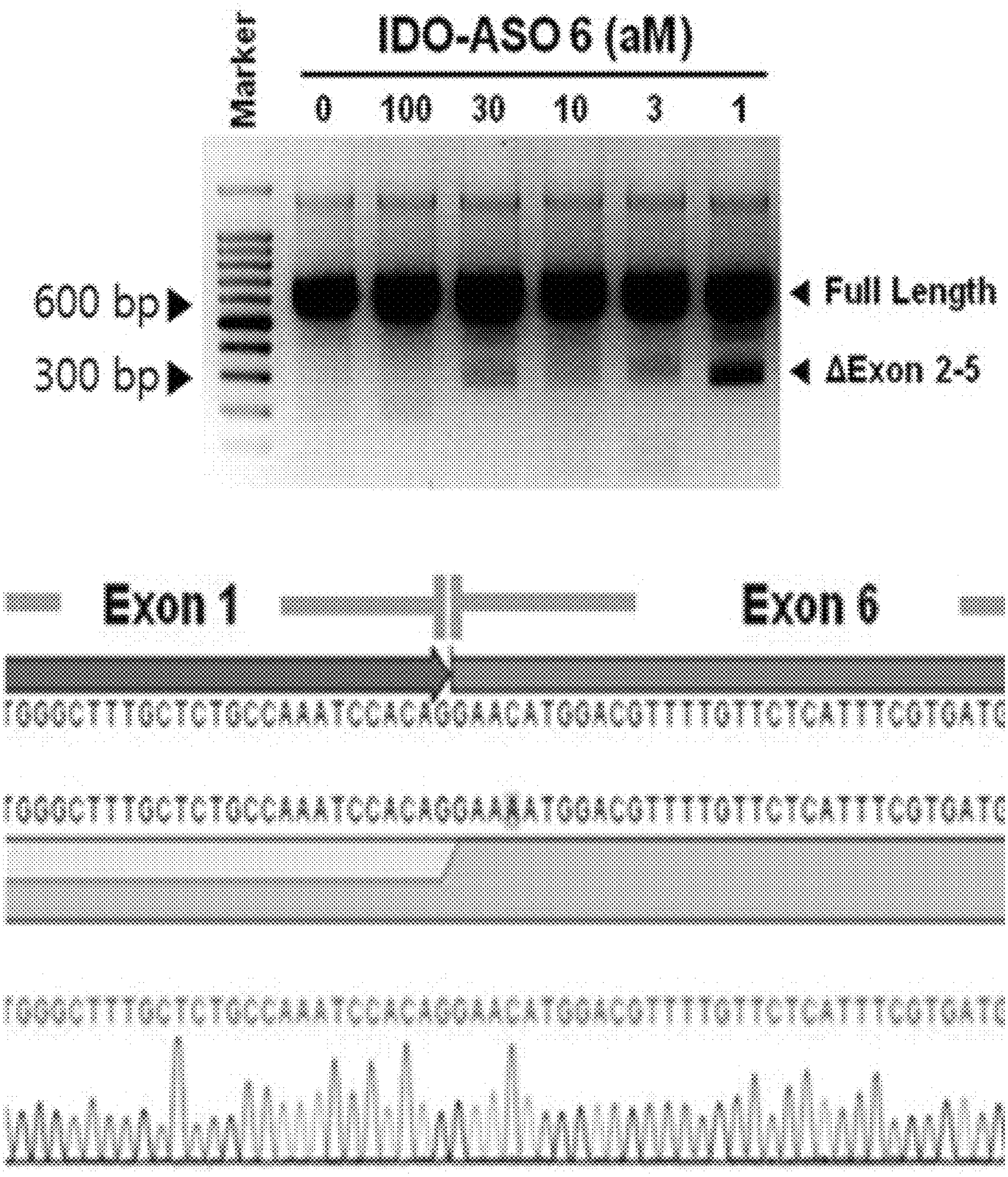
FIG. 47C. Electrophoresis data for the IDO-1 nested PCR products in SKOV3 cells treated with "IDO-ASO 6" at 0 (negative control), 1, 3, 10, 30 or 100 aM (left diagram), and Sanger sequencing data for the PCR band assigned to the skipping of exons 2-5 (right diagram).

[Nested PCR Products Data] FIG. 47C provides the electrophoresis data of the nested PCR products (left diagram) along with the Sanger sequencing data for the PCR band assignable to exon skipping (right diagram). The cells treated with "IDO-ASO 6" at 1 to 30 aM clearly yielded a single mRNA splice variant lacking exons 2-5, although the exon skipping band was not detected in the cells treated with the ASO at 100 aM. The full-length mRNA intensity was stronger in the ASO treated cells than the cells without the ASO treatment, which could be due to a transcription upregulation by the "exon intron circular RNA (EIciRNA)" accumulated during the exon skipping by "IDO-ASO 1". [*Nature Struct. Mol. Biol.* vol 22(3), 256-264 (2015)]

Examples for In Vitro and Ex Vivo Activities of SNAP25 ASOs

SNAP25 (synaptosome-associated protein of 25 kDa) is a SNARE protein involved in the exocytosis of neurotransmitters in motor neuronal cells. Botulinum toxin A (Botox™) cleaves SNAP25 for its famous anti-wrinkle activity. PNA derivatives of Formula I in Table 9 were designed to complementarily target the 3' splice site of exon 7 in the human SNAP25 pre-mRNA. SNAP25 ASOs were evaluated for the SNAP25 antisense activity in SiMa (human neuroblastoma) cells and PC12 cells of rat origin, as well as for their ability to inhibit the SNAP25 expression in the skin of mice upon topical administration. Biological examples provided herein are to illustrate the exon skipping activity of the SNAP25 ASOs as examples for the compound of Formula I, and therefore should not be interpreted to limit the scope of the current invention to SNAP25 ASOs.

SNAP25 Example 1. Exon Skipping in PC12 Cells Treated with "SNAP-ASO 3"

"SNAP-ASO 3" specified in Table 9 is a 14-mer ASO fully complementary to a 14-mer sequence in the 3' splice site spanning the junction of "intron 6" and "exon 7" in the human SNAP25 pre-mRNA. "SNAP-ASO 3" complementarily overlaps with the 14-mer pre-mRNA sequence as marked "bold" and "underlined" in the 30-mer pre-mRNA sequence of

[(5'→3') cucuuuggaucccag|GGUAACAAAUGAUGC (SEQ ID NO: 124)].

"SNAP-ASO 3" possesses a 7-mer overlap with "intron 6", and another 7-mer overlap with "exon 7".

"SNAP-ASO 3" was evaluated for its ability to induce exon skipping in PC12 cells (Cat. Number CRL-1721, ATCC), although "SNAP-ASO 3" possesses a single mismatch with the 3' splice site of "exon 7" in the rat SNAP25 pre-mRNA read out from the rat genomic DNA [accessed from NCBI Reference Sequence: NC_005012]. The 14-mer ASO possesses a 13-mer complementary overlap with the rat SNAP25 pre-mRNA as marked "bold" and "underlined" in the 25-mer pre-mRNA sequence of

[(5'→3') ugg"c"<u>ucccag</u>|<u>GGUAACA</u>AACGAUGC (SEQ ID NO: 125)], in which the single mismatch marked with a quote (" ") sign.

[Cell Culture & ASO Treatment] PC12 cells were maintained in RPMI 1640 medium supplemented with 5% FBS, 10% horse serum, 1% streptomycin/penicillin, 1% L-glutamine, and 1% sodium pyruvate under 5% $CO_2$ atmosphere at 37° C. Cells grown in 60 mm culture dish containing 5 mL culture medium were treated with "SNAP-ASO 3" at 0 (negative control), 10, 100 or 1,000 zM.

[RNA Extraction & cDNA Synthesis by One-step PCR] Following an incubation with "SNAP-ASO 3" for 42 hours, the cells were treated with 100 μg/mL cycloheximide for another 6 hours in order to freeze the ribosomal translation. Then total RNA was extracted using "Universal RNA Extraction Kit" (Cat. Number 9767, Takara) according to the manufacturer's instructions. 200 ng of RNA template was subjected to a 25 μL reverse transcription reaction using Super Script® One-Step RT-PCR kit with Platinum® Taq polymerase (Cat. Number 10928-042, Invitrogen) against a set of exon-specific primers of [SNAP-exon 1_forward: (5'→3') ATGGCCGAGGACGCAGACA (SEQ ID NO: 126); and SNAP-exon 14_reverse: (5'→3') AGCATCTTTGTTGCACGTTG (SEQ ID NO: 127)] according to the following cycle conditions: 50° C. for 30 min and 94° C. for 2 min, which was followed by 40 cycles of 30 sec at 94° C., 30 sec at 50° C., and 1 min at 72° C.

[Nested PCR Amplification] 1 μL of cDNA was subjected to a 20 μL nested PCR reaction (Cat. Number K2612, Bioneer) against a set of exon specific primers of [SNAP-exon 1_forward: (5'→3') ATGGCCGAGGACGCAGACA (SEQ ID NO: 128); SNAP-exon 14n_reverse: (5'→3') TTGTTGGAGTCAGCGCCT (SEQ ID NO: 129)] according to the following cycle conditions: 95° C. for 2 min followed by 34 cycles of 30 sec at 95° C., 30 sec at 55° C., and 1 min at 72° C.

[Identification of Exon Skipping Products] The PCR products were subjected to electrophoretic separation on a 2% agarose gel. The bands of target size were collected and analyzed by Sanger Sequencing.

Figure 48A:
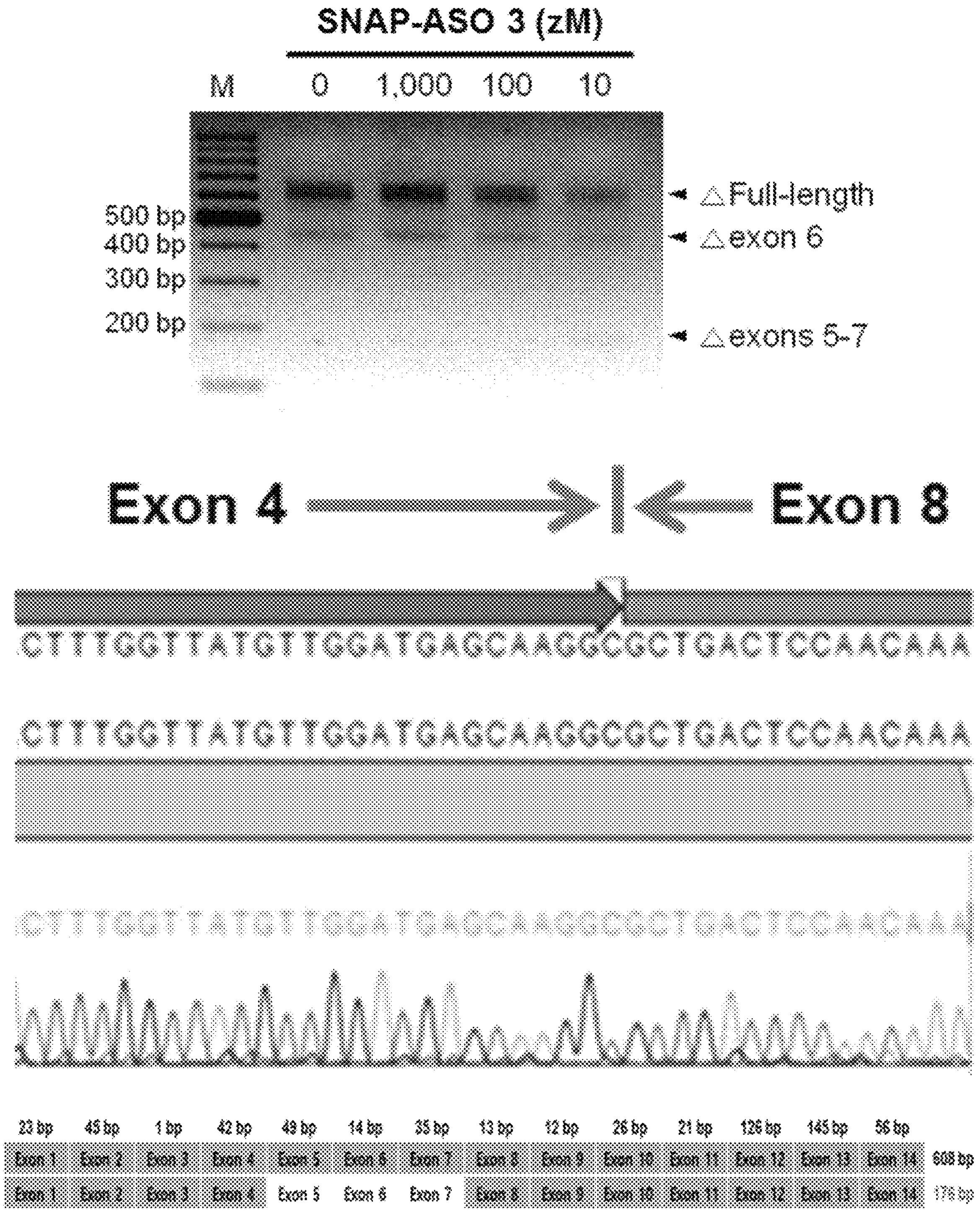
FIG. 48A. Electrophoretic analysis of the SNAP25 nested PCR products in PC12 cells treated with 0 (negative control), 10, 100 or 1,000 zM "SNAP-ASO 3" (left diagram), and Sanger sequencing data for the PCR band for the skipping of exons 5-7.

FIG. 48A provides the electrophoresis data of the PCR products, in which the 10 zM ASO treatment sample yielded a faint PCR band assignable to the skipping of exons 5-7 (cf. left diagram). Even if the cells were treated with cycloheximide to destabilize the full-length mRNA by freezing the ribosomal translation, the exon skipping band was detected only faintly. Thus the SNAP25 mRNA splice variant assignable to the skipping of exons 5-7 is likely to show poor metabolic stability in cells compared to the full-length mRNA. The exon skipping PCR product was sequenced to be the skipping of exons (5-7) as shown in FIG. 48A. (cf. right diagram) Given that the PCR product assignable to the skipping of exon 6 was observed regardless of the ASO concentration, the skipping of exon 6 is considered to occur spontaneously.

The intensity of the full-length SNAP25 mRNA decreased most in the cells treated with 10 zM "SNAP-ASO 3". The full-length mRNA intensity gradually increased to that of the negative control (i.e., without ASO treatment), as the ASO concentration was increased from 10 to 1,000 zM. The inverted dose response pattern in the nested PCR data could be due to a transcription upregulation by the "exon intron circular RNA (EIciRNA)" accumulated during the exon skipping with "SNAP-ASO 3". [*Nature Struc. Mol. Biol.* vol 22(3), 256-264 (2015)]

SNAP25 Example 2. qPCR for SNAP25 mRNA in PC12 Cells Treated with "SNAP-ASO 3"

"SNAP-ASO 3" was evaluated by SNAP25 nested qPCR for its ability to induce changes in the rat SNAP25 mRNA level in PC12 cells as follows.

[Cell Culture & ASO Treatment] PC12 cells grown in 60 mm culture dish containing 5 mL culture medium were treated with "SNAP-ASO 3" at 0 (negative control), 10, 100 or 1,000 zM. (2 culture dishes per ASO concentration)

[RNA Extraction & cDNA Synthesis by One-step RT-PCR] Following an incubation with "SNAP-ASO 3" for 42 hours, the cells were treated 100 μg/mL cycloheximide for another 6 hours to freeze the ribosomal translation. Then total RNA was extracted from cells using "Universal RNA Extraction Kit" (Cat. Number 9767, Takara) according to the manufacturer's instructions. 200 ng of RNA template was subjected to a 25 μL reverse transcription reaction using One Step RT-PCR kit (Invitrogen, USA) against a set of exon-specific primers of [SNAP-exon 1_forward: (5'→3') ATGGCCGAGGACGCAGACA (SEQ ID NO: 130); and SNAP-exon 14_reverse: (5'→3') AGCATCTTTGTTGCACGTTG (SEQ ID NO: 131)] according to the following cycle conditions: 50° C. for 30 min and 94° C. for 2 min, which was followed by 20 cycles of 30 sec at 94° C., 30 sec at 55° C., and 1 min at 72° C.

[Nested qPCR Amplification] 1 μL of each cDNA solution diluted by 100× was subjected to a 20 μL Real-Time PCR reaction against a set of exon-specific primers of [SNAP-exon 7q_forward: (5'→3') ATGGATGAAAACCTAGAGC (SEQ ID NO: 132); and SNAP-exon 8q_reverse: (5'→3') CTTCCCAGCATCTTTGTT (SEQ ID NO: 133)] according to the following cycle conditions: 95° C. for 3 min followed by 40 cycles 10 sec at 95° C., and 30 sec at 60° C. The qPCR reaction was followed with a Taqman probe of [(5'→3') 5,6-FAM-CAGCCTTCT-ZEN-CCATGATCCT-3IABkFQ (SEQ ID NO: 134)] targeting the junction of exon 7 and exon 8 in order to quantify the full-length SNAP25 mRNA.

Figure 48B:
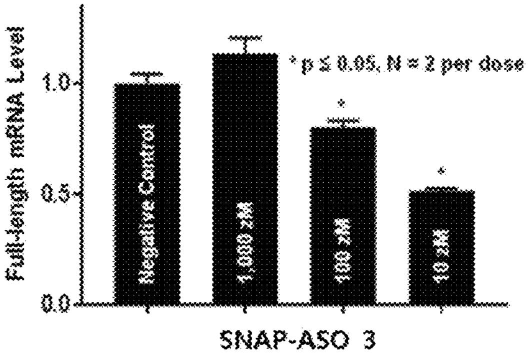
FIG. 48B. Changes in the full-length rat SNAP25 mRNA level in PC12 cells treated with "SNAP-ASO 3" at 0 (negative control), 10, 100 or 1,000 zM. (error bar by standard error)

FIG. 48B provides the qPCR data, in which the full-length mRNA level significantly decreased (student's t-test) in the cells treated with "SNAP-ASO 3" at 10 zM and 100 zM by ca 50% and 20%, respectively. However, the full-length mRNA level in the cells treated with 1,000 zM "SNAP-ASO 3" was slightly higher than the level of the cells without ASO treatment (i.e., negative control).

The inverted dose response pattern of the qPCR data is consistent fairly much with the dose response pattern of the full-length mRNA level during the exon skipping described in "SNAP25 Example 1", suggesting a transcription upregulation as the ASO dose was increased from 10 to 1,000 zM. Thus the 13-mer complementary overlap with the rat SNAP25 pre-mRNA would not be sufficient enough to knock down the transcription upregulation induced by the EIciRNA(s) accumulating during the exon skipping.

SNAP25 Example 3. qPCR for SNAP25 mRNA in PC12 Cells Treated with "SNAP-ASO 1"

"SNAP-ASO 1" specified in Table 8 is a 16-mer ASO fully complementary to a 16-mer sequence of the 3' splice site spanning the junction of intron 6 and exon 7 in the human SNAP25 pre-mRNA. “SNAP-ASO 1” complementarily overlaps with the 16-mer target sequence as marked “bold” and “underlined” in the 30-mer human pre-mRNA sequence

[(5'→3') cucuuuggaucccag|GGUAACAAAUGAUGC (SEQ ID NO: 135)].

“SNAP-ASO 1” possesses a 6-mer overlap with intron 6 and a 10-mer overlap with exon 7. However, the ASO possesses a single mismatch with the rat SNAP25 pre-mRNA as marked “bold” and “underlined” in the 25-mer pre-mRNA sequence of

[(5'→3') uggcucccag|GGUAACAAA"C"GAUGC (SEQ ID NO: 136)], in which with the single mismatch is marked with a quote (“ ”) sign.

“SNAP-ASO 1” was evaluated by SNAP25 nested qPCR for its ability to induce changes in the rat SNAP25 mRNA level in PC12 cells as described in “SNAP25 Example 2”, unless noted otherwise.

Figure 48C:
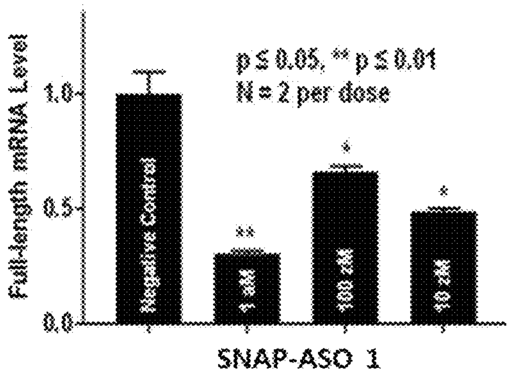
FIG. 48C. Changes in the full-length rat SNAP25 mRNA level in PC12 cells treated with "SNAP-ASO 1" at 0 (negative control), 10, 100 or 1,000 zM. (error bar by standard error)

FIG. 48C provides the qPCR data, in which the full-length mRNA level significantly decreased (student's t-test) in the cells treated with “SNAP-ASO 1” at 10 zM, 100 zM and 1,000 zM by ca 50%, 40% and 70%, respectively.

Like in the case of “SNAP-ASO 3”, the inverted dose response pattern was partly reproduced with “SNAP-ASO 1” as the dose was increased from 10 to 100 zM. Given that the full-length mRNA level decreased further as the ASO concentration was increased to 1,000 zM, however, the exon skipping efficacy of “SNAP-ASO 1” appears to be stronger than that of “SNAP-ASO 3”. The 15-mer complementary overlap of “SNAP-ASO 1” with the rat pre-mRNA would be responsible for the higher exon skipping efficacy.

SNAP25 Example 4. Inhibition of SNAP25 Protein Expression in PC12 Cells by “SNAP-ASO 3”

“SNAP-ASO 3” was evaluated for its ability to inhibit the expression of the SNAP25 protein in PC12 cells as follows.

PC12 cells were grown in 60 mm culture dish containing 5 mL culture medium, and treated with “SNAP-ASO 3” at 0 zM (negative control), 1 zM, 10 zM, 30 zM, 100 zM, 300 zM, 1 aM, 3 aM or 10 aM for 48 hours. There were 4 culture dishes of the negative control to compensate for potential technical artifacts during the western blot analysis.

[Cell Lysis] Then the cells were subjected to lysis on ice with 200 μL 1×RIPA buffer (Cat. Number 9806, Cell Signaling Tech) supplemented with 1% SDS and 1× proteinase inhibitors cocktail (cOmplete Mini, Roche). The lysates were collected in 1.5 mL e-tube, mixed with 100 μL 5× sample buffer, and boiled for 5 min.

[Western Blot] The lysates were subjected to electrophoretic separation on a 4-15% TGX-PAGE gradient gel (Cat. Number 456-1086, Bio-Rad) and then transferred onto a 0.45 μm PVDF membrane. The membrane was probed with an anti-SNAP25 antibody (Cat. Number S9684, Sigma) and an anti-β-actin antibody (Cat. Number A3845, Sigma).

Figure 49A:
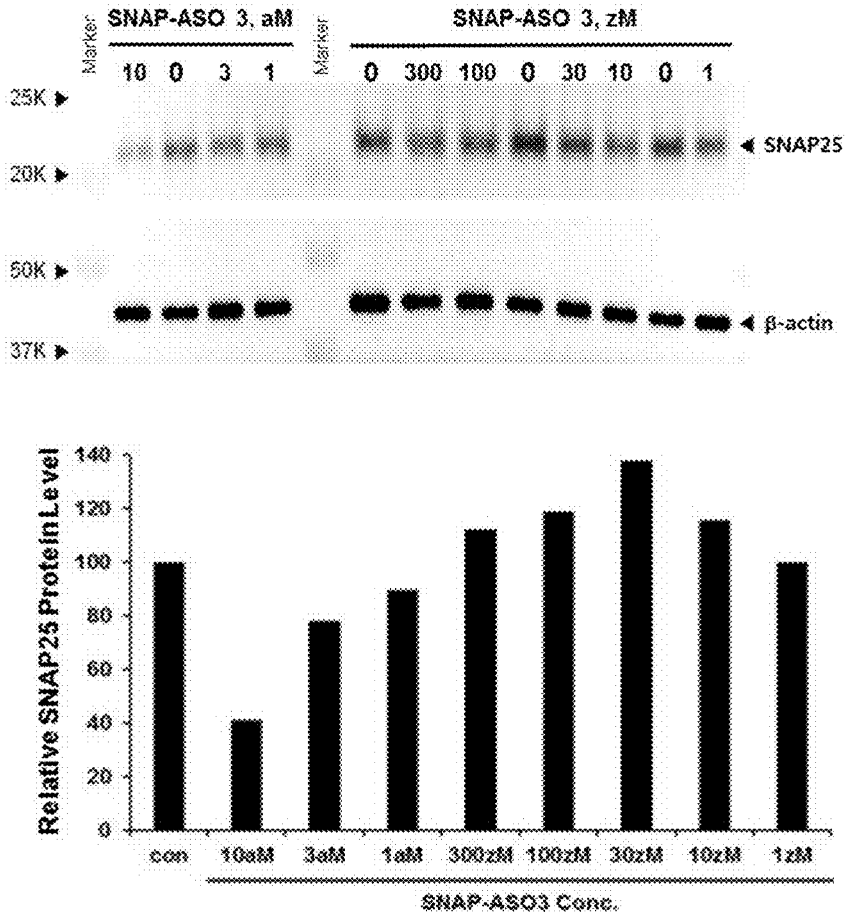
FIG. 49A. SNAP25 western blot data (top diagram) and relative SNAP25 expression levels normalized against β-actin (bottom diagram) in PC12 cells treated with "SNAP-ASO 3" for 48 hours at 0 zM (negative control), 1 zM, 10 zM, 30 zM, 100 zM, 300 zM, 1 aM, 3 aM or 10 aM.

FIG. 49A provides the SNAP25 western blot data obtained with the PC12 cell lysates (top diagram) along with the relative SNAP25 expression levels normalized against β-actin by densitometry (bottom diagram). The SNAP25 protein level decreased by 10 to 60% in the cells treated with “SNAP-ASO 3”. The expression level of the negative control (i.e., 0 zM “SNAP-ASO 3”) is the average expression level of the 4 samples.

SNAP25 Example 5. Inhibition of SNAP25 Protein Expression in PC12 Cells by “SNAP-ASO 1”

Figure 49B:
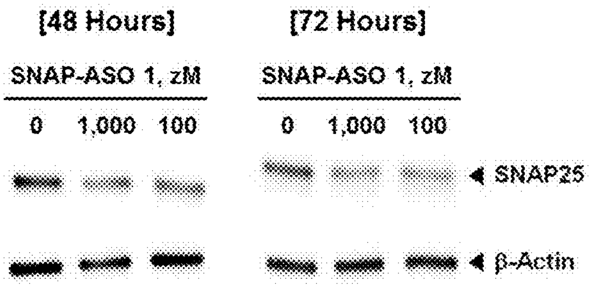
FIG. 49B. SNAP25 western blot data in PC12 cells treated with "SNAP-ASO 1" at 0 (negative control), 0.1 or 1 aM either for 48 hours or for 72 hours.

“SNAP-ASO 1” was evaluated for its ability to inhibit the SNAP25 protein expression in PC12 cells as described in “SNAP25 Example 4”, unless noted otherwise. PC12 cells were treated with “SNAP-ASO 1” at 0 (negative control), 100 or 1,000 zM either for 48 hours or for 72 hours. (One culture dish for each ASO concentration) FIG. 49B provides the western blot data for the ASO treatment of 48 hour (left) and 72 hours (right). “SNAP-ASO 1” considerably inhibited the expression of the SNAP25 protein in PC12 cells at both time points.

SNAP25 Example 6. Inhibition of SNAP25 Protein Expression in SiMa Cells by “SNAP-ASO 3”

“SNAP-ASO 3” was evaluated for its ability to inhibit the expression of the SNAP25 protein in SiMa human neuroblastoma cells as follows.

[Cell Culture and ASO Treatment] SiMa cells (Cat. Number ACC164, DSMZ) were maintained in RPMI 1640 medium supplemented with 10% FBS, 1% streptomycin/penicillin, 1% L-glutamine, and 1% sodium pyruvate under 5% $CO_2$ atmosphere at 37° C. SiMa cells were grown in 60 mm culture dish containing 5 mL culture medium, and were treated for 48 hours with “SNAP-ASO 3” at 0 zM (negative control), 1 zM to 100 aM. There were 3 culture dishes for the negative control to compensate for potential technical artifacts during the western blot analysis.

[Lysis] The cells were subjected to lysis on ice with 200 μL 1×RIPA buffer (Cat. Number 9806, Cell Signaling Tech) supplemented with 0.1% SDS and 1× proteinase inhibitors cocktail (cOmplete Mini, Roche). Then the lysates were collected in 1.5 mL e-tube, mixed with 100 μL 5× sample buffer, and boiled for 5 min.

[Western Blot] The lysates were subjected to electrophoretic separation on a 12% SDS-PAGE gel, and transferred onto a 0.2 μm polyvinylidene difluoride (PVDF) membrane. The membrane was probed with an anti-SNAP25 antibody (Cat. Number ab41455, Sigma) and an anti-β-actin antibody (Cat. Number A3845, Sigma).

Figure 50A:
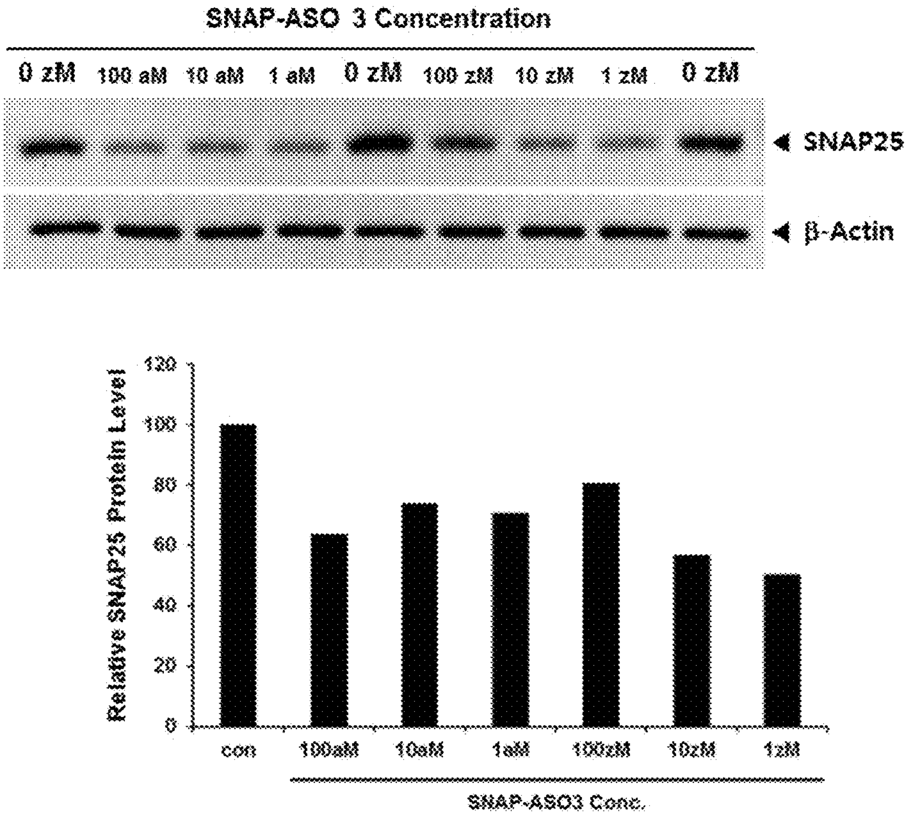
FIG. 50A. SNAP25 western blot data (top diagram) and relative SNAP25 expression levels normalized against β-actin (bottom diagram) in SiMa cells treated with "SNAP-ASO 3" for 48 hours at 0 zM (negative control), 1 zM, 10 zM, 100 zM, 1 aM, 10 aM, or 100 aM.

FIG. 50A provides the SNAP25 western blot data obtained with the SiMa cell lysates (top diagram) along with the relative SNAP25 expression levels normalized against β-actin by densitometry (bottom diagram). The SNAP25 protein level decreased by 40 to 50% in the cells treated with “SNAP-ASO 3”.

SNAP25 Example 7. qPCR for SNAP25 mRNA in SiMa Cells Treated with “SNAP-ASO 3”

“SNAP-ASO 3” was evaluated by SNAP25 nested qPCR for its ability to induce changes in the human SNAP25 mRNA level in SiMa cells as follows.

[Cell Culture & ASO Treatment] SiMa cells were grown in 60 mm culture dish containing 5 mL culture medium, and were treated with “SNAP-ASO 3” at 0 zM (negative control), 1 zM, 10 zM, 100 zM or 1 aM, 10 aM, or 100 aM. (2 culture dishes per ASO concentration)

[RNA Extraction & cDNA Synthesis] Total RNA was extracted from cells using “RNeasy Mini Kit” (Cat. Number 74106, Qiagen) according to the manufacturer's instructions. 200 ng of RNA template was subjected to a 25 μl reverse transcription reaction using PrimeScript 1st strand cDNA synthesis Kit (Cat. No. 6110B, Takara) against random hexamers.

[qPCR Amplification] The PCR reactions were monitored with a Taqman probe [(5' 3') 56-FAM-CGGCTTCAT-ZEN-CCGCAGGGTAACAA-3IABkFQ (SEQ ID NO: 137)] targeting the junction of exon 6 and exon 7 against a set of exon-specific primers [SNAP-exon 6_forward: (5'→3') GACGAACGGGAGCAGATG (SEQ ID NO: 138); and SNAP-exon 8_reverse(2): (5'→3') ATCTCATTGCCCATATCCAGG (SEQ ID NO: 139)]. Cycle Conditions: 95° C. for 3 min followed by 40 cycles 15 sec at 95° C., and 30 sec at 60° C.

Figure 50B:
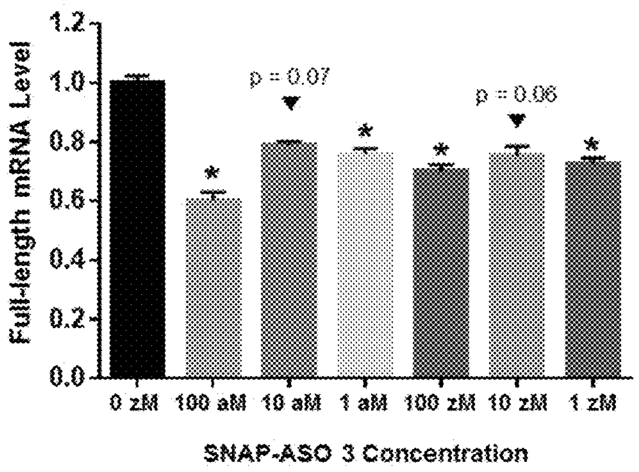
FIG. 50B. Changes in the full-length human SNAP25 mRNA level in SiMa cells treated with "SNAP-ASO 3" at 0 zM (negative control), 1 zM, 10 zM, 100 zM, 1 aM, 10 aM, or 100 aM. (error bar by standard error)

FIG. 50B provides the qPCR data, in which the full-length human SNAP25 mRNA level significantly decreased (student's t-test) in the cells treated with "SNAP-ASO 3" at 1 zM, 100 zM, 1 aM and 100 aM by 20 to 40%. The cells treated with the ASO at 100 aM showed the strongest inhibition of 40%.

SNAP25 Example 8. Inhibition of SNAP25 Protein Expression in the Skin of Mouse Topically Administered with "SNAP-ASO 1"

"SNAP-ASO 1" is a 16-mer ASO fully complementary to the 3' splice site spanning the junction of intron 6 and exon 7 in the mouse SNAP25 pre-mRNA read out from the mouse genomic DNA [accessed from NCBI Reference Sequence: NC_000068]. "SNAP-ASO 1" was evaluated for its ability to inhibit the expression of SNAP25 protein in the skin upon topical administration as follows.

[Hair Cut and Grouping] In Day 0, 8 female C57BL/6 mice (5 weeks old) were anesthetized with zoletil/rompun, and the hair in the back (ca 3 cm×4 cm) was cut with a clipper. The mice were randomly assigned into 4 groups, i.e., no ASO treatment group (negative control) and 3 treatment groups of 1 fM, 10 fM and 100 fM "SNAP-ASO 1". (2 animals per group)

[Topical Administration] Topical solutions were prepared by serially diluting an aqueous stock solution of "SNAP-ASO 1" in 30% (v/v) aqueous ethanol supplemented with 3% (v/v) glycerin to 0, 1, 10 and 100 fM "SNAP-ASO 1". Each animal was topically administered with ca 100 μL of topical solution in the back skin with hair removal using a cotton ball twice per day during Days 0 to 4.

[Skin Sampling] In the afternoon of Day 4, the animals were anesthetized with zoletil/rompun in order to sample the skin part topically treated with the ASO. The skin samples were then subjected to IHC against the SNAP25 protein as described below.

[SNAP25 IHC] Skin samples were cryo-sectioned and immunostained in series with a primary anti-SNAP25 antibody (Cat. Number ab41455, Abcam) at 1:200 dilution, with a secondary anti-IgG (Cat Number BA-1100, Vector) at 1:200 dilution, and then with Dylight 594-streptavidin (Cat Number SA-5594, Vector, CA, USA) at 1:200 dilution for red fluorescence tagging. The anti-SNAP25 antibody probes the C-terminal of the SNAP25 protein. IHC images were captured on a Zeiss slide scanner to evaluate the expression of SANP25 protein. DAPI staining was performed to visualize the skin microstructure.

Figure 51:
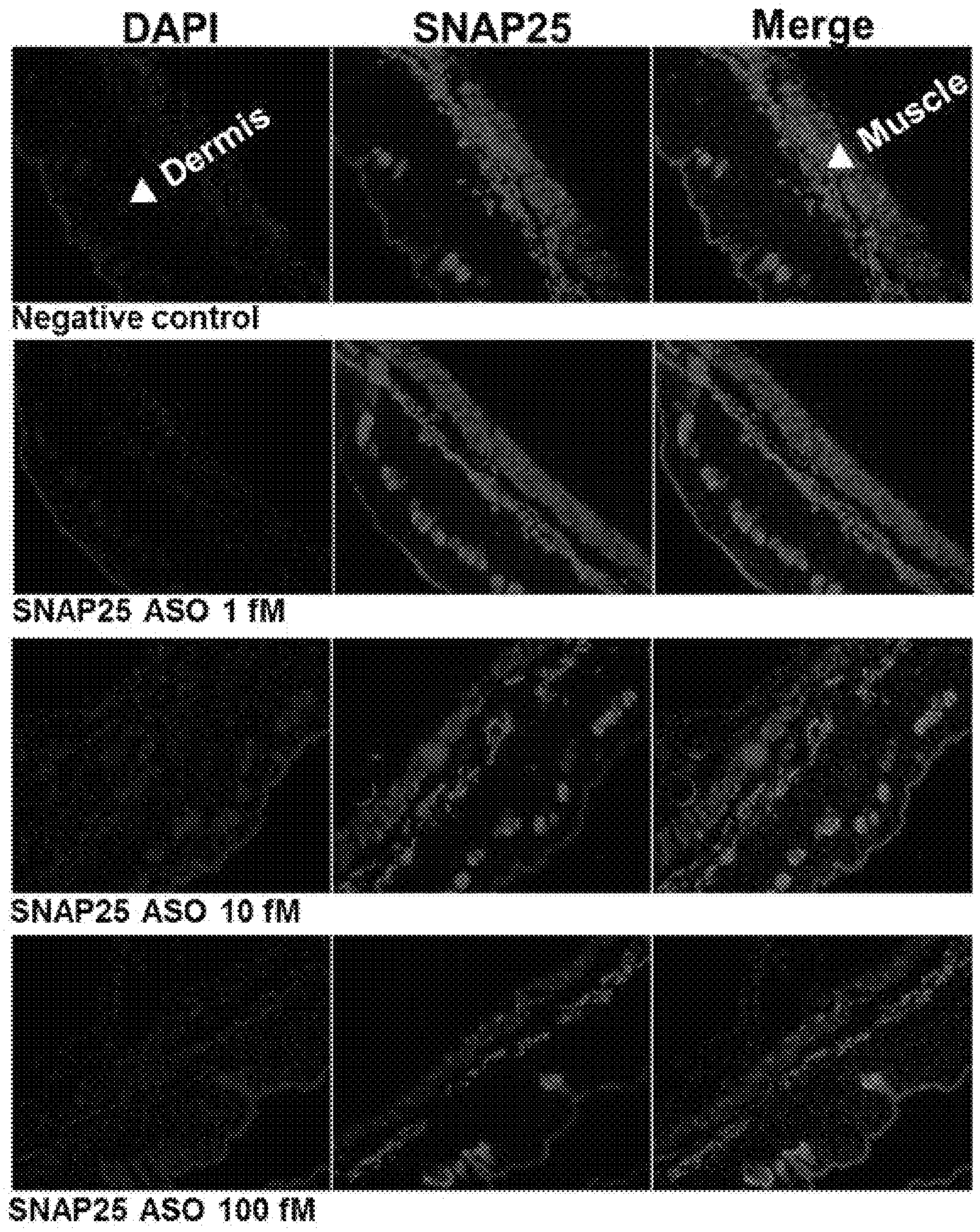
FIG. 51. SNAP25 IHC images for the skin samples of mice topically administered with "SNAP-ASO 1" at 0 (negative control), 1, 10 or 100 fM, BID over a period of 4 days.

FIG. 51 provides a representative set of SNAP25 IHC images by group. In the negative control group, the SNAP25 protein expression was high in the muscle layer right underneath the dermis. The SNAP25 protein expression in the muscle layer is considered to originate from the SNAP25 protein expression in the motor-neuronal axons embedded in the muscle layer. The SNAP25 protein expression in the muscle layer gradually decreased as the dose was increased. The most notable decrease was observed in the 100 fM treatment group.

The inhibition of the full-length SNAP25 protein expression in the skin by IHC appears to be stronger than the inhibition by western blot observed in PC12 cells (cf. "SNAP25 Example 5"). The transcriptional upregulation by the EIciRNA(s) in primary cells, if there is any, dosen't appear to be as marked as the upregulation implicated in cancer cells including PC12 and SiMa cells.

Examples for In Vitro Activity of TYR ASOs

Tyrosinase (TYR) is an enzyme involved in the melanogenesis or skin pigmentation. PNA derivatives of Formula I in Table 10 were designed to complementarily target the 3' splice site of exon 2 in the human or mouse TYR pre-mRNA. TYR ASOs were evaluated for the TYR antisense exon skipping activity in human melanocytes as well as in B16F10 (mouse melanoma) cells. Biological examples provided herein are to illustrate the exon skipping activity of TYR ASOs as examples for the compound of Formula I, and therefore should not be interpreted to limit the scope of the current invention to TYR ASOs.

TYR Example 1. Exon Skipping Induced by "TYR-ASO 4" in B16F10 Cells

"TYR-ASO 4" specified in Table 10 is a 13-mer TYR ASO fully complementary to the 3' splice site spanning the junction of intron 1 and exon 2 in the mouse TYR as marked "bold" and "underlined" in the 30-mer mouse TYR pre-mRNA sequence of

[(5'→3') aauuguuuuucacag|AUCAUUUGUAGCAGA (SEQ ID NO: 140)].

In the meantime, "TYR-ASO 4" possesses 4 mismatches with the 3' splice site spanning the junction of intron 1 and exon 2 in the human TYR pre-mRNA as marked with quote (" ") sign in the 30-mer pre-mRNA sequence of [(5'→3') ggguguuuug"u"acag|AU"UG"U"C"UGUAGCCGA (SEQ ID NO: 141)].

"TYR-ASO 4" was evaluated for its ability to induce the skipping of the mouse TYR exon 2 in $B_{16}F10$ melanoma cells as follows. "TYR-ASO 4" may serve as a good surrogate compound for "TYR-ASO 1" which is fully complementary to the human TYR pre-mRNA.

[Cell Culture & ASO Treatment] B16F10 mouse melanoma cells (Cat. Number CRL-6475, ATCC) were maintained in DMEM (Dulbecco's modified Eagle's essential minimum medium) supplemented with 10% FBS, 1% streptomycin/penicillin, and 0.01 mg/ml bovine insulin. B16F10 cells grown in 60 mm culture dish containing 5 mL DMEM were incubated for 5 hours with "TYR-ASO 4" at 0 (negative control), 1, 10, 100 or 1000 aM.

[RNA Extraction & cDNA Synthesis by One-step PCR] Total RNA was extracted using "Universal RNA Extraction Kit" (Cat. Number 9767, Takara) according to the manufacturer's instructions. 200 ng of RNA template was used for a 25 μL reverse transcription reaction using Super Script® One-Step RT-PCR kit with Platinum® Taq polymerase (Cat. Number 10928-042, Invitrogen) against a set of exon-specific primers of [TYR-exon 1_forward: (5'→3') GTAAGTTTGGATTTGGGG (SEQ ID NO: 142); and TYR-exon 4_reverse: (5'→3') AGAGCGGTAT-GAAAGGAA (SEQ ID NO: 143)] according to the following cycle conditions: 50° C. for 30 min and 94° C. for 2 min, which was followed by 15 cycles of 30 sec at 94° C., 30 sec at 52° C., and 40 sec at 72° C.

[Nested PCR Amplification] 1 µL of cDNA was further amplified in a 20 µL nested PCR reaction (Cat. Number K2612, Bioneer) against a set of exon-specific primers of [TYR-exon 1n_forward: (5'→3') GAGAACTAACTGGG-GATGA (SEQ ID NO: 144); and TYR-exon 4n_reverse: (5'→3') CGATAGGTGCATTGGCTT (SEQ ID NO: 145)] according to the following cycle conditions: 95° C. for 5 min followed by 30 cycles of 30 sec at 95° C., 30 sec at 52° C., and 40 sec at 72° C.

[Identification of Exon Skipping Products] The PCR products were subjected to electrophoretic separation on a 2% agarose gel. The bands of target size were collected and analyzed by Sanger Sequencing.

Figure 52A:
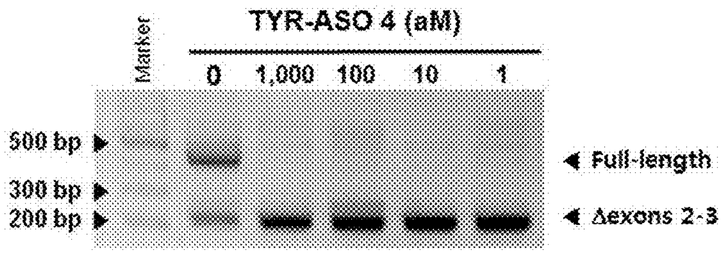
FIG. 52A. Electrophoretic analysis of the nested PCR products in B16F10 mouse melanoma cells treated with "TYR-ASO 4" at 0 (negative control), 1, 10 or 1,000 aM.

FIG. 52A provides the electrophoresis data of the PCR products. The cells without ASO treatment yielded two PCR bands, one for the full-length TYR mRNA and the other for the splice variant TYR mRNA lacking exons 2 and 3, suggesting a spontaneous skipping of exons 2-3. The cells treated with "TYR-ASO 4" at 1 to 1,000 aM, however, yielded essentially only the splice variant TYR mRNA lacking exons 2 and 3. Thus "TYR-ASO 4" increases the propensity of the skipping of exons 2-3 in B16F10 melanoma cells.

Figure 52B:
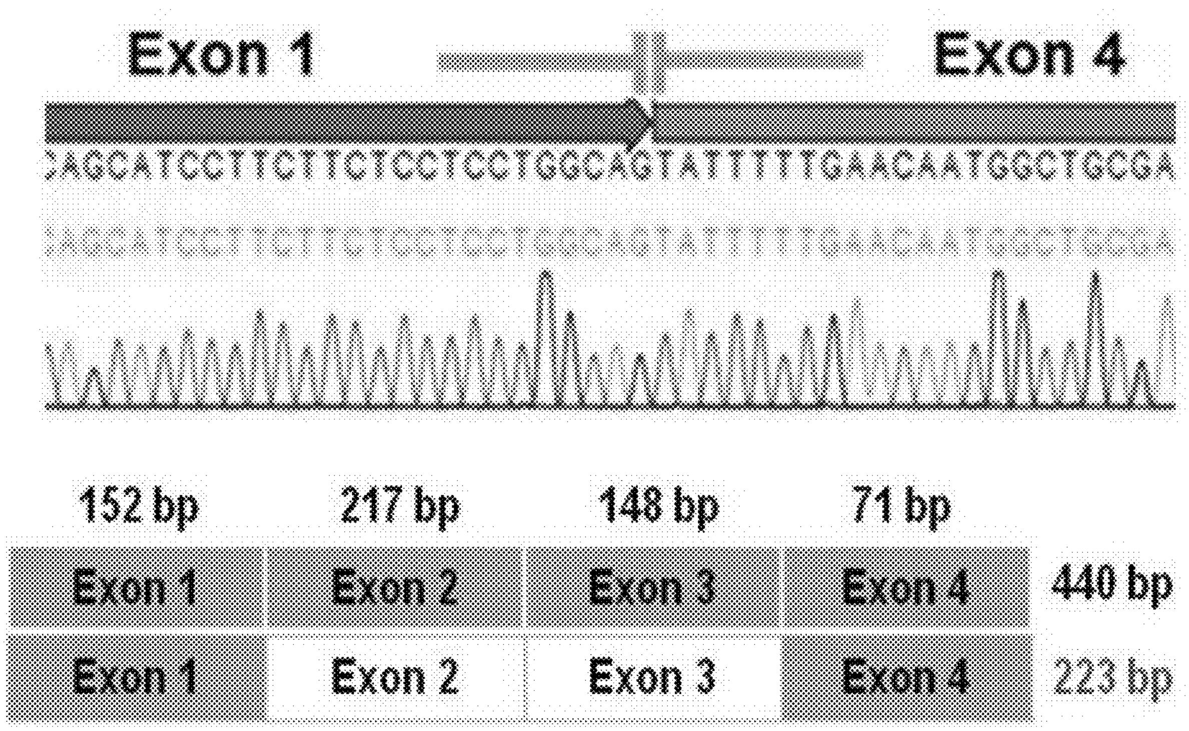
FIG. 52B. Sanger sequencing for the PCR product assigned to the skipping of exons 2-3.

The PCR product for the exon skipping was sequenced to be the mRNA splice variant lacking exons 2-3 as shown in FIG. 52B.

TYR Example 2. qPCR for TYR mRNA in B16F10 Cells Treated with "TYR-ASO 4"

"TYR-ASO 4" was evaluated by TYR nested qPCR for its ability to induce changes in the mouse TYR mRNA level in B16F10 cells as follows.

[Cell Culture & ASO Treatment] B16F10 cells grown in 60 mm culture dish containing 5 mL culture medium were treated with "TYR-ASO 4" at 0 (negative control), 1, 10, 100 or 1000 aM. (2 culture dishes per dose)

[RNA Extraction & cDNA Synthesis by One-step PCR] Total RNA was extracted and subjected to cDNA synthesis as described in "TYR Example 1".

[Nested qPCR Amplification] 1 µL of each cDNA solution diluted by 100× was subjected to a 20 µL Real-Time PCR reaction against a Taqman probe set targeting the junction of exon 2 and exon 3 (Cat. No. Mm00495818_m1, Thermo Fisher Scientific) according to the following cycle conditions: 95° C. for 3 min followed by 30 cycles 10 sec at 95° C., and 30 sec at 60° C.

[Statistical Analysis] The nested qPCR experiment was repeated independently four times, and individual mRNA levels from each experiment were normalized against the mRNA level without ASO treatment. The mRNA levels obtained from all the 4 separate experiments were pooled for statistical analysis by student's t-test. Thus the number of RNA samples is 8 per ASO concentration.

Figure 52C:
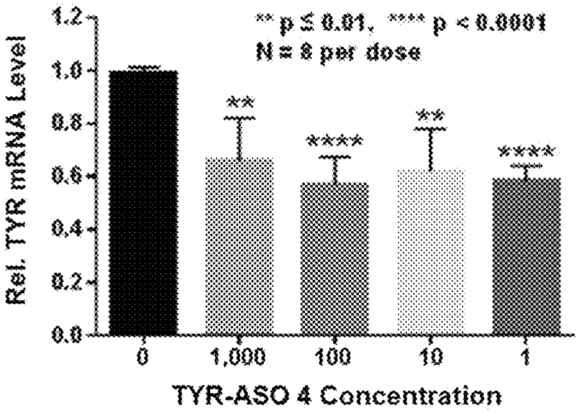
FIG. 52C. Changes in the full-length TYR mRNA level by qPCR in B16F10 mouse melanoma cells treated with "TYR-ASO 4" at 0 (negative control), 1, 10, 100 or 1,000 aM. (error bar by standard error)

FIG. 52C provides the pooled qPCR data, in which the full-length mRNA level significantly (student's t-test) decreased by ca 40% in the cells treated with "TYR-ASO 4" at 1 to 1,000 aM.

TYR Example 3. Inhibition of TYR Protein Expression by "TYR-ASO 4" in $B_{16}F10$ Cells "TYR-ASO 4" was evaluated for its ability to inhibit the expression of TYR protein in B16F10 cells as described below.

B16F10 cells grown in 60 mm culture dish containing 5 mL culture medium were treated with "TYR-ASO 4" for 24 hours at 0 zM (negative control), 10 zM, 100 zM, 1 aM or 10 aM, and subjected to lysis with 200 µL 1× cell lysis buffer (Cat. No. 9803, Cell Signaling Tech) supplemented with 1× protease inhibitors cocktail (Cat. No. P8340, Sigma). 200 µL of each lysate was mixed with 100 µL 5× sample buffer, and boiled at 100° C. for 5 min. 20 µL of each lysate was subjected to electrophoretic separation on a 4-15% gradient TGX gel (Cat No. 456-1086, Bio-Rad), and protein transfer onto a 0.45 µm PVDF membrane. The membrane was probed with an anti-TYR antibody (Cat. No. 9319, Cell Signaling Tech) and an anti-3-actin antibody (Cat. No. a3845, Sigma).

Figure 53A:
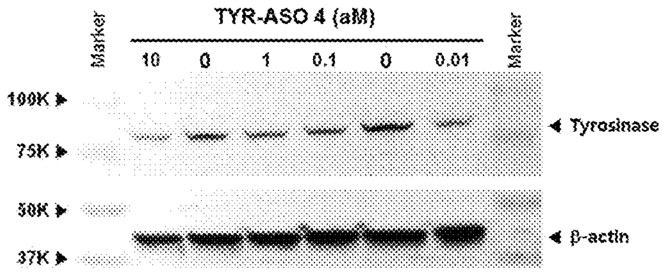
FIG. 53A. TYR western blot data in B16F10 cells treated with "TYR-ASO 4" for 24 hours at 0 (negative control), 0.01, 0.1, 1, or 10 aM.

FIG. 53A provides the TYR western blot data obtained with the B16F10 cell lysates. The TYR protein level was considerably higher in the lysates of the negative control than the lysates of the cells treated with "TYR-ASO 4".

TYR Example 4. Inhibition of Melanogenesis by "TYR-ASO 4" in B16F10 Cells

"TYR-ASO 4" was evaluated for its ability to inhibit the melanogenesis in B16F10 cells as described below.

B16F10 cells grown in 60 mm culture dish containing 5 mL culture medium were treated either with "TYR-ASO 4" at 0 (negative control) or 1 to 1,000 aM, or with 10 or 100 µg/mL arbutin as a positive control. (2 culture dishes per dose) 24 hours later, the cells were subjected to lysis with 200 µL 1N NaOH. Each lysate was collected in 1.5 mL e-tube, and kept overnight at room temperature. The melanin content in each lysate was determined by absorbance at 475 nm on an ELISA reader. The experiment was repeated four times using cells at different passage. The four sets of the melanin content data were pooled for statistical analysis by student's t-test against the melanin content without treatment (negative control).

Figure 53B:
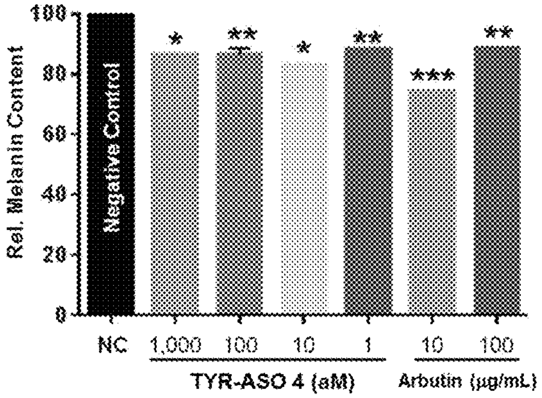
FIG. 53B. Changes in the melanin content in B16F10 mouse melanoma cells treated either with "TYR-ASO 4" at 0 (negative control) 1, 10, 100 or 1,000 aM, or with 10 μg/mL or 100 μg/mL arbutin. (error bar by standard error, * for $p<0.05$,  for $p<0.01$, and * for $p<0.001$)

FIG. 53B summarizes the changes in the melanin content in B16F10 cells following a 24 hours incubation either with "TYR ASO 4" or with arbutin. The melanin content significantly decreased ca by 15% and 25% in the cells treated with 10 µg/mL and 100 µg/mL arbutin, respectively. In case of the cells treated with "TYR-ASO 4", the melanin content significantly decreased by ca 15% without much dose dependency. The inhibitory activity of "TYR-ASO 4" was comparable to that of 10 µg/mL arbutin.

TYR Example 5. qPCR for TYR mRNA in Human Melanocytes Treated with "TYR-ASO 1"

"TYR-ASO 1" specified in Table 10 is a 13-mer TYR ASO fully complementary to the 3' splice site spanning the junction of intron 1 and exon 2 in the human TYR as marked "bold" and "underlined" in the 30-mer human TYR pre-mRNA sequence of

```
[(5'→3') ggguguuuuguacag|AUUGUCUGUAGCCGA
(SEQ ID NO: 146)].
```

"TYR-ASO 1" was evaluated by TYR nested qPCR for its ability to induce changes in the TYR mRNA level in human primary epidermal melanocytes as follows.

[Cell Culture & ASO Treatment] Primary epidermal melanocytes (Cat. Number PCS-200-013, ATCC) cells were maintained in Dermal Cell Basal Medium (Cat Number PCS-200-030, ATCC) supplemented with Adult Melanocyte Growth Kit Component (Cat. Number PCS-200-042, ATCC). Melanocytes grown in 60 mm culture dish containing 5 mL culture medium were treated with "TYR-ASO 1" at 0 zM (negative control), 1 zM, 100 zM, or 10 aM. (3 culture dishes per concentration)

[RNA Extraction & cDNA Synthesis by One-step PCR] Following an incubation with "TYR-ASO 1" for 5 hours, total RNA was extracted using "RNeasy Mini Kit" (Cat. Number 74106, Qiagen) according to the manufacturer's instructions. 200 ng of RNA template was subjected to a 25 μL reverse transcription reaction using Super Script® One-Step RT-PCR kit with Platinum® Taq polymerase (Cat. No. 10928-042, Invitrogen) against a set of exon-specific primers of [TYR-exon 1_forward(2): (5'→3') CTCTTTGTCTGGATGCATT (SEQ ID NO: 147); and TYR-exon 5_reverse: (5'→3') CTGTGGTAATCCTCTTTCT (SEQ ID NO: 148)] according to the following cycle conditions specified: 50° C. for 30 min and 94° C. for 2 min, which was followed by 15 cycles of 30 sec at 94° C., 30 sec at 50° C., and 1 min at 72° C.

[Nested PCR Amplification] 1 μL of cDNA was further amplified in a 20 μL nested PCR reaction (Cat. No. K2612, Bioneer) against a set of exon-specific primers of [TYR-exon 2n_forward: (5'→3') GATAAAGCTGCCAATTTC (SEQ ID NO: 149); and TYR-exon 3n_reverse: (5'→3') TTGTGCATGCTGCTTTGA (SEQ ID NO: 150)] against a Taqman probe [(5'→3') 5,6-FAM-CACTGG-ZEN-AAGGATTTGCTAGTCCAC-3IABkFQ (SEQ ID NO: 151)]. Cycle Conditions: 95° C. for 3 min followed by 40 cycles 10 sec at 95° C., and 30 sec at 60° C.

Figure 53C:
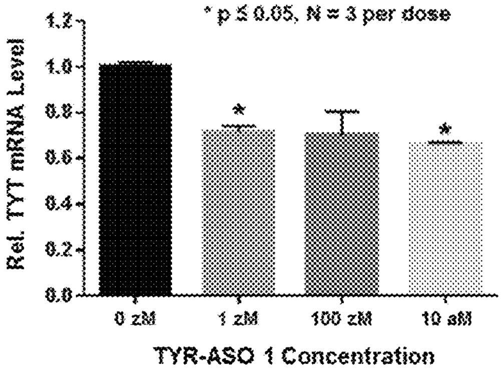
FIG. 53C. Changes in the full-length TYR mRNA level by qPCR in human primary epithelial melanocytes treated with "TYR-ASO 1" at 0 zM (negative control), 1 zM, 100 zM or 10 aM. (error bar by standard error)

FIG. 53C provides the qPCR data, in which the full-length TYR mRNA level decreased by ca 30% in the human melanocytes treated with "TYR-ASO 1" at 1 zM to 10 aM. The observed decreases were significant (student's t-test) in the cells treated with "TYR-ASO 1" at 1 zM and 10 aM.

Examples for Biological Activities of PD-1 ASOs

PD-1, also known as programmed cell death protein 1 or CD279, is a cell surface receptor expressed in immune cells. PD-1 is an immune check-point protein involved in the down-regulation of the immune response. PD-1 monoclonal antibodies such as nivolumab and pembrolizumab have been used to treat solid tumors by increasing the immune response.

PD-1 ASOs of Formula I in Table 11 were designed to complementarily target either the 3' splice site or the 5' splice site of exon 2 in the human or mouse PD-1 pre-mRNA. PD-1 ASOs were evaluated for the antisense exon skipping activity in Jurkat cells, and also for the antitumor activity in wild type mice loaded with syngeneic tumor. Biological examples provided herein are to illustrate the exon skipping activity of PD-1 ASOs as examples for the compound of Formula I, and therefore should not be interpreted to limit the scope of the current invention to PD-1 ASOs.

PD-1 Example 1. Exon Skipping Induced by "PD-ASO 3" in Jurkat Cells

"PD-ASO 3" specified in Table 11 is a 14-mer PD-1 ASO fully complementary to the 5' splice site spanning the junction of exon 2 and intron 2 in the human PD-1 pre-mRNA as marked "bold" and "underlined" in the 30-mer human PD-1 pre-mRNA sequence of

[(5'→3') AGCUCAGGGUGACAG|gugcggccucggagg (SEQ ID NO: 152)].

"PD-ASO 3" possesses a 9-mer overlap with exon 2 and a 5-mer overlap with intron 2.

"PD-ASO 3" was evaluated for its ability to induce the skipping of the human PD-1 exon 2 in Jurkat cells as follows.

[Cell Culture & ASO Treatment] Jurkat cells (Cat. Number TIB-152, ATCC) were maintained in RPMI-1640 supplemented with 10% FBS and 1% streptomycin/penicillin. Jurkat cells grown in 60 mm culture dish containing 5 mL culture medium were treated for 5 hours with "PD-ASO 5" at 0 (negative control), 10, 100 or 1,000 aM.

[RNA Extraction and cDNA Synthesis by One Step RT-PCR] Total RNA was extracted using RNAeasy mini prep kit (Qiagen, USA) according to the manufacturer's protocol. 500 ng of RNA template was subjected to a 25 μL reverse transcription reaction using One Step RT-PCR kit (Invitrogen, USA) against a set of exon-specific primers [PD-exon 1_forward: (5'→3') GTCGTCTGGGCGGTGCTACAAC (SEQ ID NO: 153); and PD-exon 5_reverse: (5'→3') GGGTGTGGAA-ATAGATGGG (SEQ ID NO: 154)]. Cycle conditions: 50° C. for 30 minutes and 94° C. for 2 minutes, which was followed by 30 cycles of 30 seconds at 94° C., 30 seconds at 53° C., and 1 minutes at 72° C.

[Nested PCR Amplification] 1 μL of cDNA diluted by 100× was further amplified in a 20 μL nested PCR (Invitrogen, USA) using the following cycle conditions: 20 seconds at 95° C., 30 seconds at 56° C., and 40 seconds at 72° C. for 40 cycles against a set of exon-specific primers [PD-exon 1n_forward: (5'→3') GGCTGGCGGCCAGGATGGTTC (SEQ ID NO: 155); and PD-exon 5n_reverse: (5'→3') GAAAGACAATGGTGGCATACTCC (SEQ ID NO: 156)].

[Identification of Exon Skipping Products] The resulting nested PCR products were subjected to electrophoretic separation on a 2% agarose gel. The bands of target size were collected and analyzed by Sanger sequencing.

Figure 54A:
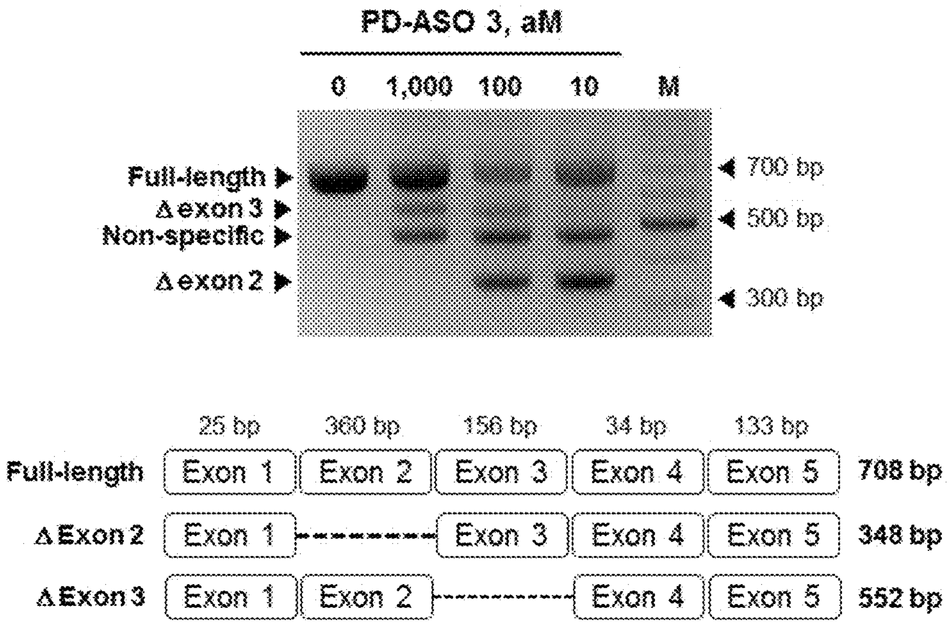
FIG. 54A. Electrophoretic analysis of the nested PCR products in Jurkat cells treated with "PD-ASO 3" at 0 (negative control), 10, 100 or 1,000 aM.

FIG. 54A provides the electrophoresis data of the PCR products. The cells without ASO treatment yielded only the PCR product band of the full-length mRNA. In the meantime, there were three PCR product bands newly formed in the cells treated with the PD-1 ASO. Of the three PCR product bands, the band of ca 470 bp size (marked as "non-specific" in FIG. 54A) was not a PD-1 mRNA splice variant with exon skipping according to a Sanger sequencing analysis.

Figure 54B:
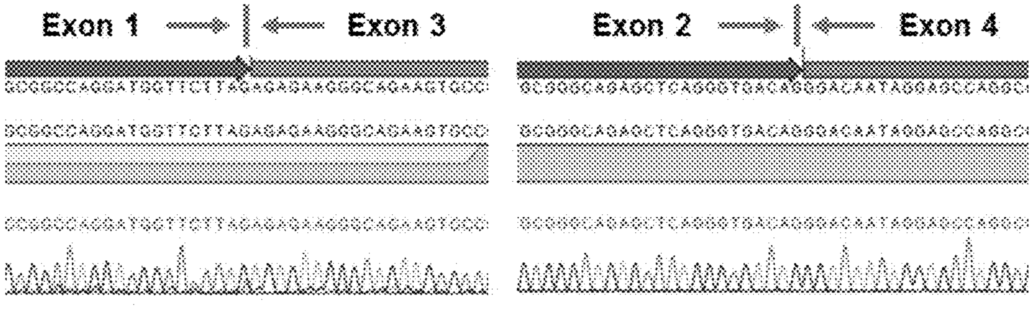
FIG. 54B. Sanger sequencing for the PCR products assigned to the skipping of exon 2 (left) and exon 3 (right), respectively.

The cells treated with "PD-ASO 3" at 10 and 100 aM yielded a PCR product band corresponding to the skipping of exon 2 by Sanger sequencing. In the cells treated with 1,000 aM "PD-ASO 3", however, the PCR product of exon 2 skipping disappeared and the full-length mRNA level was higher than the full-length level in the cells treated at the lower ASO concentrations. The two PCR products assigned to the skipping of exon 2 and exon 3 were confirmed by Sanger sequencing. (cf. FIG. 54B) The inverted dose response pattern in the nested PCR data could be due to a transcription upregulation by the "exon intron circular RNA (EIciRNA)" accumulated during the exon skipping with "PD-ASO 3". [*Nature Struc. Mol. Biol. vol* 22(3), 256-264 (2015)]

PD-1 Example 2. qPCR for PD-1 mRNA in Jurkat Cells Treated with “PD-ASO 3”

“PD-ASO 3” was evaluated by PD-1 nested qPCR for its ability to induce changes in the human PD-1 mRNA level in Jurkat cells as follows.

[Cell Culture & ASO Treatment] Jurkat cells grown in 60 mm culture dish were activated with an anti-CD3 antibody (Cat. Number 16-0037, eBioscience) at 1 g/mL and an anti-CD28 antibody (Cat. No. 16-0289, eBioscience) at 0.5 μg/mL for 48 hours. Then the culture medium was replaced with fresh medium, and treated with “PD-ASO 3” at 0 (negative control), 10, 100 or 1,000 aM for 24 hours. (4 culture dishes per ASO concentration)

[RNA Extraction and cDNA Synthesis by One Step RT-PCR] Total RNA was extracted using RNAeasy mini prep kit (Qiagen, USA) according to the manufacturer's protocol. 500 ng of RNA template was subjected to a 25 μL reverse transcription reaction using One Step RT-PCR kit (Invitrogen, USA) against a set of exon-specific primers [PD-exon 1_forward: (5'→3') GTCGTCTGGGCGGTGC-TACAAC (SEQ ID NO: 157); and PD-exon 5_reverse: (5'→3') GGGTGTGGAA-ATAGATGGG (SEQ ID NO: 158)]. Cycle conditions: 50° C. for 30 minutes and 94° C. for 2 minutes, which was followed by 30 cycles of 30 seconds at 94° C., 30 seconds at 53° C., and 1 minutes at 72° C.

[Nested qPCR by SYBR] 1 μL of each cDNA solution diluted by 100× was subjected to a 20 μL nested qPCR amplifications against a set of exon-specific primers [PD-exon 2_forward: (5'→3') ACAACGCCACCTTCACCTGC (SEQ ID NO: 159); and PD-exon 2_reverse: (5'→3') GCCAGCTTGTCCGTCTGGTTG (SEQ ID NO: 160)] according to the following cycle conditions: 20 seconds at 95° C., 30 seconds at 56° C., and 40 seconds at 72° C. for 40 cycles. The qPCR reaction was probed with SYBR (Bio-Rad, USA).

Figure 55A:
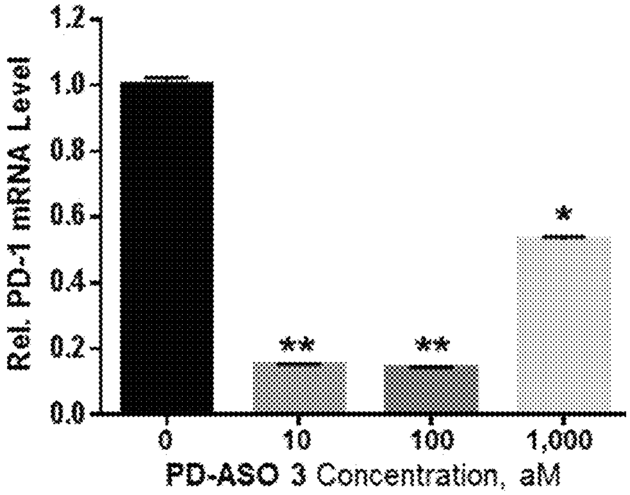
FIG. 55A. Changes in the human PD-1 mRNA level by nested qPCR in Jurkat cells treated with "PD-ASO 3" at 0 (negative control), 10, 100 or 1,000 aM. (error bar by standard error, ** for $p<0.01$, and * for $p<0.05$)

FIG. 55A provides the qPCR data, in which the PD-1 mRNA level significantly (student's t-test) decreased by >80% in the cells treated with “PD-ASO 3” at 10 and 100 aM. In case of the cells treated with the ASO at 1,000 aM, the PD-1 mRNA level rebounded to ca 55% of the negative control level. The rebound of the mRNA level at 1,000 aM is consistent with the inverted dose response pattern observed in “PD-1 Example 1”. (cf. FIG. 54A)

PD-1 Example 3. qPCR for IL-2 mRNA in Jurkat Cells Treated with “PD-ASO 3”

Down-regulation of the PD-1 activity has been known to upregulate the expression of interleukin 2 (IL-2). [*Am. J. Clin. Oncol. Vol* 39(1), 98-106 (2016)] “PD-ASO 3” was evaluated by IL-2 nested qPCR for its ability to induce changes in the human IL-2 mRNA level in Jurkat cells as follows.

[Cell Culture & ASO Treatment] Jurkat cells grown in 60 mm culture dish were activated with an anti-CD3 antibody (Cat. Number 16-0037, eBioscience) at 1 μg/mL and an anti-CD28 antibody (Cat. No. 16-0289, eBioscience) at 0.5 μg/mL for 48 hours. Then the culture medium was replaced with fresh medium, and treated with “PD-ASO 3” at 0 (negative control), 10, 100 or 1,000 aM for 24 hours. (4 culture dishes per ASO concentration)

[RNA Extraction and cDNA Synthesis] Total RNA was extracted using RNeasy mini prep kit (Qiagen, USA) according to the manufacturer's protocol. 500 ng of RNA template was subjected to a 25 μL reverse transcription reaction using PrimeScript™ 1$^{st}$ strand cDNA synthesis kit (Takara, Japan) according to the manufacturer's protocol.

[qPCR by SYBR] 1 μL of each cDNA solution was subjected to a 20 μL qPCR amplifications against a set of primers targeting the IL-2 mRNA [IL-2_forward: (5'→3') GTCACAAACAGTGCACCTAC (SEQ ID NO: 161); and IL-2_reverse: (5'→3') GGTGAGTTTGGGATT-CTTGTA (SEQ ID NO: 162)] according to the following cycle conditions: 20 seconds at 95° C., 30 seconds at 56° C., and 40 seconds at 72° C. for 40 cycles. The qPCR reaction was probed with SYBR (Bio-Rad, USA).

Figure 55B:
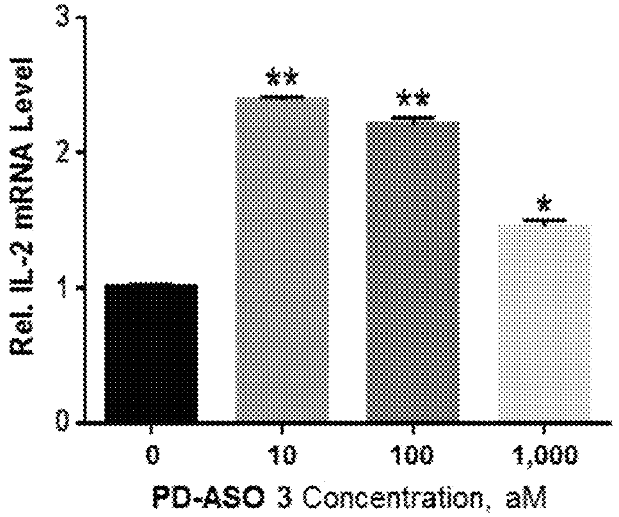
FIG. 55B. Changes in the human IL-2 mRNA level by qPCR in Jurkat cells treated with "PD-ASO 3" at 0 (negative control), 10, 100 or 1,000 aM. (error bar by standard error, ** for $p<0.01$, and * for $p<0.05$)

FIG. 55B provides the IL-2 qPCR data, in which the IL-2 mRNA level significantly (student's t-test) increased by ca 140%, 120%, and 40% in the cells treated with “PD-ASO 3” at 10, 100 and 1,000 aM, respectively. The inverted dose response pattern is consistent with the inverted dose response pattern observed in “PD-1 Example 1” and “PD-1 Example 2”. (cf. FIG. 54A and FIG. 55A)

PD-1 Example 4. qPCR for PD-1 mRNA in Jurkat Cells Treated with “PD-ASO 1”

“PD-ASO 1” specified in Table 11 is a 14-mer PD-1 ASO fully complementary to the 3' splice site spanning the junction of intron 1 and exon 2 in the human PD-1 pre-mRNA as marked “bold” and “underlined” in the 30-mer human PD-1 pre-mRNA sequence of

[(5'→3') cucuccaucucucag|ACUCCCCAGACAGGC (SEQ ID NO: 163)].

“PD-ASO 1” possesses a 5-mer overlap with intron 1 and a 9-mer overlap with exon 2.

“PD-ASO 1” was evaluated by PD-1 nested qPCR for its ability to induce changes in the human PD-1 mRNA level in Jurkat cells as described in “PD-1 Example 2”, unless noted otherwise.

FIG. 56A provides the qPCR data, in which the PD-1 mRNA level significantly (student's t-test) decreased by ca 60% in the cells treated with “PD-ASO 1” at 100 and 1,000 aM. Unlike the case with “PD-ASO 3”, “PD-ASO 1” showed no clear suggestion of the inverted dose response pattern.

PD-1 Example 5. Antitumor Activity of “PD-ASO 2” Against B16F10 Melanoma in C57BL/6 Mice “PD-ASO 2” specified in Table 11 is a 16-mer PD-1 ASO fully complementary to the 5' splice site spanning the junction of exon 2 and intron 2 in the mouse PD-1 pre-mRNA as marked “bold” and “underlined” in the 30-mer mouse PD-1 pre-mRNA sequence of

[(5'→3') AGCUCGUGGUAACAG|gugaggcuaguagaa (SEQ ID NO: 164)].

“PD-ASO 2” possesses a 10-mer overlap with exon 2 and a 6-mer overlap with intron 2.

In the meantime, “PD-ASO 2” possesses four mismatches with the human PD-1 pre-mRNA as marked “bold” and “underlined” in the 30-mer human PD-1 pre-mRNA sequence of [(5'→3') AGCUC“AG”GGU“G”ACAG-|gug“c”ggccucggagg (SEQ ID NO: 165)], where the four mismatches were marked with the quote (“ ”) sign. “PD-ASO 2” may be taken as surrogate ASO of “PD-ASO 3” for the human PD-1 pre-mRNA.

"PD-ASO 2" was evaluated for its antitumor activity in male C57BL/6 mice (4 weeks old) injected with B16F10 melanoma cells as provided below.

[Inoculation of B16F10 Melanoma Cells] B16F10 mouse melanoma cells (Cat. Number CRL-6475, ATCC) were maintained in 150 mm culture dish containing DMEM supplemented with 10% FBS, 1% streptomycin/penicillin, and 0.01 mg/ml bovine insulin. In Day 0, ca $1\times10^5$ B16F10 cells dissolved in 50 μL PBS were injected to each animal at the right rear flank.

[Grouping & ASO Treatment] In Day 3, the animals were randomly assigned by weight to 4 groups of 0 (negative control), 2, 10 and 50 pmole/Kg "PD-ASO 2". (N=15 per group)

Injection solutions were prepared by serially diluting an aqueous mother stock solution of "PD-ASO 2" in PBS to 0 nM (PBS only), 0.4 nM, 2 nM and 12.5 nM "PD-ASO 2" for the negative control, 2, 10 and 50 pmole/Kg "PD-ASO 2" group, respectively.

The animals were subcutaneously administered with an injection solution at 5 mL/Kg, 2× per week during Day 3 to Day 17.

[Anti-tumor Activity] The anti-tumor activity was assessed by changes in the tumor volume between each ASO treatment group and the negative control group.

FIG. 56B provides the observed tumor volumes by group during Day 0 to Day 19. The tumor growth of in the 2 pmole/Kg was significantly inhibited during Day 10 to Day 19. The observed inhibition in Day 19 was ca 55% (ca 375 $mm^3$ and 850 $mm^3$ with the 2 pmole/Kg and negative control group, respectively). The antitumor activity of the 50 pmole/Kg group was comparable to that of the 2 pmole/Kg group during Day 10 to Day 17. However the antitumor activity of the 50 pmole/Kg group disappeared in Day 19. The antitumor activity of the 10 pmole/Kg group was marginal without significance throughout the whole period.

The strange dose response pattern could be due to a transcription upregulation by the "exon intron circular RNA (EIciRNA)" accumulated during the exon skipping with "PD-ASO 2". [*Nature Struc. Mol. Biol*. vol 22(3), 256-264 (2015)] Given that nivolumab, a PD-1 monoclonal antibody drug approved by the US FDA, showed a dose response pattern of bell shape in tumor patients [*J. Clin. Oncol*. Vol 33(18), 2013-2020 (2015)], however, the strange dose response pattern of "PD-ASO 2" could be due to the intrinsic pharmacology of PD-1 inhibition.

In Day 19, the animals were sacrificed to measure the tumor weight by group. The average tumor weights were ca 0.35 g and 1.20 g for the 2 pmole/Kg group and the negative control group, respectively. Thus the tumor growth by weight was significantly inhibited in the 2 pmole/Kg group by ca 70%. ($p<0.01$ by student's t-test).

The invention claimed is:

1. A peptide nucleic acid derivative represented by Formula I, or a pharmaceutically acceptable salt thereof, for inducing exon skipping by targeting intron/exon or exon/intron junction of pre-mRNA:

Formula I

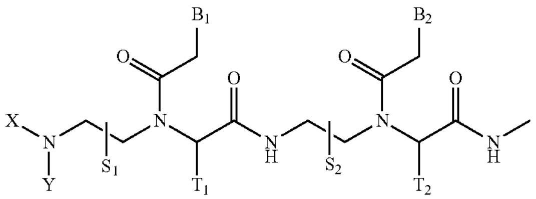

-continued

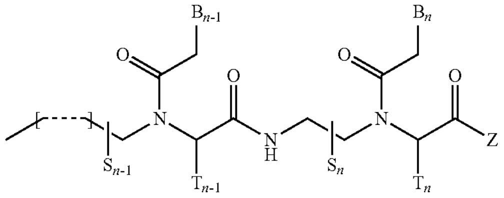

wherein, n is an integer between 11 and 20;

the compound of Formula I possesses at least a 10-mer complementary overlap with a 14-mer target splice site sequence that consists of 7-mer from intron and 7-mer from exon within a target pre-mRNA;

the compound of Formula I is fully complementary to the target pre-mRNA sequence, or partially complementary to the target pre-mRNA sequence with one or two mismatches;

$S_1, S_2, \ldots, S_{n-1}, S_n, T_1, T_2, \ldots, T_{n-1}$, and $T_n$ are hydrido radical;

X is hydrido radical;

Y is substituted or non-substituted alkyloxycarbonyl radical;

Z is amino radical;

$B_1, B_2, \ldots, B_{n-1}$, and $B_n$ are independently selected from natural nucleobases including adenine, thymine, guanine, cytosine and uracil, and unnatural nucleobases; and at least five of $B_1, B_2, \ldots, B_{n-1}$, and $B_n$ are independently selected from unnatural nucleobases represented by Formula II, Formula III, or Formula IV:

Formula II

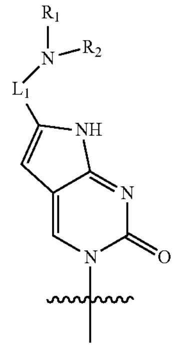

Formula III

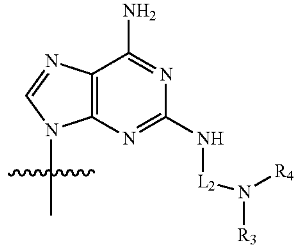

Formula IV

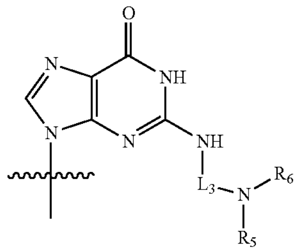

wherein, $R_1$, $R_2$, $R_3$, $R_4$, $R_5$ and $R_6$ are hydrido radical;

$L_1$, $L_2$ and $L_3$ are a covalent linker represented by Formula V covalently linking the basic amino group to the nucleobase moiety:

Formula V

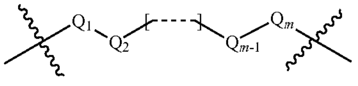

wherein, $Q_1$ and $Q_m$ are substituted or non-substituted methylene ($—CH_2—$) radical, and $Q_m$ is directly linked to the basic amino group;

$Q_2, Q_3, \ldots$, and $Q_{m-1}$ are independently selected from substituted or non-substituted methylene or oxygen radical; and m is an integer between 1 and 15.

2. The peptide nucleic acid derivative according to claim 1, or a pharmaceutical salt thereof:

wherein, n is an integer between 11 and 19;

the compound of Formula I possesses at least a 10-mer complementary overlap with a 14-mer target splice site sequence that consists of 7-mer from intron and 7-mer from exon within a target pre-mRNA;

the compound of Formula I is fully complementary to the target pre-mRNA sequence;

$S_1, S_2, \ldots, S_{n-1}, S_n, T_1, T_2, \ldots, T_{n-1}$, and $T_n$ are hydrido radical;

X is hydrido radical;

Y is substituted or non-substituted alkyloxycarbonyl radical;

Z is amino radical;

$B_1, B_2, \ldots, B_{n-1}$, and $B_n$ are independently selected from adenine, thymine, guanine, cytosine, and unnatural nucleobases;

at least five of $B_1, B_2, \ldots, B_{n-1}$, and $B_n$ are independently selected from unnatural nucleobases represented by Formula II, Formula III, or Formula IV;

$R_1$, $R_2$, $R_3$, $R_4$, $R_5$, and $R_6$ are hydrido radical;

$L_1$ represents $—(CH_2)_2—O—(CH_2)_2—$, $—CH_2—O—(CH_2)_2—$, $—CH_2—O—(CH_2)_3—$, $—CH_2—O—(CH_2)_4—$, $—CH_2—O—(CH_2)_5—$, $—CH_2—O—(CH_2)_6—$, or $—CH_2—O—(CH_2)_7—$ with the right end is directly linked to the basic amino group; and $L_2$ and $L_3$ are independently selected from $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—(CH_2)_2—O—(CH_2)_2—$, $—(CH_2)_3—O—(CH_2)_2—$, and $—(CH_2)_2—O—(CH_2)_3—$ with the right end is directly linked to the basic amino group.

3. The peptide nucleic acid derivative of claim 1, wherein the target splice site sequence is not [(5'→3') UAAGUAG-GAUAAGU (SEQ ID NO: 5)] within the human HIF-1α pre-mRNA.

4. A method of inducing in cells the skipping of the target exon within the target pre-mRNA comprising contacting the cells with the peptide nucleic acid derivative of claim 1.

5. A method of inducing in a subject the skipping of the target exon within the target pre-mRNA comprising administering the peptide nucleic acid derivative of claim 1.

6. A method of treating a disease or condition involving the expression of the target gene comprising administering the peptide nucleic acid derivative of claim 1.

7. A method of modulating in cells the functional activity of the target gene comprising contacting the cells with the peptide nucleic acid derivative of claim 1.

8. A method of modulating in a subject the functional activity of the target gene comprising administering the peptide nucleic acid derivative of claim 1.

* * * * *

SEQUENCE LISTING

```
<160> NUMBER OF SEQ ID NOS: 193

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gatgctgttt gaacta                                                  16


<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gatgctggcc ttgtg                                                   15


<210> SEQ ID NO 3
<211> LENGTH: 14
<212> TYPE: RNA
<213> ORGANISM: Homo sapiens

<400> SEQUENCE: 3

uugccuggua agga                                                    14


<210> SEQ ID NO 4
<211> LENGTH: 14
<212> TYPE: RNA
<213> ORGANISM: Homo sapiens

<400> SEQUENCE: 4
```

-continued uuuuugcgua agua 14

<210> SEQ ID NO 5
<211> LENGTH: 14
<212> TYPE: RNA
<213> ORGANISM: Homo sapiens

<400> SEQUENCE: 5
uaaguaggau aagu 14

<210> SEQ ID NO 6
<211> LENGTH: 14
<212> TYPE: RNA
<213> ORGANISM: Homo sapiens

<400> SEQUENCE: 6
aucccagggu aaca 14

<210> SEQ ID NO 7
<211> LENGTH: 14
<212> TYPE: RNA
<213> ORGANISM: Homo sapiens

<400> SEQUENCE: 7
uguuuaggua cacu 14

<210> SEQ ID NO 8
<211> LENGTH: 14
<212> TYPE: RNA
<213> ORGANISM: Homo sapiens

<400> SEQUENCE: 8
uguacagauu gucu 14

<210> SEQ ID NO 9
<211> LENGTH: 40
<212> TYPE: RNA
<213> ORGANISM: Homo sapiens

<400> SEQUENCE: 9
uucuuguugu uguuaaguag gauaaguucu gaacgucgaa 40

<210> SEQ ID NO 10
<211> LENGTH: 14
<212> TYPE: RNA
<213> ORGANISM: Homo sapiens

<400> SEQUENCE: 10
uaaguaggau aagu 14

<210> SEQ ID NO 11
<211> LENGTH: 40
<212> TYPE: RNA
<213> ORGANISM: Homo sapiens

<400> SEQUENCE: 11
gaggaaacuu cuggaugcug gugaguuauu uuacaagggu 40

<210> SEQ ID NO 12
<211> LENGTH: 14
<212> TYPE: RNA
<213> ORGANISM: Homo sapiens

<400> SEQUENCE: 12
gaugcuggug aguu 14

<210> SEQ ID NO 13
<211> LENGTH: 30
<212> TYPE: RNA
<213> ORGANISM: Homo sapiens

<400> SEQUENCE: 13
guuguuguua aguaggauaa guucugaacg 30

<210> SEQ ID NO 14
<211> LENGTH: 14
<212> TYPE: RNA
<213> ORGANISM: Homo sapiens

<400> SEQUENCE: 14
uaaguaggau aagu 14

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cagaacttat cctac 15

<210> SEQ ID NO 16
<211> LENGTH: 30
<212> TYPE: RNA
<213> ORGANISM: Homo sapiens

<400> SEQUENCE: 16
guuguuguua aguaggauaa guucugaacg 30

<210> SEQ ID NO 17
<211> LENGTH: 14
<212> TYPE: RNA
<213> ORGANISM: Homo sapiens

<400> SEQUENCE: 17
uaaguaggau aagu 14

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
ctcatcctac ttaac 15

<210> SEQ ID NO 19
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide -continued

<400> SEQUENCE: 19
guuguuguua aguaggauaa guucugaacg 30

<210> SEQ ID NO 20
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
uaaguaggau aagu 14

<210> SEQ ID NO 21
<211> LENGTH: 30
<212> TYPE: RNA
<213> ORGANISM: Homo sapiens

<400> SEQUENCE: 21
cgucauuguu uuugcguaag uacuuucagc 30

<210> SEQ ID NO 22
<211> LENGTH: 14
<212> TYPE: RNA
<213> ORGANISM: Homo sapiens

<400> SEQUENCE: 22
uuuuugcgua agua 14

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
acttacgcaa aaacaa 16

<210> SEQ ID NO 24
<211> LENGTH: 30
<212> TYPE: RNA
<213> ORGANISM: Homo sapiens

<400> SEQUENCE: 24
cgucauuguu uuugcguaag uacuuucagc 30

<210> SEQ ID NO 25
<211> LENGTH: 14
<212> TYPE: RNA
<213> ORGANISM: Homo sapiens

<400> SEQUENCE: 25
uuuuugcgua agua 14

<210> SEQ ID NO 26
<211> LENGTH: 25
<212> TYPE: RNA
<213> ORGANISM: Homo sapiens

<400> SEQUENCE: 26
gauuuuagua cacucauauc cuuuu 25

<210> SEQ ID NO 27
<211> LENGTH: 25
<212> TYPE: RNA
<213> ORGANISM: Rattus sp.

<400> SEQUENCE: 27
gaucuuagug cacucauauc cuuuc 25

<210> SEQ ID NO 28
<211> LENGTH: 25
<212> TYPE: RNA
<213> ORGANISM: Homo sapiens

<400> SEQUENCE: 28
gauuuuagua cacucauauc cuuuu 25

<210> SEQ ID NO 29
<211> LENGTH: 25
<212> TYPE: RNA
<213> ORGANISM: Homo sapiens

<400> SEQUENCE: 29
cagcacagau ucaggguaug uaaua 25

<210> SEQ ID NO 30
<211> LENGTH: 25
<212> TYPE: RNA
<213> ORGANISM: Homo sapiens

<400> SEQUENCE: 30
uugcuuuuag cuccgagucu ucaag 25

<210> SEQ ID NO 31
<211> LENGTH: 25
<212> TYPE: RNA
<213> ORGANISM: Rattus sp.

<400> SEQUENCE: 31
uuauuucuag cuccgagucu ucaag 25

<210> SEQ ID NO 32
<211> LENGTH: 20
<212> TYPE: RNA
<213> ORGANISM: Homo sapiens

<400> SEQUENCE: 32
uguuaaguag gauaaguucu 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cttgcctttc cttctcttct 20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
aacccagaca tatccacc 18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
tgaagacatc gcggggac 18

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
tttttcacaa ggccatttct 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
cttgcctttc cttctcttct 20

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
aacccagaca tatccacc 18

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
cttgctcatc agttgccact tc 22

<210> SEQ ID NO 40
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 40
aagtttcctc acacgcaaat ag 22

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gaaagcacag atgaattgc 19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcatgtcacc atcatctgt 19

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctaactggac acagtgtgtt tg 22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctgtgtgta agcatttctc tc 22

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccttgtgaa aaagggtaaa g 21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
ccatgttgca gactttatgt 20

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
cgcgaacgac aagaaaaa 18

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
ctgtggtgac ttgtccttt 19

<210> SEQ ID NO 49
<211> LENGTH: 20
<212> TYPE: RNA
<213> ORGANISM: Homo sapiens

<400> SEQUENCE: 49
uguuaaguag gauaaguucu 20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cgcgaacgac aagaaaaa 18

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ctgtggtgac ttgtccttt 19

<210> SEQ ID NO 52
<211> LENGTH: 23
<212> TYPE: RNA
<213> ORGANISM: Homo sapiens

<400> SEQUENCE: 52
uguuaaguag gauaaguucu gaa 23

-continued

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
uguuuacagu uugaactaac 20

<210> SEQ ID NO 54
<211> LENGTH: 20
<212> TYPE: RNA
<213> ORGANISM: Homo sapiens

<400> SEQUENCE: 54
gccuugccug guaaggaaaa 20

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgggtgtcac tatggagc 18

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gggtgtggaa atagatggg 19

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgggtgtcac tatggagc 18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggggtgattt ggagccat 18

<210> SEQ ID NO 59

<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tgggtgtcac tatggagc 18

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
gggtgtggaa atagatggg 19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
gaccatgttt tgcccattg 19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ggctcttttg aagaagacc 19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
gaaacagaag tacctgtgc 19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
gtcatccctg cttcataac 19

<210> SEQ ID NO 65
<211> LENGTH: 19

<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
cggaagctga agaaacttg 19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
cacttgacca cgtgtacaag 20

<210> SEQ ID NO 67
<211> LENGTH: 20
<212> TYPE: RNA
<213> ORGANISM: Homo sapiens

<400> SEQUENCE: 67
gccuugccug guaaggaaaa 20

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
tgggtgtcac tatggagc 18

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
gggtgtggaa atagatggg 19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
ttgtccatct tgtcgtctt 19

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 71
cctctccttc ctcctgta 18

<210> SEQ ID NO 72
<211> LENGTH: 11
<212> TYPE: DNA
<213> ORGANISM: Artificial Sequence
<220> FEATURE:
<223> OTHER INFORMATION: Description of Artificial Sequence: Synthetic probe

<400> SEQUENCE: 72
cttccgggct c 11

<210> SEQ ID NO 73
<211> LENGTH: 20
<212> TYPE: RNA
<213> ORGANISM: Homo sapiens

<400> SEQUENCE: 73
uuguuuuugc guaaguacuu 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ctttctcctt tcagtcctct 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
cgtctgttgg taaaggtttt 20

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ggaccaaaaa tgtcgagtat tt 22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 77

-continued

```
gctaagaagg cccagctgaa                                              20


<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

ctttctcctt tcagtcctct                                              20


<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

ttgcctggtt ctgttctt                                                18


<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

gtacactttt actggaatat atac                                         24


<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

aatgacgaca aaatccagc                                               19


<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

gtatttaaca gaatttgtaa acct                                         24


<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

ctgggattac agaaatagtt ttca                                         24
```

-continued

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
gaagacaatt gtaggggc 18

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
gtcttcttca ctctctaggg 20

<210> SEQ ID NO 86
<211> LENGTH: 20
<212> TYPE: RNA
<213> ORGANISM: Homo sapiens

<400> SEQUENCE: 86
uuguuuuugc guaaguacuu 20

<210> SEQ ID NO 87
<211> LENGTH: 20
<212> TYPE: RNA
<213> ORGANISM: Homo sapiens

<400> SEQUENCE: 87
uuguuuuugc guaaguacuu 20

<210> SEQ ID NO 88
<211> LENGTH: 20
<212> TYPE: RNA
<213> ORGANISM: Homo sapiens

<400> SEQUENCE: 88
uuguguuuag guacacuuuu 20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
ccaccggact ggaccaaaaa 20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
gctaagaagg cccagctgaa 20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
ggaccaaaaa tgtcgagcct 20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gctaagaagg cccagctgaa 20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
ctttctcctt tcagtcctct 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
cgtctgttgg taaaggtttt 20

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
tgaccatgaa taacccac 18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gcaaggattt ttacaagt 18

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Synthetic probe

<400> SEQUENCE: 97
atgtcgagta cac 13

<210> SEQ ID NO 98
<211> LENGTH: 20
<212> TYPE: RNA
<213> ORGANISM: Rattus sp.

<400> SEQUENCE: 98
uuuccuuuag guacacuuuu 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
caatcttccg tttcaacgcc 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
accacagcca ggatcaagtt 20

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 101
uaauuuugag gcucugcaaa gttct 25

<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 102
uaauuuugag gcucugcaaa gttct 25

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
caaagagaaa gagctacaga ca 22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
ctgggctgaa ttgtttgaat 20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
atccagcagt cagaaagcaa a 21

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
actaaaagtc tgcattgt 18

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
cagaattctg ccaattgctg ag 22

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
ttcttcagct tgtgtcatcc 20

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
cccagtctac caccctatca gagc 24

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
cctgccttta aggcttcctt 20

<210> SEQ ID NO 111
<211> LENGTH: 20
<212> TYPE: RNA
<213> ORGANISM: Mus sp.

<400> SEQUENCE: 111
uaauuuugag gcucugcaaa 20

<210> SEQ ID NO 112
<211> LENGTH: 25
<212> TYPE: RNA
<213> ORGANISM: Mus sp.

<400> SEQUENCE: 112
aaaauuucag guaagccgag guuug 25

<210> SEQ ID NO 113
<211> LENGTH: 20
<212> TYPE: RNA
<213> ORGANISM: Homo sapiens

<400> SEQUENCE: 113
uuuguuuuag guaauuccua 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
ttcattgcta aacatctgcc 20

<210> SEQ ID NO 115
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 115
tgaaaggaca aactcacgga 20

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
ccttactgcc aactctcc 18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
ctgctttggc ctgcactg 18

<210> SEQ ID NO 118
<211> LENGTH: 20
<212> TYPE: RNA
<213> ORGANISM: Homo sapiens

<400> SEQUENCE: 118
uguccguaag guuuggagau 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
aaaactcctg gacaatcagt 20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
acttgaaggg ctttctcc 18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
tattgatgaa gaagtggg 18

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 122
gttcacatga tcgtggattt g 21

<210> SEQ ID NO 123
<211> LENGTH: 20
<212> TYPE: RNA
<213> ORGANISM: Homo sapiens

<400> SEQUENCE: 123
uuuuaaucag gucuugccaa 20

<210> SEQ ID NO 124
<211> LENGTH: 30
<212> TYPE: RNA
<213> ORGANISM: Homo sapiens

<400> SEQUENCE: 124
cucuuuggau cccaggguaa caaaugaugc 30

<210> SEQ ID NO 125
<211> LENGTH: 25
<212> TYPE: RNA
<213> ORGANISM: Rattus sp.

<400> SEQUENCE: 125
uggcucccag gguaacaaac gaugc 25

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 126
atggccgagg acgcagaca 19

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
agcatctttg ttgcacgttg 20

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
atggccgagg acgcagaca 19

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
ttgttggagt cagcgcct 18

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
atggccgagg acgcagaca 19

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
agcatctttg ttgcacgttg 20

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
atggatgaaa acctagagc 19

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
cttcccagca tctttgtt 18

<210> SEQ ID NO 134
<211> LENGTH: 10
<212> TYPE: DNA
<213> ORGANISM: Artificial Sequence
<220> FEATURE:
<223> OTHER INFORMATION: Description of Artificial Sequence: Synthetic probe

<400> SEQUENCE: 134
ccatgatcct 10

<210> SEQ ID NO 135
<211> LENGTH: 30
<212> TYPE: RNA
<213> ORGANISM: Homo sapiens

<400> SEQUENCE: 135
cucuuuggau cccaggguaa caaaugaugc 30

<210> SEQ ID NO 136
<211> LENGTH: 25
<212> TYPE: RNA
<213> ORGANISM: Rattus sp.

<400> SEQUENCE: 136
uggcucccag gguaacaaac gaugc 25

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic probe

<400> SEQUENCE: 137
ccgcagggta acaa 14

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
gacgaacggg agcagatg 18

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
atctcattgc ccatatccag g 21

<210> SEQ ID NO 140
<211> LENGTH: 30
<212> TYPE: RNA
<213> ORGANISM: Mus sp.

<400> SEQUENCE: 140
aauuguuuuu cacagaucau uuguagcaga 30

<210> SEQ ID NO 141
<211> LENGTH: 30
<212> TYPE: RNA
<213> ORGANISM: Homo sapiens

<400> SEQUENCE: 141 gggugguuuug uacagauugu cuguagccga 30

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
gtaagtttgg atttgggg 18

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
agagcggtat gaaaggaa 18

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
gagaactaac tggggatga 19

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
cgataggtgc attggctt 18

<210> SEQ ID NO 146
<211> LENGTH: 30
<212> TYPE: RNA
<213> ORGANISM: Homo sapiens

<400> SEQUENCE: 146 gggugguuuug uacagauugu cuguagccga 30

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
ctctttgtct ggatgcatt 19

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 148
ctgtggtaat cctctttct 19

<210> SEQ ID NO 149
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 149
gataaagctg ccaatttc 18

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 150
ttgtgcatgc tgctttga 18

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
probe

<400> SEQUENCE: 151
aaggatttgc tagtccac 18

<210> SEQ ID NO 152
<211> LENGTH: 30
<212> TYPE: RNA
<213> ORGANISM: Homo sapiens

<400> SEQUENCE: 152
agcucagggu gacaggugcg gccucggagg 30

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 153
gtcgtctggg cggtgctaca ac 22

<210> SEQ ID NO 154
<211> LENGTH: 19

<212> TYPE: DNA
<213> ORGANISM: Artificial Sequence
<220> FEATURE:
<223> OTHER INFORMATION: Description of Artificial Sequence: Synthetic
primer

<400> SEQUENCE: 154
gggtgtggaa atagatggg 19

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 155
ggctggcggc caggatggtt c 21

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 156
gaaagacaat ggtggcatac tcc 23

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 157
gtcgtctggg cggtgctaca ac 22

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 158
gggtgtggaa atagatggg 19

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 159
acaacgccac cttcacctgc 20

<210> SEQ ID NO 160
<211> LENGTH: 21
<212> TYPE: DNA

<213> ORGANISM: Artificial Sequence
<220> FEATURE:
<223> OTHER INFORMATION: Description of Artificial Sequence: Synthetic primer

<400> SEQUENCE: 160
gccagcttgt ccgtctggtt g 21

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
gtcacaaaca gtgcacctac 20

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
ggtgagtttg ggattcttgt a 21

<210> SEQ ID NO 163
<211> LENGTH: 30
<212> TYPE: RNA
<213> ORGANISM: Homo sapiens

<400> SEQUENCE: 163
cucuccaucu cucagacucc ccagacaggc 30

<210> SEQ ID NO 164
<211> LENGTH: 30
<212> TYPE: RNA
<213> ORGANISM: Mus sp.

<400> SEQUENCE: 164
agcucguggu aacaggugag gcuaguagaa 30

<210> SEQ ID NO 165
<211> LENGTH: 30
<212> TYPE: RNA
<213> ORGANISM: Homo sapiens

<400> SEQUENCE: 165
agcucagggu gacaggugcg gccucggagg 30

<210> SEQ ID NO 166
<211> LENGTH: 300
<212> TYPE: DNA
<213> ORGANISM: Homo sapiens

<400> SEQUENCE: 166
atttgcgtgt gaggaaactt ctggatgctg gtgatttgga tattgaagat gacatgaaag 60
cacagatgaa ttgcttttat ttgaaagcct tggatggttt tgttatggtt ctcacagatg 120
atggtgacat gatttacatt tctgataatg tgaacaaata catgggatta actcagtttg 180

-continued

```
aactaactgg acacagtgtg tttgatttta ctcatccatg tgaccatgag gaaatgagag    240

aaatgcttac acacagaaat ggccttgtga aaaagggtaa agaacaaaac acacagcgaa    300


<210> SEQ ID NO 167
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167

gatgctgttt gaacta                                                    16


<210> SEQ ID NO 168
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

gatgctggcc ttgtg                                                     15


<210> SEQ ID NO 169
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

gatgctgttt gaact                                                     15


<210> SEQ ID NO 170
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

gagggcgccg gcggcgcgaa cgacaagaaa aagtgatttg gatattgaag atgacatgaa     60

agcacagatg                                                           70


<210> SEQ ID NO 171
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171

caccatggag ggcgccggcg gcgcgaacga caagaaaaat ttgaactaac tggacacagt     60

gtgtttga                                                             68


<210> SEQ ID NO 172
<211> LENGTH: 41
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 172
ggcggcgcga acgacaagaa aaagccttgt gaaaaagggt a 41

<210> SEQ ID NO 173
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 173
gcgaacgaca agaaaaagcc ttgtgaaaaa gggta 35

<210> SEQ ID NO 174
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 174
gtctctgcga acgacaagaa aaagccttgt gaaaaagggt a 41

<210> SEQ ID NO 175
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
gaagctgcaa ggtcttcttc aaaagagccg ctgaaggctt ccgcaactta cacg 54

<210> SEQ ID NO 176
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
cggaaatgtt atgaagcagg gatgactctg ggaggcttcc gcaacttac 49

<210> SEQ ID NO 177
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
ggaccaaaaa tgtcgagtat ttaacagaat ttgtaaac 38

<210> SEQ ID NO 178
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 178
gaccaaaaat gtcgagcctg aagacaattg tagg 34

<210> SEQ ID NO 179
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
ggaccaaaaa tgtcgagcct gaaga 25

<210> SEQ ID NO 180
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180
atatgaaata atggaggaga gactcgggaa attacagaat cacataaaaa ccttacagaa 60
atg 63

<210> SEQ ID NO 181
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
tcagagccaa cagcaattaa aagccagtta aaaatttgta agaatcacat aaaaacctta 60
cagaaatgga tggctga 77

<210> SEQ ID NO 182
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
tcagagccaa cagcaattaa aagccagtta aaaatttgta aaaatcacat aaaaacctta 60
cagaaatgga tggctga 77

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
gcccctgact tatgaatcat gtgaacccaa aagcattttt 40

<210> SEQ ID NO 184

<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aagtgggctt tgctctgcca aatccacagg aacatggacg ttttgttctc atttcgtgat     60
ggag                                                                  64

<210> SEQ ID NO 185
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aagaagtggg ctttgctctg ccaaatccac aggtaattcc tactgtattc aaggcaatgc     60
aaatgcaa                                                              68

<210> SEQ ID NO 186
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tgggctttgc tctgccaaat ccacaggaac atggacgttt tgttctcatt tcgtgat        57

<210> SEQ ID NO 187
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgggctttgc tctgccaaat ccacaggaaa atggacgttt tgttctcatt tcgtgat        57

<210> SEQ ID NO 188
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ctttggttat gttggatgag caaggcgctg actccaacaa a                         41

<210> SEQ ID NO 189
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cagcatcctt cttctcctcc tggcagtatt tttgaacaat ggctgcga                  48

-continued

<210> SEQ ID NO 190
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gcggccagga tggttcttag agagaagggc agaagtgcc 39

<210> SEQ ID NO 191
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gcgggcagag ctcagggtga cagggacaat aggagccagg c 41

<210> SEQ ID NO 192
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agtgatctac 10

<210> SEQ ID NO 193
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
agugaucuac 10